(12) United States Patent
Hetz

(10) Patent No.: US 12,144,999 B2
(45) Date of Patent: Nov. 19, 2024

(54) DEVICE FOR DELIVERING PRECISION PHOTOTHERAPY

(71) Applicant: GlobaLaseReach, LLC, Manitowoc, WI (US)

(72) Inventor: Robert Nolan Hetz, Manitowoc, WI (US)

(73) Assignee: GlobaLaseReach, LLC, Manitowoc, WI (US)

( * ) Notice: Subject to any disclaimer, the term of this patent is extended or adjusted under 35 U.S.C. 154(b) by 112 days.

(21) Appl. No.: 17/682,988

(22) Filed: Feb. 28, 2022

(65) Prior Publication Data

US 2022/0176148 A1 Jun. 9, 2022

Related U.S. Application Data

(60) Division of application No. 17/000,254, filed on Aug. 21, 2020, now Pat. No. 11,318,323, which is a
(Continued)

(51) Int. Cl.
*A61N 5/06* (2006.01)
*A61B 18/22* (2006.01)
(Continued)

(52) U.S. Cl.
CPC ............ *A61N 5/0613* (2013.01); *A61B 18/22* (2013.01); *A61B 18/24* (2013.01);
(Continued)

(58) Field of Classification Search
CPC ................ A61N 5/0613; A61N 5/0616; A61N 2005/007; A61N 2005/0628;
(Continued)

(56) References Cited

U.S. PATENT DOCUMENTS

| 5,344,435 A | 9/1994 | Turner et al. |
| 6,565,555 B1 | 5/2003 | Ryan et al. |

(Continued)

FOREIGN PATENT DOCUMENTS

WO WO-2016/154664 A1 10/2016

OTHER PUBLICATIONS

International Search Report and Written Opinion for International Application No. PCT/US2019/019286, mailed Jun. 25, 2019, 32 pages.

(Continued)

*Primary Examiner* — Jonathan T Kuo
(74) *Attorney, Agent, or Firm* — FOLEY & LARDNER LLP

(57) ABSTRACT

Systems and method relate to administering phototherapy. A device includes a hollow structure having at least a first open end. The hollow structure includes a rotatable member, one or more coherent light generators, and, for each coherent light generator, one or more lenses or mirrors optically connected to the coherent light generator and configured to alter at least one aspect of a beam of coherent light. The device further includes a processing circuit including a processor and a memory storing instructions. The instructions, when executed by the processor, cause the processor to accept an input from an operator and generate one or more beams of coherent light according to a plurality of settings configured to produce a therapeutic effect at a targeted treatment site. Additionally, the rotatable member is configured to be rotated to direct the one or more beams of coherent light to the targeted treatment site.

50 Claims, 106 Drawing Sheets

Related U.S. Application Data continuation-in-part of application No. PCT/US2019/019286, filed on Feb. 22, 2019.

(60) Provisional application No. 62/634,655, filed on Feb. 23, 2018.

(51) Int. Cl.
*A61B 18/24* (2006.01)
*A61N 5/00* (2006.01)

(52) U.S. Cl.
CPC . *A61B 2018/2253* (2017.05); *A61N 2005/007* (2013.01); *A61N 2005/0628* (2013.01); *A61N 2005/0644* (2013.01); *A61N 2005/066* (2013.01); *A61N 2005/0666* (2013.01)

(58) Field of Classification Search
CPC ...... A61N 2005/066; A61N 2005/0666; A61N 2005/0659; A61N 2005/0644; A61N 5/067; A61N 2005/0651; A61N 5/0625; A61N 2005/0604; A61N 2005/0608; A61N 2005/0609; A61N 2005/0611; A61N 2005/063; A61N 2005/0643; A61N 5/06–2005/073; A61B 5/4848; A61B 2018/2253; A61B 5/0077; A61B 5/015; A61B 2017/00061; A61B 2018/00642; A61B 2018/00678; A61B 2018/00702; A61B 2018/00708; A61B 2018/00791; A61B 2018/2261; A61B 18/20–18/28
See application file for complete search history.

(56) References Cited

U.S. PATENT DOCUMENTS

| | | |
|---|---|---|
| 6,676,654 B1 * | 1/2004 | Balle-Petersen ..... A61B 18/203 606/17 |
| 6,974,450 B2 | 12/2005 | Weber et al. |
| 7,145,651 B2 | 12/2006 | Li et al. |
| 7,218,655 B2 | 5/2007 | Wang et al. |
| 7,245,369 B2 | 7/2007 | Wang et al. |
| 7,245,371 B2 | 7/2007 | Wang et al. |
| 7,265,830 B2 | 9/2007 | Wang |
| 7,355,155 B2 | 4/2008 | Wang |
| 7,357,530 B2 | 4/2008 | Wang et al. |
| 7,366,214 B2 | 4/2008 | Liu et al. |
| 7,378,983 B2 | 5/2008 | Wang et al. |
| 7,420,663 B2 | 9/2008 | Wang et al. |
| 7,446,877 B2 | 11/2008 | Li et al. |
| 7,497,593 B2 | 3/2009 | Wang |
| 7,545,493 B2 | 6/2009 | Wang et al. |
| 7,671,986 B2 | 3/2010 | Yao |
| 7,684,036 B2 | 3/2010 | Li et al. |
| 7,755,513 B2 | 7/2010 | Wang et al. |
| 7,804,251 B2 | 9/2010 | Wang |
| 8,135,249 B2 | 3/2012 | Li et al. |
| 8,159,665 B2 | 4/2012 | Wang et al. |
| 8,167,459 B2 | 5/2012 | Wang |
| 8,189,975 B2 | 5/2012 | Sullivan et al. |
| 8,308,642 B2 | 11/2012 | Zhou et al. |
| D677,185 S | 3/2013 | Zhou et al. |
| 8,494,012 B2 | 7/2013 | Heller et al. |
| 8,518,094 B2 | 8/2013 | Wang |
| 8,574,177 B2 | 11/2013 | Pryor et al. |
| 8,699,020 B1 | 4/2014 | Zhou et al. |
| 8,709,056 B2 | 4/2014 | Wang |
| 8,749,793 B2 | 6/2014 | Wang |
| 8,795,264 B2 | 8/2014 | Zipper |
| 8,801,600 B2 | 8/2014 | Zipper |
| 8,813,756 B1 * | 8/2014 | Shanks ................ A61N 5/0613 128/898 |
| 8,882,685 B2 | 11/2014 | Pryor et al. |
| 8,887,731 B2 | 11/2014 | Zipper |
| 8,968,221 B2 | 3/2015 | Pryor et al. |
| 8,993,829 B2 | 3/2015 | Zipper |
| 9,186,091 B2 | 11/2015 | Mainini et al. |
| 9,216,300 B2 | 12/2015 | Pryor et al. |
| D748,510 S | 2/2016 | Zhou et al. |
| 9,253,851 B2 | 2/2016 | Hoffer et al. |
| 9,259,594 B2 | 2/2016 | Wang |
| 9,283,036 B2 | 3/2016 | Wang |
| 9,358,403 B2 | 6/2016 | Pryor et al. |
| 9,366,634 B2 | 6/2016 | Wang et al. |
| 9,370,465 B2 | 6/2016 | Wang |
| 9,498,640 B2 | 11/2016 | Pryor et al. |
| 9,504,847 B2 | 11/2016 | Pryor et al. |
| 9,610,214 B2 | 4/2017 | Zipper |
| 9,649,506 B2 | 5/2017 | Pryor et al. |
| 9,764,155 B2 | 9/2017 | Pryor et al. |
| 9,766,182 B2 | 9/2017 | Zhou et al. |
| 9,797,776 B2 | 10/2017 | Wang et al. |
| 9,816,934 B2 | 11/2017 | Li et al. |
| 9,909,923 B2 | 3/2018 | Wang et al. |
| 9,952,159 B2 | 4/2018 | Wang et al. |
| 9,958,395 B2 | 5/2018 | Zhou et al. |
| 10,086,211 B2 | 10/2018 | Pryor et al. |
| 10,113,969 B2 | 10/2018 | Zhao et al. |
| 10,119,916 B2 | 11/2018 | Zhao et al. |
| 10,119,917 B2 | 11/2018 | Zhao et al. |
| 10,126,244 B2 | 11/2018 | Zhao et al. |
| 10,130,550 B2 | 11/2018 | Zipper |
| 10,215,703 B2 | 2/2019 | Zhao et al. |
| 10,238,889 B2 | 3/2019 | Pryor et al. |
| 10,345,242 B2 | 7/2019 | Zhao et al. |
| 10,413,473 B2 | 9/2019 | Zipper |
| 10,413,746 B1 | 9/2019 | Pryor et al. |
| 10,564,105 B2 | 2/2020 | Zhao et al. |
| 2002/0198575 A1 | 12/2002 | Sullivan |
| 2003/0114901 A1 | 6/2003 | Loeb et al. |
| 2004/0158301 A1 * | 8/2004 | Tucek ................ A61N 5/0616 607/89 |
| 2005/0158877 A1 | 7/2005 | Wang et al. |
| 2006/0052661 A1 | 3/2006 | Gannot et al. |
| 2006/0083017 A1 | 4/2006 | Wang et al. |
| 2006/0092491 A1 | 5/2006 | Wang |
| 2006/0167531 A1 | 7/2006 | Gertner et al. |
| 2006/0278897 A1 | 12/2006 | Heller et al. |
| 2006/0285350 A1 | 12/2006 | Wang |
| 2007/0031777 A1 | 2/2007 | Wang et al. |
| 2007/0127258 A1 | 6/2007 | Wang et al. |
| 2007/0195548 A1 | 8/2007 | Wang |
| 2007/0213696 A1 * | 9/2007 | Altshuler ............ A61N 5/0616 606/9 |
| 2008/0033412 A1 | 2/2008 | Whelan et al. |
| 2008/0091249 A1 | 4/2008 | Wang |
| 2008/0137350 A1 | 6/2008 | Tian et al. |
| 2008/0195087 A1 | 8/2008 | Wang et al. |
| 2008/0201826 A1 | 8/2008 | Pryor et al. |
| 2008/0234787 A1 | 9/2008 | Kaphan et al. |
| 2008/0306472 A1 | 12/2008 | Pryor et al. |
| 2009/0012587 A1 | 1/2009 | Wang et al. |
| 2009/0082759 A1 | 3/2009 | Pryor et al. |
| 2009/0153837 A1 | 6/2009 | Wang et al. |
| 2009/0216072 A1 | 8/2009 | Zipper |
| 2009/0216073 A1 | 8/2009 | Zipper |
| 2009/0216195 A1 | 8/2009 | Zipper |
| 2009/0216250 A1 | 8/2009 | Zipper |
| 2010/0049282 A1 | 2/2010 | Wang |
| 2010/0198236 A1 | 8/2010 | Zipper |
| 2010/0228123 A1 * | 9/2010 | Brennan .................. A61B 3/10 606/41 |
| 2010/0234836 A1 | 9/2010 | Wang |
| 2010/0241038 A1 | 9/2010 | Sullivan et al. |
| 2010/0256541 A1 | 10/2010 | Pryor et al. |
| 2010/0286576 A1 | 11/2010 | Pryor et al. |
| 2010/0315631 A1 | 12/2010 | Zhou et al. |
| 2011/0004202 A1 | 1/2011 | Zipper |
| 2011/0004203 A1 | 1/2011 | Zipper |
| 2011/0009852 A1 | 1/2011 | Pryor et al. |
| 2011/0020173 A1 | 1/2011 | Pryor et al. |
| 2011/0034973 A1 | 2/2011 | Wang |

(56) References Cited

U.S. PATENT DOCUMENTS

| | | |
|---|---|---|
| 2011/0059116 A1* | 3/2011 | Onikienko ............... C12N 7/00 424/184.1 |
| 2011/0144724 A1 | 6/2011 | Pryor et al. |
| 2011/0144725 A1 | 6/2011 | Pryor et al. |
| 2011/0172746 A1 | 7/2011 | Porter |
| 2012/0041521 A1 | 2/2012 | Oron et al. |
| 2012/0215289 A1* | 8/2012 | Tucek ................. A61B 18/203 607/91 |
| 2012/0303100 A1 | 11/2012 | Pryor et al. |
| 2013/0030249 A1 | 1/2013 | Vazales et al. |
| 2013/0035746 A1 | 2/2013 | Bouboulis |
| 2013/0067782 A1 | 3/2013 | Hoffer et al. |
| 2013/0085485 A1 | 4/2013 | Van Valen et al. |
| 2013/0338654 A1 | 12/2013 | Wang |
| 2014/0088575 A1 | 3/2014 | Loeb |
| 2014/0128881 A1 | 5/2014 | Tyc et al. |
| 2015/0182757 A1* | 7/2015 | Levine .................. G16H 20/30 606/9 |
| 2015/0346103 A1 | 12/2015 | Wang et al. |
| 2016/0074672 A1 | 3/2016 | Schomacker et al. |
| 2016/0279436 A1 | 9/2016 | Wang et al. |
| 2017/0027645 A1 | 2/2017 | Ben Oren et al. |
| 2017/0059475 A1 | 3/2017 | Zhao et al. |
| 2017/0172658 A1 | 6/2017 | Zipper |
| 2017/0304646 A1 | 10/2017 | Pryor et al. |
| 2018/0250072 A1* | 9/2018 | Rogers ................. A61B 5/0059 |
| 2018/0289874 A1 | 10/2018 | Wang |
| 2019/0060664 A1 | 2/2019 | De Taboada et al. |
| 2019/0083355 A1 | 3/2019 | Zipper |
| 2019/0090895 A1 | 3/2019 | Zipper |
| 2019/0125448 A1 | 5/2019 | Zipper |
| 2019/0201712 A1 | 7/2019 | Pryor et al. |

OTHER PUBLICATIONS

Invitation to Pay Additional Fees for International Application No. PCT/US2019/019286, mailed Apr. 19, 2019, 2 pages.

\* cited by examiner

SECTION A-A
SCALE 2

DETAIL B
SCALE 5

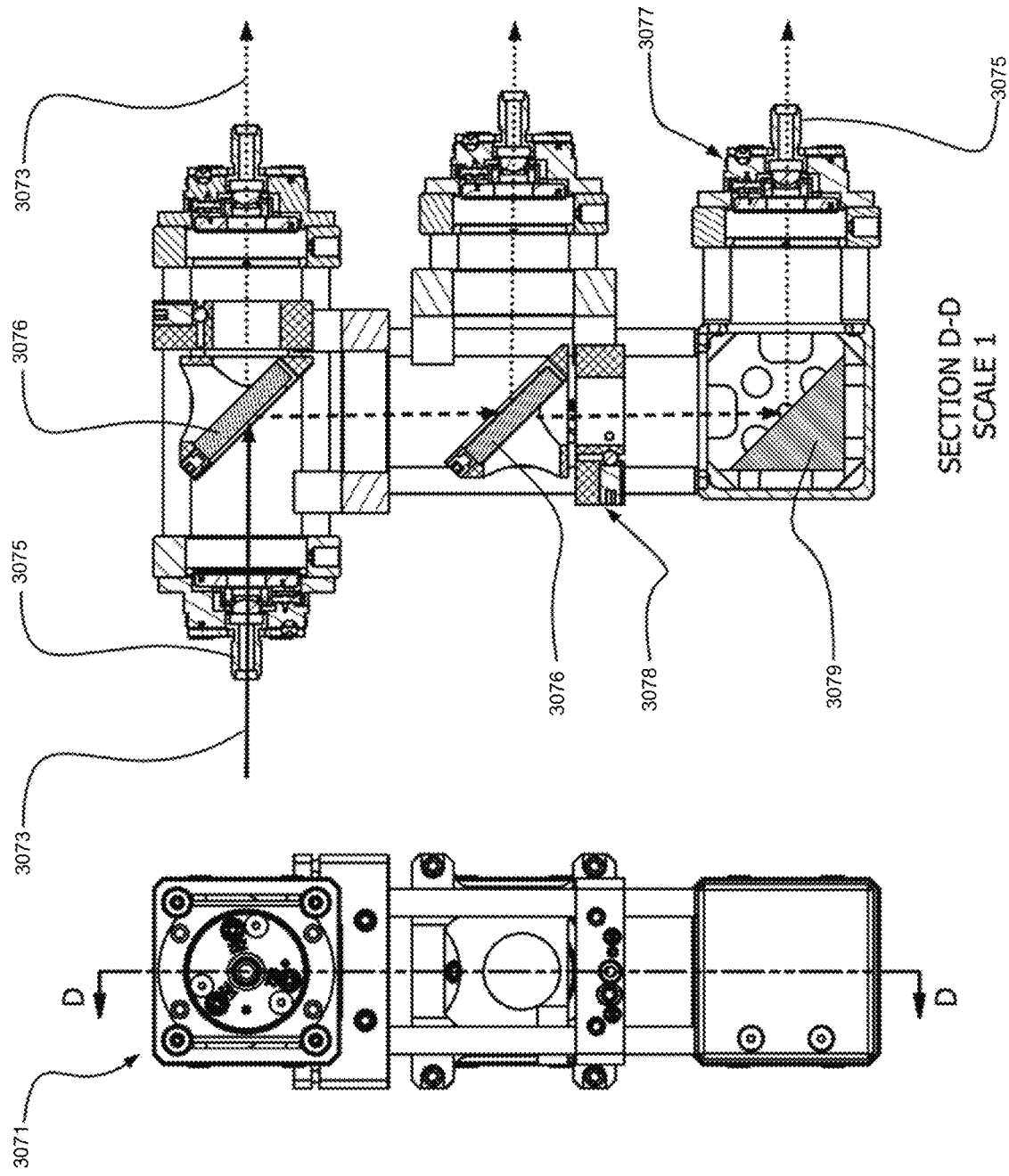

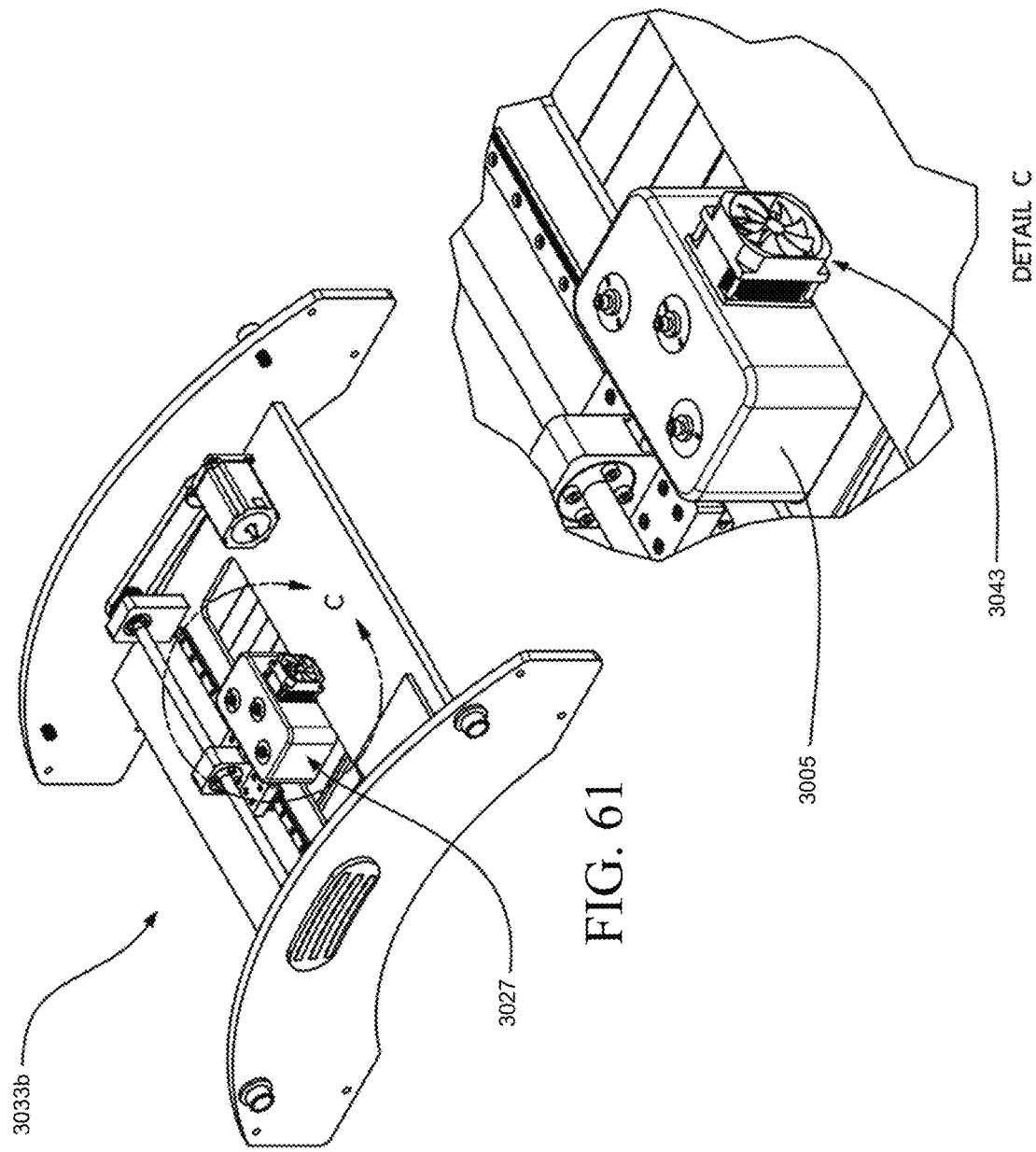

Beam-Widening Ball Lens

Negative Lens

FIG. 82
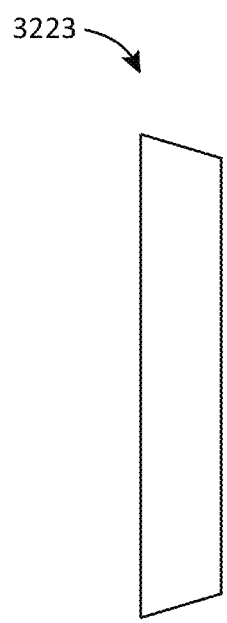 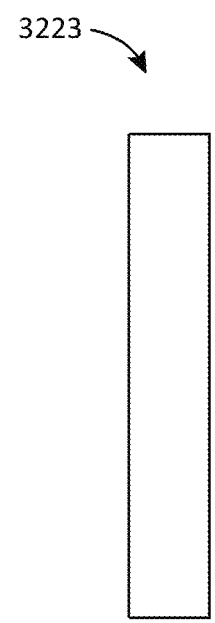
FIG. 83                     FIG. 84

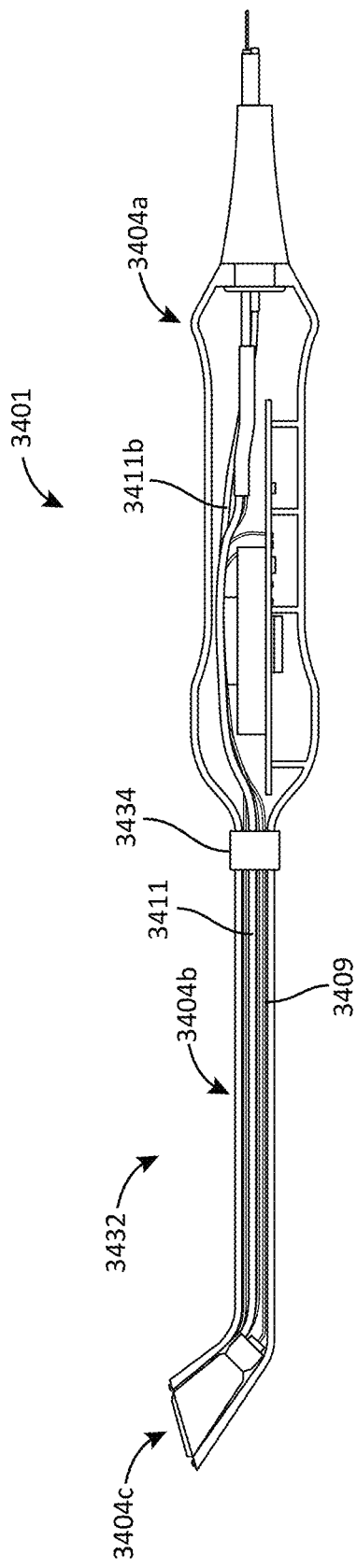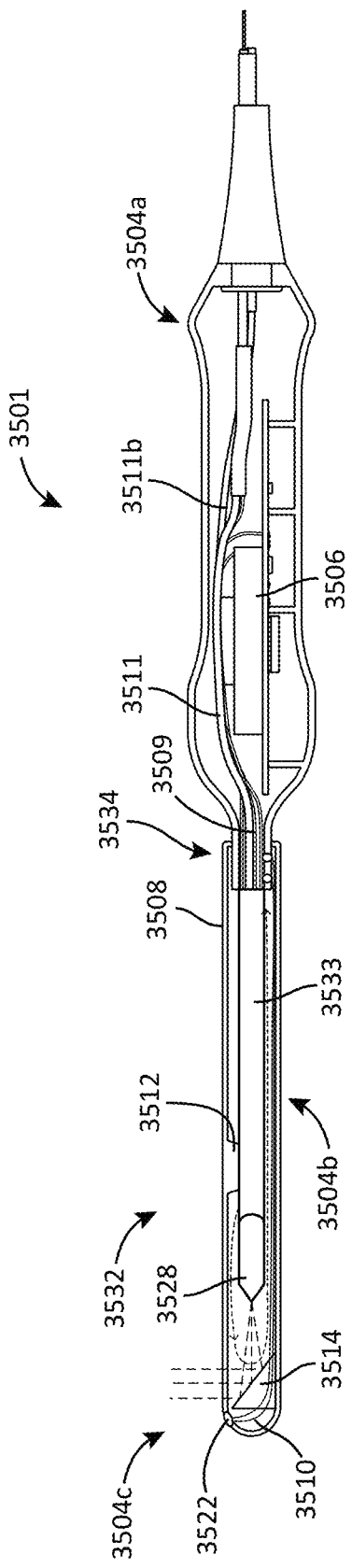
FIG. 88
FIG. 89

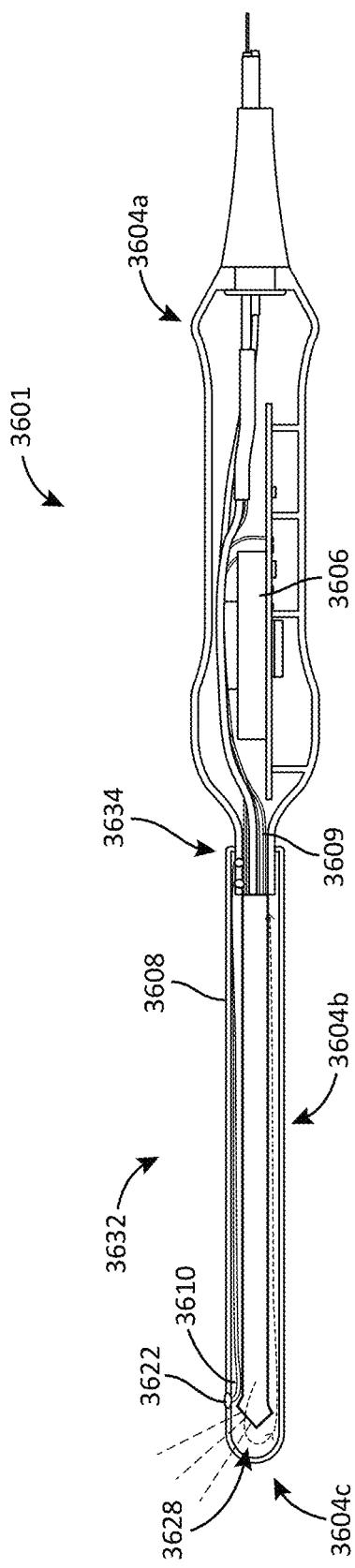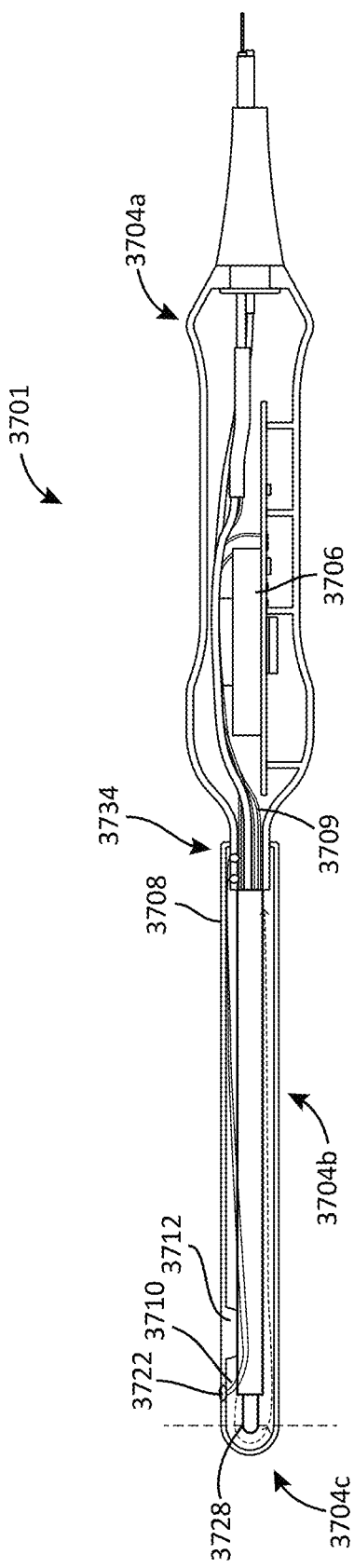
FIG. 90
FIG. 91

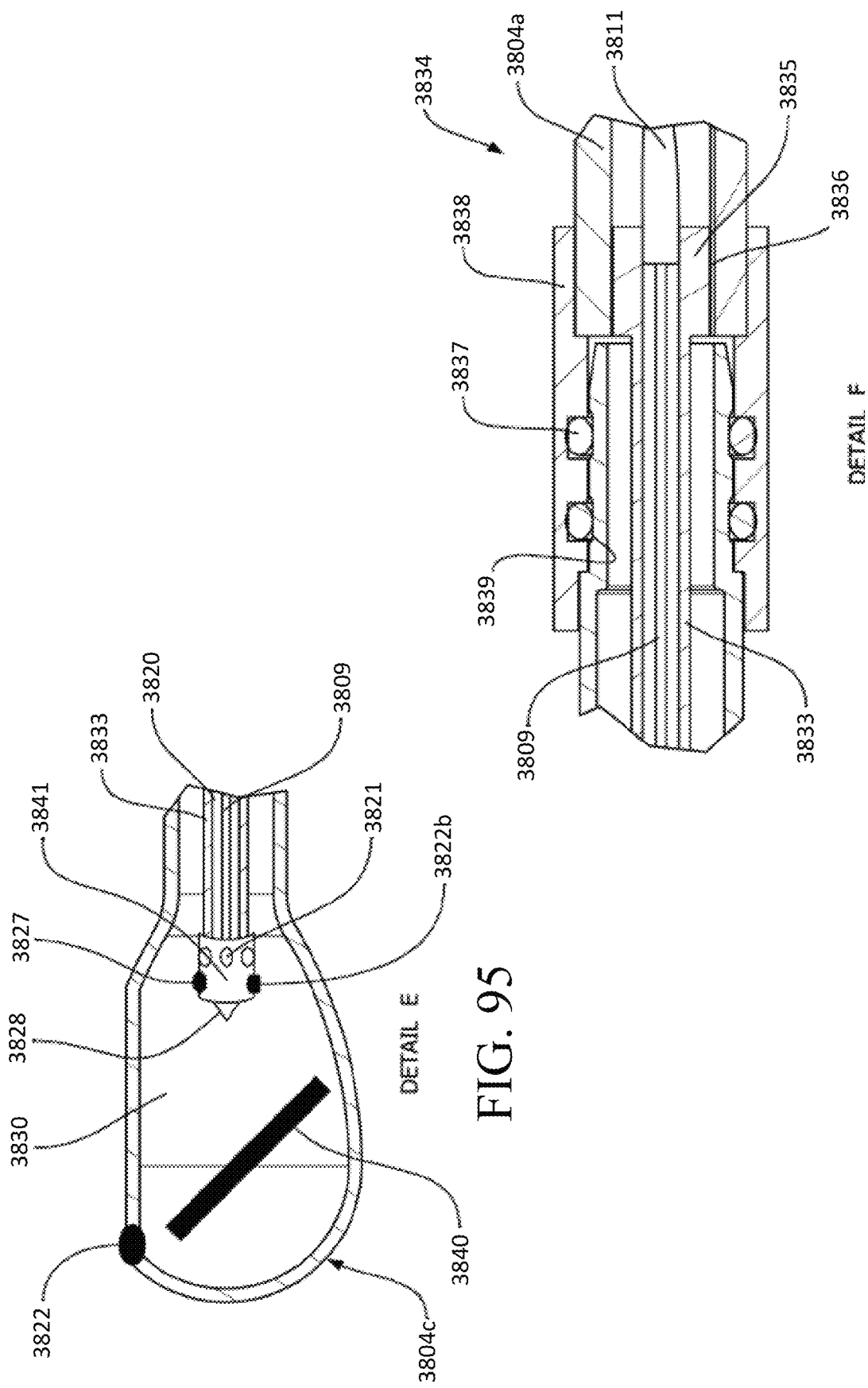

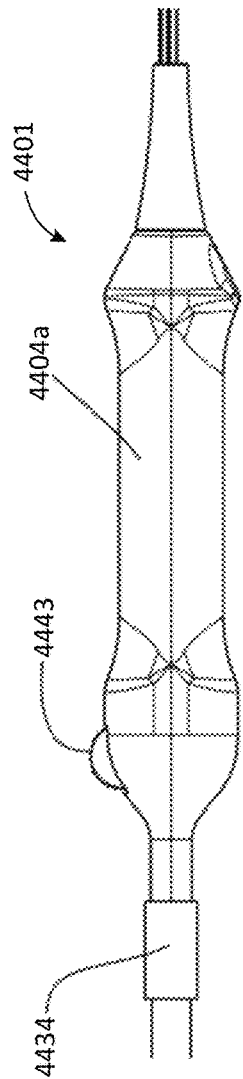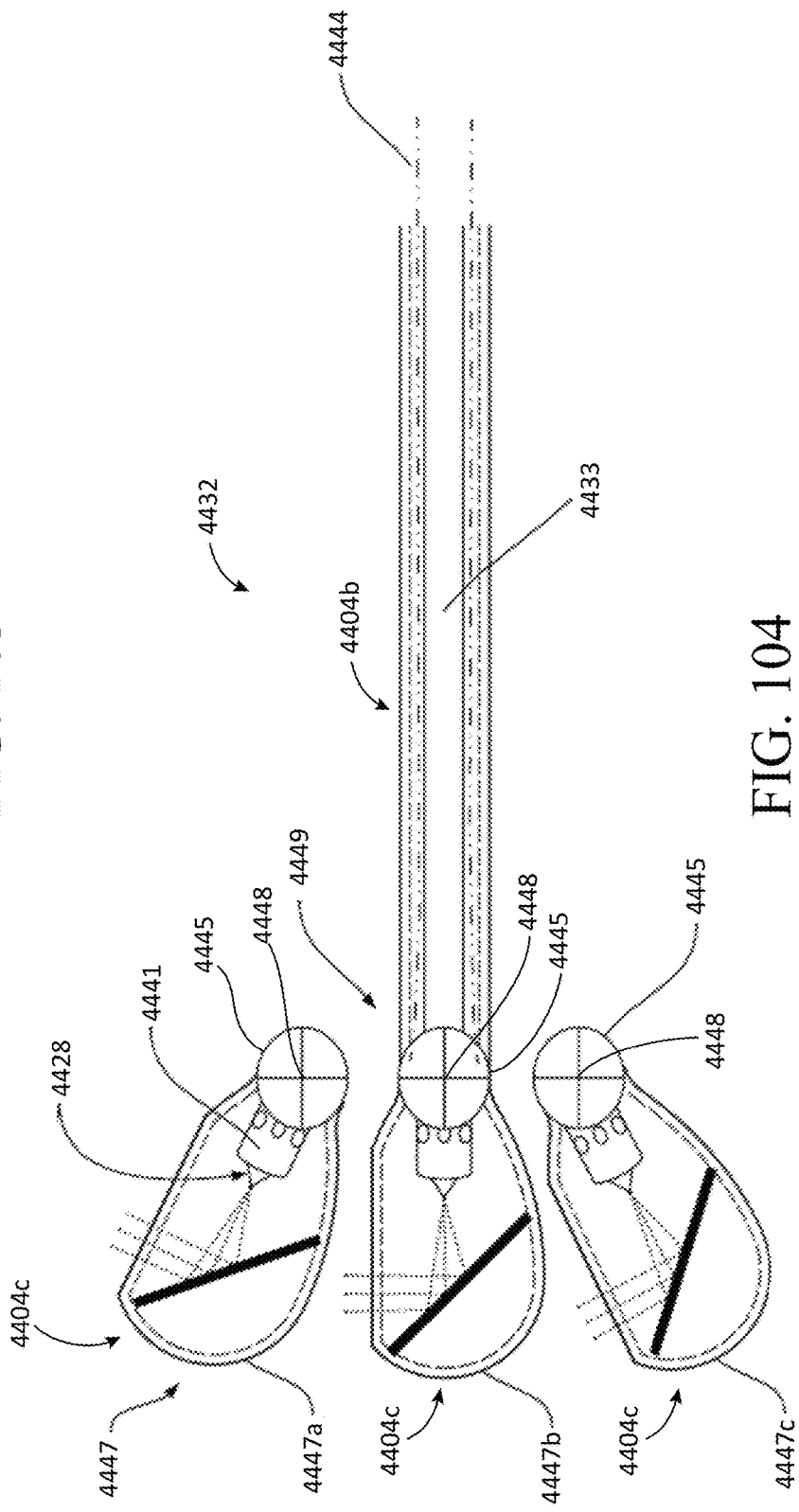
FIG. 103
FIG. 104

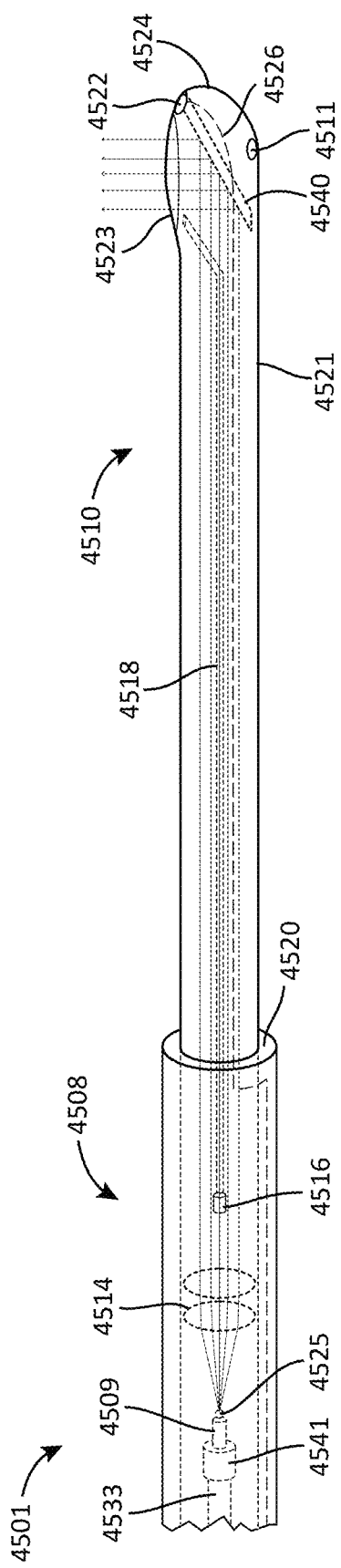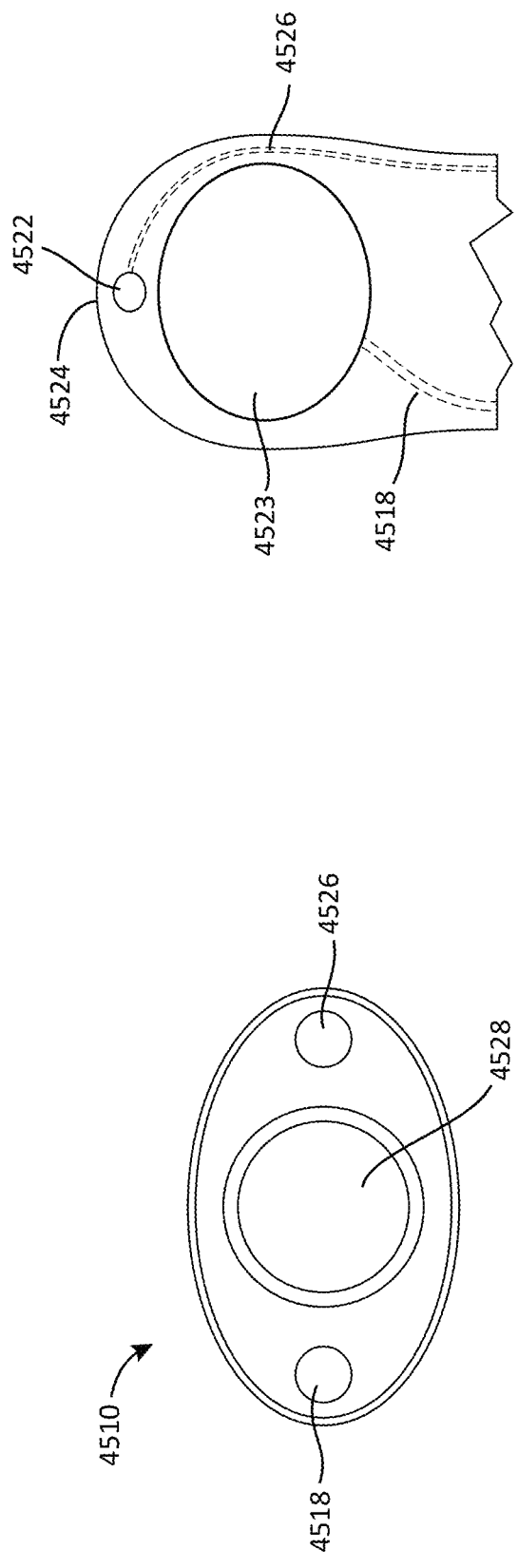
FIG. 105
FIG. 107
FIG. 106

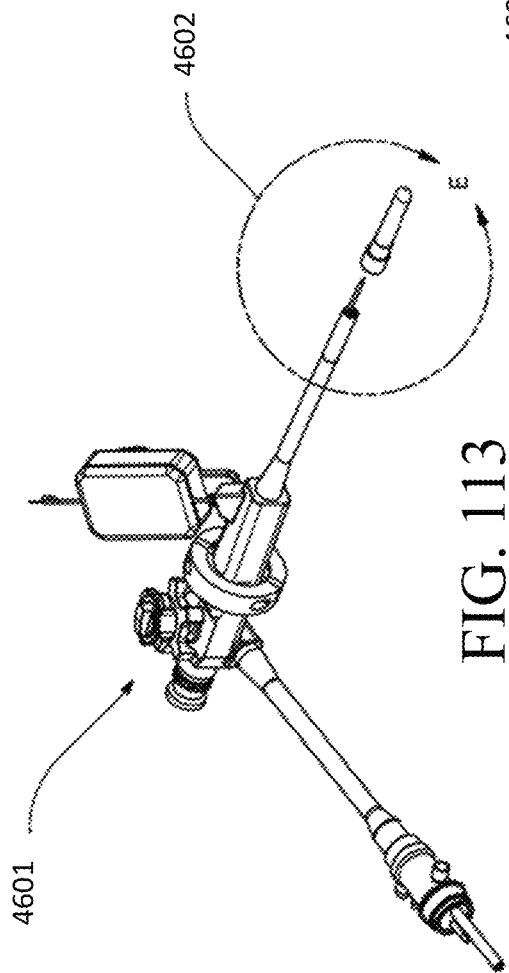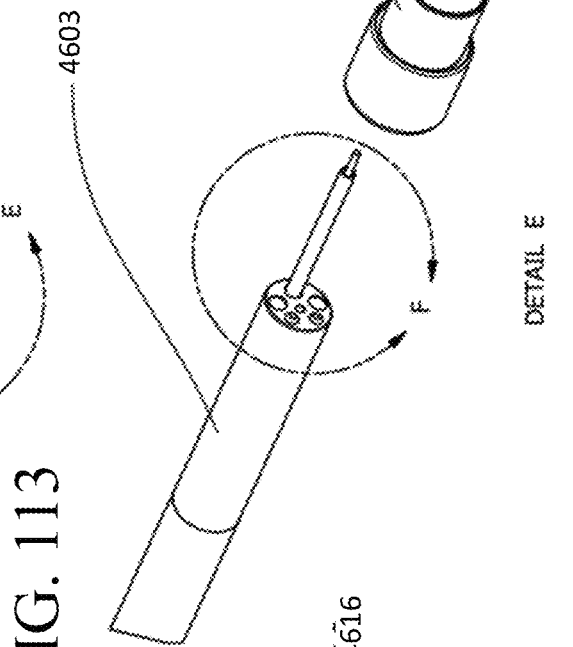
FIG. 113
FIG. 114
FIG. 115

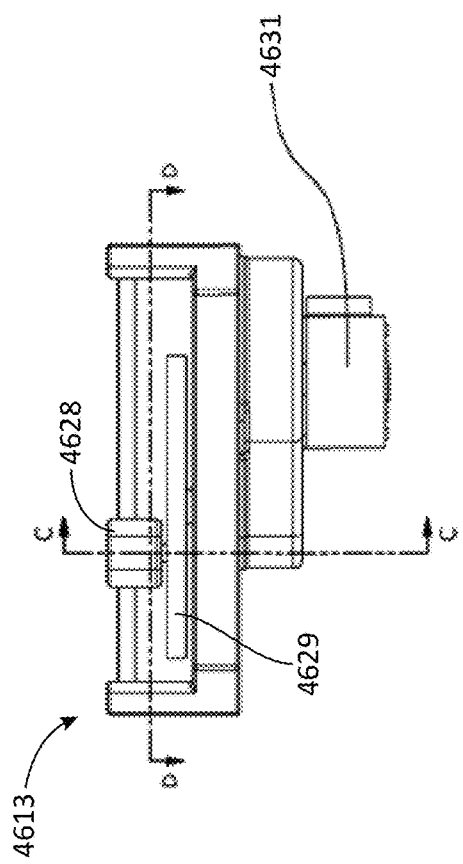
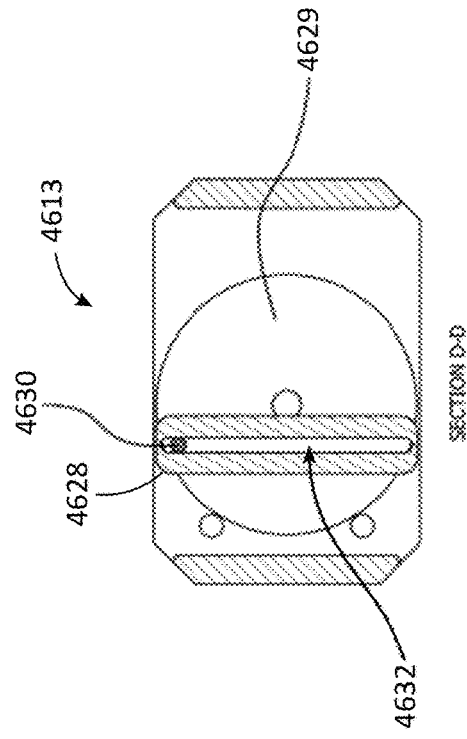
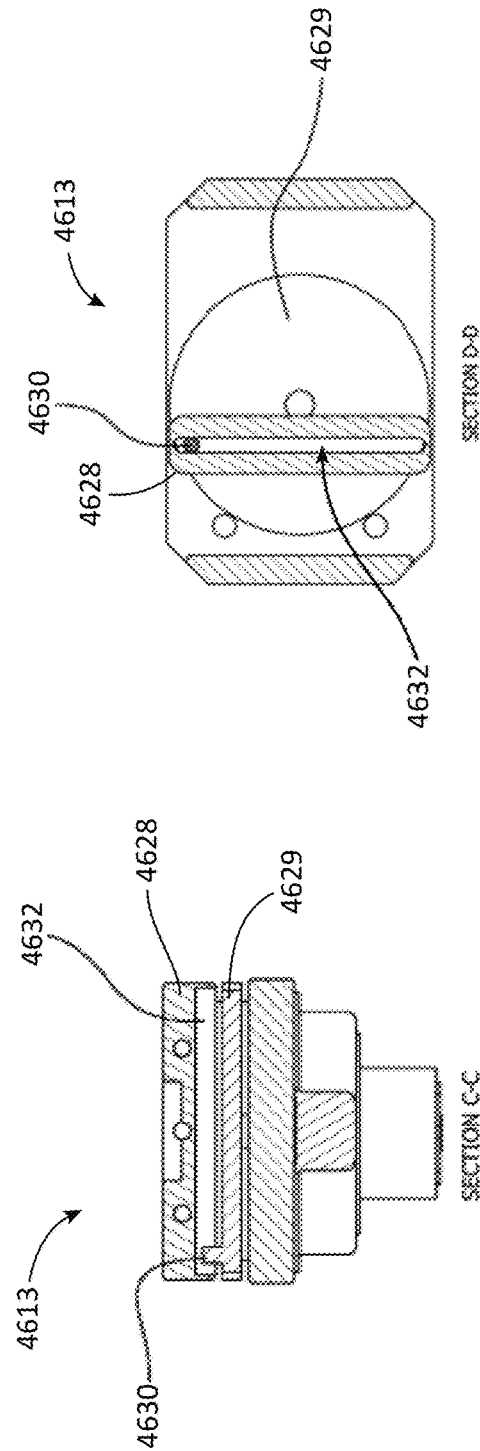

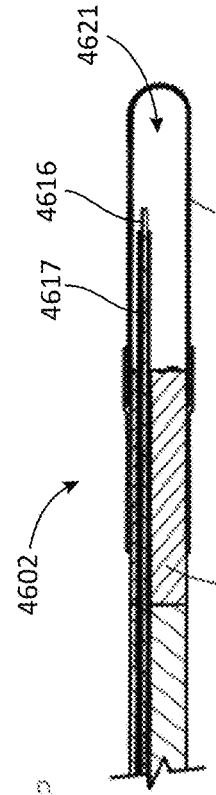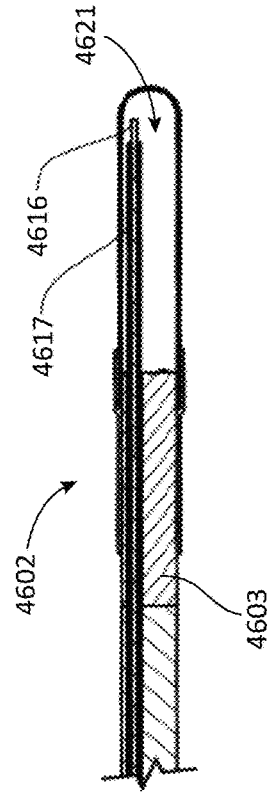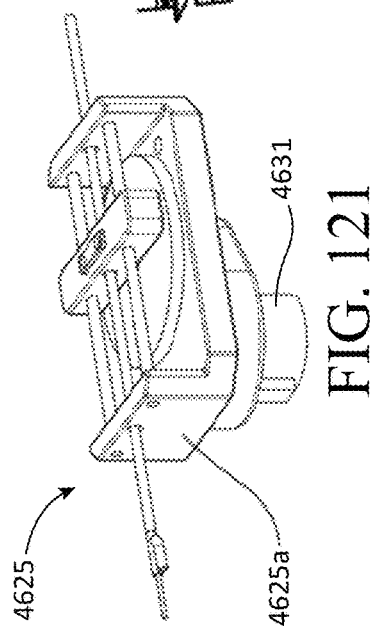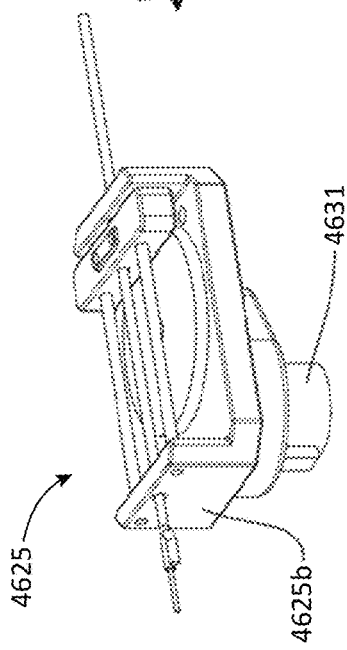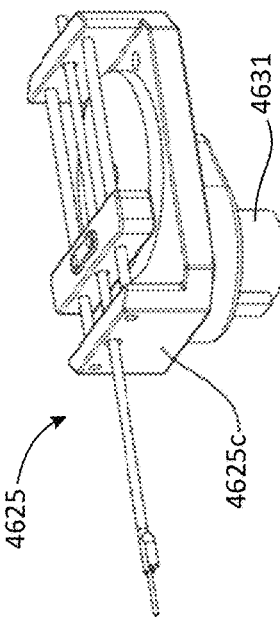

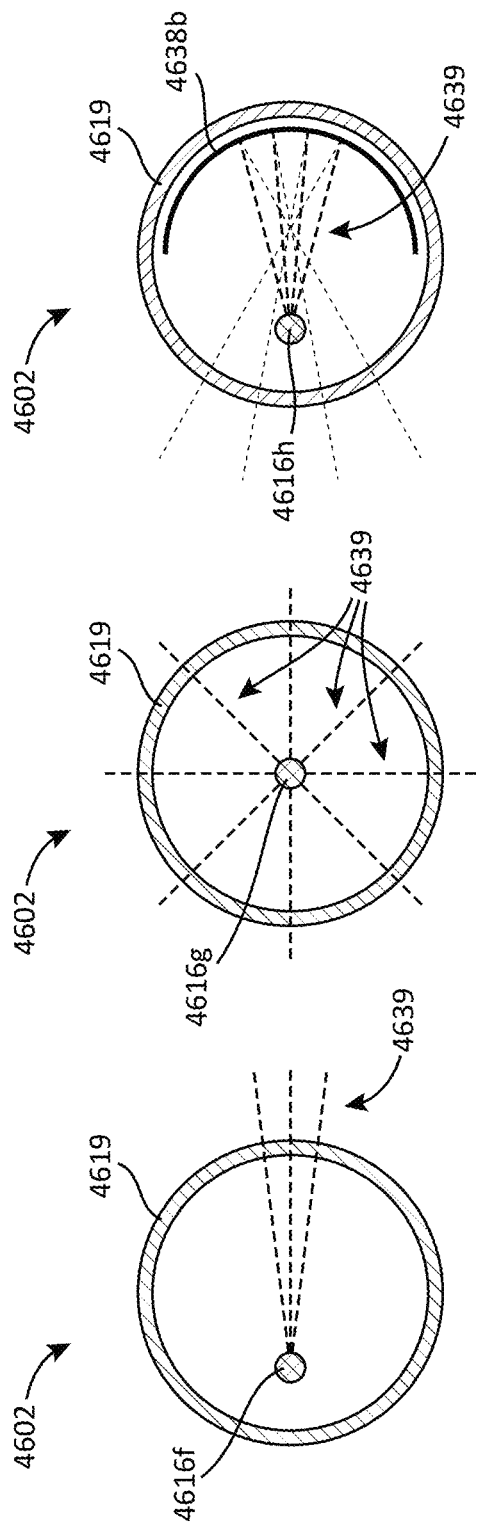

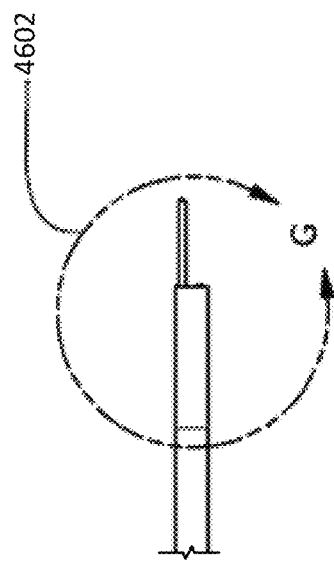
FIG. 135
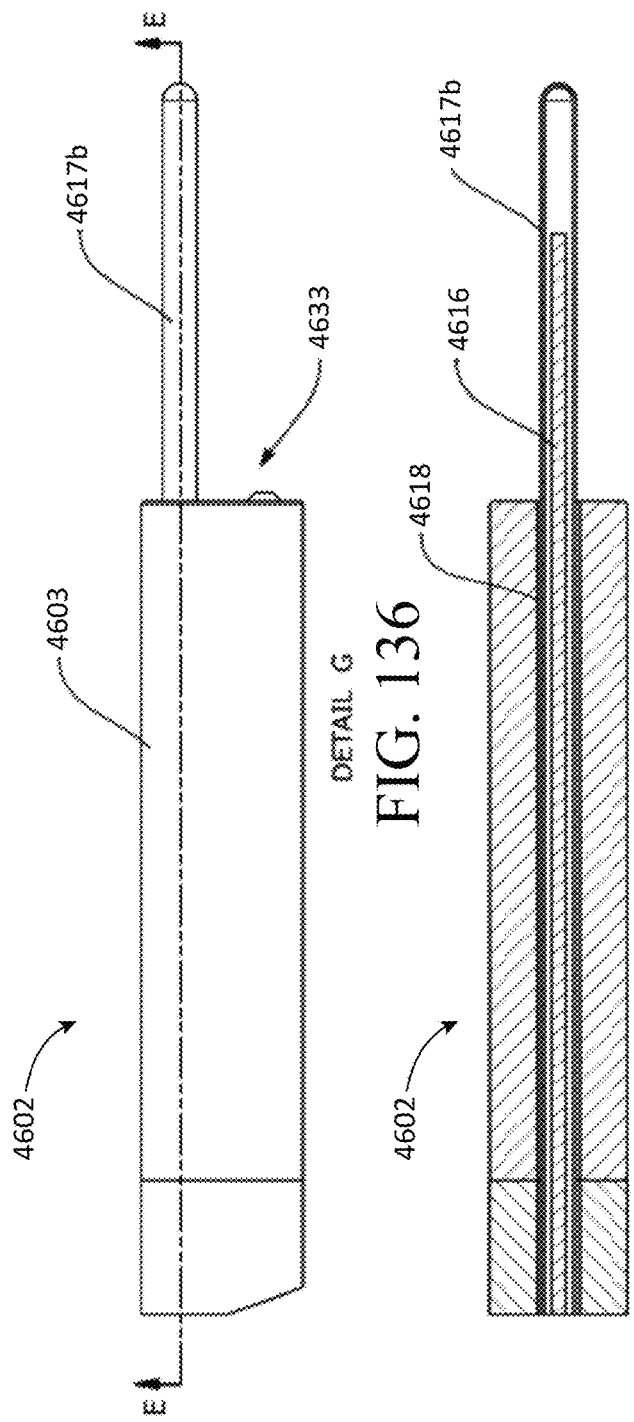
DETAIL G
FIG. 136
SECTION E-E
FIG. 137

DEVICE FOR DELIVERING PRECISION PHOTOTHERAPY

CROSS-REFERENCE TO RELATED PATENT APPLICATIONS

This application is a Divisional Application of U.S. application Ser. No. 17/000,254, entitled "DEVICE FOR DELIVERING PRECISION PHOTOTHERAPY," filed Aug. 21, 2020, which is a Continuation-In-Part application of International Application No. PCT/US2019/019286, entitled "DEVICE FOR DELIVERING PRECISION PHOTOTHERAPY," filed Feb. 22, 2019, which claims priority from U.S. Provisional Patent Application No. 62/634,655, entitled "DEVICE FOR DELIVERING PRECISION PHOTOTHERAPY," filed Feb. 23, 2018, each of which is incorporated herein by reference in its entirety.

BACKGROUND

The present disclosure relates to a device for delivering precision phototherapy, also known more specifically as photodynamic phototherapy or photobiomodulation therapy ("PBMT"). Light (photonic radiation) at certain wavelengths is more readily absorbed by molecules in certain tissues, identified as "chromophores," which in turn can stimulate or retard certain metabolic processes. This can include stimulating, suppressing, or denaturing cellular tissues, interstitial tissues, and intracellular tissue components. The deliberate exposure of tissues to light for this purpose is known as "phototherapy," "photobiomodulation therapy," "low level light therapy," "photodynamic therapy," or "laser physiotherapy" in various applications. The oldest and most well-known phototherapy is the administration of natural sunlight to human skin, which stimulates the production of Vitamin D. In this case, it is radiation at the 280-315 nm wavelength, also known as "UV-B" radiation, that stimulates the process.

SUMMARY

One embodiment relates to a device for administering phototherapy. The device includes a hollow structure having at least a first open end through which the hollow structure receives at least a portion of patient anatomy. The hollow structure includes a rotatable member configured to rotate around at least one rotary axis. The device also includes one or more coherent light generators mounted to the hollow structure. Each coherent light generator is configured to generate a beam of coherent light. The device further includes, for each coherent light generator, one or more lenses or mirrors optically connected to the coherent light generator and mounted to the hollow structure. The one or more lenses or mirrors are configured to alter at least one aspect of the beam of coherent light generated by the coherent light generator. The device further includes a processing circuit including a processor and a memory storing instructions. The instructions, when executed by the processor, cause the processor to accept an input from an operator and generate one or more beams of coherent light via the one or more coherent light generators according to a plurality of settings configured to produce a therapeutic effect at a targeted treatment site on the patient anatomy. Additionally, the rotatable member is configured to be rotated to direct the one or more beams of coherent light to the targeted treatment site on the patient anatomy.

In some embodiments, the device further comprises a spectroscopic sensor configured to obtain spectroscopic data. The instructions, when executed by the processor, may further cause the processor to analyze the spectroscopic data to estimate a change in at least one of reflectivity or absorbance of the patient's skin and surface tissues. The instructions, when executed by the processor, may further cause the processor to adjust at least one of a power, a duration, or a wavelength of a subsequent coherent light beam to maintain an optimal temperature.

Another embodiment relates to a device for administering phototherapy. The device includes a handheld probe configured to be optically connected to a coherent light generator configured to generate a beam of coherent light. The handheld probe is configured to receive the beam of coherent light from the coherent light generator. The handheld probe includes a closed tip from which coherent light is emitted after the beam of coherent light is received. The device further includes a processing circuit including a processor and a memory storing instructions. The instructions, when executed by the processor, cause the processor to accept an input from an operator and generate a beam of coherent light via the coherent light generator optically connected to the handheld probe. The beam is generated according to a plurality of settings configured to produce a therapeutic effect at a targeted treatment site on a patient.

Another embodiment relates to a device for administering phototherapy. The device includes a handheld probe configured to be optically connected to a coherent light generator configured to generate a beam of coherent light of at least 10 W. The handheld probe is configured to receive the beam of coherent light from the coherent light generator and emit the coherent light from the handheld probe after the beam of coherent light is received. The handheld probe further includes a cooling structure configured to deliver a coolant to at least a portion of the handheld probe or a portion of anatomy of a patient. The device further includes a processing circuit including a processor and a memory storing instructions. The instructions, when executed by the processor, cause the processor to accept an input from an operator and generate a beam of coherent light via the coherent light generator optically connected to the handheld probe. The beam is generated according to a plurality of settings configured to produce a therapeutic effect at the targeted treatment site.

In some embodiments, the coolant is compressed air and the cooling structure includes a vortex tube configured to cool the compressed air.

In some embodiments, the device further comprises a fiber optic cable, a diffusing lens, and an emission lens. The fiber optic cable may be configured to transmit the beam of coherent light from the coherent light generator into the diffusing lens. The diffusing lens may be configured to spread the beam of coherent light and transmit the beam of coherent light onto the emission lens. The emission lens may be configured to collimate the beam of coherent light received from the diffusing lens and emit the collimated beam of coherent light. The diffusing lens may be a ball lens. The ball lens may be held in place adjacent to and in a concentric orientation with a fiber end of the fiber optic cable by a lens retention cap having a lens retention aperture that is shaped to receive and retain the ball lens. The fiber optic cable may include a fiber ferrule and a fiber core. The fiber core may be recessed into the fiber ferrule at the fiber end such that the ball lens is held against the lens retention cap by the fiber ferrule and a surface of the ball lens abuts an end surface of the fiber core or is separated from the end surface of the fiber core by a gap. The device may further comprise an optical box having a hollow reflection portion defining a hollow cylindrical shape and including a reflective inner surface. The emission lens may be held in place at a distal end of the optical box by a retention flange. The hollow reflection portion may further include a distal side and a proximal side. The distal side may be longer than the proximal side such that the emission lens is angled with respect to a light emission path of the beam of coherent light traveling from the ball lens to the emission lens and a portion of the beam of coherent light is reflected off of the distal side into the emission lens.

In some embodiments, the device further comprises a fiber optic cable and an articulation mechanism. The fiber optic cable may be configured to emit the beam of coherent light from the coherent light generator onto a treatment tissue. The articulation mechanism may include a carriage that is fixed to a portion of the fiber optic cable and axially moveable to selectively articulate the fiber optic cable in an axial direction to allow for different areas of the treatment tissue to be treated by the beam of coherent light.

Another embodiment relates to a device for administering phototherapy. The device includes a hollow structure having at least a first open end through which the hollow structure receives at least a portion of patient anatomy. The hollow structure includes a rotatable member configured to rotate around at least one rotary axis. The device also includes one or more coherent light generators mounted to the hollow structure. Each coherent light generator is configured to generate a beam of coherent light. The device further includes, for each coherent light generator, one or more lenses or mirrors optically connected to the coherent light generator and mounted to the hollow structure. The one or more lenses or mirrors are configured to alter at least one aspect of the beam of coherent light generated by the coherent light generator. The device further includes a handheld probe configured to be optically connected to a coherent light generator. The handheld probe is configured to receive a beam of coherent light from the coherent light generator and emit the coherent light from the handheld probe after the beam of coherent light is received. The device further includes a processing circuit including a processor and a memory storing instructions. The instructions, when executed by the processor, cause the processor to accept an input from an operator and generate one or more beams of coherent light via the one or more coherent light generators and/or the coherent light generator optically connected to the handheld probe according to a plurality of settings configured to produce a therapeutic effect at a targeted treatment site on the patient anatomy.

Another embodiment relates to a method for administering phototherapy. The method includes accepting an input from an operator and generating one or more beams of coherent light via one or more coherent light generators. The one or more beams are generated according to a plurality of settings configured to produce a therapeutic effect at a targeted treatment site on a patient. The one or more coherent light generators are mounted to a hollow structure. The hollow structure includes at least a first open end through which the hollow structure receives at least a portion of patient anatomy including the targeted treatment site. The hollow structure further includes a rotatable member configured to rotate around at least one rotary axis. Each coherent light generator is optically connected to one or more lenses or mirrors mounted to the hollow structure. The one or more lenses or mirrors are configured to alter at least one aspect of the beam of coherent light generated by the coherent light generator. The rotatable member is configured to be rotated to direct the one or more beams of coherent light to the targeted treatment site.

Another embodiment relates to a method for administering phototherapy. The method includes optically connecting a handheld probe to a coherent light generator configured to generate a beam of coherent light. The handheld probe is configured to receive the beam of coherent light from the coherent light generator. The handheld probe also includes a closed tip from which coherent light is emitted after the beam of coherent light is received. The method further includes accepting an input from an operator and generating a beam of coherent light via the coherent light generator optically connected to the handheld probe according to a plurality of settings configured to produce a therapeutic effect at a targeted treatment site on a patient.

Another embodiment relates to a method for administering phototherapy. The method includes optically connecting a handheld probe to a coherent light generator configured to generate a beam of coherent light of at least 10 W. The handheld probe is configured to receive the beam of coherent light from the coherent light generator and emit the coherent light from the handheld probe after the beam of coherent light is received. The handheld probe further includes a cooling structure. The method further includes accepting an input from an operator, generating a beam of coherent light via the coherent light generator optically connected to the handheld probe according to a plurality of settings configured to produce a therapeutic effect at a targeted treatment site on a patient, and delivering, by the cooling structure, a coolant to at least one of a portion of the handheld probe or a portion of anatomy of the patient.

Another embodiment relates to a method for administering phototherapy. The method includes optically connecting a handheld probe to a coherent light generator configured to generate a beam of coherent light. The handheld probe is configured to receive the beam of coherent light from the coherent light generator and emit the coherent light from the handheld probe after the beam of coherent light is received. The method further includes accepting an input from an operator and generating one or more beams of coherent light via one or more coherent light generators and/or the coherent light generator optically connected to the handheld probe. The one or more beams are generated according to a plurality of settings configured to produce a therapeutic effect at a targeted treatment site on a patient. The one or more coherent light generators are mounted to a hollow structure. The hollow structure includes a first open end through which the hollow structure receives at least a portion of patient anatomy including a targeted treatment site. The hollow structure further includes a rotatable member configured to rotate around at least one rotary axis. Each of the one or more coherent light generators is optically connected to one or more lenses or mirrors mounted to the hollow structure. The one or more lenses or mirrors are configured to alter at least one aspect of the beam of coherent light generated by the coherent light generator.

Another embodiment relates to a device for administering phototherapy. The device includes a stationary hollow structure having at least a first open end through which the hollow structure receives at least a portion of patient anatomy and at least one coherent light generator. Each coherent light generator is configured to generate a beam of coherent light. The device also includes at least one of a plurality of coherent light generators mounted to an interior of the hollow structure, the plurality of coherent light generators including the one or more coherent light generators, or a plurality of lenses mounted to the interior of the hollow structure. The device further includes a processing circuit comprising a processor and a memory storing instructions. The instructions, when executed by the processor, cause the processor to accept an input from an operator and generate one or more beams of coherent light, via the at least one coherent light generator or the plurality of coherent light generators, according to a plurality of settings configured to produce a therapeutic effect at a targeted treatment site on the patient anatomy. The instructions further cause the processor to direct the one or more beams of coherent light to the targeted treatment site by generating the one or more beams of coherent light in a sequence.

In some embodiments, the total of the plurality of coherent light generators and/or the plurality of lenses mounted to the interior of the hollow structure is at least 200. In some embodiments, the instructions further cause the processor to direct the one or more beams of coherent light to the targeted treatment site via adjacent coherent light generators and/or lenses in a sweeping sequence. In some embodiments, the input relates to a treatment plan for the patient, and the instructions further cause the processor to generate the one or more beams of coherent light in a sequence based on the treatment plan input. In some embodiments, the device further comprises a cooling structure configured to deliver a coolant to at least a portion of the device or a portion of the patient anatomy.

BRIEF DESCRIPTION OF THE DRAWINGS

FIG. 52 depicts a side view of a representative embodiment of the beam splitting device shown in FIGS. 48 and 50.

FIG. 53 depicts a section view of the beam splitting device shown in FIG. 52, shown from the perspective of line D-D in FIG. 52 and illustrating the associated optical elements, as well as their configuration with the path of light through the device.

FIG. 61 depicts a perspective view of an illustrative embodiment of the coherent light emission optics carriage with another possible embodiment of the optics cooler attached to the optical box of the coherent light emission optics.

FIG. 62 depicts a detail view of the optics cooler of FIG. 61, shown from the perspective of detail line C in FIG. 61.

FIG. 82 depicts a convex-concave emission lens for implementation within the handheld probe device of FIG. 65.

FIG. 83 depicts a trapezoidal emission lens for implementation within the handheld probe device of FIG. 65.

FIG. 84 depicts a planar emission lens for implementation within the handheld probe device of FIG. 65.

FIG. 88 depicts a side view of a partially disposable handheld probe device for use with the phototherapy system of FIG. 66, showing various internal components.

FIG. 89 depicts a side view of the partially disposable handheld probe device of FIG. 88, shown with another disposable probe tip.

FIG. 90 depicts a side view of the partially disposable handheld probe device of FIG. 88, shown with another disposable probe tip.

FIG. 91 depicts a side view of the partially disposable handheld probe device of FIG. 88, shown with another disposable probe tip.

FIG. 95 depicts a detail view of a probe tip of the partially disposable handheld probe device of FIG. 93, showing the components within the area enclosed by callout "E" in FIG. 93.

FIG. 96 depicts a detail view of a probe tip connection feature of FIG. 93, showing the components within the are enclosed by callout "F" in FIG. 93.

FIG. 98 depicts a side view of another disposable probe tip for implementation with the partially disposable handheld probe device of FIG. 88.

FIG. 99 depicts a side view of another disposable probe tip for implementation with the partially disposable handheld probe device of FIG. 88.

FIG. 100 depicts a side view of another disposable probe tip for implementation with the partially disposable handheld probe device of FIG. 88.

FIG. 101 depicts a side view of another disposable probe tip for implementation with the partially disposable handheld probe device of FIG. 88.

FIG. 102 depicts a side view of another disposable probe tip for implementation with the partially disposable handheld probe device of FIG. 88.

FIG. 103 depicts a handle for a handheld probe device including a probe tip angling mechanism.

FIG. 104 depicts a probe tip having a rotatable tip end showing the tip end in straight forward, tilted up, and tilted down configurations.

FIG. 105 depicts a side view of another partially disposable handheld probe device.

FIG. 106 depicts a sectional view of a probe tip of the partially disposable handheld probe device of FIG. 105.

FIG. 107 depicts a top view of a probe tip end of the probe tip of the partially disposable handheld probe device of FIG. 105.

FIG. 108 depicts a schematic representation of another phototherapy system.

FIG. 109 depicts a front view of a handheld probe device assembly of the phototherapy system of FIG. 108.

Figures 109, 110:
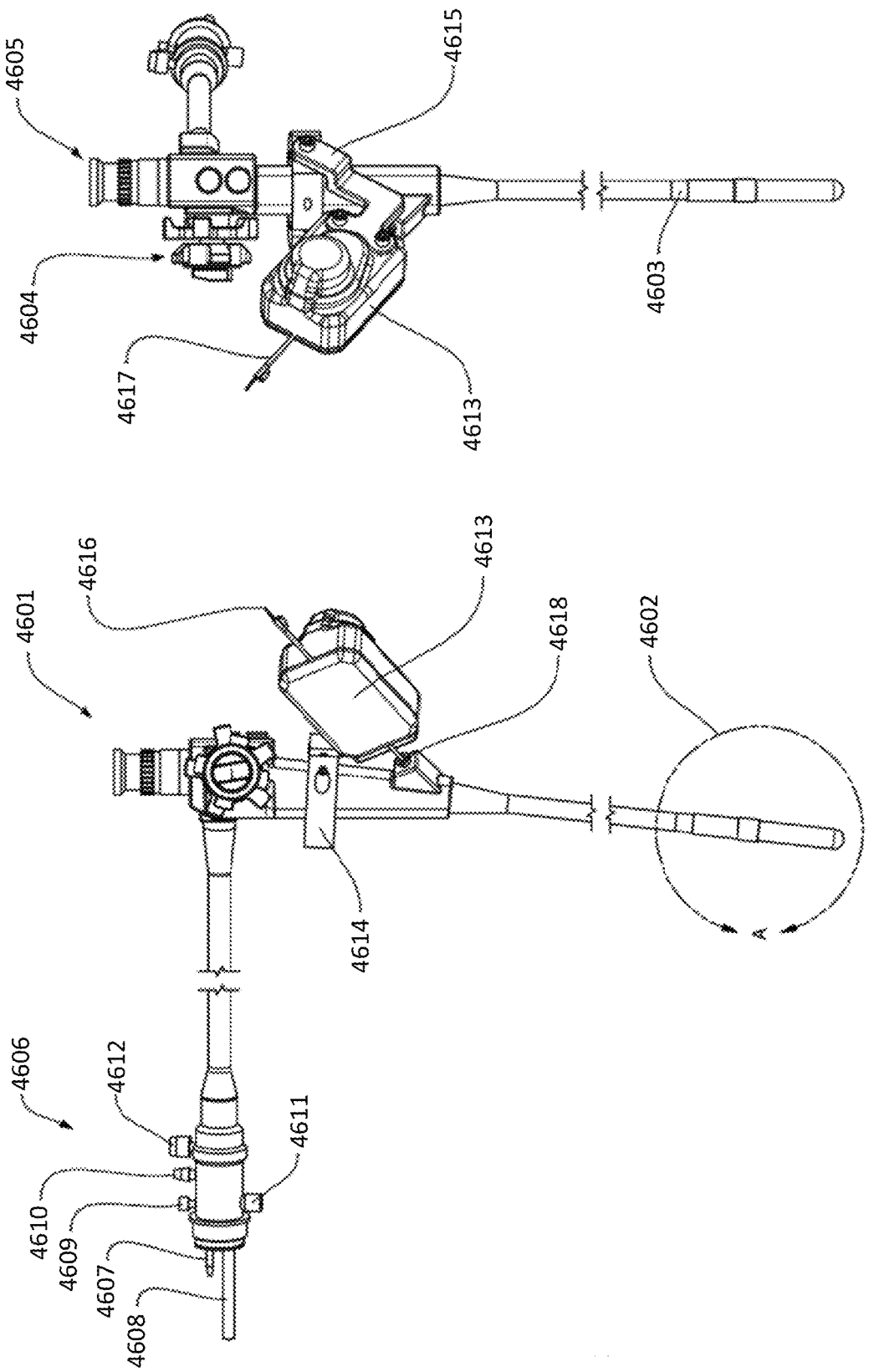

FIG. 110 depicts a side view of the handheld probe device assembly of FIG. 109.

Figure 111:
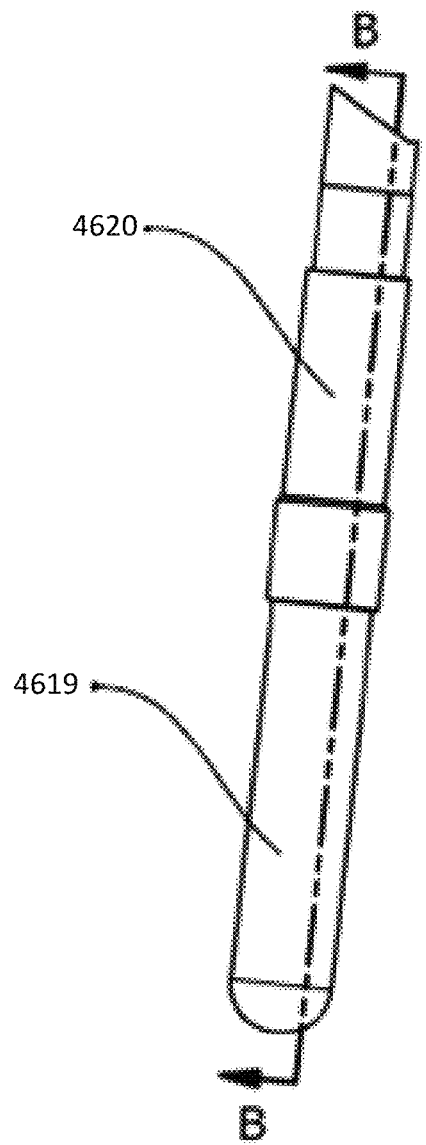

FIG. 111 depicts a detail view of a handheld probe device of the handheld probe device assembly of FIG. 109.

Figure 112:
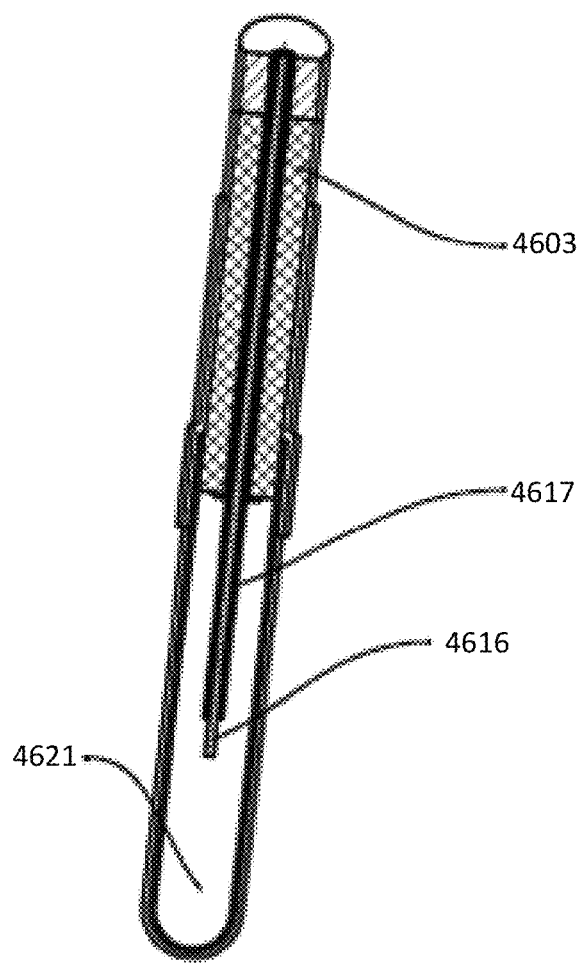

FIG. 112 depicts a section view of the handheld probe device of FIG. 111, taken along line B-B in FIG. 111.

FIG. 113 depicts a perspective view of the handheld probe device assembly of FIG. 109, shown with a probe sheath removed from a probe tip of the handheld probe device.

FIG. 114 depicts a detail view of the probe sheath and the probe tip of FIG. 113.

FIG. 115 depicts a detail view of the probe tip of FIG. 114.

Figure 116:
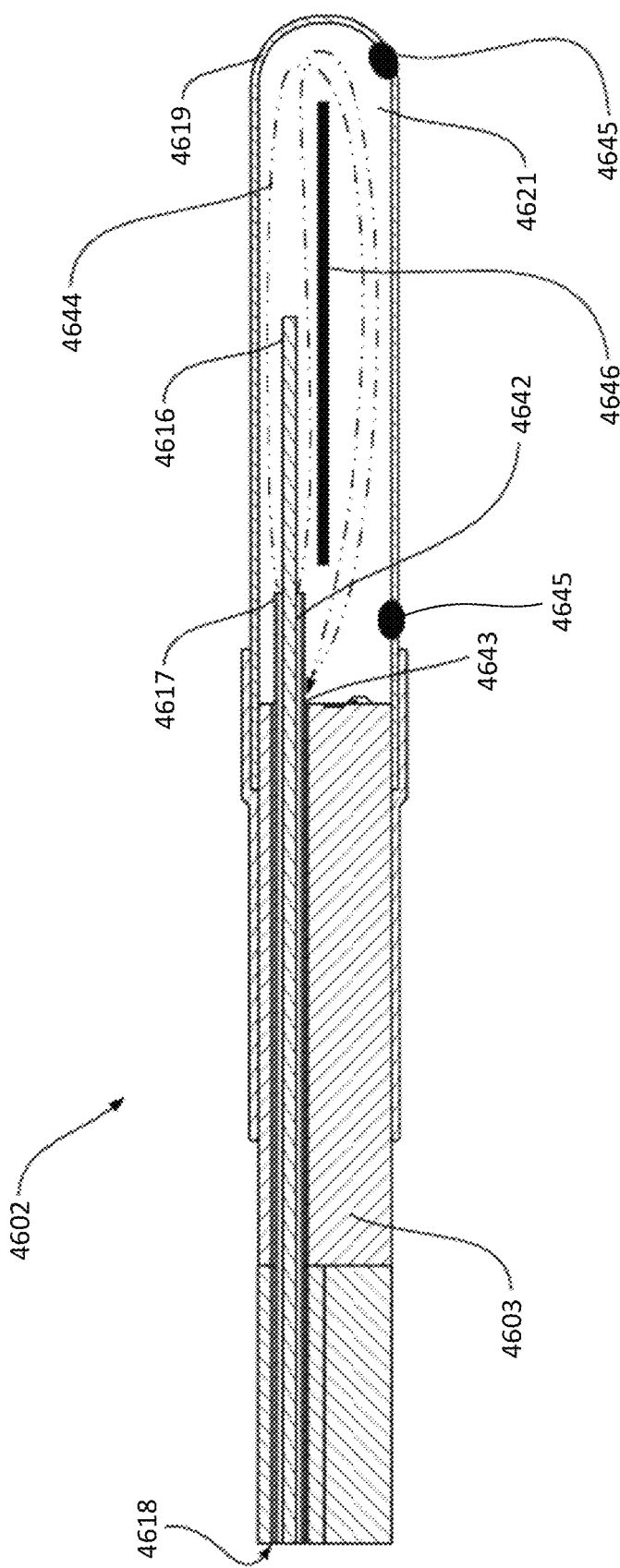

FIG. 116 depicts a section view of the handheld probe device of FIG. 111.

Figure 117:
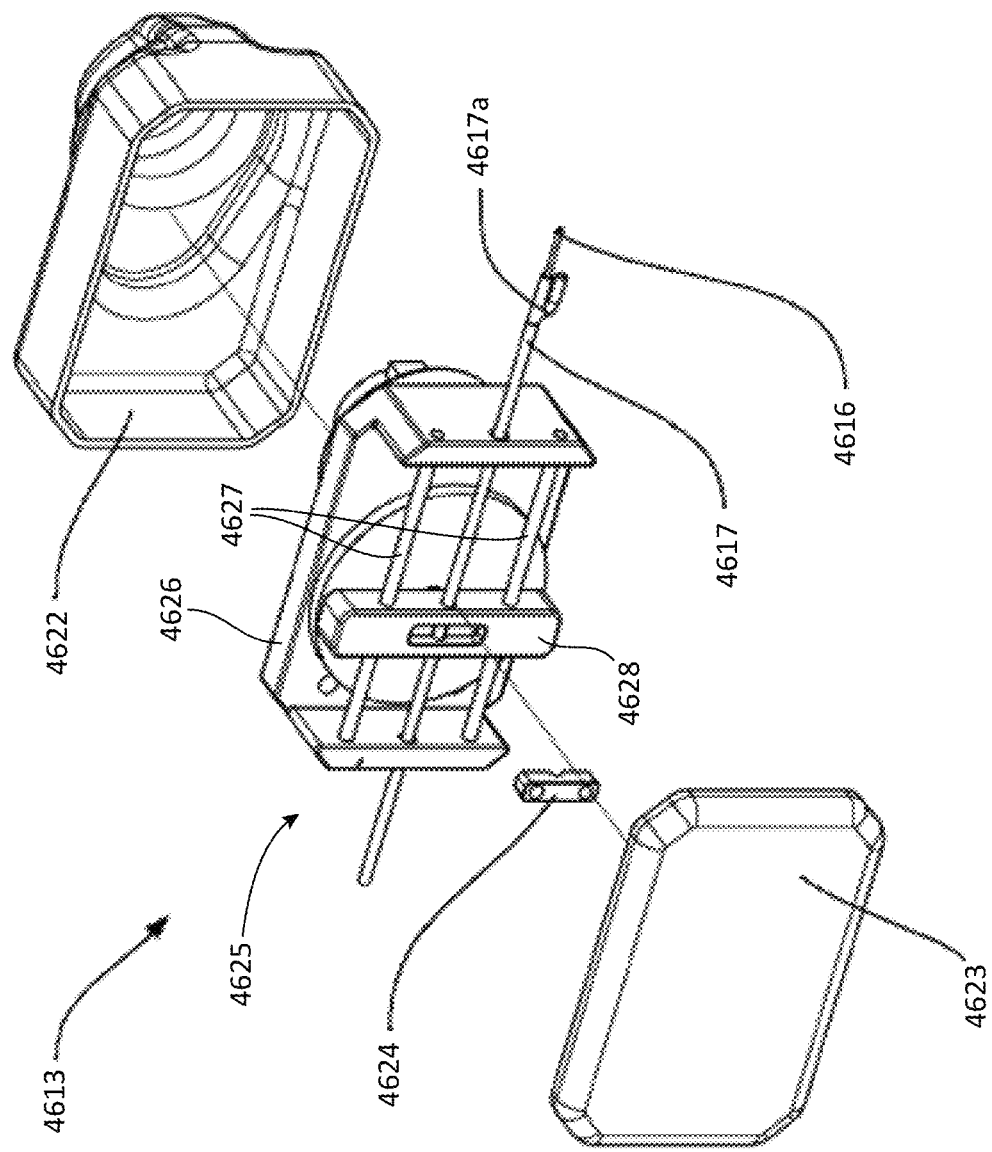

FIG. 117 depicts an exploded view of a fiber articulating assembly of the handheld probe assembly of FIG. 109.

FIG. 118 depicts a side view of an internal fiber articulating mechanism of the fiber articulating assembly of FIG. 117.

FIG. 119 depicts a section view of the internal fiber articulating mechanism of FIG. 118, taken along line C-C in FIG. 118.

FIG. 120 depicts a section view of the internal fiber articulating mechanism of FIG. 118, taken along line D-D in FIG. 118.

FIG. 121 depicts a perspective view of the internal fiber articulating mechanism in a nominal position.

FIG. 122 depicts a section view of the handheld probe device of the handheld probe assembly of FIG. 109 when the internal fiber articulating mechanism is in the nominal position.

FIG. 123 depicts a perspective view of the internal fiber articulating mechanism in an extended position.

FIG. 124 depicts a section view of the handheld probe device of the handheld probe assembly of FIG. 109 when the internal fiber articulating mechanism is in the extended position.

FIG. 125 depicts a perspective view of the internal fiber articulating mechanism in a retracted position.

FIG. 126 depicts a section view of the handheld probe device of the handheld probe assembly of FIG. 109 when the internal fiber articulating mechanism is in the retracted position.

Figures 127, 128, 129, 130, 131:
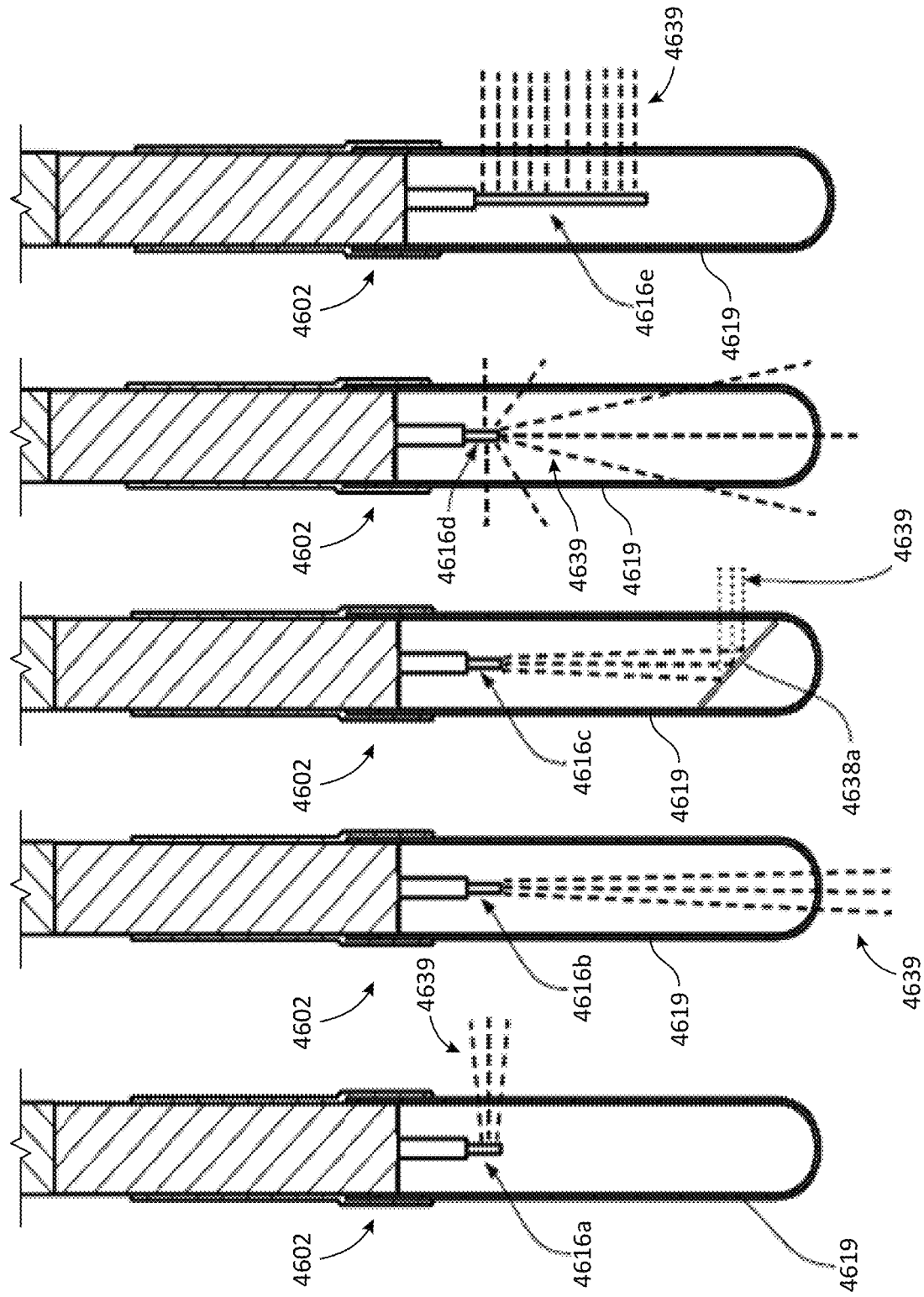

FIG. 127 depicts a section view of the handheld probe device of the handheld probe assembly of FIG. 109 showing the fiber optic cable and its associated light ray configuration.

FIG. 128 depicts a section view of the handheld probe device of the handheld probe assembly of FIG. 109 showing an alternative fiber optic cable and its associated light ray configuration.

FIG. 129 depicts a section view of the handheld probe device of the handheld probe assembly of FIG. 109 showing another alternative fiber optic cable and its associated light ray configuration.

FIG. 130 depicts a section view of the handheld probe device of the handheld probe assembly of FIG. 109 showing another alternative fiber optic cable and its associated light ray configuration.

FIG. 131 depicts a section view of the handheld probe device of the handheld probe assembly of FIG. 109 showing another alternative fiber optic cable and its associated light ray configuration.

FIG. 132 depicts an axially taken section view of the handheld probe device of the handheld probe assembly of FIG. 109, showing an off-center fiber optic cable emitting light tangentially.

FIG. 133 depicts an axially taken section view of the handheld probe device of the handheld probe assembly of FIG. 109, showing a centered fiber optic cable emitting light circumferentially.

FIG. 134 depicts an axially-taken section view of the handheld probe device of the handheld probe assembly of FIG. 109, showing an off-center fiber optic cable emitting light tangentially onto a concave mirror.

FIG. 135 depicts a side view of the handheld probe device of the handheld probe assembly of FIG. 109, shown with a sheathed fiber optic cable.

FIG. 136 depicts a detail view of the handheld probe device of FIG. 135, showing the components within the area enclosed by callout "G" in FIG. 135.

FIG. 137 depicts a section view of the handheld probe device of FIG. 136, taken along line E-E in FIG. 136.

Figure 138:
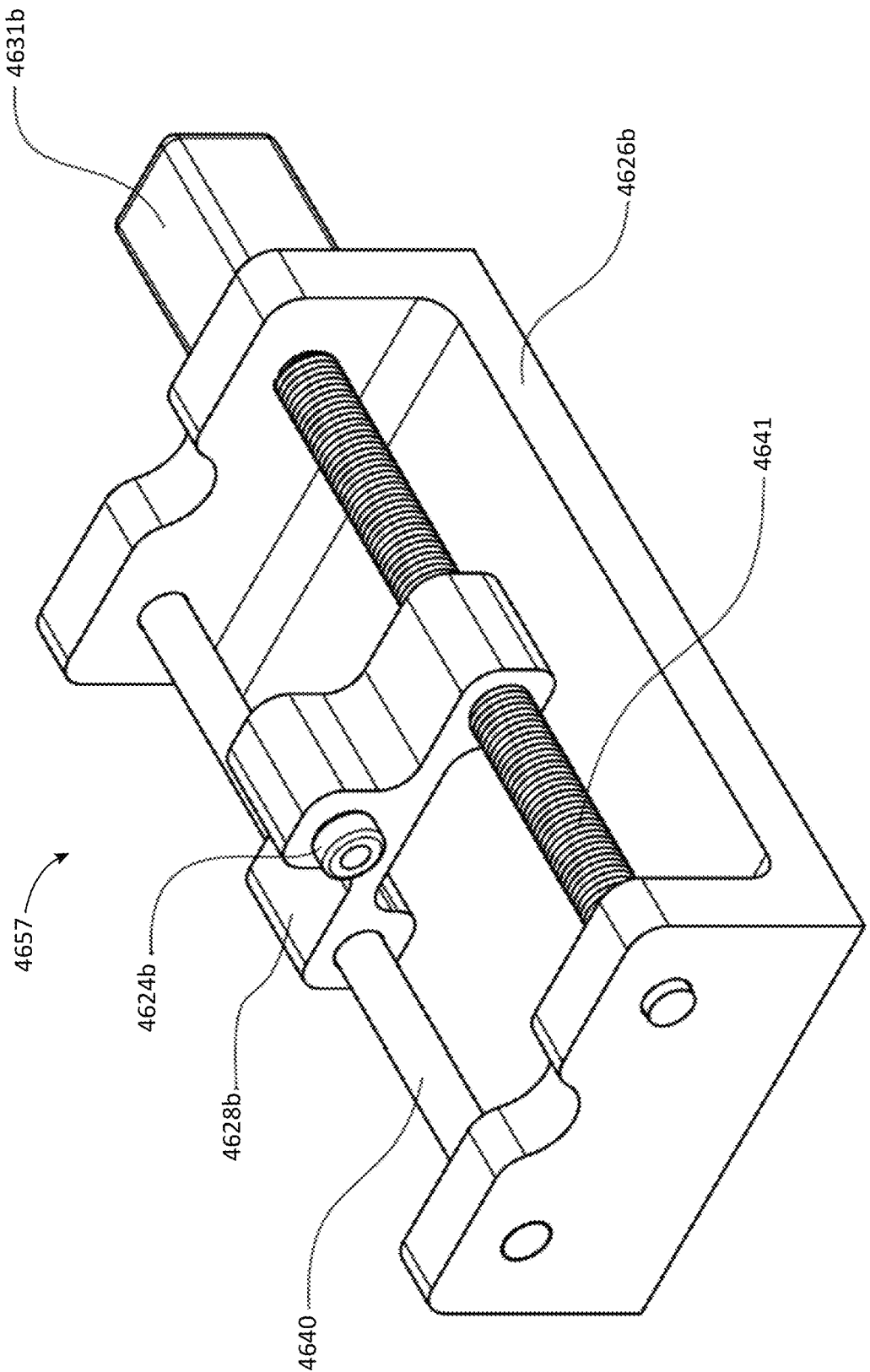

FIG. 138 depicts an alternative internal fiber actuating mechanism for implementation within the fiber articulating assembly of FIG. 117.

DETAILED DESCRIPTION

Detailed descriptions of various embodiments are described herein. The disclosure illustrates embodiments of a treatment cylinder device and various probe devices for the administration of precision phototherapy. However, it is to be understood that the devices of the present disclosure may be embodied in various forms. Therefore, specific details disclosed herein are not to be interpreted as limiting in scope of the invention in any manner, but rather as a basis for claims and as a representative basis for teaching one skilled in the art to employ the features of the present disclosure in virtually any appropriately detailed system, structure, or manner.

Physiotherapy energy of various wavelengths in the entire light spectrum may include infrared (e.g., 700 nm to 1 mm) and near-infrared wavelengths (e.g., 700 nm to 1400 nm). The administration of light in the near-infrared can reduce pain in muscles and the tissues of the lower back. Laser energy at various wavelengths of the entire spectrum, including the 694 nm wavelength of ruby lasers, is useful for photothermolysis (energetic hair removal).

There are multiple areas in which the administration of phototherapy is limited and/or of limited effectiveness. First and foremost, the phototherapy must be targeted with precision to avoid the light energy either being absorbed by tissues that are not meant to be treated, or not absorbed by the tissues toward which it is being directed. A device that could more precisely target phototherapy would be desirable.

Most systems for administering phototherapy use a human operator to target and deliver the phototherapy. While humans can become very skilled at this task, human administration is inherently inconsistent and imprecise. A device for allowing a human operator to administer phototherapy that allows more consistent and precise administration of the phototherapy would be desirable.

Most systems for administering phototherapy have only one exit portal that directs the light energy, and that exit portal has only a single directional axis of operation. Optimal phototherapy treatment often requires treatment of a volume of tissues, which may require the administration of phototherapy from a specific locus of angles that are dependent on the wavelength of the light and the depth of the tissue to be treated. A device for allowing the administration of phototherapy from a controlled locus of angles, taking into account the depth of the tissue to be treated and the physical characteristics of the light energy used would be desirable.

Most systems for administering phototherapy target only relatively shallow tissues. There are multiple subsurface tissue types that would benefit from the administration of phototherapy, but targeting subsurface tissues for phototherapy is inherently difficult, especially for a human operator. A device for allowing the efficient and precise targeting of subsurface tissues for phototherapy would be desirable.

The simultaneous delivery of multiple wavelengths of light for phototherapy has the potential to increase the benefits of phototherapy. Such delivery is difficult to do with known phototherapy devices. A device that can simultaneously target the same or closely-located tissues with multiple wavelengths of light would be desirable.

The delivery of light for phototherapy toward a volume of tissues to be treated may require delivery of light from a locus of angles circumferential to the volume of tissues to be treated, at a precise angle relative to the surface of those tissues. A device that can deliver light from a locus of angles circumferential to the volume of tissues to be treated, at a precise angle to the surface of those tissues, would be desirable.

The delivery of phototherapy to tissues can cause excess heating and tissue damage if not precisely controlled. When using higher power sources for phototherapy, this becomes more likely. A device that can deliver relatively high-powered phototherapy while allowing tissues to cool between applications and still deliver the phototherapy in a fast and efficient manner would be desirable. The present disclosure addresses these and other concerns according to various illustrative embodiments.

References will be made in detail to the embodiments of the disclosure that are illustrated in the accompanying drawings. Identification of like or similar elements and features depicted in the drawings will be referenced using common numerals wherever possible. Elements which are illustrated multiple times are generally only identified once in each figure unless multiple identifications are required for clarity. Drawings are in simplified form and are not intended to depict precise scale. It is to be understood for convenience and clarity that directional terms such as: top, bottom, left, right, up down, over, above, below, beneath, rear and front may be used in reference to relationships or interfaces depicted within the drawings and are in no way to be construed to limit the scope of the disclosure in any way. Words that depict an interface such as: attach, couple, connect and similar terms with similar inflectional morphemes refer to their direct relationship or connections via mediate elements or devices. References to a series of articles prefaced by articles like: include, includes, including, and similar conjugates are intended to be understood as without limitation or necessity of the articles listed but instead as reference to what may or may not be included.

It should be noted that while some embodiments are configured for use with human patients, the devices described herein can be used with any animal that would benefit from phototherapy, including but not limited to higher mammals such as dogs, cats, or horses. The word "patient" as used herein refers to any animal, including a human being, to which phototherapy may usefully be applied by the devices described herein. Further, unless otherwise indicated, the example embodiments can be utilized with any biological systems, including human patients, other animal patients, or any portions thereof. The "anatomy" refers to any part of the patient which PBMT can be applied.

Additionally, it should be understood that while the phototherapy devices described herein are primarily described as providing phototherapy to a patient, these devices may also be used for non-biological functions. For example, some embodiments of the device described herein may be used to heat polymers and other materials; and/or substrates to target temperatures to support forming, annealing, processing, or otherwise desirable applications; benefiting from controlled application of phototherapy in the form of targeted and dose-controlled light.

The present disclosure relates to devices for delivering precision phototherapy (e.g., "phototherapy devices") in the form of targeted and dose-controlled light. In various embodiments, a phototherapy device partially or wholly surrounds the part of the body to be treated and allows the targeting of specific tissues at specific depths while minimizing energy transfer to non-targeted tissues. In some embodiments, the phototherapy device includes a rotating device containing optical elements that is used to target the tissue to be treated (e.g., the "targeted treatment site") from a plurality of angles and a plurality of wavelengths. In some embodiments, the phototherapy device includes galvanometrically-controlled optical elements that allow targeting of a volume of tissues from a plurality of angles. In some embodiments, the phototherapy device includes a probe that may be used to provide targeted phototherapy. The probe may be used with the aforementioned embodiments, or the probe may be used separately (e.g., with an independent light source for the phototherapy). Additionally, in some embodiments the phototherapy device may include a mounting system for various phototherapy elements.

The person(s) operating the phototherapy device may be referred to herein as "therapists," "operators," or "doctors." While the persons operating the device may be licensed medical doctors, it is not required. Where safe, useful, and within the bounds of applicable law and regulation, the phototherapy device embodiment(s) may or may not be operated by a licensed health care professional.

Additionally, various phototherapy device embodiments described herein may be operated manually, partially robotically (e.g., with some automation, such as using robotic system to guide a human operator), or fully robotically (e.g., with full automation). In manual operation a user would input the desired parameters and motions independently or as a sequence to define the treatment scheme. Partial or full robotic guidance of the phototherapy device may be provided to deliver therapy to a treatment area for a specific time period and then systematically move the treatment to another area, thereby allowing for delivery of the maximum dose without creating too much heat in one area. In various embodiments, a computer control unit, which is described in further detail below, may provide this partial or full robotic guidance. Further, in some embodiments, this robotic guidance may be provided at least partially through one or more robotic arms, which may be controlled by the operator and/or the computer control unit. Thus, it should be understood that, in some embodiments, where input or other action is described as being received from or taken by an "operator" or "user", such "operator" or "user" may be or include a robotic system or other manner of computing device.

The phototherapy devices described herein should not be used to treat, cure, or prevent disease or injury in any way not compliant with applicable regulatory controls. Such regulatory controls will vary by jurisdiction and do not form part of the embodiment(s) of the disclosure or their basic operation, and will not be further described herein. To the extent that any regulatory controls apply, security controls may be incorporated into the devices described herein that restrict operation of the device by other than authorized operators in compliance with applicable regulatory controls.

For purposes of this application, phototherapy applied by the device takes the form of light of a selected and controlled wavelength or tight group of wavelengths. If multiple wavelengths are used, the light may be formed of a plurality of light beams, each having a specific selected and controlled wavelength or tight group of wavelengths. In some embodiments, the light used is coherent light (e.g., with the photons of the light having the same or nearly the same wavelengths, being in phase, and identical or nearly identical in amplitude). Further, in some embodiments, the coherent light used is generated by a laser. Many coherent light generators, as the term is used herein, are laser generators (which may also be referred to as "laser power sources"): lasers produce coherent light by means of a process called "lasing." Other devices or systems of coherent light generation and/or the generation of light of a controlled wavelength or tight group of wavelengths can also be used.

The wavelengths used to provide the phototherapy described herein may be selected based on the depth of desired penetration into the patient anatomy, as each wavelength may be associated with a different depth of soft tissue penetrance. Additionally, limited penetration of wavelengths may be addressed by applying phototherapy partially or completely around the targeted tissue site circumferentially. For example, in an arthritic knee, 7.5 cm may be the deepest that laser photons will propagate into soft tissues. As such, greater therapeutic effects may be achieved in treating the average 15 cm-diameter arthritic knee of a male patient, for instance, when the therapy is delivered completely around the knee. Delivering the therapy circumferentially around the knee will help the most Joules of photon energy penetrate into the deepest areas of the knee joint where most of the destructive inflammatory disease state exists that is causing the chronic and progressive knee pain.

For consistency and preference, the term "coherent light" will be used in this application, with the understanding that this refers to a selected and controlled wavelength or tight group of wavelengths. However, it should be understood that at least some of the embodiments described herein may be operated with non-coherent light. For purposes of this application, if a particular beam of coherent or non-coherent light is referred to as having a specific wavelength, it should be understood that so long as the coherent or non-coherent light beam is tightly grouped around that wavelength (e.g., with a bandwidth of not more than 20 nm for at least 90% of the total energy output of the beam), that beam of coherent or non-coherent light "has" that specific wavelength.

Additionally, other suitable sources of coherent or non-coherent light that may be used with the phototherapy devices described herein include, without limitation, the following: (1) non-coherent light sources such as light emitting diodes ("LEDs") or incandescent lamps (e.g., halogen lamps) connected to filters; (2) organic LEDs ("OLEDs") using small organic molecules as the electroluminescent material, which allow emission from large and/or flexible surfaces; and (3) specifically, lasers with very narrow spectral-emission bandwidths and the ability to produce 'pulses' of light with durations on the order of 12 attoseconds, often referred to as "superpulse" lasers. These sources may be used based on the type of phototherapy to be applied, the location and type of the treatment site tissue, and/or the type of injury or disease state to be treated. For example, superpulse lasers may have the ability to administer high levels of energy while allowing time for the relaxation of tissue, which may be beneficial in delivering therapy to treat diseases with higher intense vascularity (e.g., a case of higher acute injury as opposed to a chronic disease state). As another example, LEDs may provide low-level therapy, thereby allowing for longer treatment times with lower energy photons. This may be beneficial for cellular adenosine triphosphate ("ATP") generation.

It should be understood that the phototherapy devices described herein may be used to provide therapy to a variety of tissue types, including bone. For example, the phototherapy devices described herein may be used to provide phototherapy that penetrates and is absorbed by bone marrow and bone matrix (e.g., cortical and trabecular bone) or phototherapy that passes through bone.

Figure 1:
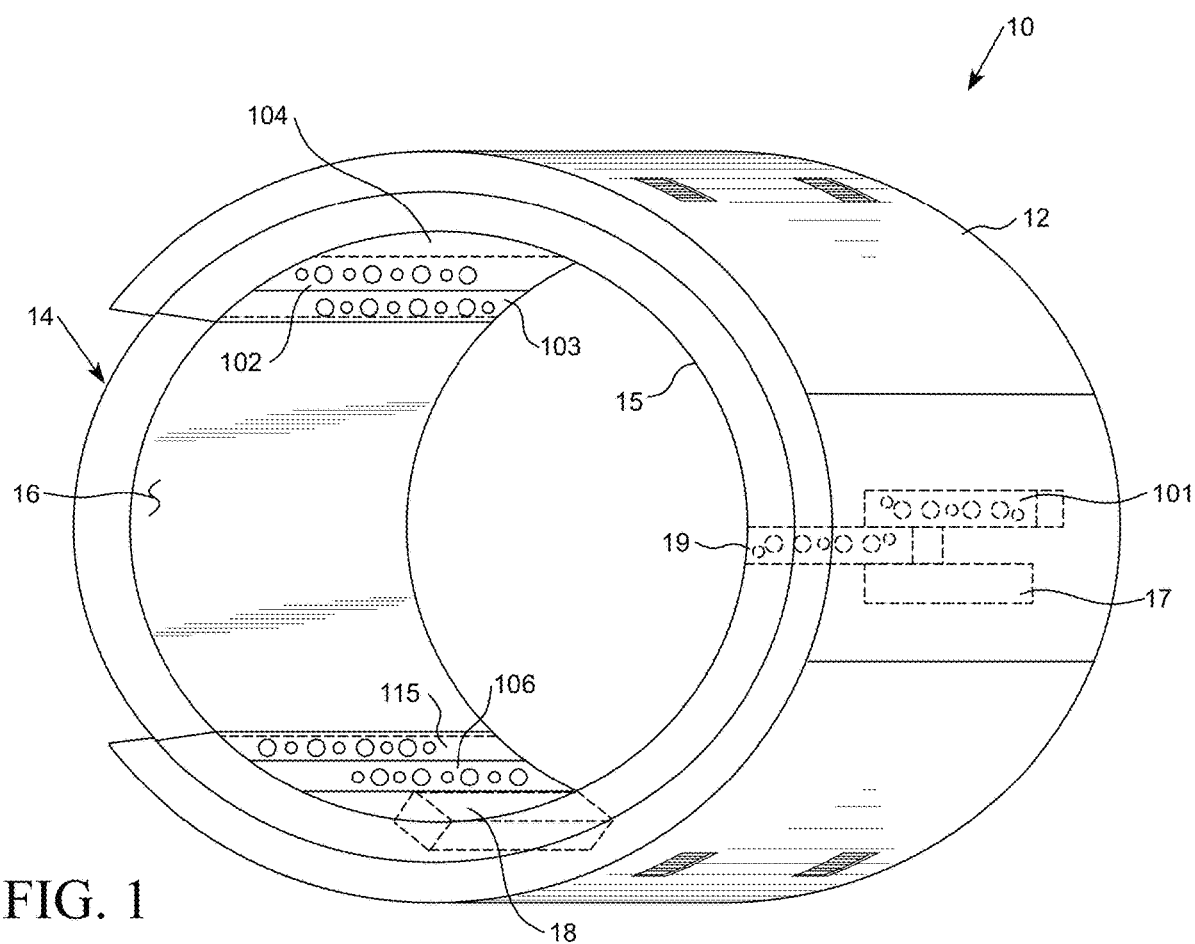
FIG. 1 depicts a perspective view of an embodiment of a treatment cylinder portion of a phototherapy device.
Figure 1A:
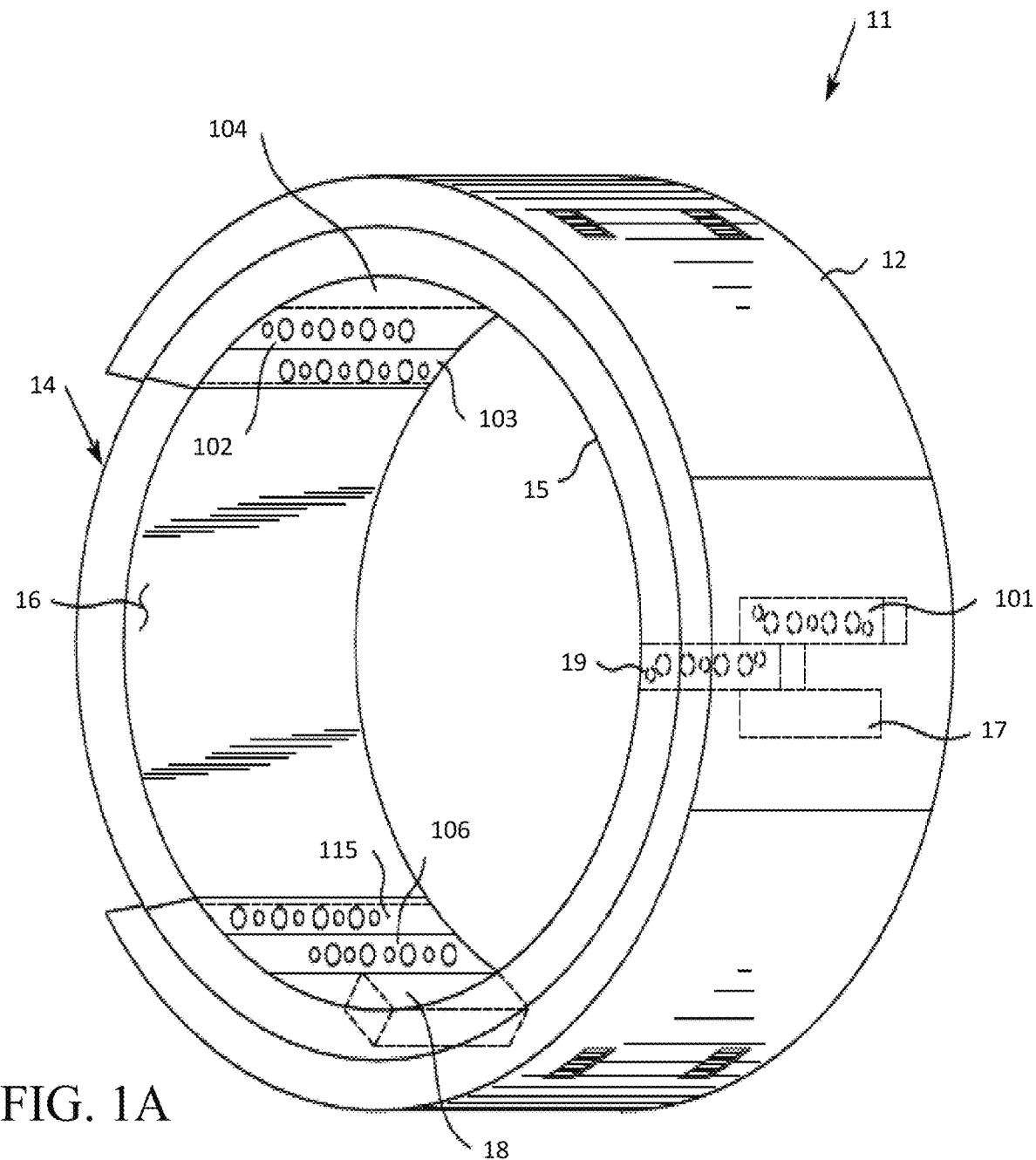
FIG. 1A depicts a perspective view of another embodiment of a treatment cylinder portion of a phototherapy device.

By referring to the exemplary embodiment of FIG. 1, the basic function of the systems and methods described herein can be easily understood. In various embodiments, including the embodiment shown in FIG. 1, a phototherapy device includes a hollow structure with at least a first open end through which at least a portion of patient anatomy can be inserted into the hollow structure. This hollow structure may take on a variety of geometrical shapes, such as a cylinder, tube, drum, sphere, or dome. While this hollow structure is referred to herein as a "treatment cylinder" based on the configurations shown in most of the Figures (e.g., treatment cylinder 10 of FIG. 1), it should be understood that structures performing the functions of the treatment cylinder described below may not necessarily be cylindrical. For example, FIG. 1A illustrates an embodiment of a treatment cylinder 11 that includes the same components as treatment cylinder 10, shown in FIG. 1, but is configured as an elliptic cylinder rather than a circular cylinder. Treatment cylinder ("TC") 10 includes exterior member 12, which is an open-ended cylinder interrupted by gap 16, and rotatable member 15. Rotatable member 15 can be rotated within TC 10 independently of exterior member 12 around a rotary axis, which may or may not be located through the center of TC 10. Gap 16 can be closed by cap 14, which slides into rotatable member 15 when the device is not in use. When used to provide treatment, the portion of the patient's body to be treated is inserted into TC 10 either through one of its open ends or through gap 16. Additionally, in various arrangements, TC 10 is connected to a computer control unit, described in further detail below. The computer control unit may also allow finite movement of TC 10 (e.g., limited movement in the x, y, and z directions) for proper positioning of the patient anatomy within TC 10.

In some embodiments, the phototherapy device includes gap 16 to make it easier to insert the patient's body into TC 10. Further, if gap 16 is included, cap 14 may be used to close gap 16 during treatment. This both prevents coherent light from escaping and reduces the chance (a) that foreign objects will be inserted during treatment that may interfere with or damage the moving parts of the device or (b) that the patient's body will be engaged by the rotatable member 15, potentially causing injury. Alternatively, cap 14 may be a hinged member of TC 10 configured to swing open to allow insertion of the patient's anatomy and swing closed to close gap 16. This hinged member may further be provided with a locking mechanism to keep the hinged member in place and closed during operation of the phototherapy device. In some embodiments, one end of TC 10 may also be closed (not shown). This provides further protection from the escape of coherent light and the introduction of foreign objects but may make TC 10 much less versatile in relation to how the patient's body can be introduced into TC 10.

It should be understood, however, that the configuration of the treatment cylinder shown in FIG. 1 is intended to be exemplary. Treatment cylinder may be configured differently in other embodiment. For example, in one embodiment, the treatment cylinder may alternatively be thin with a diameter much greater with its width (e.g., shaped like a hula hoop). The treatment cylinder may deliver focused energy and moved in the x, y, and z directions to provide therapy over the treatment area.

Figure 1B:
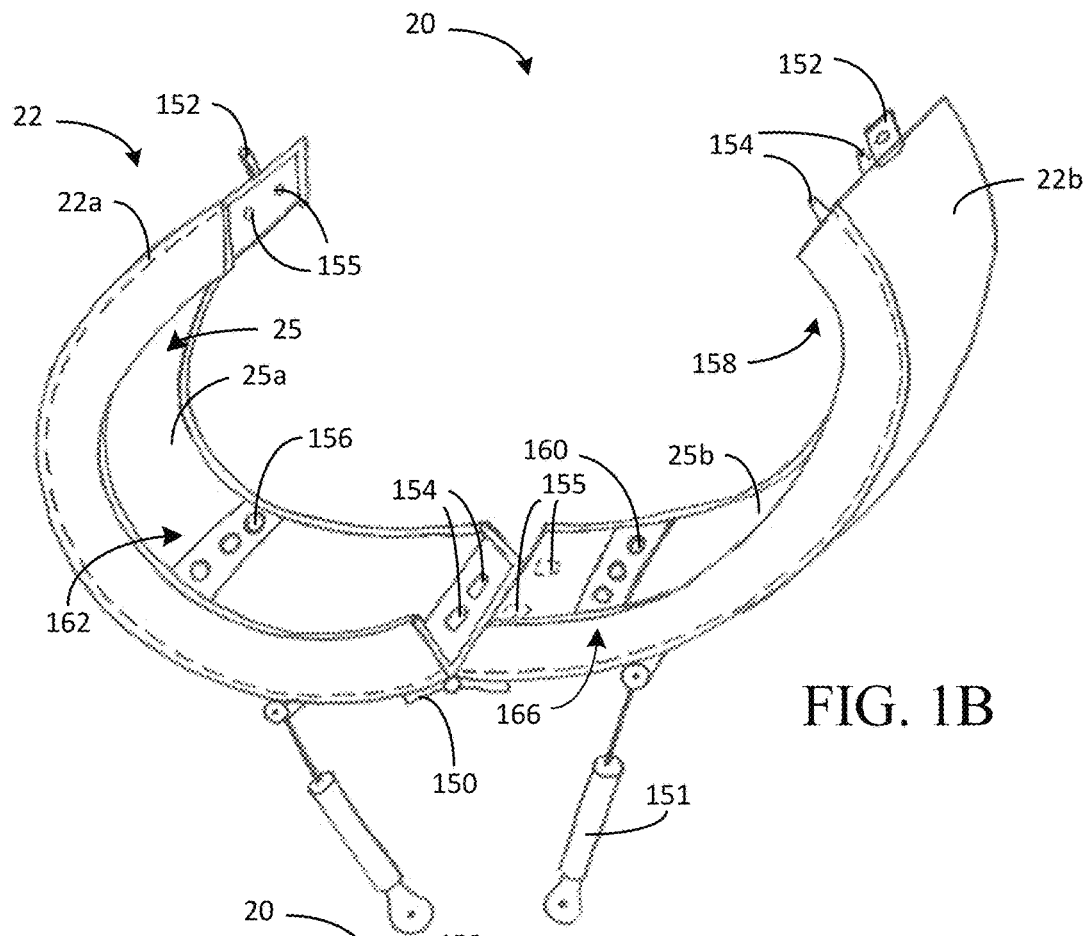
FIG. 1B depicts a perspective view of another embodiment of a treatment cylinder portion of a phototherapy device.
Figure 1C:
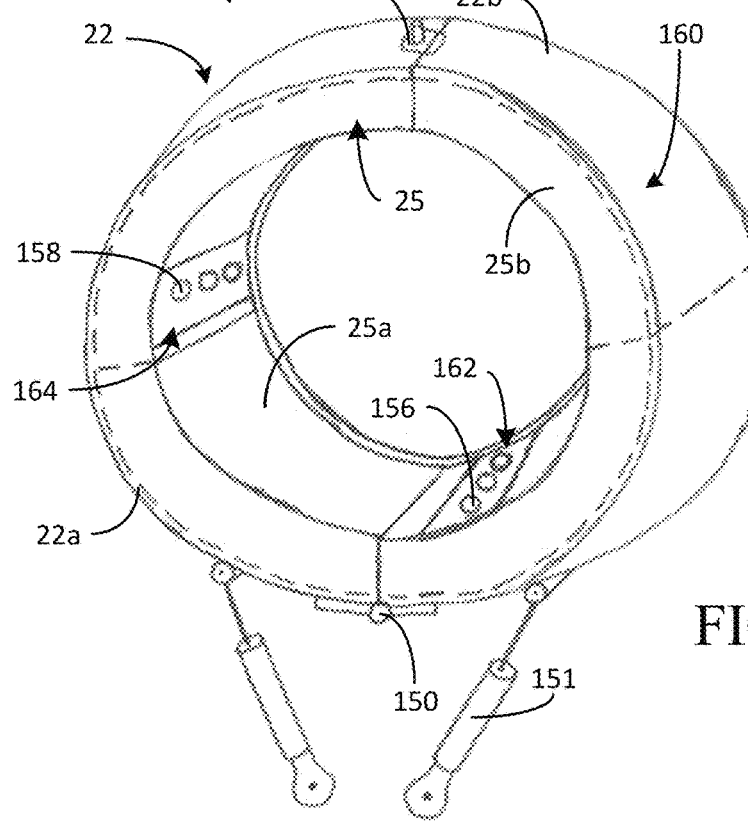
FIG. 1C depicts another perspective view of the treatment cylinder portion of FIG. 1B.

FIGS. 1B and 1C show another alternate embodiment of a treatment cylinder. TC 20 includes exterior member 22 and includes rotatable member 25 separated into two halves. Exterior member 22 includes a first exterior member half 22a and a second exterior member half 22b, and rotatable member 25 includes a first rotatable member half 25a and a second rotatable member half 25b. Exterior member halves 22a and 22b are configured to receive rotatable member halves 25a and 25 b, which may rotate within exterior member halves 22a and 22b. All of these halves (e.g., to receive the patient anatomy to be treated), as shown in FIG. 1B, and brought back together to form the whole exterior member 22 and whole rotatable member 25, as shown in FIG. 1C. Accordingly, TC 20 has the appearance of a clam shape. In some arrangements, first rotatable member half 25a must be flush with first exterior member half 22a and second rotatable member half 25b must be flush with second exterior member half 22b, as shown in FIG. 2B, before exterior member 22 and rotatable member 25 may be separated. TC 20 may be configured for treating smaller areas of anatomy (e.g., TC 20 may have a diameter of 30 cm) or treating larger areas of anatomy (e.g., TC 20 may have a diameter of 70 cm). TC 20 may also have a width appropriate for treating a certain amount of patient anatomy (e.g., TC 20 may have a width of 32 cm).

As shown, exterior member 22 and rotatable member 25 include spring hinge system 150 to facilitate the separation of halves 22a, 22b, 25a, and 25b, as well as piston system 151 configured to move halves 22a, 22b, 25a, and 25b apart and back together. Spring hinge system 150 may be configured to apply pressure to the halves 22a, 22b, 25a, and 25b to bias them closed or to bias them open, depending on the embodiment. Piston system 151 may be a static hydraulic piston. Alternatively, in some embodiments piston system 151 may be replaced with a counter pressure spring (e.g., configured to apply a counter pressure to spring hinge system 150 to keep the halves 22a, 22b, 25a, and 25b separated or apart) or a manual or motorized gear system for opening and closing rotatable member 15. Additionally, TC 20 includes locking mechanism 152 to lock halves 22a, 22b, 25a, and 25b together during operation of TC 20. Locking mechanism 152 may be either manual or automatic (e.g., controlled by computer control unit). TC 20 further includes stabilizing pins 154 provided on one end of each of rotatable member halves 25a and 25b, where stabilizing pins 154 configured to be received in pin holes 155 provided on the other end of each of halves 25a and 25b. In this way, stabilizing pins 154 and pin holes 155 fit together to stabilize halves 25a and 25b together during operation of TC 20 (e.g., to help prevent halves 25a and 25b from slipping relative to each other during rotation of rotatable member 15).

In some embodiments, the treatment cylinder (e.g., TC 10, TC 20) could be enclosed in a cabinet with a door or other closure structure. The door or other closure structure prevents external objects from being inserted into gap 16 when closed. Unlike cap 14, such embodiments would not protect the patient from becoming caught in gap 16 during operation of the device. However, if TC 10 has no moving parts that the patient could become caught in, the use of a cabinet may be practical. In some embodiments including a cabinet with a door, the device may have a lockout mechanism configured to prevent the rotatable member and/or the coherent light generators, discussed below, from activating unless the door is closed. Alternatively, the phototherapy device may require a positive override by the operator to activate rotatable member and/or the coherent light generators when the door is not closed.

In some embodiments, the cabinet may be provided with a motorized mechanism for opening and closing such a door or other closure structure. Similarly, some embodiments may, for example, include a motorized mechanism that closes gap 16 (not shown) with cap 14. If a motorized mechanism configured for performing either of these operations is present, the motorized mechanism may operate automatically and/or the operator may manually operate the motorized mechanism.

Referring back to FIG. 1, coherent light generators 17, 18, and 104, collectively "CLG," are mounted within TC 10. In some embodiments, the CLG are mounted directly to or within rotatable member 15. Each individual coherent light generator can be capable of generating a fixed wavelength of coherent light, or can be capable of generating multiple wavelengths of coherent light, either in the alternative or concurrently. Each individual coherent light generator can have the same coherent light generation selection parameters as any other coherent light generator, or can have its own unique coherent light generation selection parameters. Additionally, each CLG can emit a single beam of coherent light, or multiple beams of coherent light. Each beam of coherent light can be further divided by an optical mechanism, such as a beam splitter. Additionally, the CLG with various power outputs may be used, such as CLG capable of operating at less than 1 W, CLG capable of operating at 100 mW or more, and/or CLG capable of operating at greater than 200 W.

In some embodiments, the CLG emit coherent light in the form of laser energy through laser diodes. More specifically, the CLG emit illumination energy (e.g., from laser diodes, as described, or from another light source). This illumination is provided in a beam. The CLG can emit coherent light as various pulse types, including a continuous beam, as a pulsed (intermittent) beam, as a "superpulsed" beam, or in any combination thereof. For example, the CLG may pulse one wavelength and then pulse another wavelength, where the wavelengths span a broad range of wavelengths. Alternatively or additionally, the CLG can emit coherent light in a chirped beam, a chopped beam (e.g., a beam interrupted by an optical chopper), a shaped or patterned beam (e.g., a beam emitted in a non-circular shape), or in any combination thereof. As an example, the light could be emitted in a shape that best delivers phototherapy to the targeted treatment site, such as a petal formation, particularly if different areas of the treatment site require different amounts of light energy for treatment. As another example, the light could be emitted in a shape, such as a donut shape, that avoids areas that should not receive phototherapy treatment, such as a mole, a tattoo, or an implantable subcutaneous heart defibrillator. The CLG can also direct, or be directed such that, the light is moved in the x, y, and z and rotational directions, as discussed in further detail below. The CLG can also emit light using other optical sources and with a wide range of wavelengths, as also discussed in further detail below. In some embodiments, at least some of the CLG may be replaced with non-coherent light generators.

The CLG are optically connected to coherent light emitter rails, collectively "CLER." Coherent light generator 17 is optically connected to coherent light emitter rail 19 and coherent light emitter rail 101. Coherent light generator 18 is optically connected to coherent light emitter rail 106 and coherent light emitter rail 115. Coherent light generator 104 is optically connected to coherent light emitter rail 102 and coherent light emitter rail 103. In some embodiments, the CLG and the CLER are connected by fiber optics (not shown). However, it should be understood that any reasonable and efficient method of optical connection can be used to optically connect the CLG and CLER. Moreover, in an alternate embodiment (not shown), the CLG are laser diodes or similar sources of coherent light that are mounted directly on the CLER.

Any reasonable number of sources of coherent light may be mounted directly on the CLER and/or directly on the interior surface of TC 10. Additionally, although three CLG are shown herein as part of the phototherapy device, it should be understood that any number of CLG may be used to deliver any number of wavelengths of coherent light. For example, a single diode, dual diodes, or more than three diodes may be mounted on rotatable member 15. Further, in some arrangements, self-contained, removable, and swappable CLG may be used in the phototherapy device for purposes of selection of wavelength and power of the coherent light generated and for ease of replacement. If the CLG are mounted directly on the CLER or the interior surface of the TC 10, any desired number of CLG can be mounted in any desired configuration. For instance, a configuration suitable for a wide variety of phototherapy applications can include eight 60 W laser diodes on each of three CLER, which would allow the simultaneous delivery of multiple wavelengths (if the CLG are of different wavelengths) at high power to multiple sections of the volume of tissues to be treated.

The CLER contain a plurality of lenses and/or collimators (e.g., as described in further detail below with reference to FIG. 9) configured to alter at least one aspect of the coherent light produced by the CLG. As such, the CLER can, depending on the intended use(s) of the phototherapy device, diffuse, focus, or collimate coherent light as it is emitted from the CLER. The CLER may also alter the optical path of the coherent light. In some embodiments, the CLER are directed toward the rotary axis of TC 10, such that the coherent light, once emitted, will be directed toward the portion of the patient's body inside TC 10 and thus to the tissues which are to receive the administered phototherapy. In some embodiments, the lenses and/or collimators may be replaceable, manually adjustable, or automatically adjustable such that the diffusion pattern/spread/focus of the emitted coherent light can be changed according to the desired administration of phototherapy. Additionally, in some embodiments, a holographic film and/or optical system may modify the generated light field before it reaches the tissue to be treated and/or before it reaches other components of the CLER, such as lenses, prisms, films, and/or digital mirror arrays. For example, the light be projected through a holographic film including a holographic picture or other details that filter the light to better target specific areas within the treatment zone according to the holographic picture or details.

In various arrangements, the CLER are affixed to the surface of TC 10 and oriented in such a way as to deliver coherent light toward the central axis of rotation of TC 10. Alternatively, if TC 10 does not rotate, the CLER may be affixed and oriented to deliver coherent light toward the physical axis of TC 10. In some embodiments, as discussed above, the phototherapy may be delivered along the central axis of TC 10 in an orthogonal fashion relative to the patient's skin. In other embodiments, the phototherapy may be delivered along a different position relative to TC 10 and/or at a different angle, such as less than 90 degrees (within a margin of error).

Another CLER configuration is shown in FIGS. 1B and 1C. In TC 20, three CLER are provided on rotatable member 25 spaced equidistant apart, with CLER 156 including CLG 162 (e.g., emitting light at 810 nm) provided on rotatable member half 25a and with CLER 158 including CLG 164 (e.g., emitting light at 905 nm) and CLER 160 including CLG 166 (e.g., emitting light at 980 nm) provided on rotatable member half 25b.

Referring to TC 10 shown in FIG. 1, to use the phototherapy device, the portion of the patient's body to be treated is placed within TC 10. Once the portion of the patient's body to be treated is placed within TC 10, a computer control unit is activated by an operator (not shown), and one or more inputs (e.g., a command to use the TC 10, inputs relating to a saved or desired plan for the patient) are provided by the operator to the computer control unit. The computer control unit then energizes the CLG to provide the phototherapy. The computer control unit may also provide guidance to an operator or provide automatic control of the TC 10 to deliver the phototherapy to the targeted treatment site.

Figure 2:
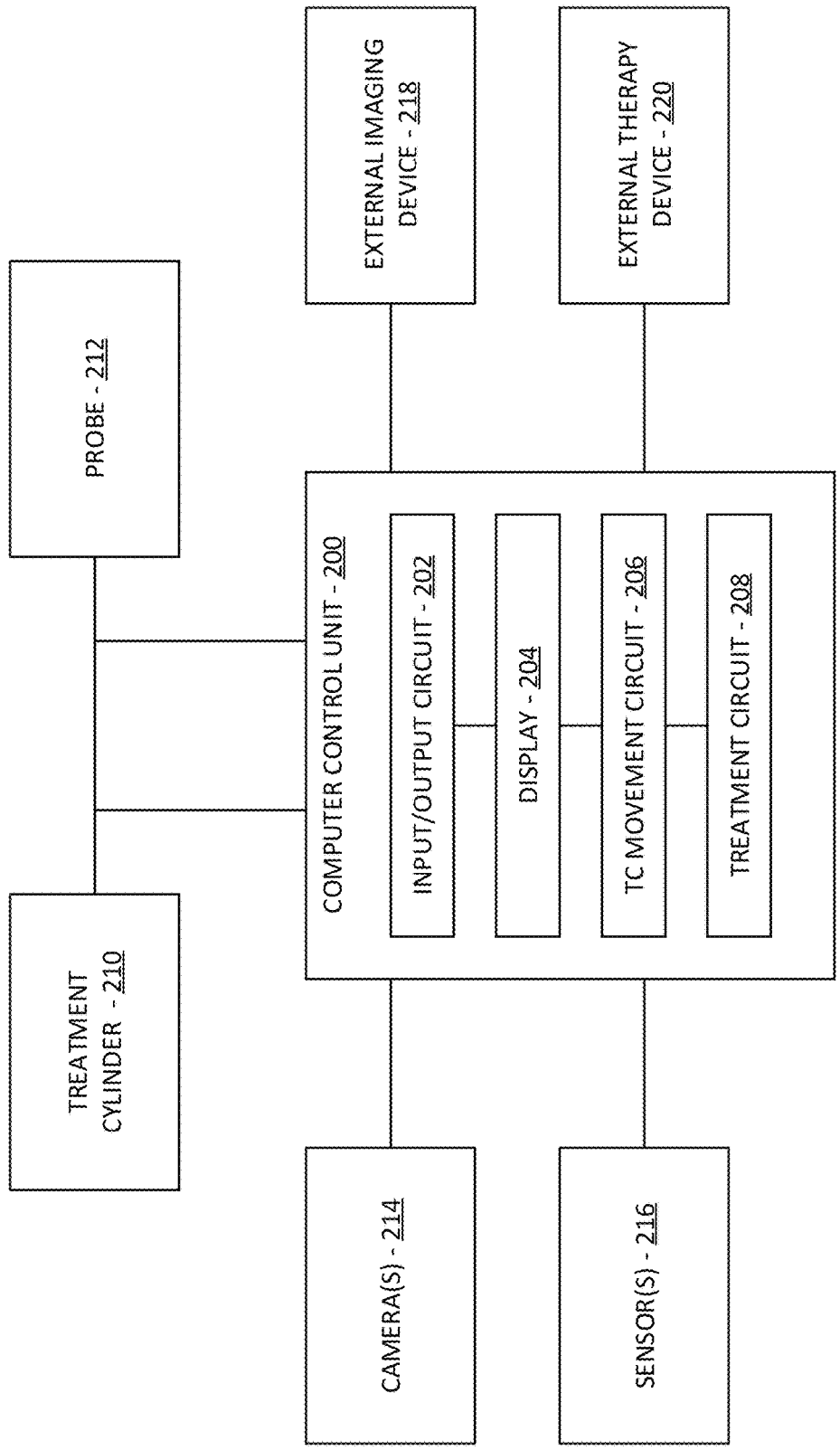
FIG. 2 depicts a block diagram of one embodiment of a computer control unit used to operate a phototherapy device.

Referring to FIG. 2, an embodiment of the computer control unit of a phototherapy device is shown. Computer control unit 200 includes input/output circuit 202, display 204, treatment cylinder movement circuit 206, and treatment circuit 208. Computer control unit 200 is also communicably coupled to treatment cylinder 210 (e.g., similar to TC 10, TC 20, or another embodiment of a treatment cylinder) and/or probe 212 (e.g., similar to a probe described below with reference to FIGS. 8-8E). As shown, computer control unit 200 may also be communicably coupled to one or more cameras 214 or other visualization devices, one or more sensors 216, an external imaging device 218, and/or an external therapy device 220. Some or all of the features of computer control unit 200 may be implemented using one or more processors and one or more computer-readable storage media. The one or more processors may be any type of processor, such as a general purpose processor, a field programmable gate array (FPGA), and application specific integrated circuit (ASIC), etc. The one or more computer-readable media may be any type of computer-readable medium or memory, such as RAM, ROM, flash media, optical media, etc. In some embodiments, various features may be implemented as instructions stored on the computer-readable media and executed by the processors to implement the functions.

These connections may be wired connections or wireless connections. For example, computer control unit 200 may include a network interface configured to communicate with devices external to computer control unit 200. A network interface may be or include, for example, any of a cellular transceiver (Code Division Multiple Access (CDMA), Global System for Mobile Communications (GSM), Long-Term Evolution (LTE), etc.), a wireless network transceiver (e.g., 802.11X, ZigBee, or Bluetooth), or a combination thereof (e.g., both a cellular transceiver and a Bluetooth transceiver). In some arrangements, a network interface includes hardware and machine-readable media sufficient to support communication over multiple channels of data communication.

Input/output circuit 202 is structured to receive communications from and provide communications to a user of computer control unit 200 (e.g., the operator). In this regard, input/output circuit 202 is structured to exchange data, communications, instructions, etc. with an input/output component (e.g., an input/output device) of computer control unit 200. An input/output device may include hardware and associated logics configured to enable the user to exchange information with computer control unit 200. For example, an input aspect of an input/output device may include a touchscreen, a mouse, a keypad, a camera, a microphone, or a user input device engageable with computer control unit 200 through a wired or wireless connection. An output aspect of an input/output device may include a display, a printer, a speaker, or an output device engageable with computer control unit 200 through a wired or wireless connection.

Display 204 may be a screen, a touchscreen, and the like. Computer control unit 200 may use display 204 to communicate information to the user (e.g., by displaying the information on display 204) and/or to receive communications from the user (e.g., through a keyboard provided on a touchscreen of display 204). In some arrangements, display 204 may be a component of an input/output device.

TC movement circuit 206 is configured to move treatment cylinder 210 (e.g., as part of delivering therapy, as part of situating the patient anatomy within treatment cylinder 210). In some embodiments, TC movement circuit 206 may also move probe 212 (e.g., through one or more robotic arms communicably connected to computer control unit 200).

Treatment circuit 208 is configured to control treatment cylinder 210 and/or probe 212 to deliver therapy to the targeted treatment site. In various embodiments, the treatment circuit 208 is configured to accept an input from an operator (e.g., a command to start treatment, an input of a setting for the treatment, a selection of a saved treatment plan for the patient, etc.). In some embodiments, treatment circuit 208 is configured to receive an input from an operator related to a treatment plan for the patient and deliver the therapy according to the treatment plan input. The treatment plan input may be a selection of the treatment area by the operator (e.g., via user interfaces provided on display 204, via markings made by the operator on the patient anatomy to indicate the treatment area and sensed by camera(s) 214), a selection of a type of therapy by the operator, a selection of parameters of the therapy by the operator, and so on. Additionally, treatment circuit 208 may use inputs from one or more external devices (e.g., from camera(s) 214, from sensor(s) 216, from external imaging device 218, and/or from external therapy device 220) to control or modify the therapy.

Example operation of computer control unit 200 to control treatment cylinder 210 and deliver phototherapy may be understood with reference to TC 10. As discussed above, in various embodiments, the operator provides computer control unit 200 with one or more inputs. The input(s) is used to determine the power setting, the duration, and the wavelength(s) of coherent light to be administered to the tissues of the patient. As an illustration, a treatment plan input may include an entirely automatic group of settings for placement (e.g., in the x, y, and z directions, as well as time of placement and time between illuminations), power, wavelength and duration, a group of manual and automatic settings, or a group of manual settings. In some embodiments, many of the settings may be predetermined to reduce the possibility of error. Further, in some embodiments, the computer control unit may have limits on any and all manual settings such that the risk of injury to the patient by the delivery of too much energy to a particular group of tissues is minimized.

As an example, computer control unit 200 may accept inputs directed to a continuous mode output or pulsed mode output, a pulse duration, a frequency (Hz), a power (W), and specific available wavelength(s) of the coherent light. As noted above, the ranges for these settings may lie between predetermined limits. To illustrate, there may be a specific ceiling of frequency settings for the pulsed mode for each millisecond level of pulse duration, and vice versa. As a more specific illustration, when using the 30 W power setting of an 810 nm laser for a probe (e.g., as described below with reference to FIGS. 8-8E) or when using the 30 to 60 W power setting of an 810 nm laser for a treatment cylinder, if the pulse duration is set to 30 ms, the frequency cannot be increased higher than 12 Hz. Similarly, if the operator has set the frequency to 12 Hz and increases the pulse duration to 31 ms, computer control unit 200 automatically reduces the frequency to 11 Hz.

In some embodiments, once computer control unit 200 receives the input, computer control unit 200 rotates rotatable member 15 such that one or more of the CLER are in a position suitable for the administration of phototherapy to the designated tissues of the patient according to the input. Computer control unit 200 then energizes one or more of the CLG so that they emit one or more beams of coherent light according to a plurality of settings (e.g., power, pulse duration, wavelength, frequency, pulse type, etc.) configured to produce a desired therapeutic effect at the targeted treatment site, which is then directed to the corresponding CLER and thus to the tissues of the patient. In various embodiments, the CLG are energized using batteries, direct coupling, induction charging, and the like. Computer control unit 200 can, according to the input, send different levels of coherent light energy to any desired number of emitters in the CLER. For example, for maximum delivery of energy, the maximum safe output of the CLG can be sent to a single emitter. Alternatively, for maximum volume of exposure at minimal energy, the minimum output of the CLG can be sent to all of the emitters on a CLER.

Additionally, as discussed above, computer control unit 200 may move TC 10 as part of delivering the phototherapy. For example, computer control unit 200 may rotate rotatable member 15 of TC 10. Computer control unit 200 may also move TC 10 along x, y, and z directions to deliver therapy (e.g., using a support or mounting system to which TC 10 is coupled, as described in further detail below). Moreover, in treatment cylinder embodiments including optical elements that may be controlled electronically, computer control unit 200 may move one or more optical elements as part of delivering the phototherapy (e.g., computer control unit 200 may move one or more galvanometrically-controlled lenses or mirrors, as described in further detail below).

By controlling the output of the CLER and/or by moving TC 10, computer control unit 200 may produce particular effects in the emitted beams making up the phototherapy, which in turn may provide particular therapeutic effects. For example, computer control unit 200 may deliver the phototherapy with specific speed and power to provide a therapeutic dose while allowing for diffusion of heat in the targeted treatment site. As one illustration, computer control unit 200 may control the output of the CLER and/or move TC 10 to provide ratcheting, rocketing, or rotating beams around and/or across portions of the targeted treatment site or multiple targeted treatment sites. As another illustration, computer control unit 200 may control the output of the CLER and/or move TC 10 to provide waving or sweeping beams across the targeted treatment site. For example, a wiping motion may involve movement of the beam from right to left, then down the width or diameter of the beam, and then left to right. A sweeping motion may involve moving a wide beam (e.g., produced by three diodes side-by-side, such as a 9 cm beam emitted by three rectangular diodes 3 cm wide by 0.2 cm thick) over a wide swath of the treatment area such that, as computer control unit 200 rotates rotatable member 15, the beam produces a sweeping motion. These motions could be slow and smooth, or these motions could be fast or very fast (e.g., beyond the physical ability of a human), which may allow the delivery of higher energy photons without overheating the skin surface or tissues below the skin's surface. As another illustration, computer control unit 200 may control the output of the CLER and/or move TC 10 to point the beam at a specific angle toward the targeted treatment site. The beam may be stationary and may be provided under, for example, Magnetic Resonance Imaging ("MRI") and/or global positioning system ("GPS") guidance. As another illustration, computer control unit 200 may control the output of the CLER to produce beams in an oval pattern that administers phototherapy but reduces heat buildup.

Additionally, in various embodiments, computer control unit 200 may vary phototherapy directed toward different treatment zones and settings or parameters of the phototherapy (e.g., intensity, speed, length, etc.) based on treatment zones. In some embodiments, a targeted treatment site includes three treatment zones. The first treatment zone is a primary treatment zone ("PTZ") that covers, for example, the mid 0 to 8 cm or more of the targeted treatment site. The size of the PTZ may vary depending on the size of the treatment site and how beneficial it may be to treat the areas surrounding the targeted treatment site. The proximal secondary treatment zone ("PSTZ") is the next 0 to 8 cm or more past the PTZ, but still within the targeted treatment site, that is closest to the heart. Similarly, the distal secondary treatment zone ("DSTZ") is the next 0 to 8 cm or more past the PTZ, but still within the targeted treatment site, that is furthest of from the heart. The treatment zones are discussed in further detail below with reference to FIGS. 10-15. It should be noted that, in other embodiments, a targeted treatment site may include any number of treatment zones, including a single treatment zone, less than three treatment zones, or greater than three treatment zones, and all such modifications are contemplated within the scope of the present disclosure.

Further, it should be understood that computer control unit 200 may produce, control, and/or modify the phototherapy automatically or semi-automatically, depending on the embodiment. For example, in one embodiment, the operator may provide the one or more inputs, and computer control unit 200 may automatically provide the phototherapy to the patient based on the input(s). In another embodiment, computer control unit 200 may automatically provide the phototherapy in certain locations but may require at least some manual control or input from the operator, such as requiring the operator to manually move TC 10 in x, y, and z directions so that computer control unit 200 may better direct the phototherapy. In another embodiment, computer control unit 200 may energize the one or more CLG according to the input(s), and the operator may be required to manually move TC 10 to deliver the phototherapy. In another embodiment, computer control unit 200 may energize the one or more CLG according to the input(s) and provide guidance to the operator (e.g., via user interfaces shown on display 204) for providing the phototherapy. As such, it should be understood that references to computer control unit 200 producing, controlling, and/or modifying the phototherapy may contemplate at least some manual input or interaction from the operator. In some embodiments, the input from the operator may be selection of a particular treatment plan stored in computer control unit 200, such that computer control unit 200 energizes one or more CLG in accordance with the selected treatment plan. In some embodiments, the input from the operator may be a command to activate one or more CLG, and the one or more CLG may be activated in response for automated and/or manual application of light to one or more treatment areas.

Depending on the size of the area to be treated and the optimal angles of incidence for the coherent light, computer control unit 200 can administer coherent light of a fixed power, wavelength, and duration from the first position of rotatable member 15, rotate rotatable member 15 to a new position, and then administer additional coherent light of the same or a different fixed power, wavelength, and duration. This cycle of rotating and administering coherent light can repeat as many times as, for example, a treatment plan input calls for or as decided by the operator. This allows for cooling of the tissues in between treatments (e.g., through the blood circulation) while allowing the delivery of the total energy required for effective treatment as fast as safely possible. It also allows the delivery of the maximum safe level of energy per administration as the delivery of the coherent light (e.g., in terms of targeted area/volume, power, duration, and wavelength) is controlled by computer control unit 200. It further allows the CLG to deliver, if appropriate, relatively high levels of power safely, which increases efficiency and reduces total treatment time as the delivery of the coherent light is controlled by computer control unit 200.

For example, in one embodiment, computer control unit 200 may administer coherent light to the targeted treatment site on the order of one to two seconds, then not administer coherent light to the site on the order of ten seconds, and then repeat the cycle until the desired level of energy has been delivered to that particular site. However, the time of administration could be less, or be greater, depending on the benefits desired. For example, in severe knee arthritis within the central part of the knee structure, the goal would be to administer the highest amount of photon energy into the deepest depths of the knee joint and surrounding tissues for maximum therapeutic benefit. As such, the time of administration may be increased relative to the above embodiment.

In some embodiments, as discussed above, the coherent light may be administered to the patient at an angle of incidence at or near 90 degrees (e.g., so that the coherent light strikes the body perpendicular to the surface). This may reduce the total amount of tissue that the light must traverse to reach the tissue to be treated. However, in other embodiments, the coherent light may be administered to the patient at an angle of incidence less than 90 degrees. For example, depending on the size of the area to be treated and the optimal angles of incidence for the coherent light, computer control unit 200 may direct the coherent light onto the patient at an angle of incidence significantly diverging from 90 degrees. In such embodiments, computer control unit 200 may be configured to adjust the power and/or duration of the coherent light administration to compensate for the additional depth of tissue that the coherent light must traverse to reach the tissue to be treated.

Treatment of the human knee may be used as an example of the operation and benefit of a treatment cylinder operating in conjunction with a computer control unit, such as TC 10 operating in conjunction with computer control unit 200. A human knee 15 cm in diameter over a 22 cm long axis extending above and below the knee joint's fulcrum produces a 1036 $cm^2$ treatment area. A typical therapeutic phototherapy dose is a radiant exposure of 8.7 Joules/$cm^2$ over this area. A coherent light beam 3 cm in diameter at the emitter diverges to a 7.1 $cm^2$ planar intersection with the area to be treated at a typical focal length and an angle of incidence at or near 90 degrees. Therefore, at least 147 individual pulses of coherent light are needed to cover the entire treatment area. For a human using a single emitter wand to deliver phototherapy, this would require at least 147 individual applications of phototherapy, carefully spaced, aimed, and timed. Advantageously, the phototherapy device described herein can completely automate this process, ensuring that the entire area to be treated is uniformly (or as otherwise most therapeutically effective) and entirely covered, at the proper distance, power setting, and duration of coherent light emission.

According to various embodiments, phototherapy may be delivered with any wavelength within the spectrum with both a narrow and broad spectrum approach, where the wavelength is based on the therapy that is required for the patient. For example, phototherapy may be delivered with an infrared or near-infrared wavelength. As another example, phototherapy may be delivered in a range of 400-1200 nm, 600-1100 nm, 800-1100 nm, and/or 400-10,000 (e.g., to allow for the use of $CO_2$ lasers). As another example, phototherapy may be delivered at or near (e.g., within 5%) the following wavelengths: (1) 980 nm, which will penetrate soft tissues to a depth of approximately 4 to 4.5 cm; (2) 905 nm, which will in some applications produce an immediate analgesic effect by reducing nerve impulses in the treated tissues; (3) 808-810 nm, which will penetrate soft tissues to a depth of approximately 8 cm, the maximum depth to which phototherapy can be safely and efficiently applied under most conditions; or (4) 1064 nm, which is less readily absorbed by the surface tissues of patients with darker skin and can penetrate to a reasonable depth without causing as much surface heating as coherent light with shorter wavelengths, increasing energy delivery to the tissues to be treated and reducing the risk of excessive surface tissue heating in such patients. Additionally, in various embodiments, the phototherapy device is configured to deliver at least a certain level of therapy, such as beams of coherent light with a radiant exposure in the range of 0.1 to 50 J/$cm^2$ of therapy (e.g., 4-12 J/$cm^2$ of therapy, 5-8 J/$cm^2$ of therapy, 8-12 J/$cm^2$ of therapy).

In one embodiment of delivering therapy using the phototherapy devices described above, an initial series of treatments with the device could deliver approximately 60 W of power, or more, to the targeted tissues for the prescribed surface area. Follow-up treatments could be delivered at the same, lower, or higher wattages of power (e.g., follow-up treatments could be delivered at approximately 20 W of power). Follow-up photon administration could be applied, for example, in maintenance therapies to manage the disease state or to treat and further suppress diseases that are prone to inflammation flare-ups. Regardless of the use of milliwatts to megawatts, the power can be controlled based on the amount of heat dissipation or cooling of the tissue. The operator and/or computer control unit 200 can change wattage, treatment area, pulse duration, frequency, pulse width, and/or overall treatment duration according to the targeted treatment site. This real-time adjustability in power allows the prescribed therapy to be tailored to the disease state.

The therapy may also be tailored to the type of disease state that is being treated. For example, specific therapy parameters may be used for certain central nervous system ("CNS") diseases or conditions (e.g., dementia, depression, post-traumatic stress disorder ("PTSD"), Alzheimer's, Parkinson, and stroke). More specifically, therapy could be applied that causes or triggers cellular changes or interstitial changes that affect the progression of these disease states.

Additionally, a variety of aspects of the light beam used for phototherapy may be manipulated, either physically (e.g., by changing out optical components) or electronically (e.g., by using the computer control unit to change out optical components or power only certain optical components), depending on the therapy. For example, the beam may be diffusing or non-diffusing. The beam may be collimated or not collimated. As discussed above, the beam's diameter, size, and shape may be adjustable, and the beam may be provided at a static spot or may be movable. The beam may also be ablative (e.g., for performing a laser vaginal rejuvenation treatment). For instance, one or more CLER may emit an ablative erbium laser beam or a $CO_2$ laser beam to perform a laser peel on the skin's surface or to penetrate through the epidermis and into the dermis for skin tightening, abdominal stretch marks appearance reduction, and age spot reduction.

In various embodiments, and as discussed above, an aim of the phototherapy device is to deliver the coherent light energy as fast as safely possible to diminish heat buildup, as heating causes vasodilation in the intervening tissues, making them absorb more energy and reducing the effectiveness of the treatment. However, if it is determined by the operator that more and slower treatments will produce better results, the operator and/or computer control unit 200 can adjust the parameters of the phototherapy device accordingly. In some embodiments, the phototherapy device may include, or the operator may separately apply, a structure for cooling the patient's surface tissues to reduce vasodilation. The cooling structure may be used before and/or during a treatment session to cool the skin's surface prior to the beam hitting the skin at the targeted treatment site. The cooling structure may also be used to decrease heat discomfort from heat buildup at the beam-skin surface interface ("BSSI") and within the dermis and subdermal tissues. For example, the cooling structure may be used to keep patient tissues from heating over 41° C. when treated by a treatment cylinder. Additionally, pretreating the skin with the cooling structure may result in vasoconstriction and skin blanching that can lead to more photons passing through the superficial skin and subdermal tissues, thereby aiding photons in penetrating into deeper soft tissues where disease states tend to reside.

The mechanism of the cooling structure could include forced-air ventilation, the application of cold water, ice, or cooling gel, or any other reasonable, safe, and efficient mechanism for cooling the surface tissues. For example, the cooling mechanism may cool patient tissues using coolants such as cooled-chilling, flowing, distilled water or sterile normal saline (e.g., 0.9% NaCl), 10% menthol, compressed $CO_2$, nitrous oxide, liquid nitrogen, nitrogen gas, and/or isopropanol or another cooled fluid from an external cooling system. Additionally, in some embodiments, the cooling mechanism may be delivered to the patient internally.

Various cooling mechanisms could be applied to both the treatment cylinder (e.g., TC 10, TC 20) and the targeted treatment area. In some embodiments, the cooling mechanism may provide direct or indirect cooling of components of the phototherapy device, such as the CLG or a probe tip of the phototherapy device (e.g., as discussed in further detail below with reference to FIGS. 8-8E), and/or indirect cooling of the surrounding tissue. For example, the phototherapy device could include a cooling mechanism at the coupling mechanisms or interfaces of the fiber optics and/or laser beam transfer structures used to move coherent light from CLG to CLER (e.g., the coupling beam laser highway). In other embodiments, the cooling mechanism could be external to the treatment cylinder (e.g., provided directly on the patient) and/or there could be a source arising from the TC 10 itself at the beam-surface interface. For example, a cooling blanket could be provided on the patient during treatment of the knee. By cooling the patient's blood upstream, the blood is cooled before reaching the treatment zone, thereby extending the photon exposure time and/or allowing for an increased amount of photon administration at any given time.

Additionally, the cooling mechanism may include various structures. For example, a cooling mechanism may include one or more pumps for pumping the coolant or cooling media to the patient site or site on the phototherapy device to be cooled. The cooling mechanism may further include tubes or conduits for guiding the coolant or the cooling media to and from the site to be cooled.

Furthermore, in some embodiments, the dermal layer, subdermal tissues, and/or subcutaneous tissues may be treated (e.g., physically, physiologically, or neurologically) before photons are administered onto the skin surface of the treatment site to improve treatment efficacy. To illustrate, the skin may be cooled, numbed, made less reflective to incoming photons, and/or vasoconstricted before administration of photons. For example, a cream, gel, oil, or spray containing a topical numbing anesthetic such as lidocaine may be applied to the skin surface. As another example, a skin cooling and vascular constricting cream, gel, oil, or spray, containing substances like menthol, $CO_2$, *Eucalyptus globulus* leaf oil, phenylephrine HCl, epinephrine, witch hazel, or menthol may be applied to the skin surface. Prior to the administration of photons, an operator can also apply agents, chemicals, or other substances that block or absorb part or all of the delivered photons to the skin and/or into deeper anatomical layers. These can include specific photon-absorbing chromophores, such as biologically friendly inks, that can enhance the absorption of photons and thus enhance the propagation of photons through tissues within the targeted treatment site.

As an illustration, a hemoglobin-enriched sterile bile acid that preferentially adheres to tumor cells could be injected into a pancreatic tumor. The chosen type of photons could then be delivered into the mid-upper abdominal skin area above the top areas of the pancreas using TC 10. Additional photons could also be delivered through MRI or GPS guidance through an independent probe or a probe coupled to a treatment cylinder, such as TC 10. For example, the probe could be interfaced with or attached to the end of an endo gastro duodenum ("EGD") endoscope. Such probes are described in further detail below with reference to FIGS. 8-8E.

As another illustration, a gel containing lidocaine and phenylephrine HCl that numbs the skin and vasoconstricts the blood vessels could be applied within the targeted treatment site. This numbing allows higher energy photon delivery into the skin without the patient sensing the usually intolerant higher temperatures of 41 to 45° C. (e.g., depending on the type of tissue being treated) produced by the photons. Additionally, the use of these topically applied vasoconstrictors could reduce the blood flow within the targeted treatment site, thus reducing the presence of the chromophore hemoglobin within these shallower surface tissues. Hemoglobin is known to preferentially absorb a 980 nm diffused beam of photons, and these vasoconstrictors could thus produce a blanched skin environment that allows more photons in such a beam to travel deeper into the subdermal tissues and beyond.

In some embodiments, the phototherapy device may be used with one or more cameras (e.g., camera(s) 214 of FIG. 2). Cameras can be used, for example, to view a body part or orifice of interest in 2D or 3D with a time circumferential view of the targeted tissue site. As another example, an infrared camera may be used to locate hot spots at the targeted tissue site. In some embodiments, the camera may be incorporated into the phototherapy device (e.g., provided on TC 10), while in other embodiments, the camera may be used separately or externally from the phototherapy device.

In various embodiments, user interfaces may be provided to the operator of the phototherapy device (e.g., on display 204 of computer control unit 200) before, during, and after use of the device to deliver therapy to a patient. These user interfaces may include various indicators, such as a power indicator, a readout of the rotation speed of the treatment cylinder, a readout of the frequency, pulse width, and rotation of the coherent light provided by the CLG, a readout of the power level of the CLG, and/or a readout of the sequence of the energy emission on the CLER. Additionally, in some embodiments, the user interfaces may be interactive (e.g., with clickable buttons on a monitor or on a touchscreen) such that the operator can control and modify delivery of the phototherapy treatment using the user interfaces. As examples, the user interfaces may include an ON/OFF button, an emergency stop button, buttons or other indicators that the operator can select to modify the power levels of the CLG (e.g., such that the operator can modify the power levels of the CLG individually and/or as a whole), and/or buttons or other indicators that the operator can select to modify the sequence of the energy emission on the CLER. The user interfaces may also allow an operator to position the CLG, individually or as a group (e.g., using robotics), into selective areas of the targeted treatment site. Moreover, the user interfaces may be provided on a touchscreen displaying the treatment site such that the operator can mark and draw areas to be treated and/or areas to avoid treatment on the displayed treatment site.

In some embodiments, the user interfaces may be used to control a camera or other imaging system used to visualize the treatment area. To illustrate, the user interfaces may allow the operator to move the camera (e.g., in a 360° rotation), show an infrared visualization of the treatment site (e.g., recording and measuring in real-time), show a visualization of the veins of the treatment site (e.g., an AccuVein® visualization of the treatment site), and/or show a visualization of a body part different from the treatment site. Further, the user interfaces may show images from other diagnostic or imaging modalities, such as MRI images, to help the operator target areas of interest on or below the body surface.

In various embodiments, the treatment cylinder (e.g., TC 10, TC 20) may be used with one or more sensors to aid in the treatment process. The sensors may produce data relating to the operation of the phototherapy device and/or a parameter of the targeted treatment site, as discussed in further detail herein. The one or more sensors may be integrated with the treatment cylinder or may be used separately from treatment cylinder and, for example, configured to feed back into treatment cylinder and/or the computer control unit (e.g., computer control unit 200). In various arrangements, the computer control unit may use sensor data may to control or modify the phototherapy treatment, such as by controlling the treatment cylinder to re-treat areas, move on to other areas for treatment (e.g., move the coherent light to other treatment areas), redirect the phototherapy (e.g., at least one beam of coherent light forming the phototherapy), or modify one or more settings for the phototherapy (e.g., by decreasing the power level for the therapy). More specific illustrations are discussed below.

As examples, a treatment cylinder may be used with one or more sensors to detect temperature (e.g., a skin temperature sensor, a device temperature sensor), to detect rotation of the phototherapy device (e.g., a motion detector or encoder), to detect movement of the phototherapy device or of the patient (e.g., an accelerometer, a linear variable differential transformer ("LVDT")), to detect an energy level of the phototherapy device, to detect an audible noise or a visual cue while the phototherapy device is in use, and/or to detect patient vital signs or monitor other biological or physiological systems (e.g., weight, heart rate, blood pressure, $PCO_2$, $PO_2$, $CO_2$). To illustrate, TC 10 may include temperature sensors positioned on rotatable member 15 to continuously capture tissue or skin temperature information before and after each CLER or CLG passes and applies energy to the treatment area. As another illustration TC 10 may be used with contact and/or non-contact temperature sensors mounted on the patient or on a control cabinet. In some embodiments, camera data (e.g., relating to a parameter of the targeted treatment site, such as the temperature of the site) may also be used similar to sensor data to modify, redirect, or otherwise control the phototherapy.

Accordingly, in some embodiments, the phototherapy device receives temperature information from one or more temperature sensors integrated into and/or separate from the phototherapy device. As such, the computer control unit may receive temperature information and may be configured to shut off the laser output at a skin temperature greater than 45° C., as determined by the one or more temperature sensors, for biological reasons (e.g., to prevent the patient's tissue from overheating and sustaining damage). Alternatively, or additionally, the treatment cylinder may include a shutter that stops the laser treatment to protect the patient if the sensor data indicates that the device has stalled or is not rotating. However, at least some embodiments of the phototherapy device may be used for non-biological applications (e.g., industrial use), and in such embodiments the temperature could range from negative degrees to very high temperatures.

As one example, the device may be used in a non-biological application to melt metals at their $T_g$ temperatures. Accordingly, the device configured for such applications may include a temperature sensor configured to sense high temperatures. As another example, for pin creation, the pin usually rotates to create threads. Using this device, the pin could remain stationary while the one or more laser beams rotate 360 degrees around the pin. As another example, the device may be used to cut deep channels or crevices (e.g., 3 cm deep) into and completely circumferentially around stationary steel columns (e.g., solid steel columns 200 feet long by 3 feet in diameter). As another example, the device may be used to laser a company's logo onto a steel column circumferentially (e.g., laser a logo 6 feet high by 15 feet wide onto a stationary 200-foot-long steel column 1.5 times the distance around the column). As another example, the device may be used to laser cut partially or completely through, from all sides, an existing support column embedded in a concrete foundation. This may be done using a device including a hollow structure with a clamshell configuration (e.g., as shown in FIGS. 1B and 1C), which allows the hollow structure to be enclosed around the support column. Once enclosed, the hollow structure may cut the column from all directions, individually or simultaneously, to a desired depth using the laser diodes on the hollow structure. As another example, again using a device including a hollow structure with a clamshell configuration, the hollow structure may be enclosed around a tree and used to cut down the tree in a rapid fashion. As another example, a device may be used to apply photons to the surface of an object, such as a meat carcass, to kill bacteria on the object. The photons could be topically applied in a sweeping fashion around the entire object in an ablative laser mode to kill surface bacteria or applied in a diffuse-beam mode that would penetrate several cm deep to kill live bacteria and parasites (e.g., living under flaps of fat and soft tissues not reachable by gamma radiation, which is a current method used to kill bacteria in meat carcasses).

Additionally, the treatment cylinder (e.g., TC 10, TC 20) may be used with one or more sensors and/or cameras capable of distinguishing sections of the human anatomy and facilitating the treatment cylinder in providing therapy to those sections. For example, as noted above, the operator may be provided with user interfaces showing the patient anatomy of the treatment site. The operator can mark, label, or otherwise identify sections of the treatment site for the application of therapy, for the application of a higher level of therapy (e.g., with additional Joules, with additional wavelengths, at a different rotational speed), and/or for the avoidance of therapy using the user interfaces. As another example, the operator may mark, label, or otherwise identify these sections directly on the patient anatomy, and the computer control unit (e.g., computer control unit 200) can identify the sections based on the markings, labels, or identifications. To illustrate, the operator may mark these sections in a specific color, place radio-frequency identification ("RFID") markers around the sections, or place optical markers around these sections, and the computer control unit may identify the sections using a camera or an RFID sensor. The computer control unit may then automatically provide therapy to the identified sections, increase therapy to the identified sections (e.g., by modifying one or more therapy settings, such as the power level), and/or avoid providing therapy to the identified sections. Alternatively, the computer control unit may guide the operator in providing therapy, providing increased therapy, and/or avoiding therapy in the identified sections.

As an illustration, the operator may mark target points directly on the patient anatomy or using user interfaces corresponding to areas of more intense soft tissue tenderness (e.g., muscle tenderness or palpitation). The computer control unit may then provide increased therapy to those areas once those areas are reachable by the diodes of the rotating treatment cylinder.

In various embodiments, and as discussed above, the phototherapy device may be used with various other imaging modalities and/or treatment devices. For example, the device may be used with an MRI machine, an x-ray machine or other imaging machine like an MRI and/or a Global Positioning System ("GPS")-like locating device (e.g., that uses chips or emitting signal beads that are implanted, for example, within a probe, which is described in further detail below), a computerized tomography ("CT") scanner, an ultrasound machine, one or more operative scopes, one or more endoscopes, one or more fluoroscopes, one or more optical/visual cameras (e.g., charge-coupled device ("CCD") cameras, color sensors, or other image sensors), and/or one or more thermal cameras. In some embodiments, the computer control unit (e.g., computer control unit 200) for the phototherapy device may be configured to interface or otherwise automatically connect to imaging and/or treatment devices to assist the operator in positioning the device, in making treatment decisions, in targeting the tissue surface, and so on.

To illustrate, the phototherapy device may include a trans-esophageal probe, and imaging modalities may be used to track the beam location with respect to targeted tissue and visualize the effects of treatment in real-time. More specifically, a rapid CT scan may be used to help the operator visualize the effects of the phototherapy and adjust both the location and parameters for the phototherapy. Alternately, ultrasonic, endoscopic, and/or fluoroscopic imaging could be used for visualization of the tissue and the phototherapy device (e.g., a probe of the phototherapy device, as discussed below, and the probe photon emission window (e.g., the beam dimensions and direction(s)) to observe the effects of adjustments to the phototherapy. The phototherapy device may also be imaged with an x-ray machine to confirm placement of the phototherapy device (e.g., placement of a treatment cylinder or a probe tip, as discussed below) over the treatment site both pre- and post-phototherapy administration (e.g., by determining the location of the phototherapy device with respect to organs and bone structures of the patient).

In various embodiments, and as discussed above, the computer control unit (e.g., computer control unit 200) may use inputs from these various external devices and/or devices incorporated as part of the phototherapy device to produce, control, and/or modify the phototherapy (e.g., as part of a feedback control loop). For example, as shown in FIG. 2, computer control unit 200 may receive inputs from camera(s) 214 and modify treatment based on the camera location. Computer control unit 200 may use various temperature sensors 216 (e.g., thermistors, thermocouples, infrared imaging, ultraviolet imaging, etc., which may be incorporated on treatment cylinder 210, external to treatment cylinder 210, provided on a cabinet for treatment cylinder 210, etc.) to modify the therapy, such as by moving the beam if computer control unit 200 senses that the targeted tissues are becoming too hot. Computer control unit 200 may also use spectrometers or spectroscopy information indicating skin ailments, temperature, or other information about the body to modify the therapy.

Further, computer control unit 200 may use internal inputs as sensed via internal electronics (e.g., via information provided to computer control unit 200 by the CLG and/or CLER components). These internal inputs may include information about the light beam itself, including the length, width, shape, profile, and Gaussian distribution of the beam. Computer control unit 200 may also be able to detect, via internal inputs, partial or total diode energy output failure of the CLG or inadequate and/or improper movement of one or more components of the phototherapy device (e.g., such that the treatment cylinder is not moving a specific way or speed for safe and efficacious treatment administration). If computer control unit 200 senses these issues, computer control unit 200 may immediately stop all laser output while alerting the operator by sound and/or user interfaces that an error has occurred. In this way, when phototherapy is controlled by a computer control unit, the therapy may be more optimized through feedback mechanisms, resulting in shorter dwell times and safer phototherapy delivery.

It should be understood that the various configurations and properties of the phototherapy device described above with respect to FIGS. 1-1C may also be applied to other phototherapy device embodiments, including or not including a treatment cylinder (e.g., instead including a standalone probe), described herein. For example, other embodiments of the phototherapy device may be used with one or more cameras, various user interfaces, one or more sensors, one or more imaging modalities, and/or one or more other treatment devices.

Figure 3:
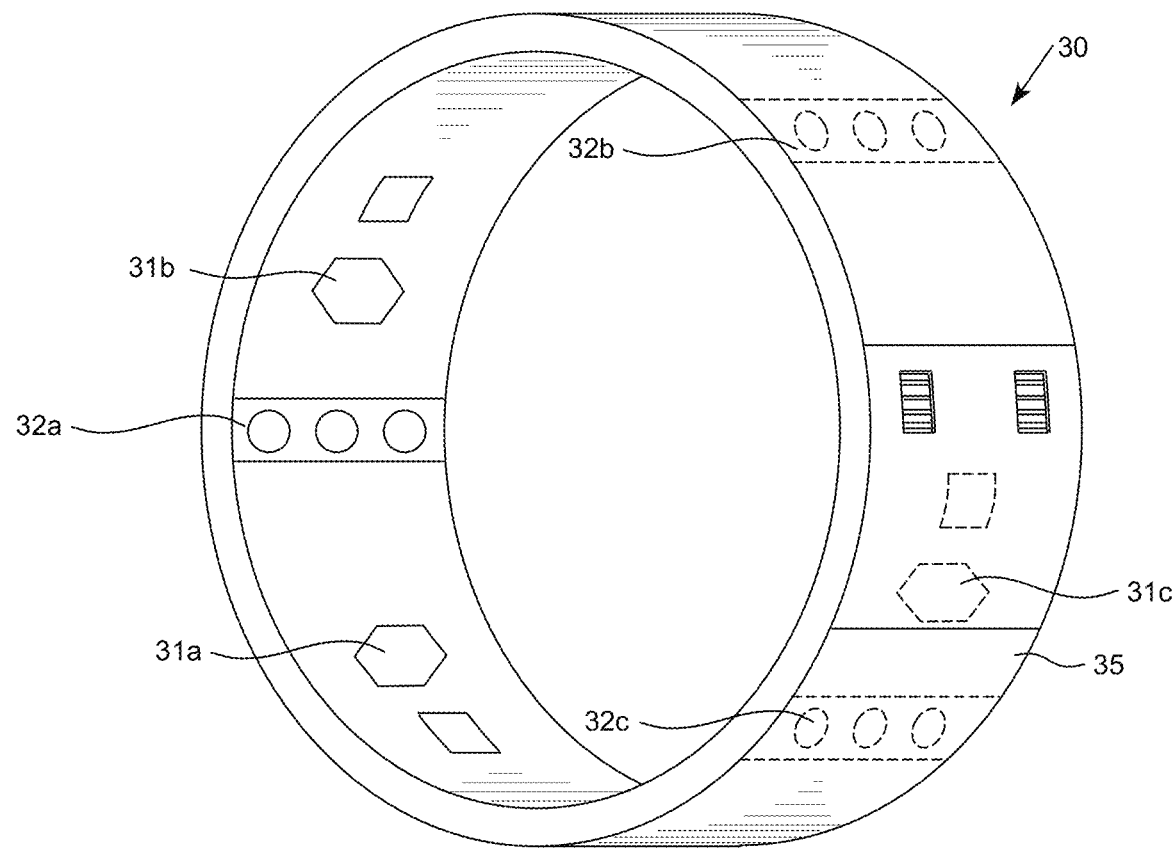
FIG. 3 depicts an abstracted perspective view of another embodiment of a treatment cylinder portion of a phototherapy device.

FIG. 3 shows an alternate embodiment of the treatment cylinder. As shown in FIG. 3, TC 30 can alternatively be a single member (shown) or an outer stationary member and an inner rotatable member (not shown). The CLG are optically connected to galvanometrically-controlled lens assemblies 32a, 32b, and 32c, collectively "GCLA." There is no limit as to how many GCLA can be used or how many emitters GCLA can contain, but it is required that each GCLA contain at least one coherent light emitter. The GCLA are operably connected to the computer control unit (e.g., computer control unit 200), which can use the GCLA to more precisely target the beams of coherent light generated by the CLG (e.g., as described in further detail with regard to FIG. 3A below). Galvanometrically-controlled mirrors 31a, 31b, and 31c (collectively "GCM") can allow light emitted from the GCLA to be aimed at a mirror and then reflected toward the patient as opposed to being directly aimed at the patient by the GCLA. Including the galvanometrically-controlled mirrors 31a, 31b, and 31c allows the coverage of more angles of transmission with the same or fewer GCLA and/or rotational increments of TC 30.

Similar to the CLER, the GCLA are configured to alter at least one aspect of the coherent light produced by the CLG (e.g., the optical path of the light, the diameter of the light, the collimation of the light, etc.), except that the GCLA are more specifically galvanometrically-controlled. In some embodiments, whether through GCLA, a lens, a mirror, or another mechanism of directing light, the light to be used for the administration of phototherapy may be directed through or toward an emitter that controls its direction and directs it toward, for example, central axis of the TC 30. In general, any "beam steering" device, as that term is used in the art, whether now known or later invented, can be used to accomplish this function. This can include, without limitation, physical devices or controlled electromagnetic fields. Further, in some embodiments, the path of the light to through the emitters may end in a type of "beam conditioner," as that term is used in the art, whether now known or later invented. These beam conditioners may include, without limitation, lenses, collimators, partial mirrors, optical ports, or diffusers.

Figure 3A:
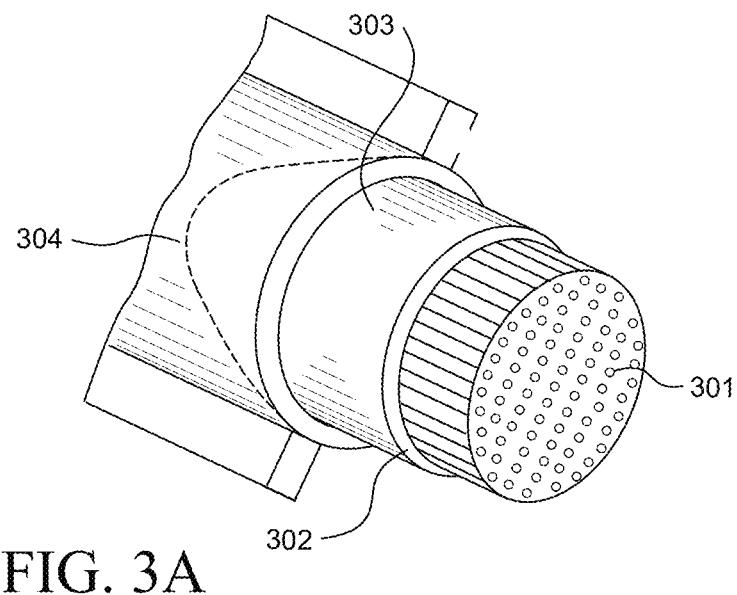
FIG. 3A depicts a perspective close-up view of one embodiment of a gimbal-mounted lens/collimator assembly.

FIG. 3A shows the detail of a single light emitter component of a GCLA. Galvanometric gimbal 304 is mounted over the end of the optical connection to one of the CLG. Coherent light travels through galvanometric gimbal 304, which can be electromagnetically positioned by signals from the computer control unit (e.g., computer control unit 200). Mounted in galvanometric gimbal 304 are first diffusing lens 303, second diffusing lens 302, and collimator 301, collectively the "diffuser assembly." By controlling the position of galvanometric gimbal 304, the lens assembly can be aimed to more precisely target the coherent light generated by the CLG and direct it to the tissues to be treated. Some embodiments may include any particular number of diffusing lenses and/or collimators, but many embodiments include at least one lens or collimator so as to give the beam of coherent light the proper dispersion/diffusion to safely and effectively transmit the beam of coherent light toward the patient.

In some embodiments, TC 30 includes CLER and GCLA. Additionally, some embodiments include more than one galvanometrically-controlled emitter in a GCLA. The GCLA, the CLER, or any other emitter for coherent light used in any embodiment described herein can be configured either to maintain a constant diameter of the illuminated area where the coherent light initially strikes the patient's body or to provide a variable diameter of the illuminated area where the coherent light initially strikes the patient's body. Selecting for a constant-diameter configuration or a variable-diameter configuration can be via electromechanical control of the optical components of the emitter (e.g., via the computer control unit), or by adding or removing a collimator or diffusing element from/to the coherent light beam's optical path where it leaves the device and enters the space between the emitter and the patient's body.

In some embodiments, the GCLA include one or more physical or electrical mechanisms for moving lens 302 on the axis of the coherent light beam toward or away from galvanometric gimbal 304 and/or collimator 301 and thus the source of the coherent light. Using this mechanism changes the net focal length of the GCLA and thus the size and energy-per-square-unit-of-area of the coherent light beam where it intersects the patient's body. The mechanism for moving lens 302 can be manually implemented by the operator or controlled by the computer control unit, either in response to a treatment plan input, a manual setting by the operator, or the computer control unit determines the optimum parameters for the delivery of phototherapy as described above or below (e.g., with reference to FIG. 6A).

Figure 4:
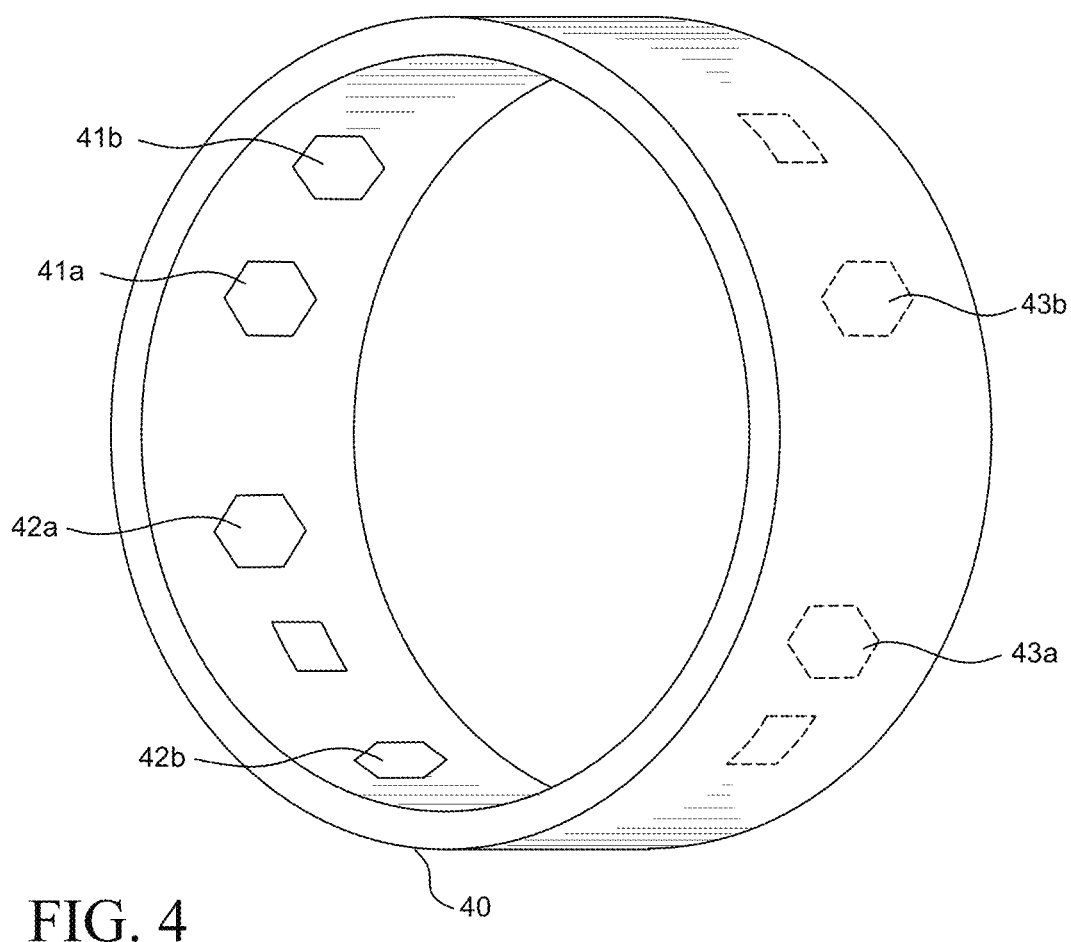
FIG. 4 depicts a perspective view of another embodiment of a treatment cylinder portion of a phototherapy device.

FIG. 4 shows another alternate embodiment of the treatment cylinder. As shown in FIG. 4, TC 40 can alternatively be a single member (shown) or an outer stationary member and an inner rotatable member (not shown). The CLG are optically connected to galvanometrically-controlled mirror assemblies 41a and 41b, 42a and 42b, and 43a and 43b, collectively "GCMA." As opposed to the prior embodiments, the emitters of the CLG are now permanently targeted toward the GCMA. As such, the GCMA may alter at least one aspect of the coherent light produced by the CLG, such as the optical path of the coherent light.

The treatment cylinder may include a single (or at least a non-rotatable) member in an embodiment using GCMA. Alternatively, the treatment cylinder may include a rotatable member that can be used without interfering with the functioning of the device. Unless a rotatable member is used, all targeting of the coherent light beams may be performed by controlling the positions of the GCMA. Further, it should be understood GCLA and/or CLER may also be included in an embodiment including GCMA.

It should further be understood that TC 10, TC 20, TC 30, and TC 40 described above are intended to be exemplary and that a phototherapy device may include another alternate embodiment of a treatment cylinder. For example, in one embodiment, the treatment cylinder does not include a rotatable member and instead includes a fixed ring. A plurality of optical fibers is permanently or temporarily mounted on the fixed ring and attached to a fiber-coupled laser provided with linear actuation. The plurality of optical fibers may be mounted in any desirable configuration, such as a vertical or a horizontal straight line or in a circular cluster. Additionally, the plurality of optical fibers may be mounted in a single area on the fixed ring or in multiple areas on the fixed ring. During therapy, the fixed ring remains stationary. Instead, the linear actuator moves from optical fiber to optical fiber, thereby illuminating different locations on the fixed ring, and thus the treatment site, based on the optical fiber(s) that are used by the laser. The treatment cylinder may also be mounted onto a frame holding the electronics for controlling the phototherapy device inside and including wheels for moving the treatment cylinder. This treatment cylinder configuration thus requires no rotational components and may be powered by remote electronics, although this configuration may require complex fiber insertion and placement accuracy and a treatment plan that avoids inconsistent hot spots.

In another embodiment, a treatment cylinder includes ring of a plurality of mirror assemblies (e.g., GCMA) mounted on the inside surface of a rotating member of the treatment cylinder. One or more laser inputs (which may be galvanometrically-controlled) are aimed at the mirror assemblies, which direct the emitted light to the treatment site within the treatment cylinder. The laser inputs may be external to the treatment cylinder and aimed at the ring of mirror assemblies, for example, directly or through additional mirrors on the treatment cylinder or external to the treatment cylinder configured to aim the laser inputs to the ring of mirror assemblies. In this way, the electronics are removed from the rotating member, and a stand is not required for the treatment cylinder itself to house the electronics. This embodiment may require complex software programmed into the computer control unit to ensure that the phototherapy reaches the treatment site and avoids light path interruptions.

In another embodiment, a treatment cylinder is fabricated with a gap, where one of the ends of member forming the gap is a mirror-polished end. A mirror side of the mirror-polished end may be accessible from within cladding of the member of the treatment cylinder. A laser (e.g., provided via a fiber optic cable) is inserted through the cladding of the member of the treatment cylinder into the core of the treatment cylinder. The emitted light is directed to the treatment site via the mirror-polished end (e.g., by mirror side accessible from within the cladding). The treatment cylinder rotates on a rotational axis, and all of the electronics are positioned outside of the rotational axis. Thus, this embodiment is advantageous because a stand is not required to house electronics (e.g., because at least some of the electronics are within the cladding of the treatment cylinder itself), though this embodiment may require complex fabrication and some insertion loss of may be incurred.

In another embodiment, instead of a treatment cylinder, the phototherapy device may instead include a treatment globe. The treatment globe may be configured similarly to embodiments of the treatment cylinder discussed above (e.g., including one or more CLER, GCLA, and/or GCMA on the inside of the treatment globe, including a rotatable member) but may instead be globe-shaped. The treatment globe may be configured to rotate on one or more axes (e.g., rotate around an axis going through the center of the treatment globe). The treatment globe may also be connected to a support arm (e.g., similar to the support arms discussed below with reference to FIGS. 7-7D), allowing for further rotation and movement of the treatment globe.

In some arrangements, the treatment globe includes a single opening to the interior of the treatment globe such that the patient anatomy to be treated can be inserted through the opening into the interior of the globe. In other arrangements, the treatment globe may include an opening extending through the treatment globe such that patient anatomy may be inserted through the treatment globe. Additionally, the treatment globe may be provided with one or more caps or coverings (e.g., photon-absorbing caps or coverings) configured to fit around the opening(s) such that the patient anatomy can be inserted into the opening(s) and the caps or coverings can be used to surround the patient anatomy and close off the opening(s). In this way, photons may be absorbed by the cap or covering such that they do not escape the treatment globe. Further, the treatment globe may also be provided with other features discussed herein with reference to the treatment cylinder (e.g., sensors, user interfaces, use with various imaging modalities, etc.).

In another embodiment, instead of a treatment cylinder, the phototherapy device may instead include a treatment chamber. The treatment chamber may be cylindrical, spherical, dome-shaped, etc. Additionally, the treatment chamber may be large enough for the patient to fit entirely within the treatment chamber, or the treatment chamber may be sized to receive only a portion of the patient's anatomy. In some arrangements, the treatment chamber includes a table for the patient to rest on during the treatment procedure, and the operator may position the patient on the table according to the disease to be treated (e.g., based on where on the patient the phototherapy should be directed). The treatment chamber is further provided with a multi-mirrored surface, such as a mirrored sphere. The multi-mirrored surface may be provided on the ceiling, wall(s), or floor of the treatment chamber. Additionally, the treatment chamber is provided with one or more laser power plants positioned on the walls or other surfaces of the treatment chamber. For example, the laser power plants may be configured similarly to the GLC discussed above (e.g., including an optical apparatus for delivering the photon beam, such as a fiber optic cable, a diffusing lens, one or more mirrors for beam reduction, and/or a beam collimator).

The laser power plants are configured to emit laser beams, and the direction of the beams may be modified via a galvanometric control by the computer control unit. Additionally or alternatively, one or more laser power plants may be provided on one or more robotic arms that are also controlled by the computer control unit. The robotic arm(s) may be mounted outside of the treatment chamber or inside the treatment chamber. In various arrangements, the laser power plants and/or robotic arms may be automatically controlled, manually controlled, or both.

In some arrangements, after the operator situates the patient on the table, the operator selects a prescribed treatment protocol from user interfaces provided to the operator (e.g., on a monitor on the outside of the treatment chamber or near the treatment chamber). Additionally, the operator may make one or more selections via the user interfaces to modify or further refine the therapy, as described above. For example, the operator can select areas shown on the user interfaces to designate sections for treatment, increased treatment, and avoiding treatment. Once the treatment has begun, at least some of the laser beams may be directed to the multi-mirrored surface, which may be stationary, turning or rotating, or moving. The target treatment site may thus receive phototherapy from one or more of the following sources: (1) directly from the laser power plants, (2) reflected off of the multi-mirrored surface (e.g., from the laser power plants mounted inside the treatment chamber and/or from the laser power plants mounted on the one or more robotic arms), and/or (3) directed by the one or more robotic arms. The phototherapy may also be applied by the operator manually, with guidance from the computer control unit, or automatically controlled by the computer control unit.

Figure 5:
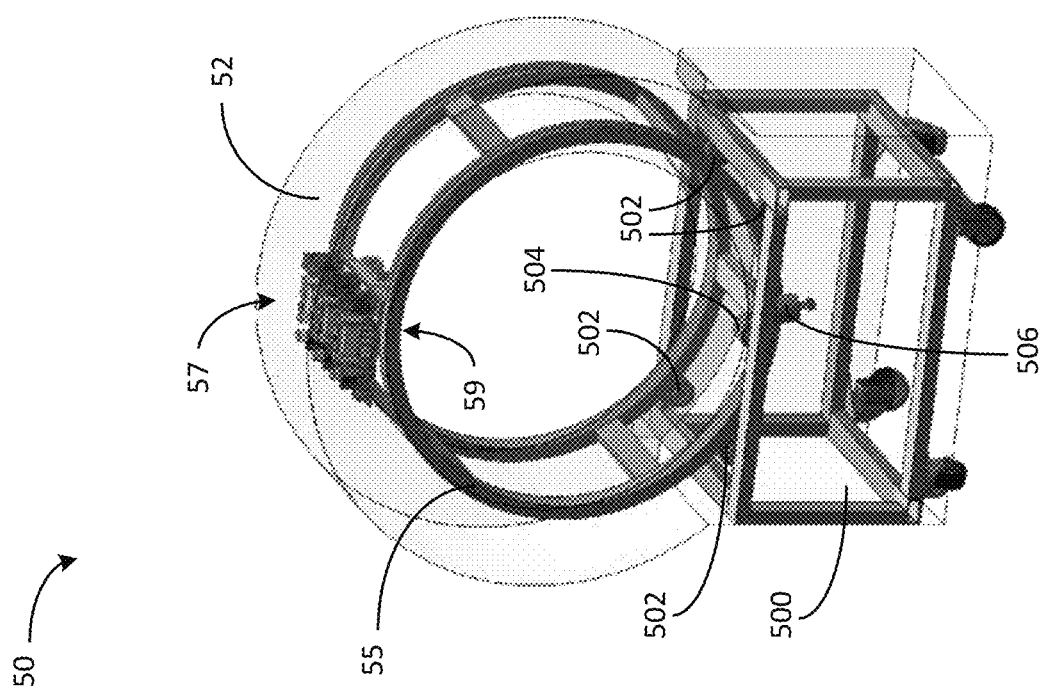
FIG. 5 depicts a perspective view of another embodiment of a treatment cylinder portion of a phototherapy device.

In some embodiments, a treatment cylinder may also be mounted on various types of supports. FIG. 5 shows an embodiment of a mounted treatment cylinder. TC 50 includes exterior member 52 and rotatable member 55. In some arrangements, rotatable member 55 includes welded cross-braces as shown in FIG. 5. One or more CLG are mounted on rotatable member 55, along with one or more CLER. Accordingly, TC 50 includes CLG 57 and CLER 59. Alternatively, TC 50 may additionally or alternatively include GCLR and/or GCMA. To avoid unnecessary rotating electronics (e.g., power cords), CLG 57 may be powered, for example, through a slip ring, through induction, or through battery packs.

The entire TC 50 assembly is mounted above cabinet 500, which may be provided as part of exterior member 52 (shown) or as a separate component (not shown). Cabinet 500 may be configured to hold electronic components for TC 50, such as some or all of the components of the computer control unit for TC 50. Additionally, cabinet 500 includes wheels to increase the portability of the phototherapy device. In this way, the phototherapy device may include most or all of the electronic components in a compact fashion (e.g., on TC 50 or within cabinet 500), while preserving the through-hole design, though this embodiment may also result in rotating electronics and a complex support system.

TC 50 may be rotated through a drive system provided between TC 50 and cabinet 500. For example, in FIG. 5, the phototherapy device includes drive wheels 502 configured to rotate TC 50. The phototherapy device also includes an idle wheel 504. In some configurations, the idle wheel 504 may be spring-loaded (e.g., biased to return TC 50 to a neutral position). The drive system, including the drive wheels 502 and the idle wheel 504, is actuated by a servo motor 506 provided below TC 50. The servo motor 506 may be manually activated by the operator and/or automatically activated by the computer control unit to rotate TC 50 via drive wheels 502 and idle wheel 504.

Figure 5A:
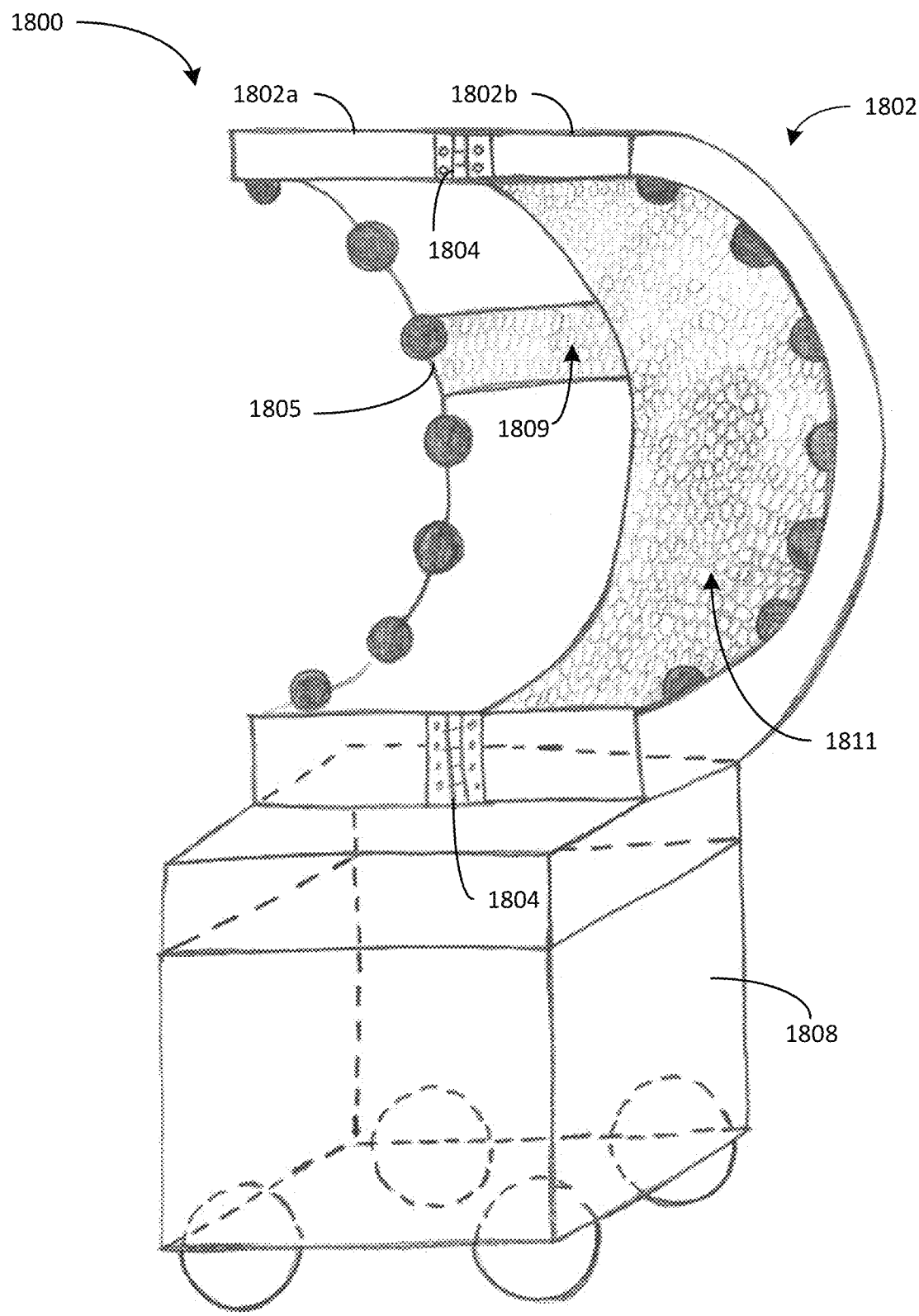
FIG. 5A depicts a perspective view of another embodiment of a treatment cylinder portion of a phototherapy device.
Figure 5B:
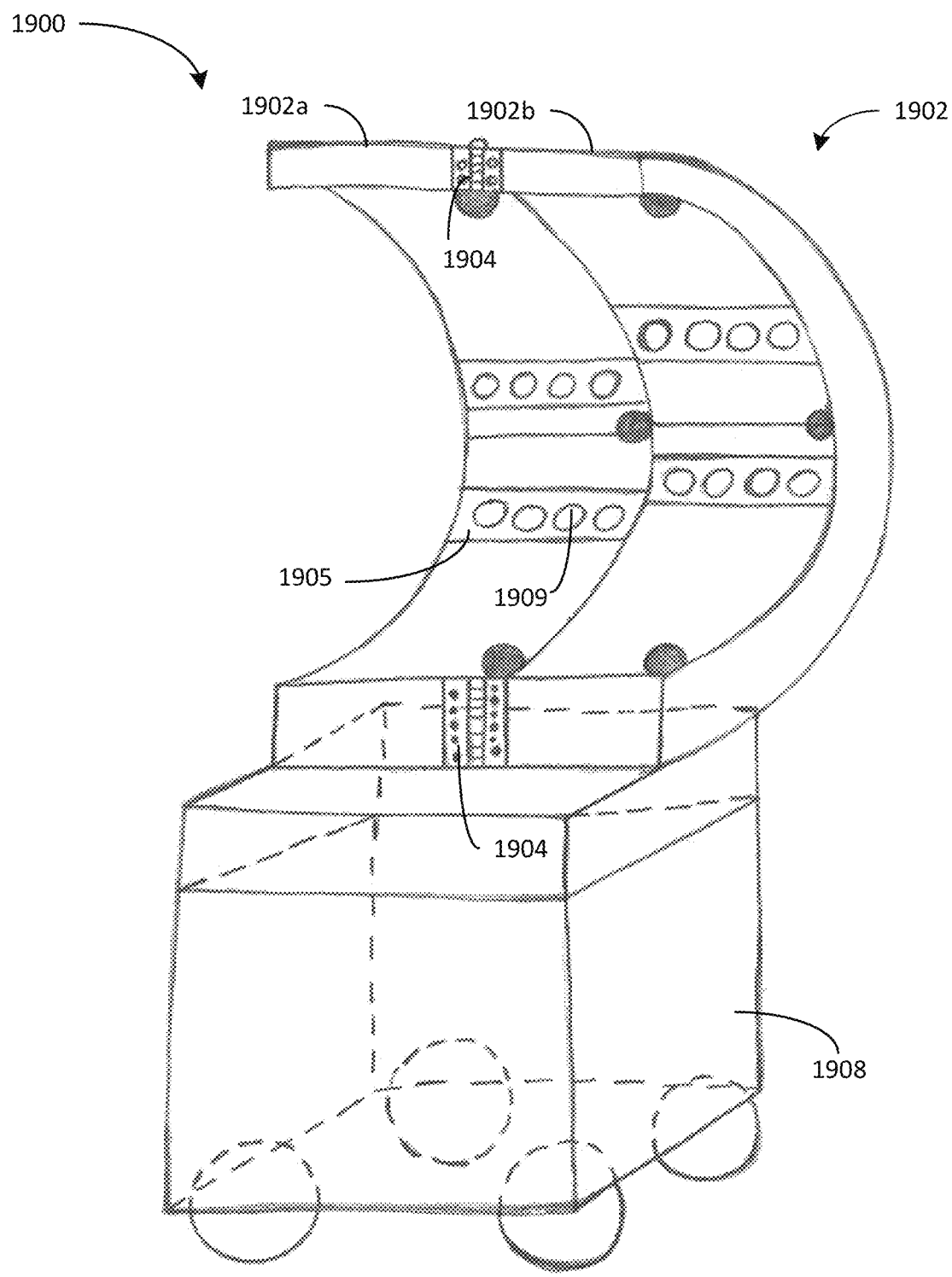
FIG. 5B depicts a perspective view of another embodiment of a treatment cylinder portion of a phototherapy device.

FIGS. 5A and 5B show alternative embodiments of mounted treatment cylinders. Referring first to FIG. 5A, TC 1800 includes TC member 1802 (e.g., configured as a cylinder that is 61 cm in diameter) split into first half 1802a and second half 1802b. TC member 1802 separate into first half 1802a and second half 1802b at hinges 1804, as shown in FIG. 5A, to allow an operator to move a patient into position with respect to TC 1800, for storage, and so on. The interior sides of first half 1802a and second half 1802b in FIG. 5A illustrate alternative configurations for delivering phototherapy via TC 1800. In some arrangements, as shown on first half 1802a, TC 1800 may include rotatable member 1805 provided with a number of optical components (e.g., 30 to 40 lenses 2 cm in diameter) arranged as one or more CLER 1809. Rotatable member 1805 rotates around a track provided on the inside of TC member 1802 to deliver phototherapy generated one or more CLG (not shown). The CLG may be chosen for TC 1800 based on the power requirements for the phototherapy (e.g., 60 W for each 2 cm lens). In other arrangements, as shown on second half 1802b, the interior of TC member 1802 may be provided with stationary optical components (e.g., 902 diffusing lenses 2 cm in diameter, which may be the most lenses required to treat the circumference of a male hip 22 cm in width with each lens capable of treating 3.14 cm$^2$) arranged as one or more stationary CLER 1811 that provide phototherapy from one or more CLG (not shown). In other arrangements, TC 1800 may include both rotatable member 1805 (e.g., on first half 1802a) and stationary CLER 1811 (e.g., on first half 1802a). For example, TC 1800 may include 30 to 40 lenses on rotatable member 1805 on first half 1802a, with the track for rotatable member 1805 provided on just the interior of first half 1802a, and 451 stationary lenses on second half 1802b (e.g., to provide 1416 cm$^2$ of emitting lenses 2 cm in diameter). Additionally, TC 1800 may be mounted on cabinet 1808, which may store various electrical components for the phototherapy device (e.g., some or all of the computer control unit) and may be provided with wheels (as shown) to allow for easy transportation and positioning of TC 1800.

TC 1900 of FIG. 5B may be configured similarly to TC 1800. As shown in FIG. 5B, TC 1900 includes TC member 1902 (e.g., configured as a cylinder that is 32 cm in diameter) split into first half 1902a and second half 1902b. Similar to TC 1800, TC member 1902 may be separated into first half 1902a and second half 1902b at hinges 1904. In various arrangements, TC 1900 includes multiple rotatable members 1905, each provided with optical components arranged as CLER, represented by CLER 1909. Rotatable members 1905 rotate around a track provided on the inside of TC member 1902 to deliver phototherapy generated by one or more CLG (not shown). For example, CLER 1909 may provide a 3.0 cm beam diameter at the skin-beam interface. The track may extend all the way around the interior of TC member 1902, or the track may be divided up according to the number of rotatable members 1905 (e.g., with a track provided in each of the four quarters of TC member 1902 in FIG. 5B). TC 1900 may also be mounted on cabinet 1908 storing, for example, electrical components for the phototherapy device and/or provided with wheels (as shown).

Figure 5C:
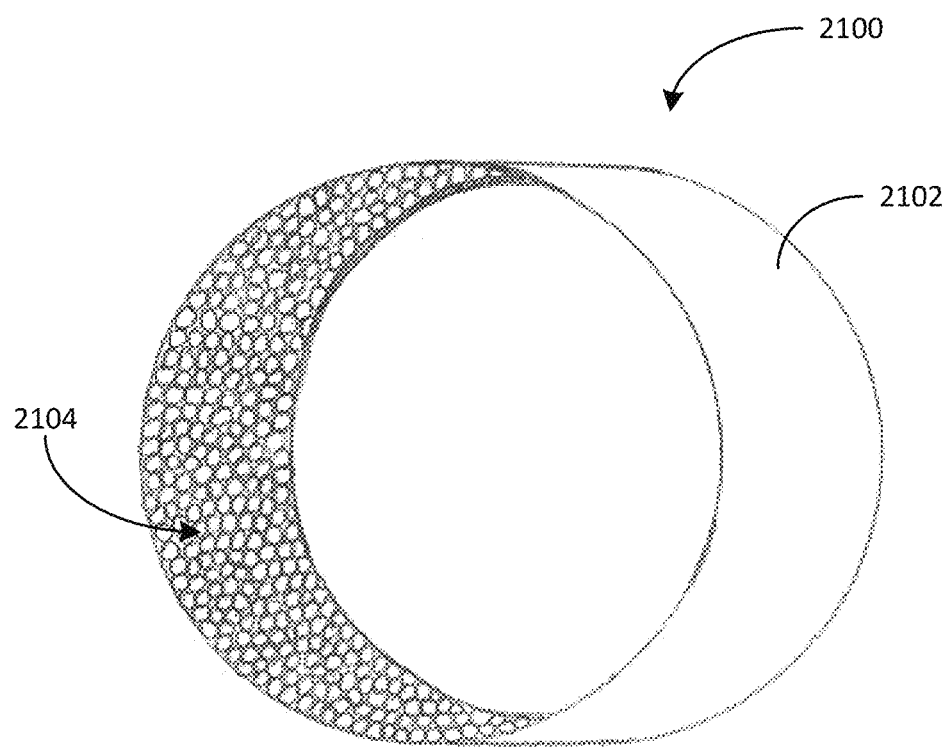
FIG. 5C depicts a perspective view of another embodiment of a treatment cylinder portion of a phototherapy device.

FIG. 5C shows another alternative embodiment of a treatment cylinder. As shown, TC 2100 is similar to second half 1802b of TC 1800. Rather than including a rotatable member, TC 2100 includes stationary member 2102. The interior of stationary member 2102 is provided with a plurality of optical components 2104. For example, optical components 2104 may be provided in a continuous stacked array across the internal surface of TC 2100 (e.g., an array of 240 to 560 optical components), as shown in FIG. 5C. In other arrangements, optical components 2104 may be provided in a different configuration, such as in rows of components 2104 spaced out from each other. Further, optical components 2104 may be provided entirely around an interior surface of stationary member 2102 (as shown), or optical components 2104 may be provided partially around or in only a band or strip of surface area around the interior surface of stationary member 2102.

In various arrangements, optical components 2104 include numerous CLG and/or numerous lenses. The CLG and/or lenses may be capable of producing (in the case of CLG) or transmitting (in the case of lenses) coherent light in one or more wavelengths towards patient anatomy provided within TC 2100. In some arrangements, optical components 2104 may be entirely or primarily CLG. In other arrangements, optical components 2104 may be entirely or primarily lenses (e.g., including a few CLG for providing the coherent light or including external CLG not mounted to TC 2100 for providing the coherent light). It should also be understood that TC 2100 may include additional types of optical components, such as mirrors (e.g., such that the interior of stationary member includes GCMA and/or GCLA).

Phototherapy in a wide range of power levels may be provided to a patient via optical components 2104 of TC 2100. As an example, the CLG and/or lenses of optical components 2104 may produce/transmit phototherapy from 0.1 W to 150 W to a targeted treatment site within TC 2100. More specifically, stationary TC 2100 may provide phototherapy to a patient by activating CLG in a particular sequence. For example, a computer control unit (e.g., computer control unit 200) may activate individual CLG of optical components 2104 to directly aim photons at a targeted treatment site, and/or to aim photons at the targeted treatment site via lenses of optical components 2104, in a pattern. As another example, the computer control unit may activate laser power sources for CLG (e.g., CLG of optical components 2104 and/or external CLG) to aim photons at the targeted treatment site in a pattern. To illustrate the foregoing, coherent beams may be directed from adjacent optical components 2104 in a sweeping motion to sequentially sweep over the targeted treatment site. However, it should be understood that coherent beams may be directed from adjacent optical components 2104 in any pattern that may provide phototherapy to the treatment site (e.g., according to a treatment plan automatically or manually selected for the patient). As such, various features and capabilities of rotating treatment cylinder embodiments described above may be implemented in stationary TC 2100 through this individual control of CLG for TC 2100.

In some embodiments, TC 2100 may be capable of rotating as well as, or in the alternative from, providing therapy as described above. In such embodiments, TC 2100 may include a rotational member and include similar capabilities and functions as rotating treatment cylinder embodiments discussed above. Additionally, it should be understood that TC 2100 may include systems, components, functionalities, etc. of various treatment cylinders discussed above. As an example, TC 2100 may include a cooling system configured to cool portions of the phototherapy device and/or portions of a patient's anatomy.

As an example of an industrial use of a phototherapy device with a stationary or fixed treatment cylinder (e.g., TC 2100), switchgrass or pond scum may be pumped through the fixed cylinder (e.g., with the fixed cylinder serving as a "laser pipe" as part of the pumping). The fixed cylinder may then be used to apply photons to the switchgrass, or similar substrate, to accelerate the process of turning the switchgrass into motor fuel (e.g., an alternative ethanol biofuel). A similar process may also be used to accelerate or scale up the production of other substances, such as nanomaterials (e.g., fullerene) and botulinum toxin and other biomolecules often limited to micro-bench scale production. Accordingly, the fixed cylinder may be used as a laser-emitting pipe as part of a fermentation system for producing pharmaceuticals; for batch, semi-batch, semi-continuous, and continuous processing of chemical, biochemical, and/or photochemical reaction processes for pure and applied research; and for therapeutic and industrial applications involving any naturally occurring or manmade substrate.

Figure 6:
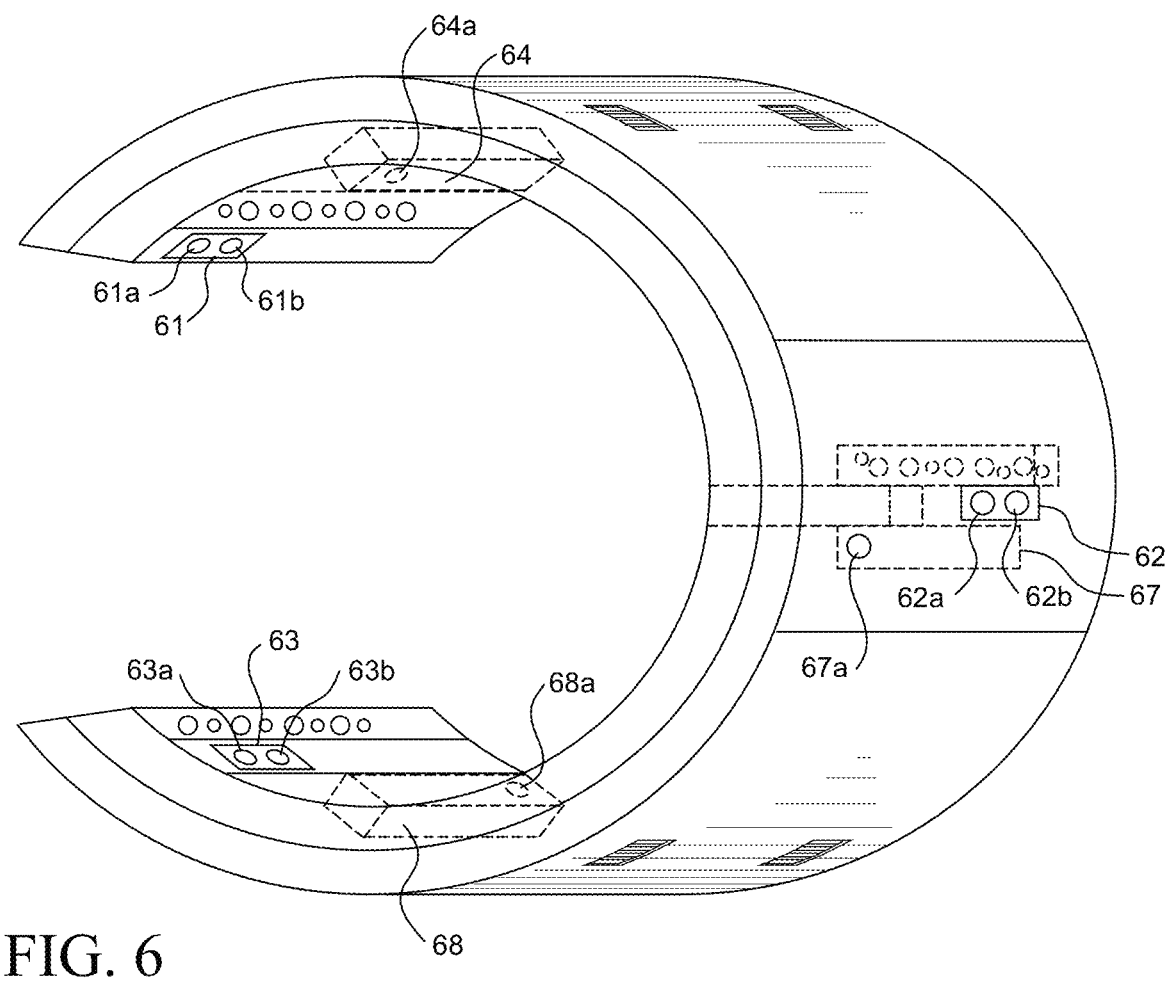
FIG. 6 depicts a perspective view of a treatment cylinder portion of a phototherapy device including an embodiment of an optical assembly.

FIG. 6 shows an embodiment of an improvement, which can be used with any of the described embodiments, including a plurality of cameras and/or spectroscopic analyzers that are in electronic communication with the computer control unit (e.g., computer control unit 200). It should be understood that spectroscopic analyzers may include a non-limiting variety of sensors and may, in some embodiments, further include cameras. Optical sensor assemblies 61, 62, and 63 individually contain cameras 61*a*, 62*a*, and 63*a* and spectroscopic sensors 61*b*, 62*b*, and 63*b*. The computer control unit follows a predefined method (e.g., as described below with reference to FIG. 6A) to use input from the optical sensor assemblies to control the administration of phototherapy. Cameras 61*a*, 62*a*, and 63*a* feed an optical view of the portion of the patient's body being treated to the computer control unit (e.g., camera views of one or more areas of the targeted tissue site). Spectroscopic sensors 61*b*, 62*b*, and 63*b* feed spectroscopic data including infrared/temperature/reflectivity information about the portion of the patient's body being treated to the computer control unit. Also shown are CLG 67, 68, and 64, with output ports 67*a*, 68*a*, and 64*a*, which can be used to provide coherent light to accessories such as the probes described in association with FIGS. 8-8E.

Figure 6A:
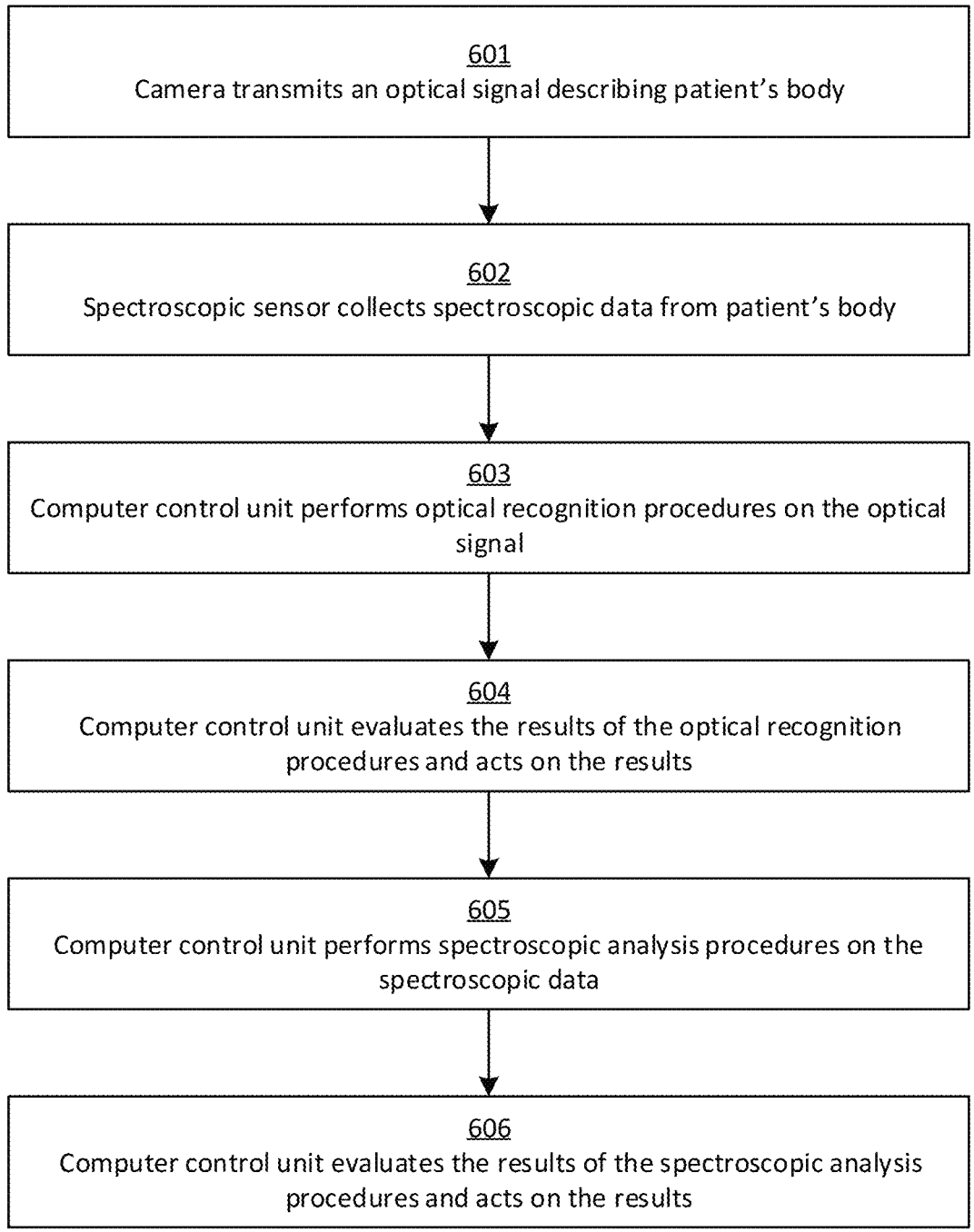
FIG. 6A depicts a flow chart setting forth steps used by a computer control unit to accept and act upon data from the optical assembly of FIG. 6.

FIG. 6A shows a method that may be implemented by the computer control unit (e.g., computer control unit 200). With reference to FIG. 6A, it should be understood that some embodiments of the phototherapy device may include fewer optical sensor assemblies (e.g., two or less). In some embodiments, such as embodiments including fewer than three optical sensor assemblies, the method may include an extra step where the computer control unit rotates the rotatable member to allow at least one optical sensor assembly to have a line-of-sight view of the area of the patient's body to be treated. Various embodiments may include one optical sensor assembly located proximately to each CLER so that the computer control unit can use data for the optical line-of-sight corresponding with that CLER to aim and control the output of coherent light from that CLER. For simplicity, FIG. 6A will discuss only those steps for using a single optical sensor assembly: if more than one optical sensor assembly is included, the method may include additional steps in which the computer control unit processes the data from the additional optical sensor assemblies.

In Step 601, camera 61*a* transmits an optical signal describing the portion of the patient's body present in the treatment cylinder to the computer control unit (e.g., computer control unit 200).

In Step 602, spectroscopic sensor 61*b* collects spectroscopic data from the portion of the patient's body and transmits it to the computer control unit. For example, spectroscopic sensor 61*b* may be one of various types of sensors, such as the sensors described herein, and may further be a camera.

In Step 603, the computer control unit performs optical recognition procedures upon the optical signal from camera 61*a*. Optical recognition procedures are well-known in the art and will not be described in detail herein. In summary, the computer control unit will look for predetermined properties of the optical signal and either process them algorithmically against predefined geometries or compare them to a number of previously obtained and stored optical signals.

In Step 604, the computer control unit evaluates the results of the optical recognition procedures and acts upon the results thereof. Acting upon the results thereof can include any reasonable step, including but not limited to one or more of the following: (1) alerting the operator to move, or tell the patient to move, the portion of the patient's body to be treated to a more optimal position; (2) allowing the operator to designate, preferably by a touchscreen, the precise areas of the patient's body to be targeted by the coherent light emissions; (3) rotating the rotatable member, if included in the embodiment being used, to more precisely target the tissues to be treated; (4) adjusting the galvanometric gimbals of either GCLA or GCMA, if either is included in the embodiment being used, to more precisely target the tissues to be treated; and/or (5) extrapolating the depth of the tissues to be treated by determining the position of the portion of the patient's body to be treated and/or determining the amount of tissue the coherent light will have to traverse to reach the tissues to be treated and adjusting the power and/or duration of the output of coherent light accordingly. If the phototherapy device includes additional sensors, the output from the additional sensors may also be incorporated into the step(s) taken.

It should be understood that, in some embodiments, the computer control unit may perform one or more of the above steps automatically such that the operator or patient does not need to make adjustments. For example, the computer control unit may automatically designate areas of the patient's body to be targeted by the coherent light emission based on results of the optical recognition procedures (e.g., based on a favorable comparison to previously obtained and stored examples of treatment sites).

In Step 605, the computer control unit performs spectroscopic analysis procedures on the spectroscopic data provided by spectroscopic sensor 61*b*. Spectroscopic analysis procedures are well-known in the art and will not be described in detail herein. In summary, the computer control unit will evaluate the spectroscopic data for parameters including but not limited to reflectance and/or absorption, color, and emission in various spectra (e.g., active infrared analysis, which provides temperature information by extrapolation).

In Step 606, the computer control unit evaluates the results of the spectroscopic analysis procedures and acts upon the results thereof. Acting upon the results thereof can include any reasonable step, including but not limited to one or more of the following: (1) automatically adjusting, or signaling a manual adjustment indication to the operator, of the power, duration, and/or wavelength of coherent light to be used to administer phototherapy based upon the estimated reflectance/absorption of the patient's skin and surface tissues; (2) automatically adjusting, or signaling a manual adjustment indication to the operator, of the power, duration, and/or wavelength of coherent light to be used to administer phototherapy based upon the estimated vascularity of the patient's skin and surface tissues; (3) if the spectroscopic analysis is performed after at least one coherent light emission, estimating the change in reflectivity/absorbance and/or vascularity of the patient's skin and surface tissues and adjusting, or signaling a manual adjustment of, the power, duration, and/or wavelength of subsequent coherent light emissions to maintain an optimal temperature; and/or (4) if the spectroscopic analysis is performed after at least one coherent light emission, measuring the temperature of the patient's skin and surface tissues and adjusting or signaling a manual adjustment of the power, duration, and/or wavelength of subsequent coherent light emissions to maintain an optimal temperature range. If the phototherapy device includes additional sensors, the output from the additional sensors may also be incorporated into the step(s) taken.

As an illustration of the foregoing, if the computer control unit is analyzing a mole, the computer control unit may analyze the patient's skin based on camera and/or spectrometer data and make adjustments to avoid harming the patient's skin. For example, the computer control can determine, via data from a camera, the patient's skin type and color based on a Fitzpatrick scale. If the patient has Fitzpatrick Skin Type V or VII, the therapy dose may be delivered more slowly due to the increased absorption of darker skin. This may be important in the 800-850 nm wavelength range when treating a patient with a higher Fitzpatrick Skin Type. Alternately, if the patient has Fitzpatrick's Skin Type I or II, the therapy dose may be administered at a higher dose and/or rate that is more rapid.

In some embodiments, the phototherapy device may include both a camera and a spectroscopic sensor. In other embodiments, only one of the two can be included in the device. If only one is included, either the computer control unit can detect that only one is present and execute only those commands and evaluations utilizing the one which is present, or the computer control unit's controlling software may not include the portions of the method of FIG. 6A that apply to the one which is not present. Accordingly, in some embodiments, the computer control unit may recognize the presence of either or both the camera and the spectroscopic sensor and execute only those commands and evaluations utilizing whichever is present.

In an optional improvement or alternate embodiment, the phototherapy device may include an illumination mechanism. This can be the light source already included for phototherapy or a separate light source. This illumination can be used, without limitation, to enhance the steps set forth above in the following ways: (1) it can provide additional illumination to help the camera obtain a better optical signal; (2) it can provide consistent and known levels of illumination to be used in spectroscopic analysis; and/or (3) it can be used to enable Light Detection and Ranging ("LIDAR") functionality for the device, which allows the computer control unit to more precisely determine the size, position, and/or volume of the portion of the patient's body to be treated.

It should be noted that while the image data must be collected before image recognition can be performed and the computer control unit can respond to the results thereof, and likewise spectroscopic data must be collected before spectroscopic analysis can be performed and the computer control unit can respond to the results thereof, otherwise the image data collection, image recognition, spectroscopic data collection and spectroscopic analysis, and the computer control unit's response to image recognition and spectroscopic analysis can be performed in any desired order.

It should be noted that the operator can manually evaluate various relevant physical parameters of the patient and the tissues to be treated and the surface tissues above them. This information can then be input into the computer control unit, which can either recommend adjustments to the operator to be manually input as part of the treatment plan or used by the computer control unit to adjust the treatment plan automatically. These parameters could include, but are not limited to the following.

(1) The presence and nature of open wounds. It should be noted that the phototherapy device can be used to treat open wounds and speed healing through the general benefits of the administration of phototherapy. A wound may require different doses inside and outside the edges of the wound. The computer control unit may use spectrometry imaging to subsequently adjust the dose differently for each section of the wound.

(2) The presence and extent of inflammation. The dose could be adjusted manually or automatically downward in an area of intense inflammation where the targeted tissue could be absorbing more photons. As the inflammation dissipates, the administration of the photon dose could be gradually increased accordingly.

The presence and extent of skin pigmentation, either as a general property of the patient's tissue (e.g., relative levels of melanin) or specifically as to the area to be treated (e.g., the presence of birthmarks or other skin pigmentation irregularities.) For example, the computer control unit may use the Fitzpatrick scale to adjust the therapy dose, as described above.

Blood flow, temperature, and/or vascularity of the tissues. Certain wavelengths could be absorbed more readily by blood within the vessels causing coagulation problems. Blood vessels and/or the flow of blood could be visualized with infrared imaging, ultrasonic imaging, and/or other vessel structure or blood flow imaging technologies and could be avoided and prevented from receiving incoming photons. These imaging techniques could also detect the temperature of the vessels to allow for real-time adjustments in dose, rate, etc.

Size and distance of the tissues to be treated from the CLER or other emitter location, including the presence and extent of atypically thick or thin skin. The beam's size and the beam's distance, if the beam is not collimated, to the targeted tissues could be adjusted given the thickness of the skin, which can vary given the patient's weight, etc. CLER or other emitter devices could detect these variations in skin thickness, and the operator can manually change the treatment dose inputs or the computer control unit can adjust the treatment dose automatically.

Reflectivity (albedo) of the patient's skin. If the spectrometer detects an abnormal reflection on or around the targeted tissue (e.g., there is an unknown gel or cream on the skin), steps can be taken before or during the administration to remove or avoid this reflectivity or account for this in the treatment dose inputs to this reflective area.

Weight of the patient and thickness of adipose tissue. A person of higher weight, such an obese person, with a thicker layer of fat tissue will have a greater distance between the skin surface and targeted tissue. Therefore, a similar therapeutic dose, relative to a thin person, within the abdominal muscles will require a higher input delivery at the beam/skin surface interface. For example, when treating the abdominal wall of an obese person, the treatment cylinder might have to rotate twice as many times, thereby delivering a radiant exposure of 12 J/cm$^2$ onto the skin surface, as opposed to the 6 J/cm$^2$ radiant exposure onto the skin surface used for a thin person, in order to get the same dose within the abdominal wall muscles and/or the target treatment area of the obese patient.

Figure 7:
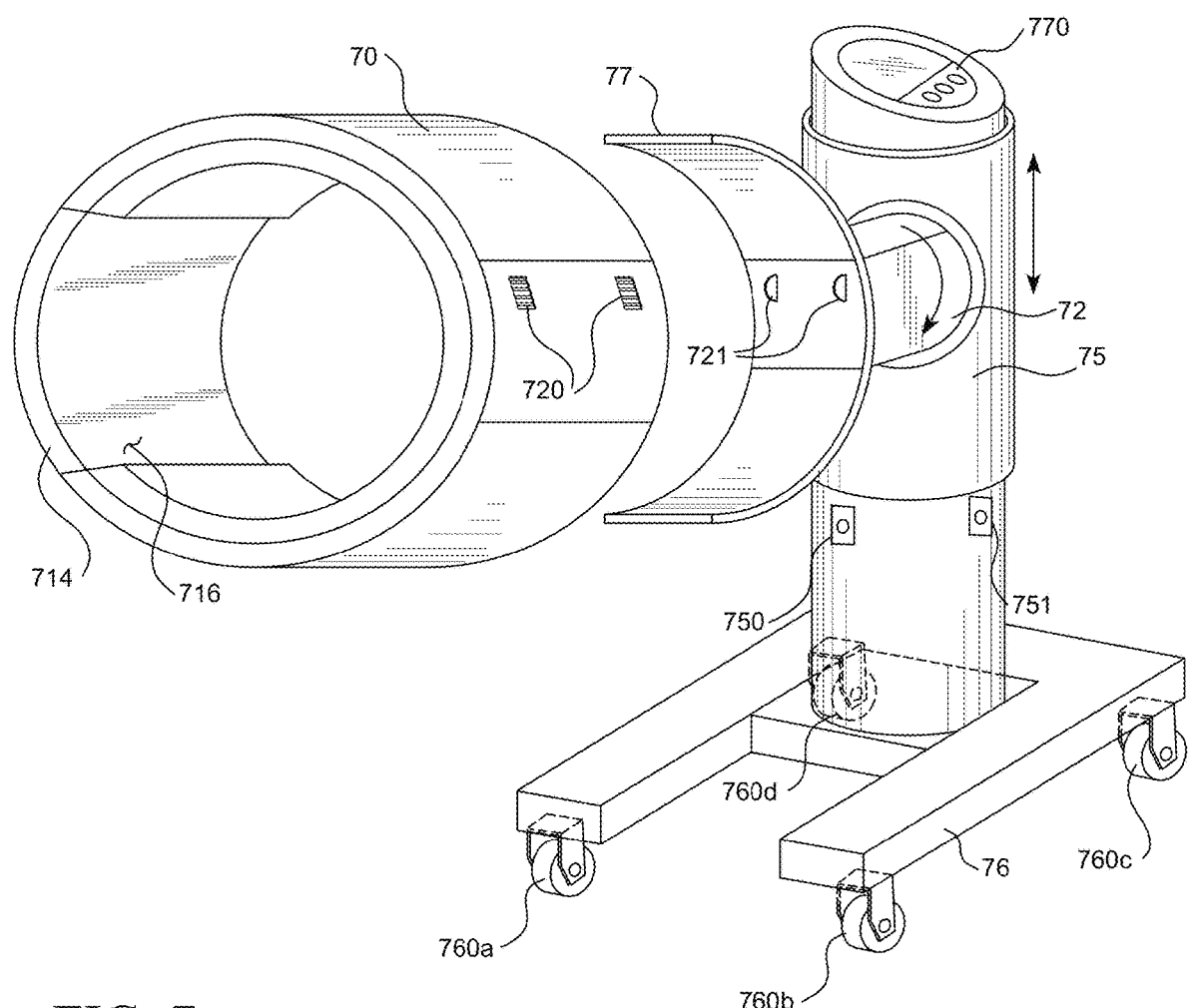
FIG. 7 depicts a perspective view of an embodiment of a horizontally rotatable gantry assembly for mounting a treatment cylinder portion of a phototherapy device.

FIG. 7 shows an embodiment of an improvement including a horizontally rotatable gantry assembly for a treatment cylinder. TC 70 is mounted in bracket 77, which is mounted on horizontal arm 72 and which is, in turn, mounted on vertical member 75. The whole assembly is mounted on base 76. (TC 70 is shown separate from bracket 77 for ease of review; normally it is mounted inside bracket 77.) TC 70 has gap 716 through which the portion of the patient's body to be treated can travel and then be closed with cap 714. By rotating horizontal arm 72 and/or rotating base 76 on casters 760a, 760b, 760c, and 760d, any portion of the patient's body, whether the patient is standing, sitting, lying or reclining, can easily and comfortably be introduced into TC 70 through gap 716. As such, TC 70 may be moved in one or more degrees of freedom due to this support structure. Drivers 721 interface with rotators 720 to rotate the components of TC 70 relative to each other.

In some embodiments, the phototherapy device according to FIG. 7 may include a cap (not shown, see FIG. 1) or an enclosing cabinet (not shown) to prevent the escape of coherent light from gap 716 and/or potential damage to the phototherapy device by the insertion of foreign objects that may prevent the rotation of TC 70 or otherwise interfere with moving parts thereof.

Figure 8:
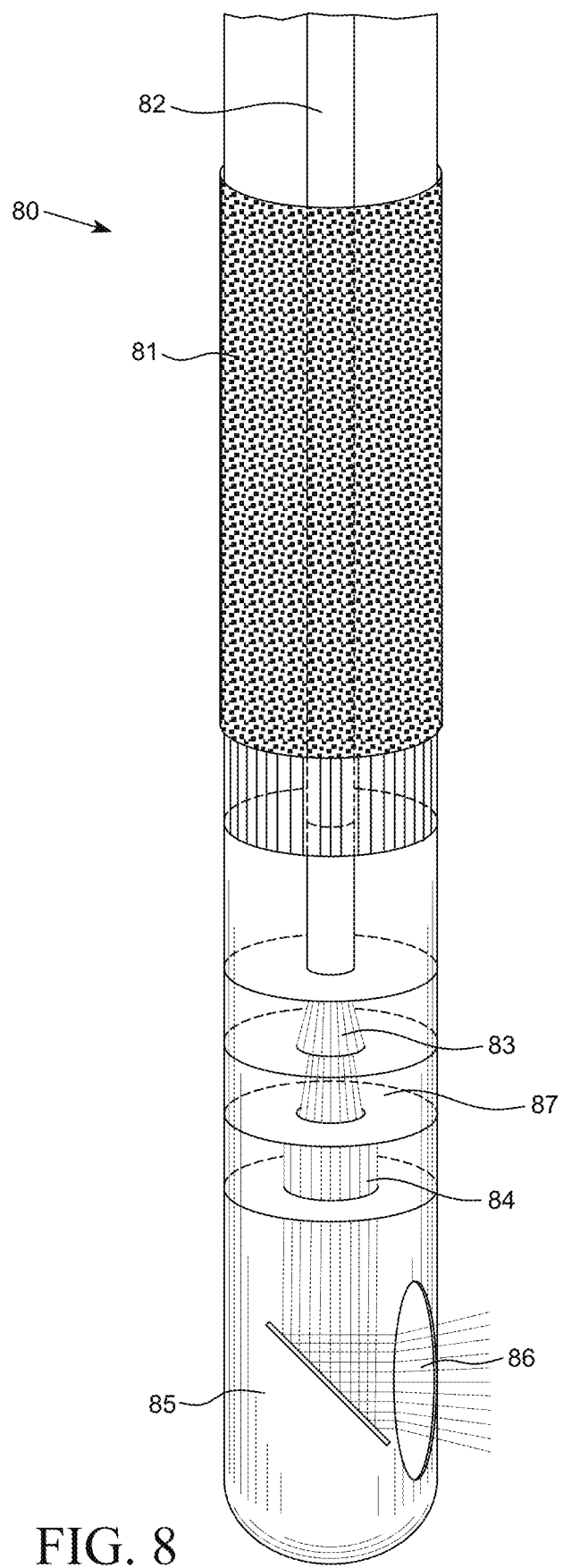
FIG. 8 depicts a cross-sectional view of an embodiment of a probe of a phototherapy device.
Figure 8A:
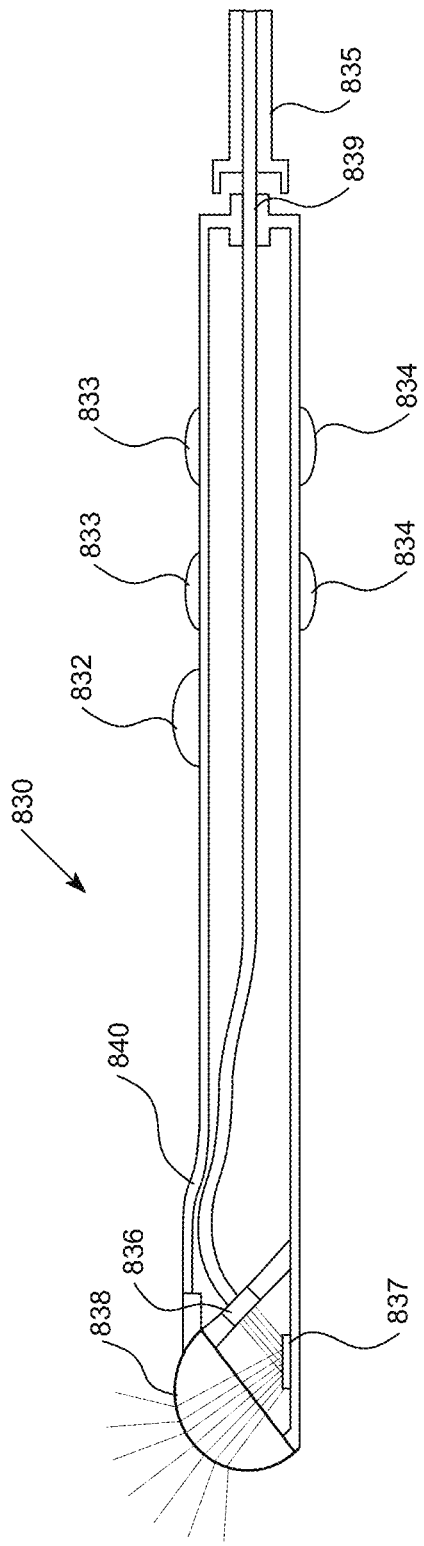
FIG. 8A depicts a cross-sectional view of another embodiment of a probe of a phototherapy device.
Figure 8B:
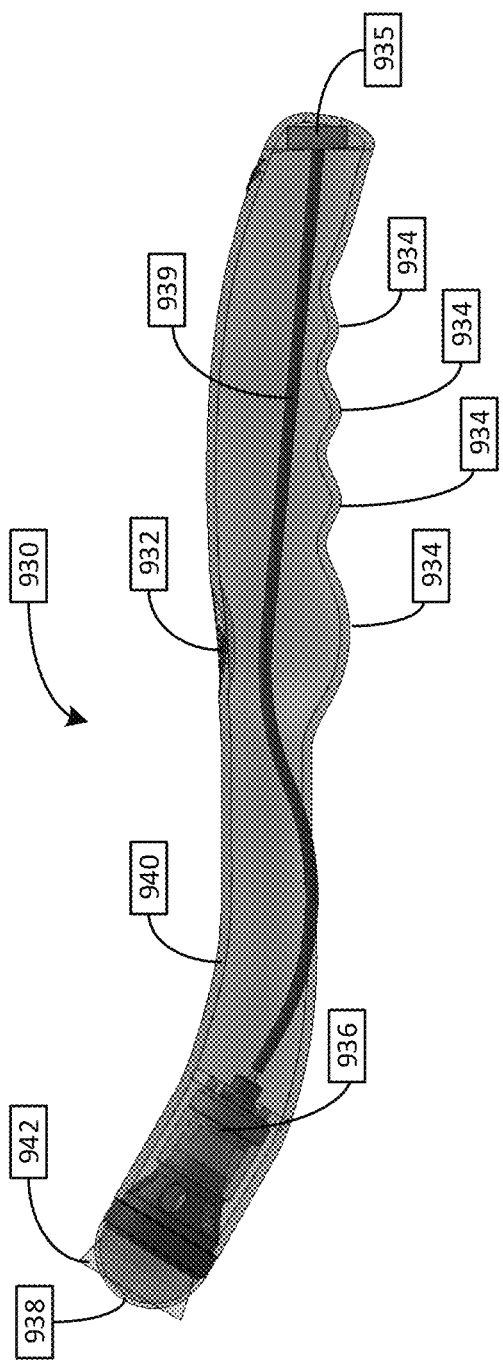
FIG. 8B depicts a cross-sectional view of another embodiment of a probe of a phototherapy device.
Figure 8C:
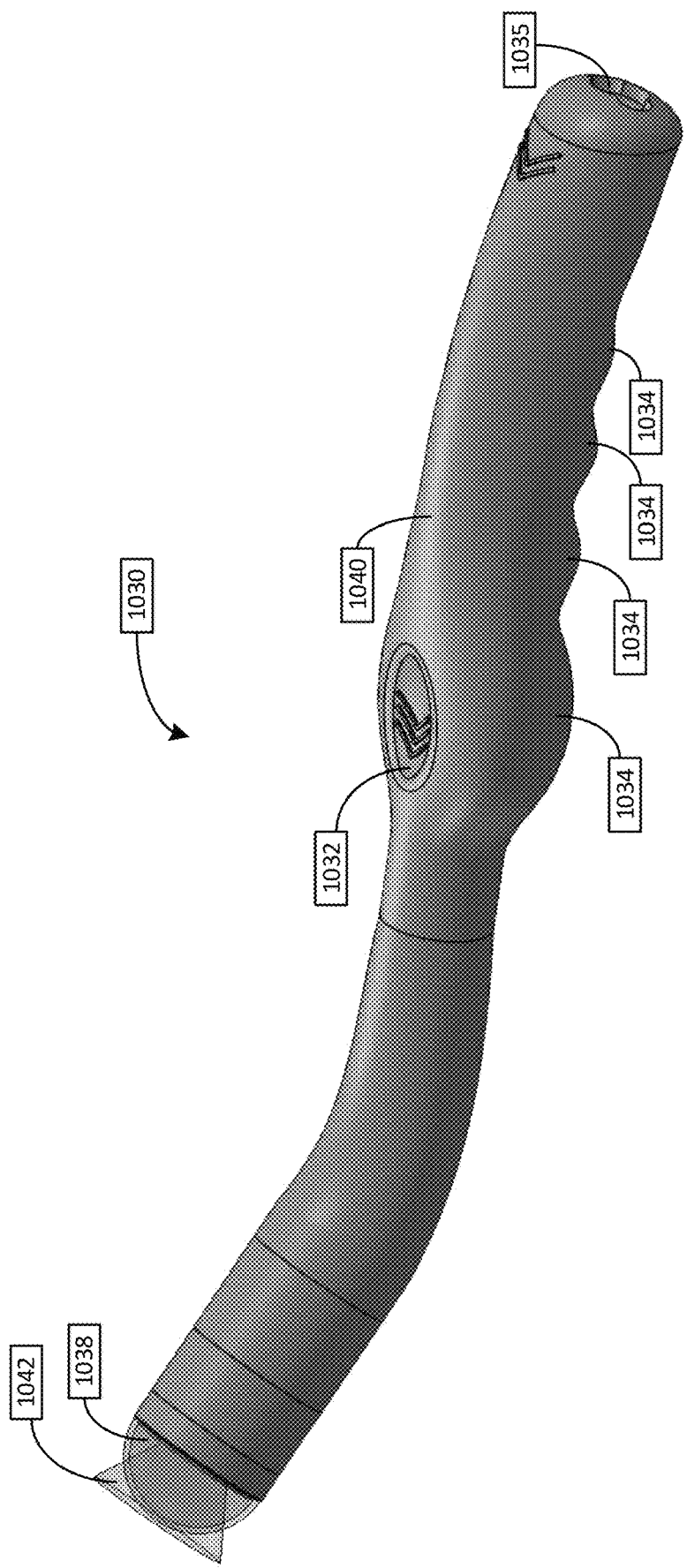
FIG. 8C depicts a perspective view of another embodiment of a probe of a phototherapy device.
Figure 8D:
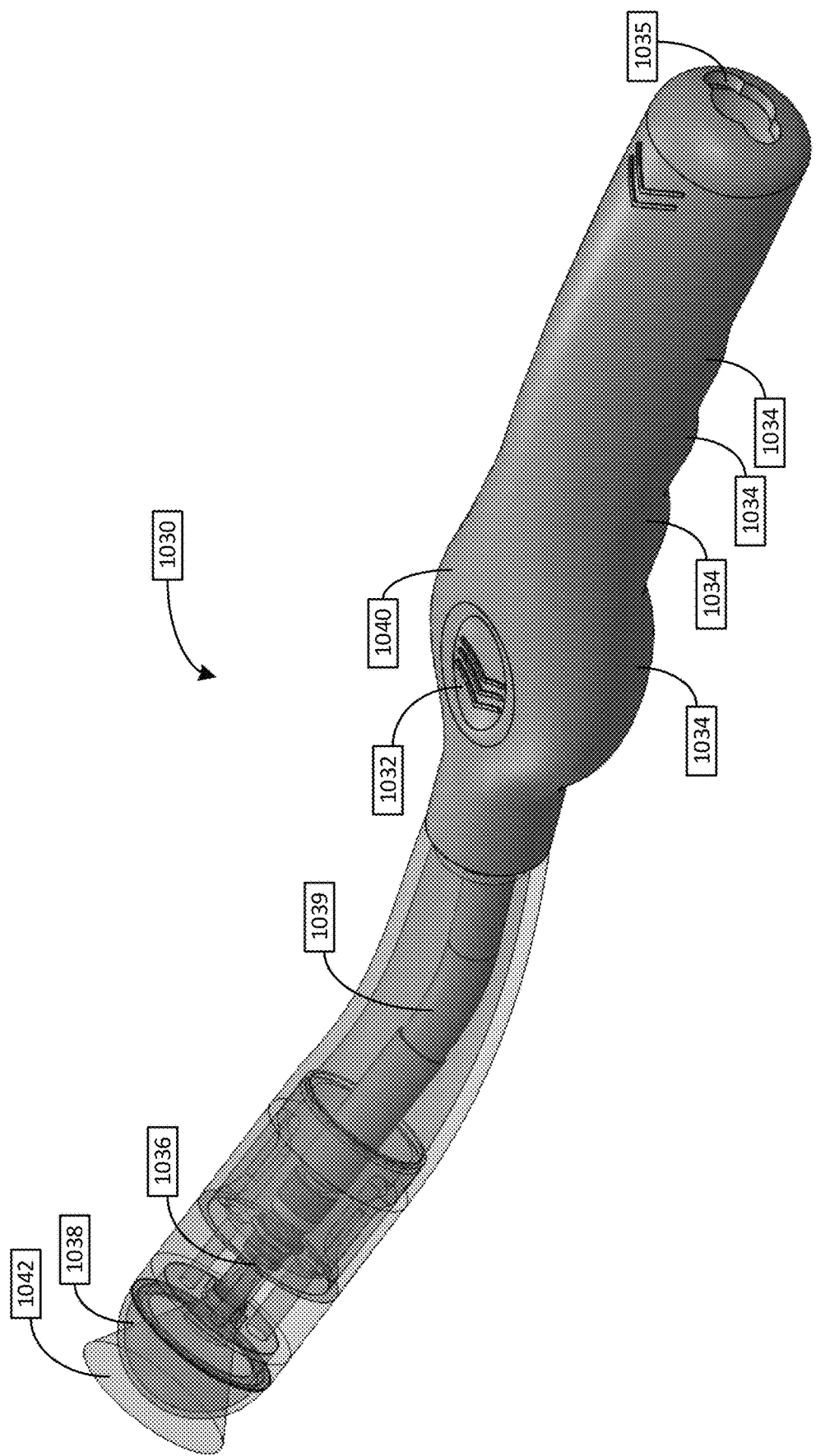
FIG. 8D depicts a perspective and cross-sectional view of the probe of FIG. 8C.
Figure 8E:
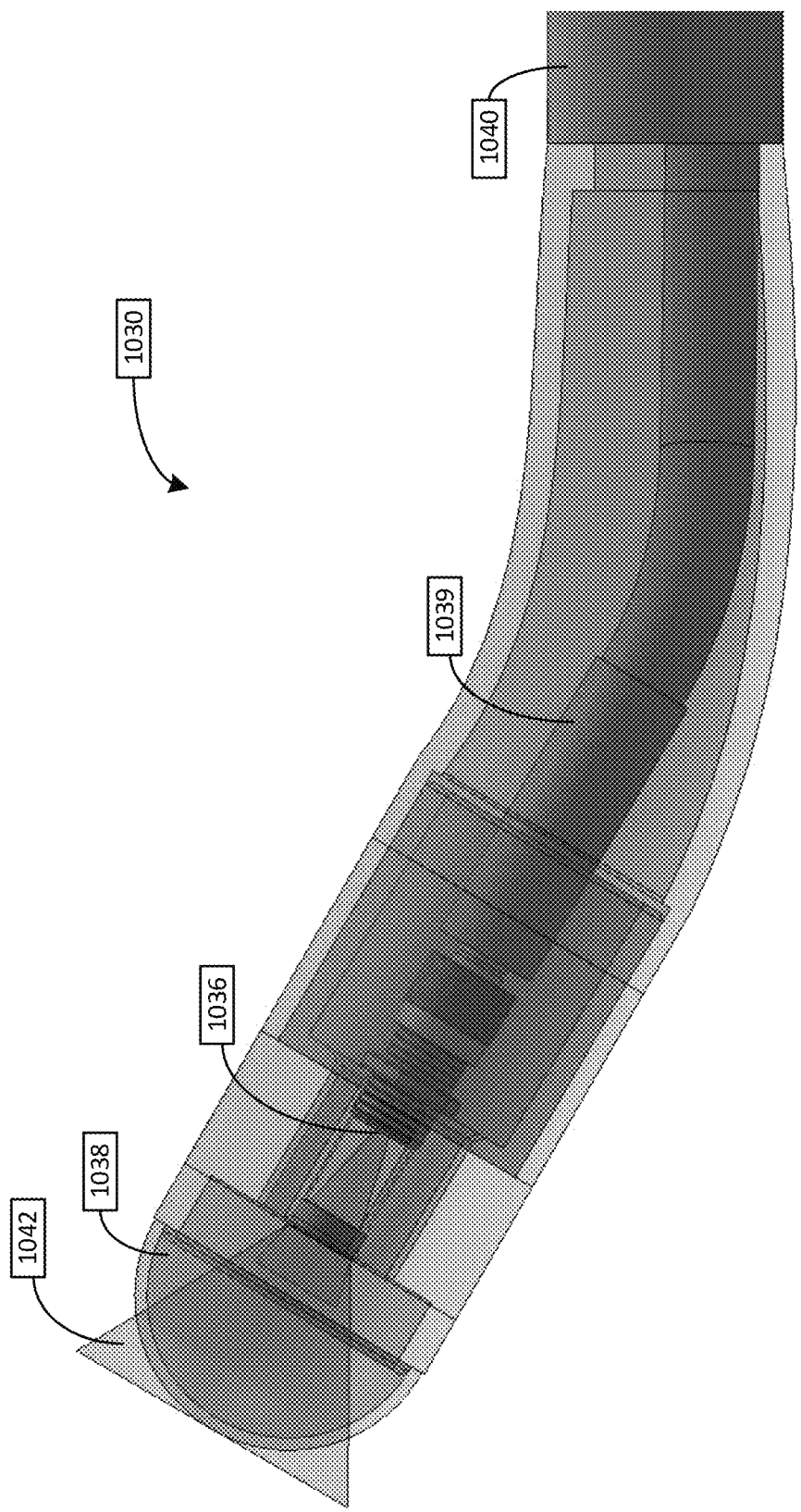
FIG. 8E depicts a cross-sectional view of a tip of the probe of FIG. 8C.

Also shown in FIG. 7 are optional additional CLG 750 and 751, which can be used to provide coherent light to accessories such as the probes shown in FIGS. 8-8E. CLG 750 and 751 may be located such that they will not interfere with the travel of horizontal arm 72, whether above its highest vertical travel or below its lowest vertical travel (the latter is shown). Additionally, optional control panel 770 is mounted on top of vertical member 75. Control panel 770 interfaces with and/or includes the computer control unit. Control panel 770 also controls the movement and rotation of the components of the gantry assembly and includes a display screen (e.g., a touchscreen) and/or control input devices such as buttons, dials, etc.

However, it should be understood that a treatment cylinder may be provided with a different support system from bracket 77 mounted on horizontal arm 72 on base 76, as shown in FIG. 7. For example, in one embodiment, a treatment cylinder is provided with one open end. The other end is closed and mounted on a support (e.g., similar to horizontal arm 72). The treatment cylinder includes one or more CLER, GCLA, and/or GCMA as described above. One or more power supplies for the CLG of the CLER, GCLA, and/or GCMA may be provided on the outside of the treatment cylinder. Additionally, power for the treatment cylinder as a whole may be provided via the support and the closed end (e.g., through cables connecting to a power source and running through the support and the closed end to the treatment cylinder). To use the treatment cylinder, the tissue to be treated is inserted through the open end into the interior of the cylinder. For example, the treatment cylinder may be 70 cm in diameter and thus sized to receive a limb of a patient.

Accordingly, this embodiment includes a clear support system for the treatment cylinder. This embodiment also includes simple connections, for example, to the power source for powering the treatment cylinder and associated electronics (e.g., the CLER, GCLA, and/or GCMA), although the patient tissue to be treated must be entirely receivable in the interior of the treatment cylinder due to the closed end and at least some of the electronics may need to be configured to remain unaffected by rotation of the treatment cylinder (e.g., the laser power supply provided on the outside of the treatment cylinder). Variations of this embodiment may include using slip rings to input the power and light into the treatment cylinder and inputting the light through the support and the closed end (e.g., by running a fiber optic cable through the support and closed end).

FIGS. 7A-7D show another embodiment of a treatment cylinder mounted on a support. TC 310 includes an exterior member 312 and a rotatable member 315. Additionally, TC 310 includes a number of CLG, represented by CLG 317, positioned around the interior of TC 310. Any number of CLG may be used, such as the configuration of six sets of three laser diodes as shown in FIGS. 7A-7D. The CLG are connected to CLER, represented by CLER 319, also positioned around the interior of TC 310. Alternatively, the CLG may be connected to GCLA and/or GCMA positioned around the interior of TC 310. The CLER, GCLA, and/or GCMA are shown as emitting coherent light beams, represented by beam 331.

Specifically, the CLER, GCLA, and/or GCMA are positioned on diode mounts, represented by diode mount 330. The diode mounts may be configured to allow the CLER, GLCA, and/or GCMA to be moved into and away from the interior of TC 10 (e.g., through galvanometric controls). Each diode mount is further positioned on a diode track, represented by diode track 332. The diode track enables the diode mount, and the CLER, GLCA, and/or GCMA on the diode mount, to be moved along the rail toward each of the open ends of TC 10. Additionally, the diode tracks are provided on rotatable member 315. In some arrangements, the diode tracks are stationary on rotatable member 315, and the diode tracks may be moved circumferentially around TC 10 by rotating rotatable member 315 as a whole. In other arrangements, the diode tracks may be individually moved around rotatable member 315 (e.g., rotatable member 315 may itself be a rail for the diode tracks). In such arrangements, rotatable member 315 may be stationary or may also be rotatable such that the diode tracks may all be rotated together. In this way, the emitted light beams may be manipulated around the patient anatomy inserted into the center of TC 10 to provide optimal therapy.

Figure 7A:
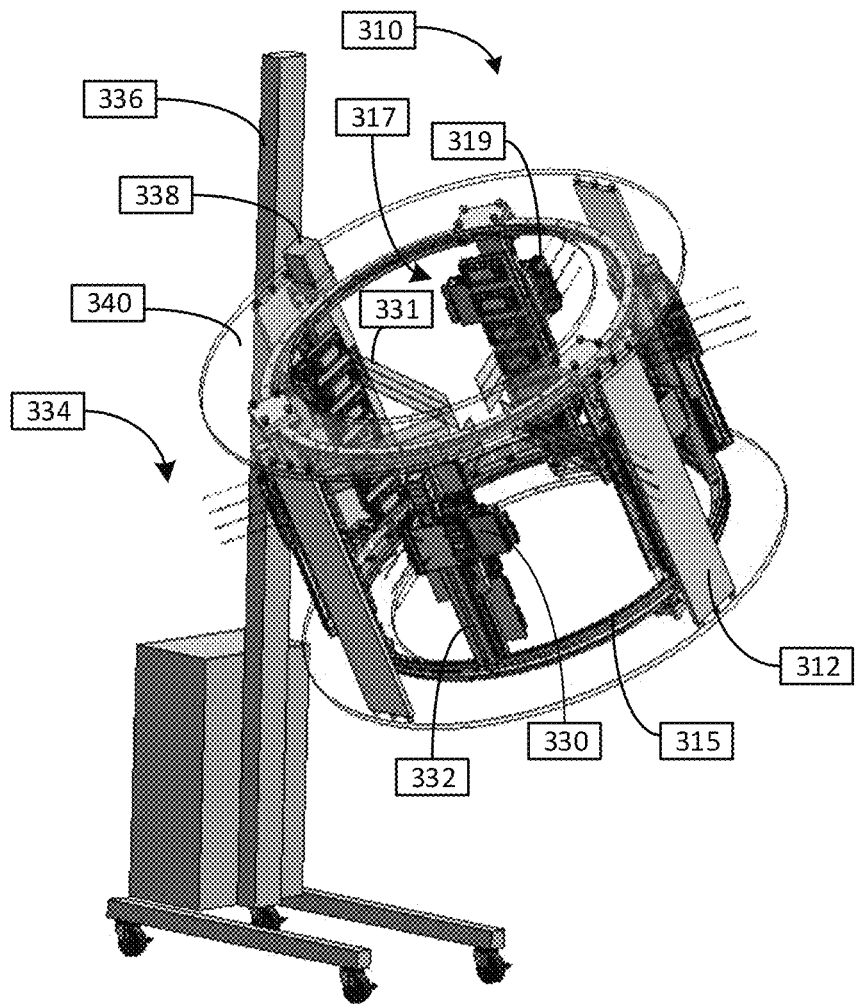
FIG. 7A depicts a perspective view of another embodiment of a treatment cylinder portion of a phototherapy device mounted on another embodiment of a support assembly.
Figure 7B:
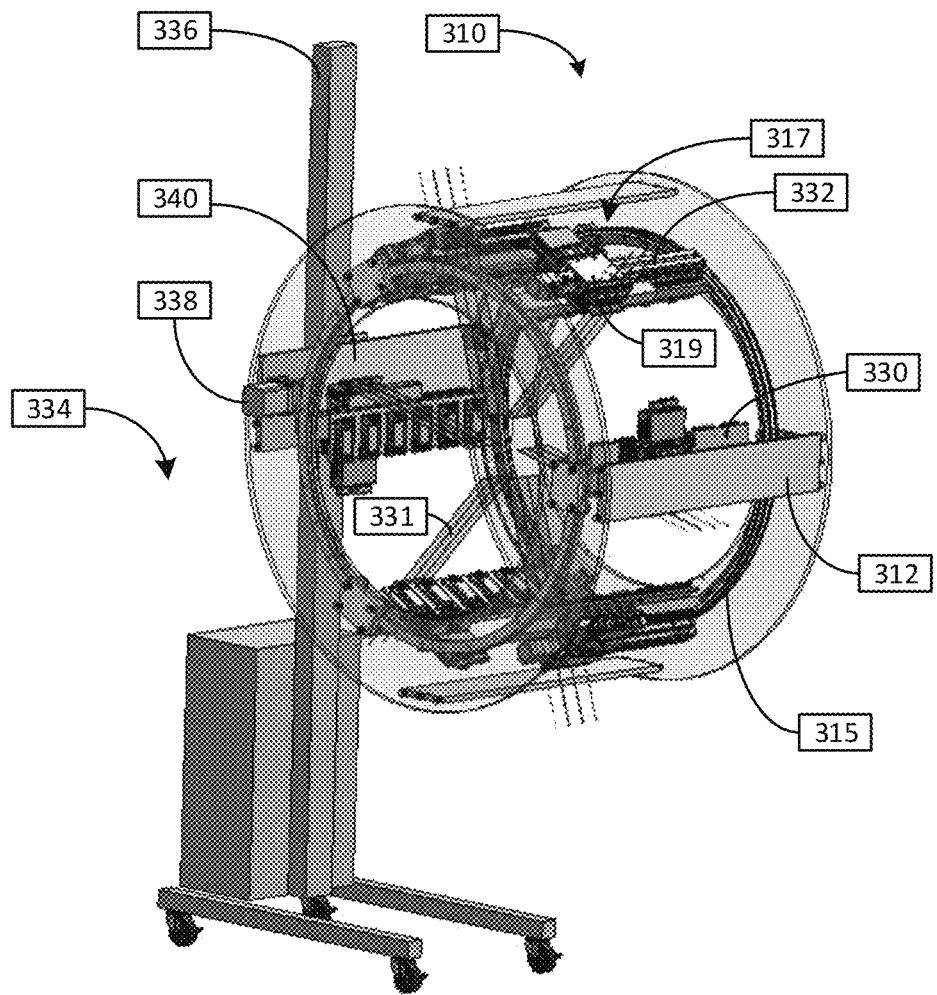
FIG. 7B depicts another perspective view of the treatment cylinder portion and support assembly of FIG. 7A.
Figure 7C:
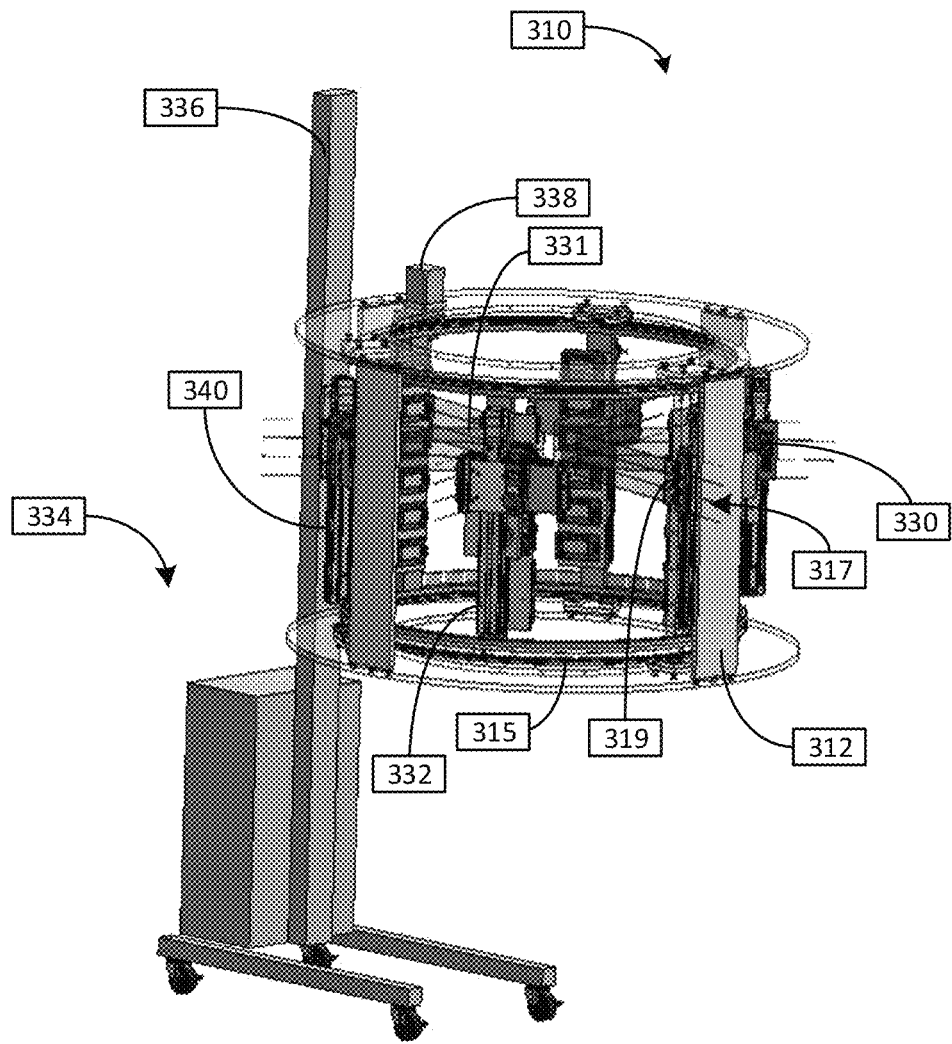
FIG. 7C depicts another perspective view of the treatment cylinder portion and support assembly of FIG. 7A.
Figure 7D:
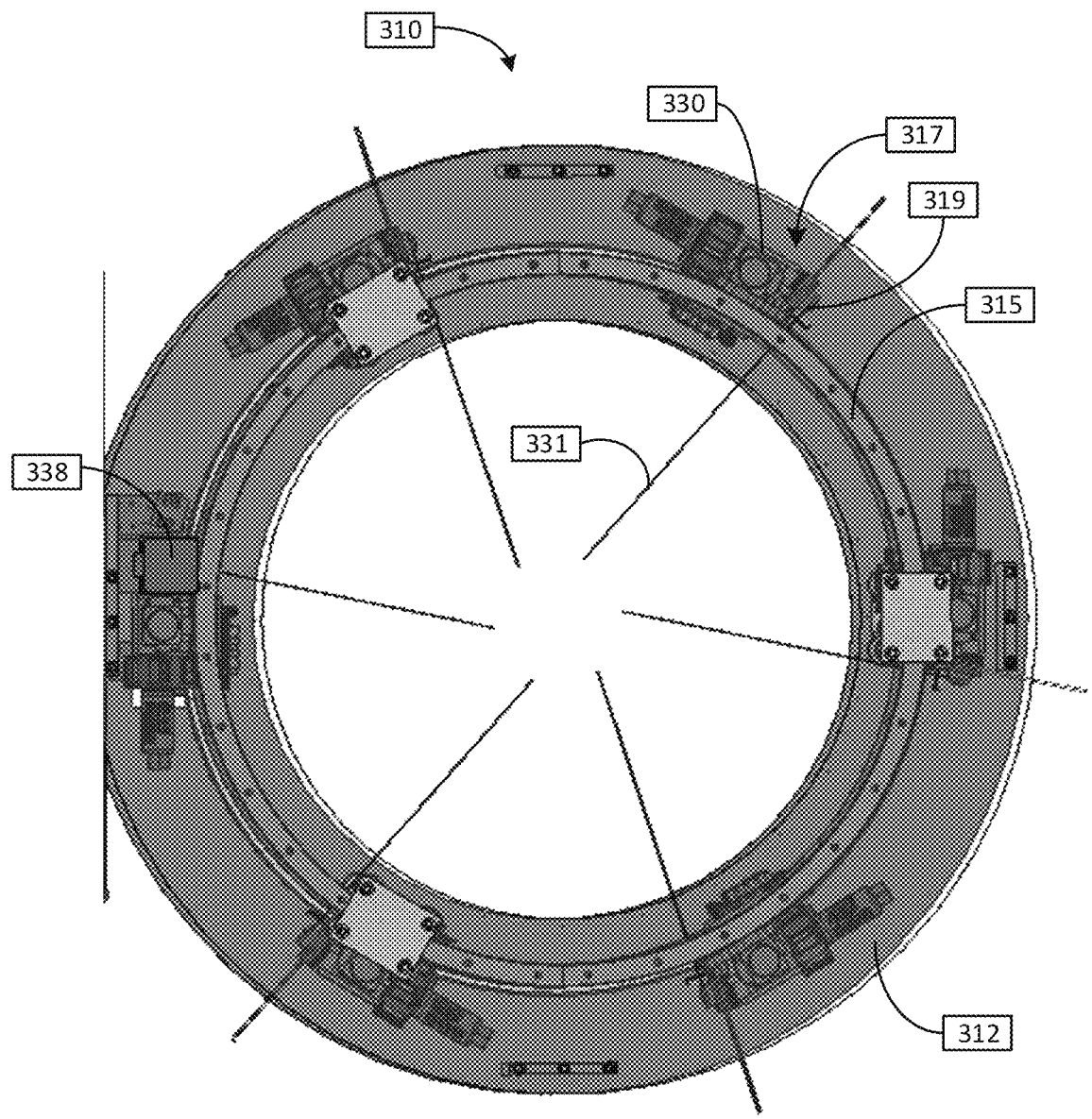
FIG. 7D depicts a top view of the treatment cylinder portion of FIG. 7A.

Furthermore, TC 10 as a whole is mounted onto a support system 334. Support system 334 includes vertical track 336 extending from a base of the support system 334; the base may be provided with wheels to facilitate maneuverability of phototherapy device as shown in FIGS. 7A-7C. Similarly, TC 10 includes a crossbar 338 extending across the width of TC 10. Crossbar 338 is mounted onto vertical track 336 via mounting plate 340. As shown in FIGS. 7A-7C, mounting plate 340 may be coupled to vertical track 336 such that mounting plate 340 can (1) rotate with respect to the plane parallel to mounting plate 340 (e.g., rotate in 360 degrees) and (2) move vertically along vertical track 336. As such, mounting plate 340 provides movement in multiple degrees of freedom to TC 10, which may assist an operator and/or the computer control unit (e.g., the computer control unit 200) in positioning TC 10 over the targeted treatment site.

FIG. 8 shows an embodiment of a handheld probe. In some arrangements, the handheld probe may work in conjunction with a treatment cylinder (e.g., TC 10, TC 20, TC 30, TC 40, TC 50, TC 70, and/or TC 310 described above).

Probe 80 has optical conduit 82, which is optically connected to one or more CLG of any of the embodiments of the treatment cylinder discussed above. If each of the CLG connected to probe 80 emits a different wavelength, this allows the operator to select the CLG that emits the desired wavelength of coherent light for a given course of treatment. If the CLG are mounted on the rotatable member of the treatment cylinder connected to probe 80, in an embodiment that uses a rotatable member, the rotatable member may be configured to be kept stationary when using probe 80 so that the connection of the CLG to probe 80 will be stable. Alternatively, in some arrangements, probe 80 may be incorporated into a compartment external to the treatment cylinder as part of a standalone machine that could be connected to, or implemented with, the treatment cylinder through one or more fiber optic cables or through laser-beam emitting and beam energy collection devices. As yet another alternative, in some arrangements, probe 80 may be implemented as an entirely standalone device not connected to a treatment cylinder and instead connected to one or more independent CLG. In some embodiments, the CLG optically connected to the probe is a 10 W or more laser diode (e.g., capable of providing 4-12 J/cm$^2$ or more of radiant exposure per treatment). In other embodiments, the CLG optically connected to the probe is a 2-15 W laser diode.

Coherent light from the CLG (not shown, see previous figures) travels into the body of probe 80 and to diffuser element 83, which diffuses it to a predetermined beam diameter. The diffused coherent light then travels through diffusing chamber 87, where it continues to spread, and then into collimator 84, which redirects the coherent light into a consistent and well-defined beam with a constant circular cross-section. The coherent light beam then travels to mirror 85 and is directed out of the body of probe 80 through portal 86 at the tip of probe 80. Portal 86 may be optically neutral or may have the property of diffusing or concentrating the beam, as is appropriate in any particular therapeutic application. For example, in some embodiments, portal 86 incorporate a second diffuser element (e.g. a lens) that further diffuses the beam, as probe 80 may be built on a scale such that the beam will still be quite small when it emerges from portal 86.

In some embodiments, the end or tip of probe 80 may be an open system such that there is an open air space bridge between the end of the emitting lens and the surface of the mucosa or skin surface being treated. Alternatively, in other embodiments, the end or tip of probe 80 may be a closed system such that a lens or transparent glass or plastic surface is in direct contact with the receiving mucosal or skin surface. Additionally, it should be understood that while probe 80 of FIG. 8 is described with reference to a single portal 86, other embodiments of probe 80 may include additional portals 86.

In various embodiments, probe 80 may be configured to include various additions or changes to manipulate and/or configure the emissions from probe 80. These additions may include the following: differently-shaped or different types of lenses (e.g., a diffusing lens, a mirror, a convex lens, a concaved lens, a dome lens, a flat lens), prisms (e.g., to change the shape of the beam), coils, fiber direct illumination, direct illumination from LEDs, other types of diodes or other energy-emitting devices, or reflections from differently shaped mirrors to change the beam profile (e.g., such that the emitted beam is in a circular, oval rectangular, linear, square, or other shape). Moreover, more than one of these additions/changes may be used simultaneously. Probe 80 may also receive one or more fiber optic cables (e.g., having a diameter less than 2 mm, of 2 mm, or greater than 2 mm) rather than having light emitted into probe 80. These additions may, for example, change the profile, diffusion, shape, and/or frequency of the emitted light beam. Alternatively, in some embodiments, probe 80 may include a straight light pathway for the beam with no changes or modifications.

Furthermore, in various embodiments, the emitted wavelength is collimated, though it should be understood that the emitted wavelength may alternatively be non-collimated. The emitted beam may also have various diameters or widths, such as less than 2 cm, equal to 2 cm, or greater than 2 cm. The emitted beam may also be configured such that the diffused beam diameter at the mucosa or skin/mucosa interface is less than 3 cm or greater than 3 cm. Further, the light used in probe 80 may be energized, for example, through batteries, direct coupling of energy, or induction charging.

To use probe 80, a human operator, a robotic operator (e.g., a robotic arm), or other manual or automated positioning system (e.g., all of which may be considered an "operator" with respect to probe 80) grips probe 80 and positions probe 80 to direct coherent light onto the tissues to be treated. Examples of grips that may be included in probe 80 include upper grips and lower grips configured for proper handling. The operator manipulates the end of probe 80 emitting phototherapy through portal 86 toward the targeted tissue site. The operator then engages a power switch, which may be on or within the probe, attached to or within a fiber optic cable harness, or a wireless switch (e.g., the operator may switch on the power via a mobile device). Once powered on, light flows from the CLG and is emitted through portal 86 (e.g., at any angle and at any power output, such as watts or Joules, depending on the configuration of probe 80 and parameters used for the therapy).

Delivery of phototherapy from probe 80 may be partially or fully controlled by the computer control unit (e.g., computer control unit 200), similar to the treatment cylinder as described above. Furthermore, various aspects of the treatment cylinder embodiments and operation of the treatment cylinder embodiments discussed above may be applied to probe 80, such as use of the probe with one or more cameras, user interfaces, one or more sensors, one or more imaging modalities, and/or one or more external treatment devices. For example, the probe may include a temperature sensor at the tip or surrounding one or more portals of the probe. Any sensors implemented in the probe may be in constant contact with the computer control system (e.g., via a wireless or wired connection).

While the probe (e.g., probe 80) can be used for surface treatments/on the exterior of the body, in various embodiments the probe is used for the delivery of coherent light to the inner core of the body not reachable by transdermal or transepithelial means. The probe can be used to deliver coherent light to the interior of the body by any reasonable means and/or through any suitable orifice, including but not limited to the following methods: (1) transesophageal insertion, which allows treatment of the interior of the mouth, the throat, the esophagus, and the interior of the torso, including the pericardial area, and further allows transintestinal insertion, allowing treatment of the intestines and other tissues proximate to the intestines; (2) transvaginal insertion, which allows treatment of the vaginal canal, the cervix, and with dilation if necessary, the uterus and other tissues proximate to the vagina and uterus; (3) transrectal insertion, which allows treatment of the rectum and other tissues proximate to the rectum, and further allows transintestinal insertion, allowing treatment of the intestines and other tissues proximate to the intestines; and/or (4) transbronchial insertion, which allows treatment of the lungs and other tissues proximate to the lungs.

In addition, the probe (e.g., probe 80) may be configured for, or configured to be modified for, insertion into the patient as a transureteral probe, a transnasal probe, a transcolonic probe, transauricular canal probe, transpharyngeal probe, translaryngeal probe, transluminal or orifice probe, intervascular probe, and joint or intermuscular probe, subcutaneous or subdermal probe. The probe may further be a handheld or robotically-controlled probe for open cavity surgery. Additionally, in some embodiments, the probe may be incorporated as part of an injectable subdermal, dermal, or deeper injection device, including an inter-joint injectable delivery device.

In some embodiments, an illuminated endoscope (not shown) may be included in the body of probe 80, such that the operator can see exactly where the coherent energy will leave portal 86 and enter the patient's tissues. For example, an illuminated endoscope may be included in the transesophageal configuration of the probe. In some embodiments, a standard flexible endoscopy system may be used to control the position of probe 80. If this is done, the standard flexible endoscopy system attaches to probe 80 somewhere under semi-rigid sleeve 81. Semi-rigid sleeve 81 then rolls up and over the connection, sealing it and allowing probe 80 to be directed by the standard flexible endoscopy system.

In some embodiments, the probe (e.g., probe 80) may be introduced into the body through an incision instead of a natural orifice. Such incision, and operation of the probe through it, may be performed by a medical doctor or someone trained and legally authorized to perform such a procedure. With a properly sized probe, introduction can be made via catheterization of a blood vessel, allowing treatment of the circulatory tissues and other tissues proximate to the circulatory system up to and including cardiac catheterization and treatment. Such catheterization, and operation of the probe through it, may be performed by a medical doctor or someone trained and legally authorized to perform such a procedure.

Each probe may include a unique identifier. This identifier could include, without limitation, a permanently or semi-permanently affixed bar code or QR code, a permanently or semi-permanently affixed RFID tag, or an integrated circuit of some kind that can be queried to retrieve an identification parameter, such as a number or string of characters permanently or semi-permanently stored on the integrated circuit, by a wired or wireless connection. In some embodiments, the unique identifier may be associated with a particular patient, such that during that patient's course of treatment with the device, that probe is used only for that patient. This can be done by any reasonable manner, from making a note in the patient's medical records as to the unique identifier of that patient's associated probe, to including software in the computer control unit that retrieves the unique identifier and checks it (e.g., against a patient identification database) and advises the operator whether the correct probe is being used, to including software in the computer control unit that will not allow the device to send coherent light from the CLG to the probe unless the probe's unique identifier matches a unique identifier associated with the patient (e.g., an optically readable code or an RFID tag on a standard medical info bracelet). In some embodiments, the probe could even require information or biometric conformation from the patient prior to use, such as reading a fingerprint from the patient or asking the operator to input information requested from the patient that only the patient would know.

In some embodiments, the unique identifier described above may be used to track the usage of the probe and to ensure that it is not used more times than is recommended by the manufacturer and/or that it is not used for a longer period after the initial use than is recommended by the manufacturer. For instance, the unique identifier can be tracked each time the probe is used, and after the sixth time, the computer control unit can advise the operator and/or not allow coherent light to be sent from the CLG to the probe. Similarly, the first day the unique identifier is used can be tracked, and after fifteen days, the computer control unit can advise the operator and/or not allow coherent light to be sent from the CLG to the probe.

In some embodiments, the probe may include a control chip that can be screwed/inserted into the handle of probe. The control chip allows a certain number of photon treatments to be administered through probe before the photon energy emission is automatically turned off through a wired or wireless connection to the source of the laser used for probe (e.g., similar to treatment cylinder with an identification number or code, as discussed above). Alternatively, a closing aperture system may close an aperture within probe or external to probe after a certain number of treatments, where the closing of the aperture prevents the emission of the photon beam down the fiber optic network connected to and through probe.

In some embodiments, the probe is configured for disposal after one or more uses. Alternatively, in other embodiments, the probe may be reusable on the same patient and/or for multiple patients after cleaning and sterilization.

If the probe is small and/or flexible enough, it can be further inserted, like an endoscope, into the intestines and eventually allow the delivery of phototherapy to almost every volume of tissue inside the abdominal cavity. A sufficiently small and flexible probe can also be inserted transurethrally, allowing treatment of the urethra, the bladder, and other tissues proximate to those organs such as the kidneys. Accordingly, the size of the probe may be provided as follows: (1) the length of the probe could be less than a rigid anoscope or more than a flexible colonoscope; (2) the width of the probe (e.g., a shaft of the probe, the end of the probe, portions of the probe, or the entire probe) could be less than 1 cm, up to 5 cm, or greater than 5 cm (e.g., the diameter of the probe could be 0.5 to 2 cm or near the diameter of existing rigid scopes or flexible scopes, such as an EGD scope or sigmoidoscope); and (3) the probe (e.g., the shaft, the end, portions, or the entire probe) could allow for no rotation, less than 90 degrees of rotation, up to 90-180 degrees of rotation, or up to 210 degrees of rotation.

Accordingly, various objectives of the probe (e.g., probe 80) can be summarized as follows. The probe acts as a device for administering precision phototherapy. As described above, the therapy may be applied via the probe either manually or robotically (e.g., controlled by the computer control unit, controlled by a robotic arm). More specifically, the probe serves as a device for administering precision phototherapy that is inserted into a lumen or an orifice of the body to provide treatment via precise targeting of the treatment site, which may be any area of the body. The probe may also be used during open surgery, or the probe may be used with endoscopic procedures. The probe may thus safely and efficiently administer the highest amount of phototherapeutic energy into deep, diseased soft tissues. When used with imaging modalities that scan the body of the patient being treated, the probe may be used to automatically target the tissues to be treated while adjusting the energy of the phototherapy accordingly (e.g., via automatic control by the computer control unit or recommended steps provided by the computer control unit). The probe may also serve as a device for administering precision phototherapy that can simultaneously deliver light of multiple wavelengths to the tissues to be treated.

Additionally, the probe (e.g., probe 80) may be used with one or more agents, chemicals, or substances that cool the treatment area, numb the treatment area, cause the treatment area to be less reflective to incoming photons, vasoconstrict the treatment area, and/or block or absorb part or all of the delivered photons, as similar to the process discussed above with reference to the treatment cylinder. For example, a substance or agent may be applied to the probe's tip or onto the surfaces of the targeted treatment site before photons are delivered to the targeted treatment site. As an illustration, a laser-photon coupling gel and/or a gel or oil mixed with phenylephrine could be placed on the tip of a transvaginal probe or inserted into the vagina minutes before administering PBMT photons transvaginally into the pelvis. The clear coupling gel or oil could help the photons travel, with less deflection and reflection off the mucosal surfaces of the vagina, thus allowing more photons to eventually propagate into the deeper pelvic structures where disease states may exist. The phenylephrine could also temporarily vasoconstrict the blood vessels within the vaginal mucosa causing mucosal blanching and thus providing a vaginal mucosa environment with less blood flow and less hemoglobin. Having less hemoglobin at the interface between the vaginal mucosal surface and submucosal tissues allows the photons from a 980 nm diffused beam to propagate into the deeper structures and tissues within the chosen targeted treatment site within the pelvis, as discussed above.

FIG. 8A shows an alternate embodiment for the probe (e.g., a configuration meant for transvaginal or transrectal use). For example, probe 830 may be connected to a treatment cylinder (e.g., TC 10, TC 20, TC 30, TC 40, TC 50, TC 70, and/or TC 310 described above), allowing for simultaneous delivery of PBMT energies into the pelvis and into the lower abdomen topically or transdermally through the suprapubic area via transvaginal probe 80. Alternatively, probe 830 may be used as a standalone device with a separate light source. It should be understood that probe 830 of FIG. 8A may include any and all of the features described above with reference to probe 80. Moreover, it should be understood that probe 830 may be configured to be or may be modified to be used as a probe in other areas of the body, such as a transesophageal probe or a transbronchial probe.

Fiber optic cable 835 optically connects probe 830 with a CLG (not shown; see, e.g., FIG. 1, 5, or 7). Coherent light flows through interior fiber optic 839 within body 840 and reaches first diffusing lens 836, where it is diffused and then directed toward mirror 837. Alternatively, in some arrangements, lens 836 may not be a "diffusing lens" but be used to shape the light to illuminate in a predictable pattern without being diffusing by definition. Mirror 837 in turn directs the coherent light through convex diffusing dome lens 838, where it is transmitted to the tissues to be treated. In some embodiments, the light emerging from diffusing lens 836 is divergent. In other embodiments, the light emerging from diffusing lens 836 may be a diffuse beam that is collimated prior to delivery of the beam/photons to the targeted tissue's surface. Furthermore, in some embodiments, the coherent light beam must be diffused by the end of its travel through probe 830. If diffusing lens 836 does not diffuse the beam significantly or at all, the optical properties of mirror 837 and/or convex diffusing dome lens 838 may need to be adjusted to produce the net diffusion desired.

The use of first diffusing lens 836, mirror 837 and convex diffusing dome lens 838 allows a very small fiber optic to be used (e.g., for most handheld applications, the fiber optic will be approximately 2 mm in diameter) and for the body of the probe to thus be smaller while producing a large and controlled diffused output of coherent light. For most handheld applications, the probe can be approximately 2 cm in diameter, the convex diffusing dome lens 838 adding only slightly to the effective diameter, and yet an effective diffused beam of at least 3 cm in diameter is readily produced for the treatment of tissues with phototherapy.

To use the probe, the operator holds probe 830 in the area of upper grips 833 and lower grips 834. Alternatively, and as described above with reference to probe 80, probe 830 may be configured to receive a rigid or flexible endoscope, and the operator may manipulate the endoscope to manipulate probe 830. The operator then inserts probe 830 (e.g., according to the medical best practices for such insertions) into the patient's vagina and aims it at the tissues to be treated. The operator then engages power switch 832. This sends a signal to the computer control unit to energize the CLG (not shown) to which fiber optic cable 835 is attached and begins the flow of coherent light into the probe. The coherent light is then delivered according to the treatment plan input and/or any manual control inputs made by the operator.

FIG. 8B shows another alternate embodiment for a probe. As with the probes discussed above, probe 930 may be configured for use with a treatment cylinder or may be configured as a standalone device with a separate light source. Additionally, probe 930 may include all the features described above with reference to probes 80 and 830 and may be modified to be used in various areas of the body.

Probe 930 is generally similar to probe 830, with a fiber optic cable connecting probe 930 to a CLG via fiber optic cable interface 935. Coherent light flows through interior fiber optic 939 within body 940 and reaches first diffusing lens 936, where it is diffused. However, probe 930 does not include a mirror; instead the coherent light is directed straight to convex diffusing dome lens 938. The light may also pass through one or more additional lenses (e.g., diffusing lenses, diffusing mirrors) or other optical elements before reaching convex diffusing dome lens 938. As such, similar to probe 830, the use of first diffusing lens and convex diffusing dome lens 938 allow a very small fiber optic to be used to still produce an emitted beam 942 with a diameter sufficient for the phototherapy application.

However, body 940 of probe 930 differs from probe 830 in that body 940 is more curved, particularly at the tip where emitted beam 942 emerges from probe 930. For example, the tip may be at a 30 degree curve from the rest of body 940. Additionally, probe 930 includes ergonomic bottom grips 934 and a button 932 (e.g., that the operator can press to turn probe 930 on and thereby provide phototherapy).

FIGS. 8C-8E show another alternate embodiment for a probe. As with the probes discussed above, probe 1030 may be configured for use with a treatment cylinder or may be configured as a standalone device with a separate light source. Additionally, probe 1030 may include all of the features described above with reference to probes 80, 830, and 930 and may be modified to be used in various areas of the body.

Probe 1030 is generally similar to probe 930, with a fiber optic cable connecting probe 1030 to a CLG via fiber optic cable interface 1035. Coherent light flows through interior fiber optic 1039 within body 1040 and reaches first diffusing lens 1036, where it is diffused. The coherent light is also directed to convex diffusing dome lens 1038, where it is emitted as beam 1042 (e.g., as shown in more detail in FIG. 8E, illustrating the tip of probe 1030). Before being emitted, the beam may also pass through one or more additional lenses or other optical elements.

Body 1040 of probe 1030 is also similar to body 940 of probe 930, though is more streamlined than body 940 of probe 930. Body 1040 additionally includes ergonomic grips 1034, which held the operator control and maneuver the photon-emitting tip of probe 1030. Further, the thumb indentation at the 11 o'clock position in ergonomic grips 1034 helps the operator of probe 1030 to better sense the location and direction of the upward curve (e.g., 30 degree curve) of the tip of probe 1030, for example, toward targeted pelvic organs and/or pelvic floor muscles and structures if probe 1030 is used as a transvaginal probe. Body 1040 also includes a button 1032 (e.g., that the operator can press to turn probe 930 on and thereby provide phototherapy).

These alternate probe embodiments may be further modified to include desirable features for providing phototherapy. For example, body 1040 of probe 1030 may include one or more openings for cooling a portion of probe 1030 (e.g., on or near the handle of probe 1030, incorporated as part of interface 1035). Stainless steel tubing forming one or more channels within body 1040 of probe 1030 may be connected to the opening(s) to transport, for instance, water coolant, compressed $CO_2$ gas, or chilled air from a source external to probe 1030, through probe 1030, and out again. The tubing may be configured to cool the targeted tissues (e.g., through an opening in convex diffusing dome lens 1038), the tip of probe 1030 (e.g., convex diffusing dome lens 1038), and/or first diffusing lens 1036 and any other optical components housed in the tip of probe 1030 (e.g., a diffusing mirror). In some arrangements, more than one section of tubing may be provided to cool probe 1030, and the different sections may be of different calibers (e.g., with smaller-diameter tubing used to transport a coolant into probe 1030 and with larger-diameter tubing used to transport used coolant out of probe 1030). Alternatively, a refrigerant coil may be provided at the base of probe 1030 and/or within the wall at the connection between body 1040 of probe 1030 and convex diffusing dome lens 1038.

In some embodiments, probe 1030 may house a temperature sensor near the optical components of the tip to detect any heat buildup with these beam-interfacing components. For example, a temperature sensor may be provided on an external surface of convex diffusing dome lens 1038 (e.g., with an insulating layer between the sensor and lens 1038) to monitor, for instance, the vaginal mucosa being treated. As another example, a ring temperature sensor could be provided around the base of lens 1038 to measure the temperature underneath convex diffusing dome lens 1038. As another example, a temperature sensor may be provided within a chamber positioned before first diffusing lens 1036 to measure the temperature at the connection between interior fiber optic 1039 and the optical assembly within probe 1030. In response to detecting heat buildup via the temperature sensor, for example, the computer control unit may automatically shut down operation of probe 1030 or warn the operator of the potential heat buildup.

Figure 8F:
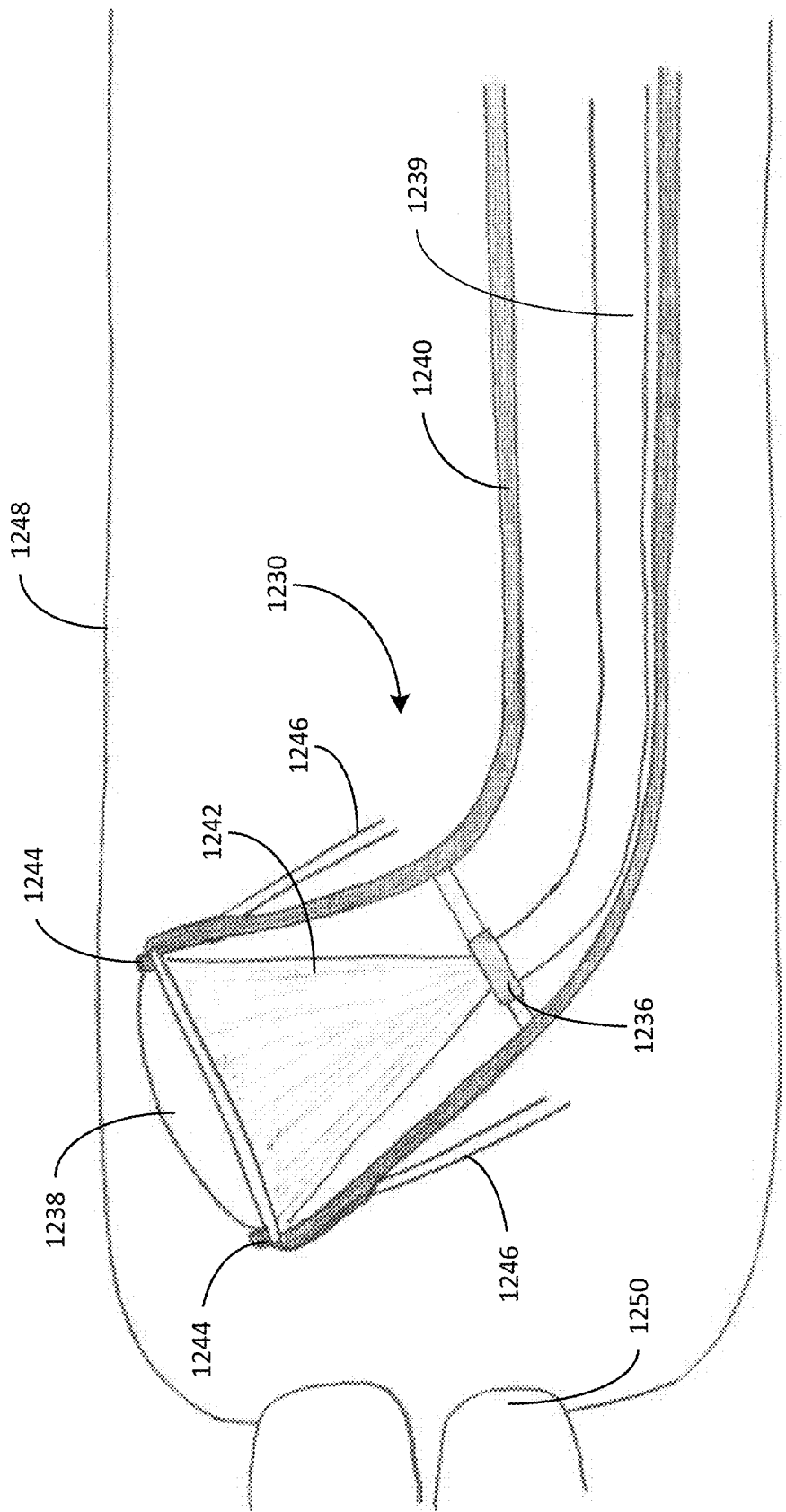
FIG. 8F depicts a cross-sectional view of another embodiment of a probe of a phototherapy device.
Figure 8G:
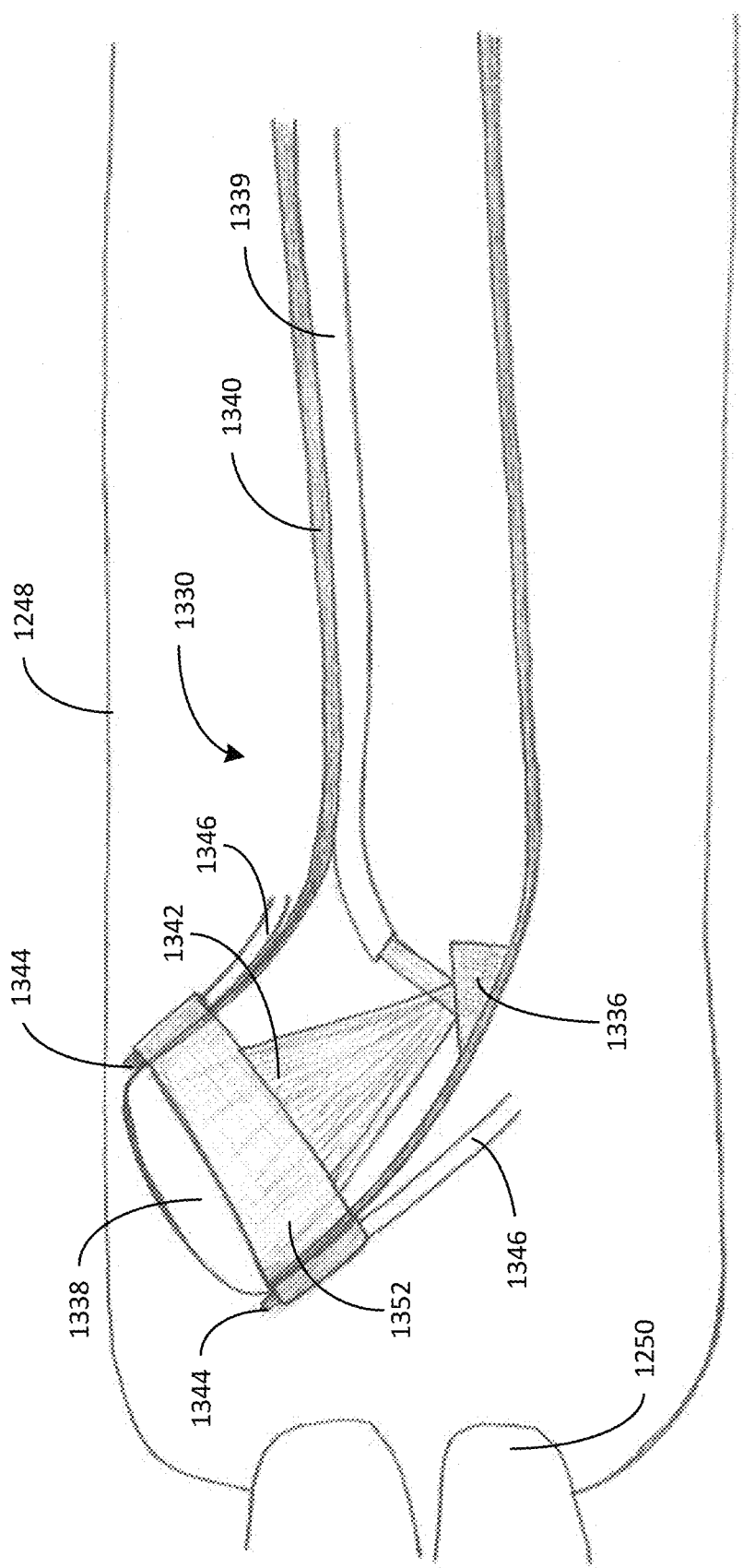
FIG. 8G depicts a cross-sectional view of another embodiment of a probe of a phototherapy device.
Figure 8H:
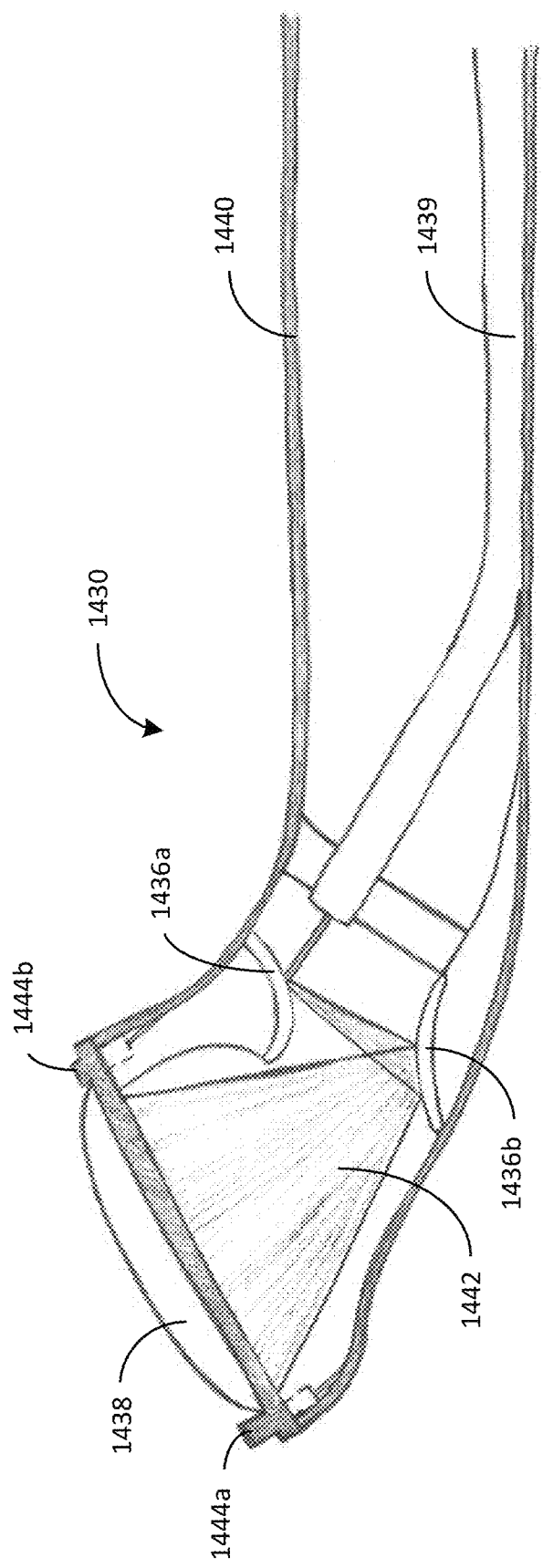
FIG. 8H depicts a cross-sectional view of another embodiment of a probe of a phototherapy device.

FIGS. 8F-8H show additional alternate embodiments for a probe. As with the probes discussed above, probe 1230, probe 1330, and probe 1430 may be configured for use with a treatment cylinder or may be configured as standalone devices with separate light sources. Additionally, probe 1230, probe 1330, and 1430 may include all of the features described above with reference to probes 80, 830, 930, and 1130 and may be modified to be used in various areas of the body.

Referring first to FIG. 8F and probe 1230, probe 1230 is generally similar to probe 1030 and probe 930, with a fiber optic cable connecting to probe 1230 (not shown). Coherent light flows through interior fiber optic 1239 within body 1240 and reaches first diffusing lens 1236, where it is diffused into diffused beam 1242. The coherent light is also directed to convex diffusing dome lens 1238, where it is emitted from the tip of probe 1230. In some arrangements, before being emitted, the beam may also pass through one or more additional lenses or other optical elements. However, as shown in FIG. 8F, dome lens 1238 is much smaller than, for example, dome lens 938 of probe 930 and dome lens 1038 of probe 1030 (e.g., dome lens 1238 being 2.5 mm high, being 5 mm high). Additionally, the tip of probe 1230 is provided with one or more temperature sensors 1244 drilled into the side of the probe (e.g., such that temperature sensors 1244 extend up to 2 mm above the base of dome lens 1038). Wires 1246 connecting to temperature sensors 1244 may be provided within probe 1230, external to probe 1230 (as shown), or extending from within probe 1230 to the exterior. The configuration of the smaller dome lens 1238 and temperature sensors 1244 may allow temperature sensors 1244 to more easily contact and collect temperature data from vaginal mucosal wall 1248 or cervix 1250 while keeping temperature sensors 1244 isolated from the components of probe 1230 that also create heat.

Probe 1330 of FIG. 8G is configured similarly to probe 1230, with interior fiber optic 1339 extending through body 1340. However, interior fiber optic 1339 ends by emitting the coherent light of interior fiber optic 1339 on first diffusing mirror 1336 positioned on the side of the interior of probe 1330 (e.g., near the upward curve at the tip), with first diffusing mirror 1336 directing the coherent light as diffused beam 1342 to convex diffusing dome lens 1338 and out of probe 1330. In some arrangements, before being emitted, the beam may also pass through one or more additional lenses or other optical elements. Similar to dome lens 1238, convex diffusing dome lens 1338 is much smaller than, for example, dome lens 938 of probe 930 and dome lens 1038 of probe 1030, but dome lens also has a larger diameter than dome lens 1238 of probe 1230 (e.g., 2.9 cm diameter instead of 2.5 cm diameter). The larger diameter of dome lens 1338 may allow dome lens 1338 to sit on top of the tip of probe 1330 (e.g., glued to the top of probe 1330). Surrounding dome lens 1338 around the circumference of body 1340 is plastic end ring 1352. End ring 1352 may help secure dome lens on the tip of probe 1330. Additionally, as shown in FIG. 8F, end ring 1352 may have a thickness wide enough that one or more holes can be drilled lengthwise through end ring 1352 and one or more temperature sensors 1344 may be inserted through the hole(s). Wires 1346 connecting to temperature sensors 1344 may be provided within probe 1330, external to probe 1330 (as shown), or extending from within probe 1330 to the exterior. Similar to probe 1230, this configuration of end ring 1352, temperature sensors 1344, and dome lens 1338 may allow temperature sensors 1344 to more easily contact and collect temperature data from vaginal mucosal wall 1248 or cervix 1250 while keeping temperature sensors 1344 isolated from the components of probe 1330 that also create heat.

As discussed above, embodiments of the probe may include a cooling structure. For example, in some arrangements, probe 1230, probe 1330, or a similar probe may include a cooling structure, such as a Peltier thermoelectric cooler cylinder or another structure described above with reference to the treatment cylinder, provided on or around the circumference of the probe just before or past a point where the coherent light is diffused (e.g., past first diffusing lens 1236 in probe 1230 or past first diffusing mirror 1336 in probe 1230). The cooling structure may be used to prevent patient tissues from reaching temperatures above 45° C.

Probe 1430 of FIG. 8H is configured similarly to probe 1230 and probe 1330, with interior fiber optic 1439 extending through body 1440, and interior fiber optic 1439 ends by emitting the coherent light of interior fiber optic 1439 on first diffusing mirror 1436a (e.g., a stage 1 convex diffusing mirror) positioned on the side of the interior of probe 1430. However, in probe 1430, first diffusing mirror 1436a diffuses and redirects the coherent light to second diffusing mirror 1436b (e.g., a stage 2 convex diffusing mirror). Second diffusing mirror 1436b redirects the coherent light as diffused beam 1442 to convex diffusing dome lens 1438 and out of probe 1430. In some arrangements, before being emitted, the beam may also pass through one or more additional lenses or other optical elements. Similar to dome lens 1238 and dome lens 1338, convex diffusing dome lens 1338 is much smaller than, for example, dome lens 938 of probe 930 and dome lens 1038 of probe 1030. Dome lens 1438 may be sized to fit on the end of probe 1430 (e.g., 2.5 cm in diameter and 2.5 mm in height). The tip of probe 1430 is also provided with multiple temperature sensors, similar to probe 1230 and probe 1330. For example, as shown in FIG. 8H, probe 1430 includes first temperature sensor 1444a is positioned at the edge of come lens 1438 and extends up to the same height as dome lens 1438 (e.g., 2.5 mm in height). As such, first temperature sensor 1444a may be used to capture the vaginal mucosa temperature distally (e.g., distal from the vaginal mucosa when probe 1430 is curved towards the vaginal mucosa as shown in FIG. 8H). Probe 1430 also includes second temperature sensor 1444b positioned lower than the top of dome lens 1438 (e.g., 1.5 mm in height), with the second temperature sensor 1444b configured to capture the vaginal mucosa temperature proximally (e.g., proximal to the vaginal when probe 1430 is curved towards the vaginal mucosa as shown in FIG. 8H).

It should be understood that other embodiments of the probe may also include more and/or different types of optical component from the optical components shown with respect to probe 1230, probe 1330, and probe 1430. For example, instead of a dome lens, any of these probe embodiments may include a glass dome or an acrylic dome that encloses the tip of the probe.

Figure 8I:
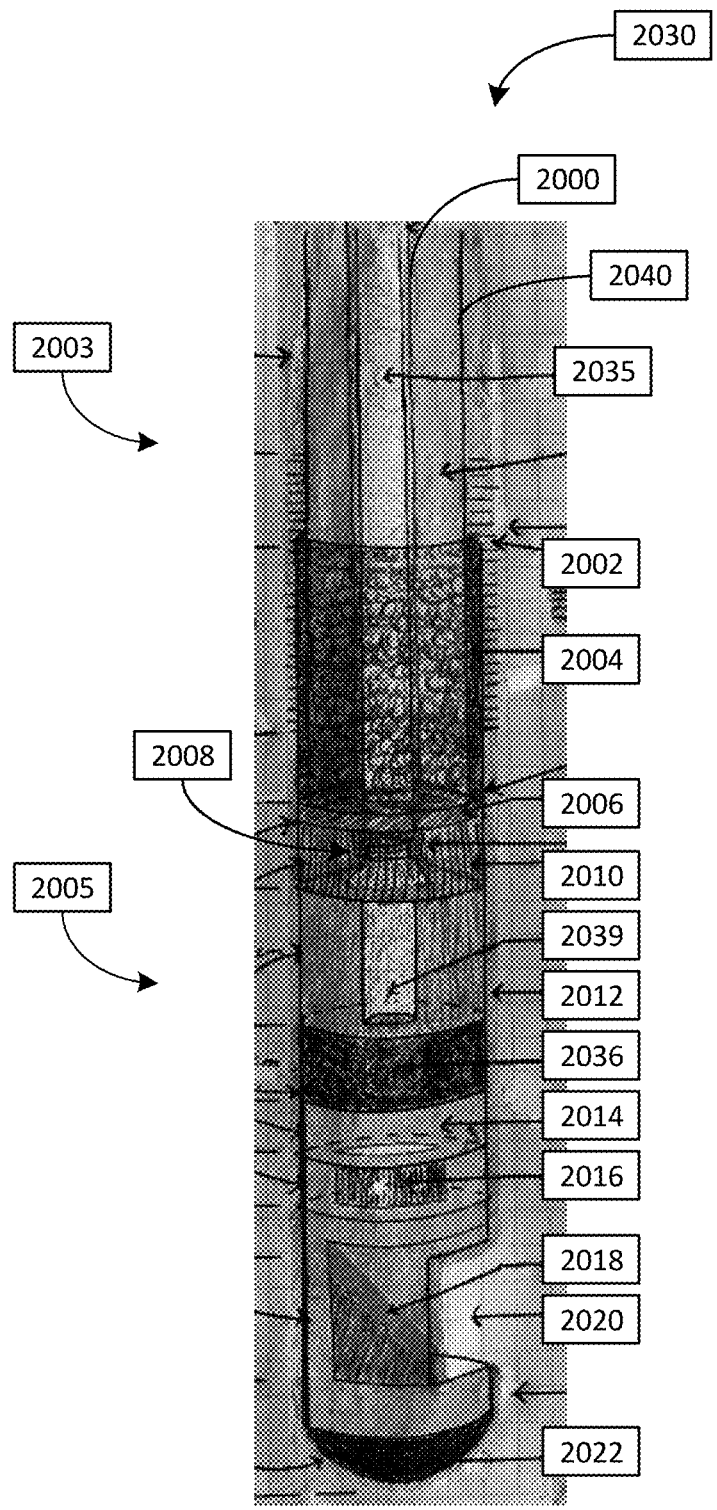
FIG. 8I depicts a perspective and cross-sectional view of another embodiment of a probe of a phototherapy device.

FIG. 8I shows another alternate embodiment for a probe. Probe 2030 may be used, for example, as an endoscopic probe for transesophageal, transgastric, or transgastric treatments. As with the probes discussed above, probe 2030 may be configured for use with a treatment cylinder or may be configured as a standalone device with a separate light source. As shown in FIG. 8I, probe 2030 is generally similar to various probes discussed above. External fiber optic 2035 connects to probe 2030 such that coherent light flows through body 2040 of probe 2030 through external fiber optic 2035 (e.g., 0.3 cm in diameter transporting a 0.2 cm in diameter laser beam). Interior fiber optic 2039 is provided within channel 2000 (e.g., having a diameter of 0.35 cm), which may also be used, for example, as a biopsy forceps channel. Body 2040 may be configured with endoscope section 2003 such that at least a portion of probe 2030 may be used as an endoscope itself, such as a pediatric flexible endoscope. For example, body 2040 may be 0.9 cm in diameter and sized to fit within a 1.2 cm diameter opening (e.g., the esophagus of a pediatric patient). To this end, body 2040 may include a flexible segment 2002 (e.g., 2.1 cm long) configured to allow articulation of probe 2030.

As external fiber optic 2035 extends through body 2040 towards the tip, body 2040 transitions to thicker transition area 2004 (e.g., 1.92 cm long). Transition area 2004 may partially overlap with flexible segment 2002 (e.g., such that only 0.31 cm of transition area 2004 do not include flexible segment 2002). The end of transition area 2004 may mark the end of endoscope section 2003 of body 2040 of probe 2030 and the beginning of combination chassis section 2005 of probe 2030 and thus be provided with endoscope-probe interface 2006. Interface 2006 may include connector 2008 (e.g., a male-female connector) for connecting external fiber optic 2035 to interior fiber optic 2039 such that coherent light is emitted into interior fiber optic 2039. As shown, connector 2008 may be provided within pipe-like bridge 2010 (e.g., such that interface 2006 and bridge 2010 are together 0.62 cm long).

Moving to the tip of probe 2030, coherent light travels through interior fiber optic 2039 within cable bridge 2012 (e.g., 1.04 cm long) to diffusing lens 2036 (e.g., 0.33 cm thick), where interior fiber optic 2039 may terminate. Diffusing lens 2036 diffuses the coherent light beam through diffusing chamber 2014 (0.25 cm long) to collimator 2016 (e.g., 0.25 cm long), which collimates the diffused coherent light beam. From collimator 2016, the coherent light is directed to convex diffusing mirror 2018 (e.g., the top of which may be positioned 0.25 cm from the end of collimator 2016 and may extend, from that end, 0.55 cm towards the tip of probe 2030). As shown in FIG. 8I, convex diffusing mirror 2018 is provided at an angle (e.g., a 45 degree angle) such that mirror 2018 redirects the coherent light out of probe 2030 via portal 2020. In some arrangements, portal 2020 may be provided with a closing aperture such that portal 2020 may be closed. The tip of probe 2030 is provided with rounded cap 2022 (e.g., for ease of insertion into a patient). In various embodiments, probe 2030 may be covered in a sheath (e.g., for ease of insertion and manipulation within the patient).

The probe, in whatever embodiment, may be connected to the CLG through a removable optical connection. This allows the probe to receive coherent light from the CLG without the addition of additional coherent light generation sources. Further, if the CLG are provided as part of a treatment cylinder, this allows the computer control unit to be aware that a probe is being used to administer phototherapy in conjunction with the treatment cylinder and to control the emission of coherent light through the probe by controlling the emission of light at the CLG. If no optical connection between the probe and a CLG exists, some other source of coherent light is instead optically connected to the probe.

The probe, in whatever embodiment, may also be removably electrically connected to other components of the phototherapy device and ultimately the computer control unit. This allows the computer control unit to detect when the probe is switched on and can also allow it to confirm the unique identity of the probe, if such can be determined electronically, and that it is appropriate to allow the probe to be used (e.g., it is not out of date, it has not been used the maximum number of times, it is correlated to the patient being treated, etc.) if such can be determined electronically.

In some embodiments, the probe may be removably connected, either optically or electronically, or both, to other components of the phototherapy device to allow the coordination of phototherapy between the treatment cylinder and the probe. If the probe is electronically connected to the computer control unit, the computer control unit may be configured to control the duration, power, and wavelength of the coherent light to be administered through the probe according to a predetermined treatment plan. Moreover, in such cases, the computer control unit may signal the operator as to the depth and alignment of the insertion of the probe, and further signal the operator as to any position adjustments that should be made as the treatment progresses. The computer control unit may also make similar signals regarding the treatment cylinder, when therapy is being delivered simultaneously via the probe and the treatment cylinder.

If the probe has an endoscope (e.g., as described above with reference to FIG. 8), the operator may be shown a live view of the endoscope's field-of-view to assist in positioning the probe. If the computer control unit allows optical recognition of the endoscope's field of view (e.g., as described above with reference to FIG. 6), the computer control unit may signal the operator as to the ongoing positioning of the probe based upon its determination as to the current location of the tissues to be treated relative to the probe.

In some embodiments, the probe includes a spectroscopic sensor in the probe. If the probe has a spectroscopic sensor (e.g., as described above with reference to FIG. 6), the computer control unit may use data from the spectroscopic sensor to control the power, duration, and wavelength of the coherent light to maximize the delivery of therapeutic energy while minimizing the risk of burning the patient's tissues.

In some embodiments, a treatment plan selected (e.g., by the computer control unit 200) based on a treatment plan input includes the administration of phototherapy by the treatment cylinder and the probe concurrently or in a predetermined sequence. As an example and without limitation, if phototherapy is being administered to address pelvic pain in a female, the treatment cylinder can direct coherent light toward the pelvic region of the patient while the probe is inserted transvaginally and simultaneously, or in a controlled alternating pattern, directs coherent light toward tissues in the interior of the pelvic region that the coherent light emitted from the treatment cylinder cannot reach.

In some embodiments, the computer control unit may track the position of the probe, such as through visual/optical tracking, inertial tracking, or radiolocation of any appropriate kind. If the computer control unit can track the position of the probe, the computer control unit may use information about the position of the probe to do one or more of the following: (1) advise the operator as to whether the probe is properly placed and/or oriented for the desired treatment plan; (2) warn the operator and/or disable the probe if it determines that the probe is not in the proper placement/orientation to administer the desired phototherapy; (3) ensure that the coherent light being emitted by the probe is not directed at the same tissues to which the treatment cylinder emitters are simultaneously administering coherent light, which could result in excessive exposure or overheating and potential tissue damage; or (4) coordinate the treatment cylinder emitters with the probe's emission of coherent light to improve the overall efficacy of the phototherapy.

As discussed above, the probe may have its own source of coherent light. If the probe has its own source of coherent light, the probe and/or its source of coherent light may have one or both of the following properties: (1) the probe and/or light source is in electronic communication with the computer control unit such that the computer control unit can coordinate the output of the probe with a treatment plan input; or (2) the probe and/or light source has a specification, and the computer control unit is able to accept a specification input such that the computer control unit can advise the operator as to the appropriate application of the probe and the power, duration, and wavelength of the coherent light to be applied with the probe during the application of phototherapy.

Additionally, any of the phototherapy device embodiments discussed above including a probe may include a network interface (e.g., provided in the probe, provided at the CLG optically connected to the probe, and/or provided at the computer control unit communicating with the probe and CLG). As such, the phototherapy device may include a wireless connection with a mobile device including a display, such as a smartphone or a tablet. Alternatively, the phototherapy device may include a wired connection with a mobile device, or the mobile device may serve as the computer control unit for the phototherapy device. In some embodiments, the mobile device may operate an application or other program that allows the operator, via the mobile device, to view data from the computer control unit communicating with the probe (e.g., data relating to the operation of the probe, sensor data from the probe). In some embodiments, the operator may also view, via the mobile device, a unique identifier for the probe (e.g., stored in a control chip implanted in or a tracking number on the probe's handle).

Various operations and settings of the phototherapy device that may be viewed by the mobile device include the selected type of wavelength; the selected number of watts output ("MNW") for the probe; the estimated corrected number of watts ("CNW") actually being emitted by the probe (e.g., which may account for Joules of energy lost as the laser beam travels from the CLG through external fiber optics, internal fiber optics, and the probe's optical components, such as a 810 nm laser set at 14.5 W having a 10 W diffused-beam actually delivered from the probe); the selected beam delivery mode of either a continuous mode or a pulsed mode, the latter including the selected frequency (Hz) and pulse width (milliseconds) of the beam; an energy delivered meter to keep track of the number of Joules being delivered during a treatment session (e.g., in CNW); and a time meter showing the number of seconds that the laser beam has been emitted for the treatment session, the number of times the laser beam has been automatically turned off due to the treatment site temperature reaching an undesirable level (e.g., 45° C.), the number of times the laser beam has been automatically turned off because rotational movement sensors detected no movement for a certain amount of time (e.g., 1.75 seconds), and/or the number of times the laser beam has been automatically turned off based on another sensor within the probe (e.g., the probe's handle) monitoring incoming $CO_2$ gas pressure per square inch ("PSI"), flow rate, and/or temperature. Additionally, in some embodiments, the operator may be able to select or modify various operations and settings of the phototherapy device via the mobile device.

In some embodiments, the probe may further include one or more markers, such as sensors or beads, that an external monitoring system can use to show the location of the probe relative to other anatomical structures of the patient. For example, the probe may include one or more radiopaque markers visible on x-rays or CT scans and/or one or more resonant markers visible on MRI images. Alternatively, the probe may include one or more markers that emit location and/or direction data of the markers, allowing the location of the probe to be tracked via an external monitoring system. As an example, the markers may be RFID markers that can be tracked via an RFID tracking system set up in a medical procedure room.

Additionally, the external monitoring system may display images showing the location of the probe relative to the anatomy of the patient via the mobile device (e.g., through a wired or wireless connection between the external monitoring system and the mobile device). Viewing the location of the probe via the mobile device may allow the operator to better position the probe and/or direct the coherent light from the probe, either completely manually or with guidance from the computer control unit. With reference to the latter, for example, the computer control unit may analyze the location of the probe relative to the anatomical structures of the patient and provide visual prompts to the display of the mobile device for altering the location and/or direction of the probe to provide the best treatment therapy. Alternatively, the computer control unit may use location/direction data for the probe provided by the external monitoring system to automatically reposition the probe or alter the direction of the coherent light emitted from the probe (e.g., by moving internal optical components of the probe, such as a mirror or diffusing lens), such as through a robotic maneuvering system controlling the probe.

As an illustration of the foregoing, a transesophageal probe including resonant markers may be manually positioned or automatically positioned in the esophagus based on MRI scanning of the esophagus-heart structures. The probe may thereby be manipulated to best apply the PBMT only to the posterior heart muscle of a struggling-to-pump ventricle chamber. As another illustration of the foregoing, a mobile device receiving location images for a transvaginal probe including markers may show that the probe deep inside the vaginal vault is actually next to the top left side of the external intravaginal cervical tip and that the PBMT beam is reaching toward and into the left upper lateral side of the bladder wall. The images and data regarding the location and operation of the probe could be used to view the probe's location, the specific areas of the pelvic organs, the direction, location, and strength of the probe's coherent light beam, and the level of coherent light being delivered to the vaginal mucosal subdermis, as well as the left upper lateral bladder wall.

In some embodiments, the mobile device may also display information about the patient being treated (e.g., retrieved based on the patient's medical records or a unique identifier for the probe associated with the patient). For example, the mobile device may display basic patient demographic data (e.g., Health Insurance Portability and Accountability Act ("HIPAA")-compliant protected data), as well as medical history data, including current medications, prior surgeries, past and present medical diagnoses, psychological history, and, depending on the targeted treatment site, pertinent prior chronic pelvic pain ("CPP") treatments, prior interstitial cystitis ("IC") treatments, prior dyspareunia treatments, prior and current gynecological diseases and problems, prior and current urology diseases and problems, prior and current gastrointestinal diseases and problems, and the current working diagnoses for planned PBMT. In some embodiments, the patient or the operator in conjunction with the patient may complete a targeted review of symptoms (e.g., "yes" and "no" answers to symptom questions or rating the applicability of symptoms on a scale of 1 to 10) via the mobile device, such as for CPP, IC, dyspareunia, urological-bladder symptoms/complaints, gynecological-reproductive tract symptoms/complaints, and gastrointestinal symptoms/complaints. The patient may need to answer these targeted review of symptoms questions before the mobile device accepts the identifier for the probe and allows the first PBMT treatment session to begin. Further, in some arrangements, before each of all or some of subsequent treatments (e.g., five treatments), the patient may similarly need to answer a series of follow-up questions, the answers of which are recorded on the mobile device before treatment can begin via the probe. Additionally, if an identifier for the probe (e.g., stored on a control chip in the probe) connected to the mobile device does not match up with an identifier stored for the patient, the mobile device may prevent follow-up treatments from being administered via the probe (e.g., to ensure the same probe is used for the first six treatment sessions). The patient's answers to the symptom questions may also be transmitted to the manufacturer of the probe (e.g., under encryption) such that the patient information may be centrally stored and, for example, retrieved by the mobile device when the patient returns for another follow-up treatment session.

Moreover, embodiments of the phototherapy device including a treatment cylinder (instead of or in addition to the probe) may also be capable of connecting to a mobile device and providing the mobile device functionalities discussed above. For example, phototherapy devices including a treatment cylinder may allow the operator to view and modify operations and settings of the treatment cylinder, view the location of the treatment cylinder relative to patient anatomy, and display information about the patient being treated via a mobile device.

In some embodiments, various components of a phototherapy device may be tested before use (e.g., use for the first time, use for the day, use before each treatment session). For example, testing a phototherapy device including a transvaginal probe may include testing the transvaginal probe itself, testing a laser machine providing power to diodes optically connected to the transvaginal probe (e.g., one or two different wavelength-generating diodes), and/or testing functions of a control unit box (e.g., incorporated as part of the computer control unit for the phototherapy device). In some arrangements, the control unit box may include different sound generators, a screen that displays incoming sensor data and the laser machine's control settings (e.g., which may be controlled on the laser machine screen and relayed to the control unit box), and a master control to control the laser machine's ON/OFF functionality (e.g., manually and/or automatically) if, for example, one of the sensors senses that a critical shutdown should occur based on temperature or lack of probe motion. In some arrangements, the control unit box may further house components storing software that operates and reacts according to the incoming sensor information to allow for safe operation of the probe during PBMT treatment. As such, the control unit box may actively receive and respond to various feedback from sensors and controls within the laser machine (e.g., ON/OFF controls).

The phototherapy device may further include, for example, a $CO_2$ gas cooling system formed from a compressed bone dry $CO_2$ gas tank, insulated tubing with an in-line filter that transports $CO_2$ gas from an adjustable regulator mounted on the tank, and a PSI meter sensing wire from the regulator. The $CO_2$ gas cooling system may further include an in-line $CO_2$ flow meter. As such, the components of the $CO_2$ gas cooling system may also be tested before the phototherapy device is used.

The phototherapy device may further include a wire-cable harness that connects the laser machine to, for instance, the end of the handle of the transvaginal probe. In some arrangements, the wire-cable harness may include a number of electronic communication wires from the laser machine to the probe, from the laser machine to the control unit box, from a $CO_2$ tank regulator to the control unit box (e.g., in embodiments of the probe including the $CO_2$ cooling structure), from the probe to the control unit box, and from sensing lead wires connected to the probes sensors (e.g., for temperature, for $CO_2$ PSI-flow, for motion) to the control unit box. Alternatively, in some arrangements, one or more of these connections may be provided wirelessly. Further, the wire-cable harness may include low voltage electrical wires from the laser machine to the probe to supply energy to the probe (e.g., to power an LED safety alarm light, discussed below) and from the laser machine to the control unit box. Further, the wire-cable harness may include the fiber optic cable that transports the laser beam from the power plant to the transvaginal probe. Accordingly, these components and connections may further be tested before the transvaginal probe is used.

Additionally, the phototherapy device may include various safety features to help ensure safe and effective phototherapy treatment. For example, a probe may include an LED alarm light on the handle of the probe, e.g., just ahead of a thumb indentation at the 12 o'clock position. When the laser beam is turned on (e.g., via a foot pedal), this LED may automatically turn on as a green color and stay green until the laser beam is turned off (e.g., by the operator taking their foot off of the foot pedal or the probe being automatically turned off) or a warning situation is reached. When any temperature sensor (e.g., either first temperature sensor 1444a or second temperature sensor 1444b) indicates that the treatment site is reaching a warning heat level (e.g., 43° C. in the vagina), the LED may change to a flashing red light. At the same time, the control unit box may start to emit a gentle beeping sound (e.g., at the same frequency as the flashing red LED light). These two safety alerts indicate to the operator that the operator should move to a different location or quadrant, for example, within the patient's vaginal vault treatment site or take their foot off the foot pedal to stop emitting the laser beam. These alerts may automatically turn off once the temperature of the patient tissue sensed by the temperature sensors drops below the warning temperature level. However, if any temperature sensor indicates that the treatment site has reached a critical heat level (e.g., 45° C. in the vagina), the control unit may automatically turn off the laser machine, and the LED may turn to a constant, non-flashing red light. The beeping from the control unit box may also be replaced, for example, with a voice that says, "Laser off temp," or a double antique car horn sound.

In some arrangements, the probe may also include a motion sensor such that when the laser beam is on, the motion sensor is automatically turned on and when the laser beam is off, the motion sensor is automatically turned off. If, when the laser beam is on, the motion sensor does not sense back-and-forth movement for a certain amount of time (e.g., 1.25 seconds), the LED may change to a flashing green light. The control unit box may further make an alarm sound, such as sound constant, quick bursts of standard car horn sounds, until movement is again detected, at which point these alerts may stop. If the motion sensor does not detect movement for a greater amount of time (e.g., 1.75 seconds), the control unit may automatically turn the laser off. Further, the alert sound may immediately go on for a certain amount of time (e.g., for a full second) and then turn off. Once the laser is off, the motion sensor also turns off automatically, but the LED may keep flashing green until the laser beam is turned back on.

Figure 9:
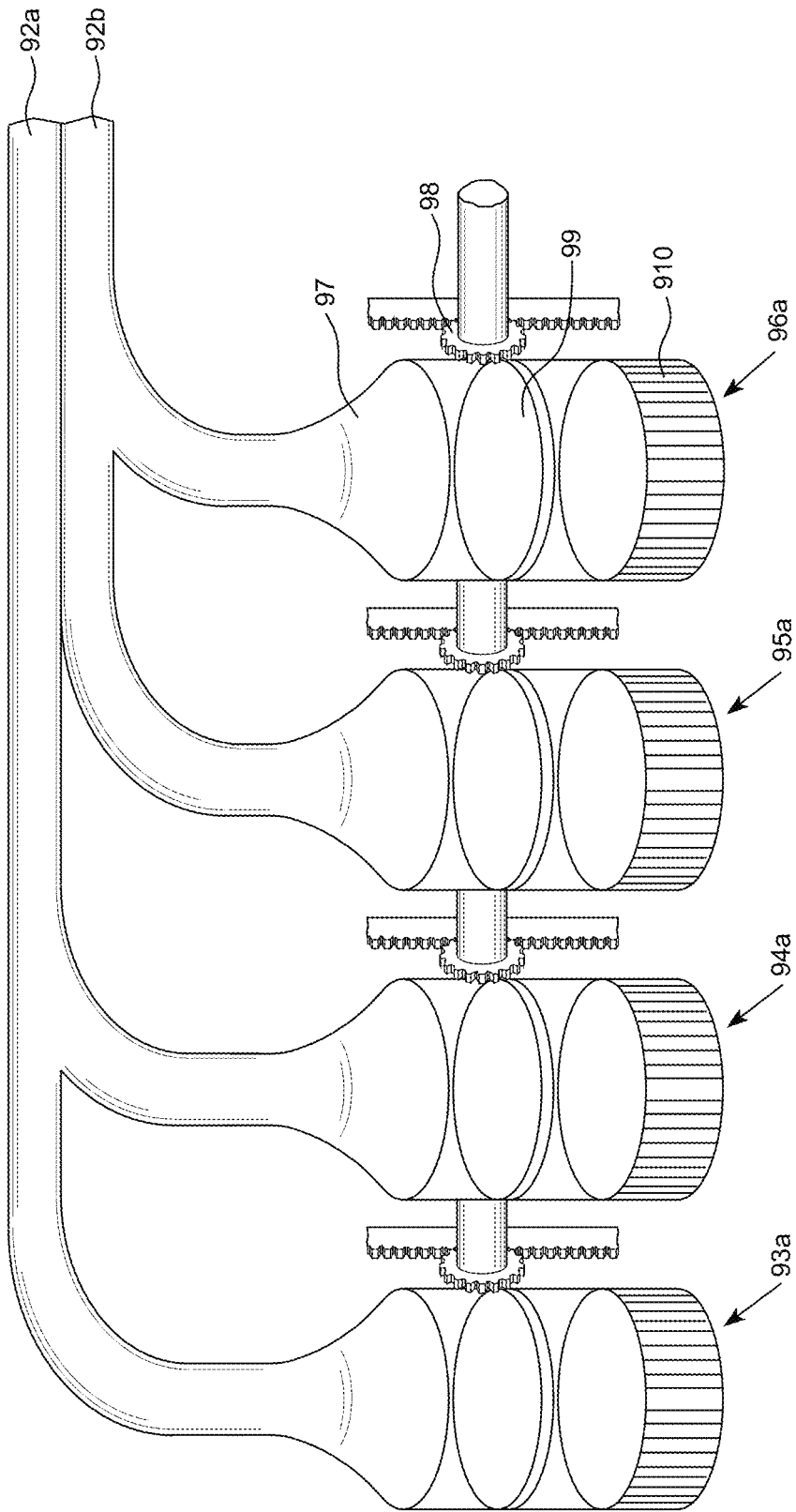
FIG. 9 depicts a perspective view of an embodiment of a coherent light emitter assembly of a phototherapy device.

FIG. 9 shows the components of one embodiment of the CLER (e.g., described above with reference to FIG. 1) in detail. First fiber optic 92a and second fiber optic 92b deliver coherent light from the CLG (not shown) to one or more of emitter assemblies 93a, 94a, 95a, and 96a. All of the emitter heads function similarly: their assembly and operation will be described in relation to emitter assembly 96a. Fiber optic 92b optically communicates with fixed diffusing lens 97. Coherent light travels from fixed diffusing lens 97 to adjustable diffusing lens 99, which can be moved toward and away from fixed diffusing lens 97 by gear assembly 98. Gear assembly 98 can be manually adjusted by the operator or adjusted by the computer control unit. Coherent light, having been diffused to the desired diameter by the diffusing lenses, travels through collimator 910, where it is collimated to the desired diameter and then directed toward the tissues to be treated. Any or all of the emitter heads can be energized at any given time, according to a treatment plan input, operator adjustment, or automatic adjustment by the computer control unit. The computer control unit can adjust the position of any individual lens or collimator with regard to any other lens or collimator, or they can be adjusted by the operator either electronically or manually. This allows the beam to be controlled to a constant diameter no matter the distance between the emitter and the patient's body and/or to allow a desired diameter of beam to be applied in any given configuration.

In some embodiments, each emitter assembly may emit only one wavelength of coherent light at a time. Additionally, in some embodiments, each emitter assembly may also have a source of visible light that is introduced into it and follows the same focal path as the coherent light, the visible light may be referred to as the "guidance light," "target light," or "safety light" (herein, "safety light"). Because the coherent light is often outside the visible spectrum (e.g., coherent light at a 1064 nm wavelength is in the near-infrared, and most human beings will not be able to see it), the use of the safety light allows the operator to see where the coherent light beam is intersecting, or will intersect, the surface of the patient's body. Safety lights can be used with any of the alternate embodiments described herein. One or more safety lights can also be used as an illumination source to assist optical or spectroscopic sensor analysis as described above. Alternatively, a coherent light beam that is in the visible spectrum may be its own safety light.

As an example, if emitter assembly 93a is emitting coherent light at 808 nm, emitter assembly 94a is emitting coherent light at 905 nm, and emitter assembly 95a is emitting coherent light at 980 nm, a blue safety light at 440 nm could be introduced into emitter assembly 93a, a green safety light at 540 nm could be introduced into emitter assembly 94a, and a red safety light at 700 nm could be introduced into emitter assembly 95a. The safety light beams may have similar initial diameters and follow the same optical paths as the corresponding coherent light beams so that the areas they illuminate will be as close as reasonably possible to the area of incidence of the corresponding coherent light beams. Because different wavelengths of light are affected differently by optical components, if it is required that the illuminated areas be exactly the same for a safety light beam and the corresponding coherent light beam, the safety light beam may either travel a different optical path or be of a slightly different initial diameter than the corresponding coherent light beam. If it is required that the illuminated areas be exactly the same at all focal lengths, they may travel a different optical path that will dynamically compensate for the different effects of optical components on the safety light beam and the coherent light beam.

There are no preferred associations of visible light wavelengths to coherent light wavelengths, though in some embodiments, the safety lights may follow the same relative length order as in the corresponding coherent light wavelengths (i.e., the shortest wavelength of coherent light used is associated with the shortest wavelength of visible light being used.) However, in various embodiments, the operator may have the ability to manually change the visible light wavelength associated with any given coherent light wavelength so that if one or more visible light wavelengths are not suitable in any given phototherapy session (e.g., one or more of the visible light wavelengths are particularly hard to see against the patient's particular skin tone), a more suitable one may be used.

Figure 10:
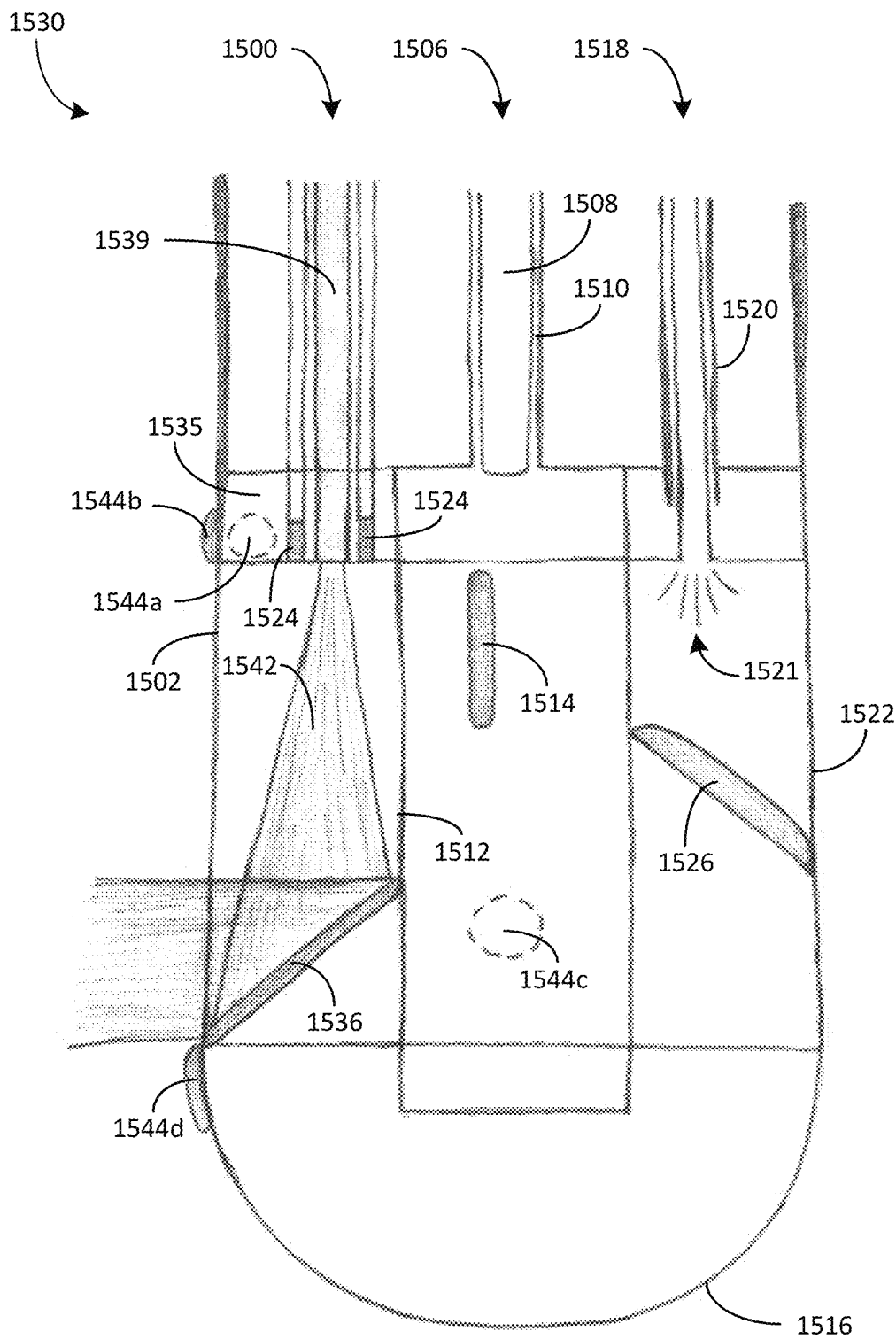
FIG. 10 depicts a cross-sectional view of another embodiment of a probe of a phototherapy device in use with an endoscope.

As an example of a phototherapy device incorporating various systems and components discussed above, including a probe, an endoscope, and a cooling system, FIG. 10 shows another alternate embodiment of a probe configured to be attached or connected to the end of a flexible EGD endoscope. Probe 1530 includes three sections. First section 1500 is similar to the probes described above. More specifically, first section 1500 houses fiber optic cable 1539 that connects to diffusing chamber 1502 (e.g., containing one or more diffusing elements, such as diffusing lenses or diffusing mirrors at or near interface 1535 between fiber optic cable 1539 and diffusing chamber 1502, or containing no optical elements). The interior of interface 1535 between fiber optic cable 1539 and diffusing chamber 1502 may include one more temperature sensors, such as temperature sensor 1544a, to monitor the temperature of the fiber optic connection. Additionally, the exterior of interface 1535 may include a secondary temperature sensor, such as temperature sensor 1544b, to monitor the temperature of the mucosa of the treatment site. As shown in FIG. 10, coherent light travels through diffusing chamber 1502 until it reaches flat mirror 1536 at the end of diffusing chamber 1502 that angles light beam 1542 (e.g., 45 degrees) out through diffusing chamber 1502. In some arrangements, diffusing chamber 1502 is transparent, or may include an optical component, such that light beam 1542 may be emitted through diffusing chamber 1502. In other arrangements, diffusing chamber 1502 may instead include a portal at the end of the diffusing chamber through which the coherent may be emitted to the target treatment site.

Second section 1506 is provided next to first section 1500 and is configured to receive EGD endoscope 1508. Specifically, the second section is configured to receive or include instrument channel 1510 for EGD endoscope 1508. A cable of EGD endoscope 1508 that may be rotated slowly (1) by an external motor, (2) by incoming cooling media pressure-flow from a third section, discussed further below (e.g., such that the rate or volume of flow of the media could be adjusted to set the rate of rotation), or (3) manually as the operator pulls EGD endoscope 1508. Instrument channel 1510 connects to mirror turbine 1512 provided parallel to diffusing chamber 1502 of first section 1500. Mirror turbine 1512 includes highly convex mirror 1514. Further, the end of mirror turbine 1512 connects to dome 1516 (e.g., similar to the convex diffusing dome lenses described above, or configured as a transparent glass or acrylic dome). Temperature sensor 1544c may be provided in mirror turbine 1512 to monitor the inside of mirror turbine 1512 and monitor the inside of dome 1516. Additionally, another temperature sensor 1544d may be provided on the outside of dome 1516 near mirror 1536 of first section 1500 to monitor the mucosal surfaces e.g., mucosal surfaces of the gastrointestinal tract) of the target treatment site receiving PBMT.

Third section 1518 is provided on the other side of second section 1506 (e.g., such that first section 1500 and third section 1518 are opposite each other across second section 1506). Third section 1518 is configured to includes irrigation (e.g., cooling) channel 1520 for EGD endoscope 1508, which may be formed of insulated stainless steel. Channel 1520 connects to tube 1522 provided parallel to mirror turbine 1512 and diffusing chamber 1502. Cooling media 1521 is received in tube 1522. Further, tube 1522 is connected to diffusing chamber 1502 via mirror turbine 1512 such that cooling media 1521 flows into tube 1522, through mirror turbine 1512, and into diffusing chamber 1502. First section 1500 is provided with one or more suction channels 1524 parallel to fiber optic cable 1539 that then suck cooling media 1521 out of diffusing chamber 1502 and back to the source. Tube 1522 may further contain convex mirror 1526 such that the degree of beam divergence coming out of first section 1500 is the same as mirror 1536 of first section 1500.

In some arrangements, probe 1530 may be provided as one piece (e.g., configured to receive a fiber optic cable and an EGD endoscope). In other arrangements, at least some sections of probe 1530 may be separable from each other (e.g., interface 1535 may serve as the connection apparatus between a section for an EGD endoscope and a section for a fiber optic cable).

Figure 11:
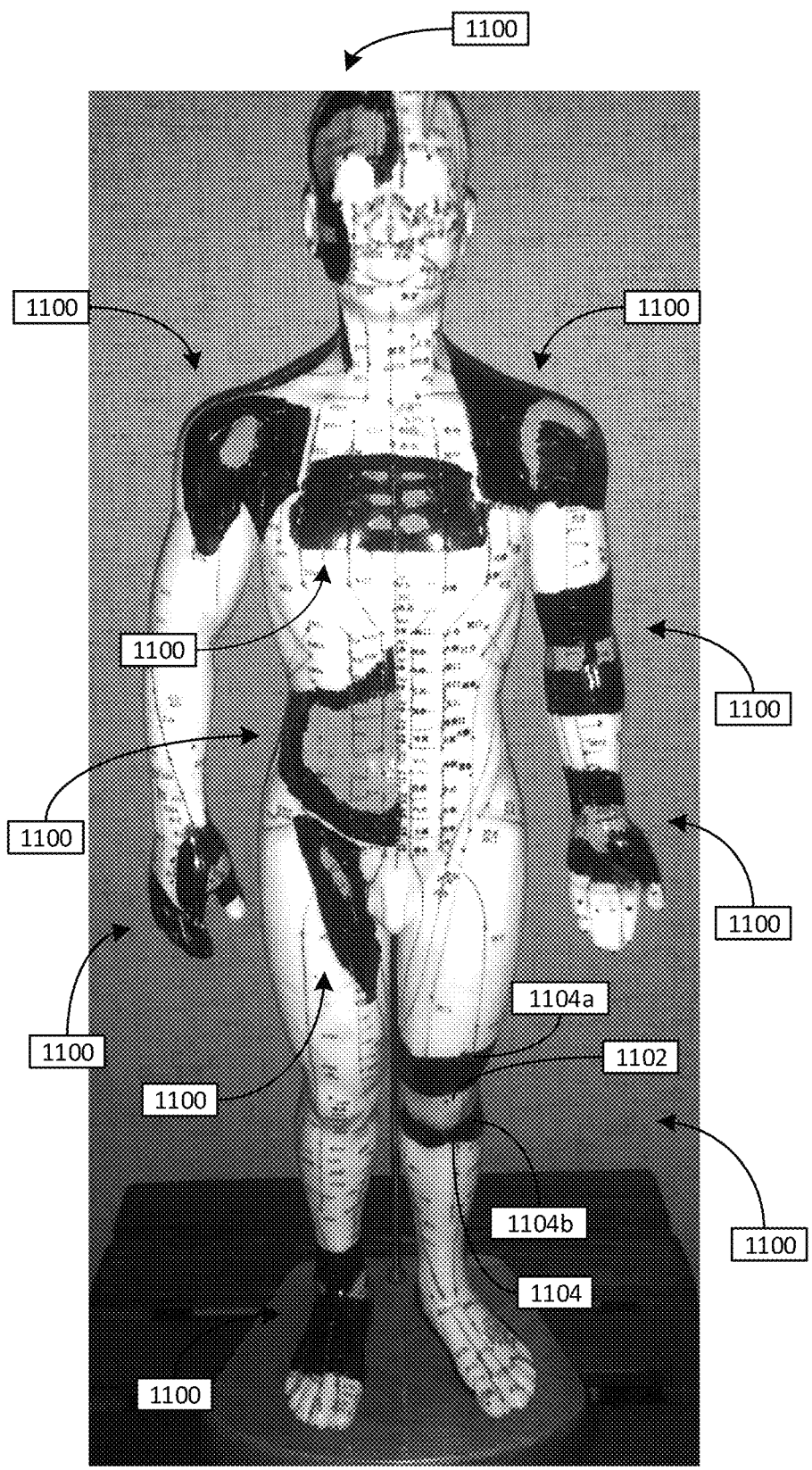
FIG. 11 depicts a front view of a first patient including example treatment areas.
Figure 12:
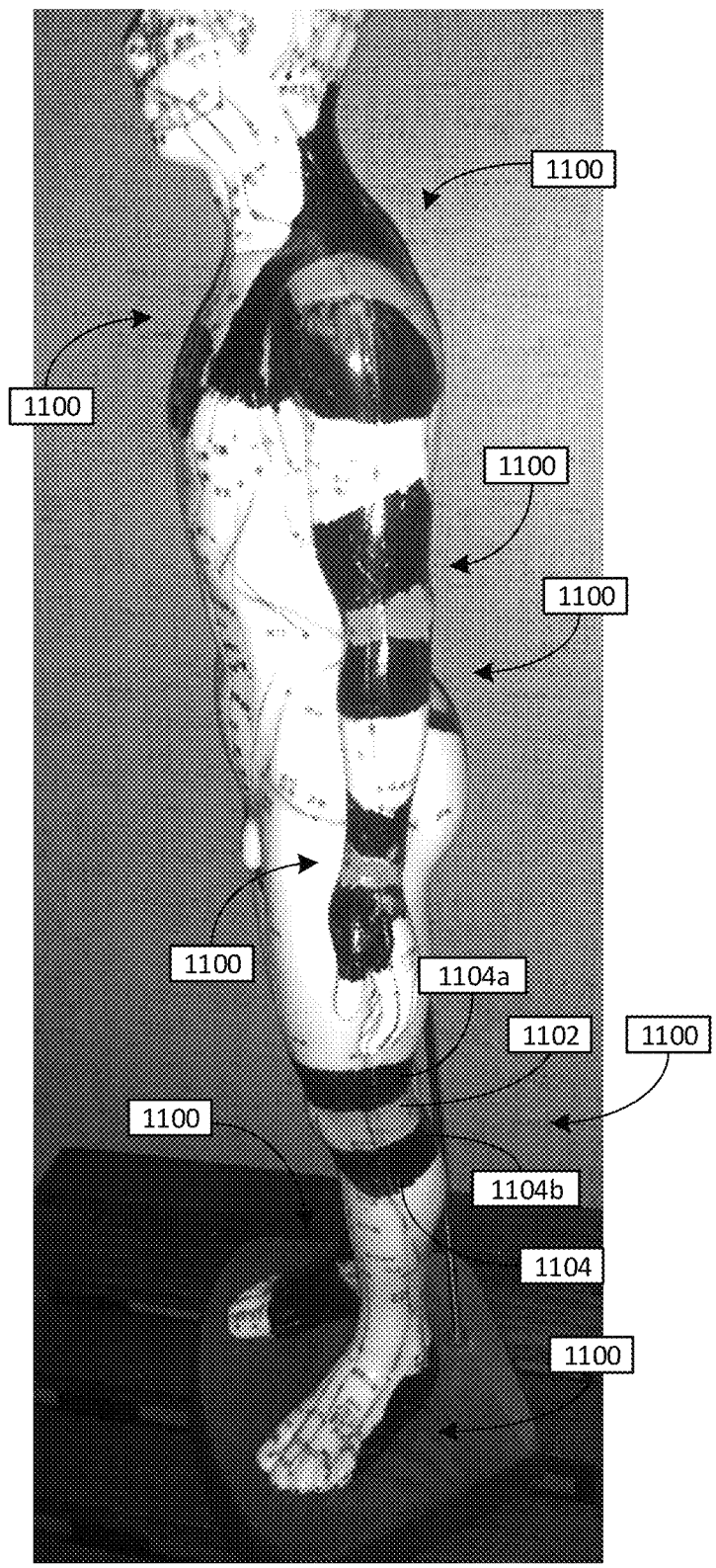
FIG. 12 depicts a side view of the patient of FIG. 11 including example treatment areas.
Figure 13:
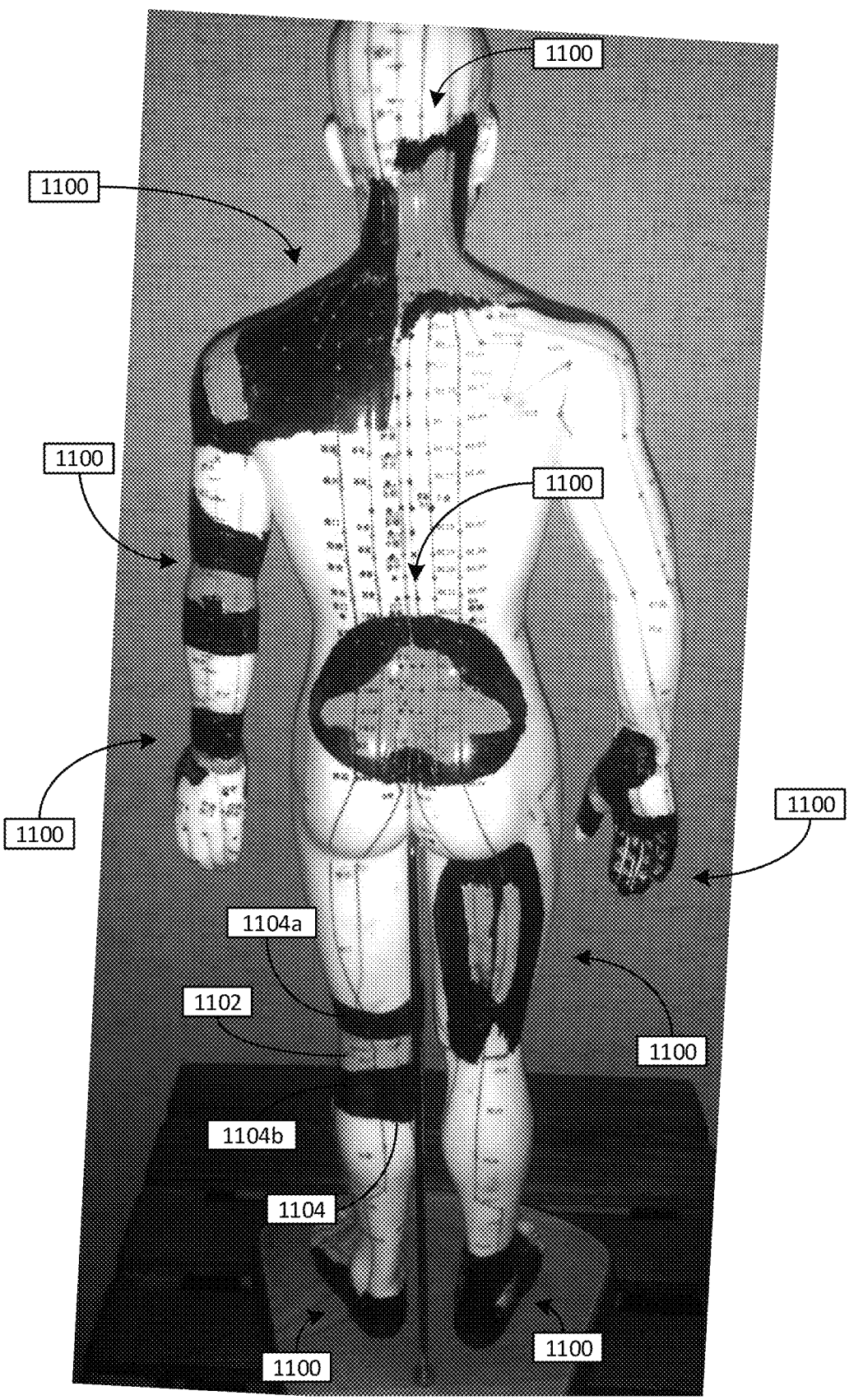
FIG. 13 depicts a back view of the patient of FIG. 11 including example treatment areas.
Figure 14:
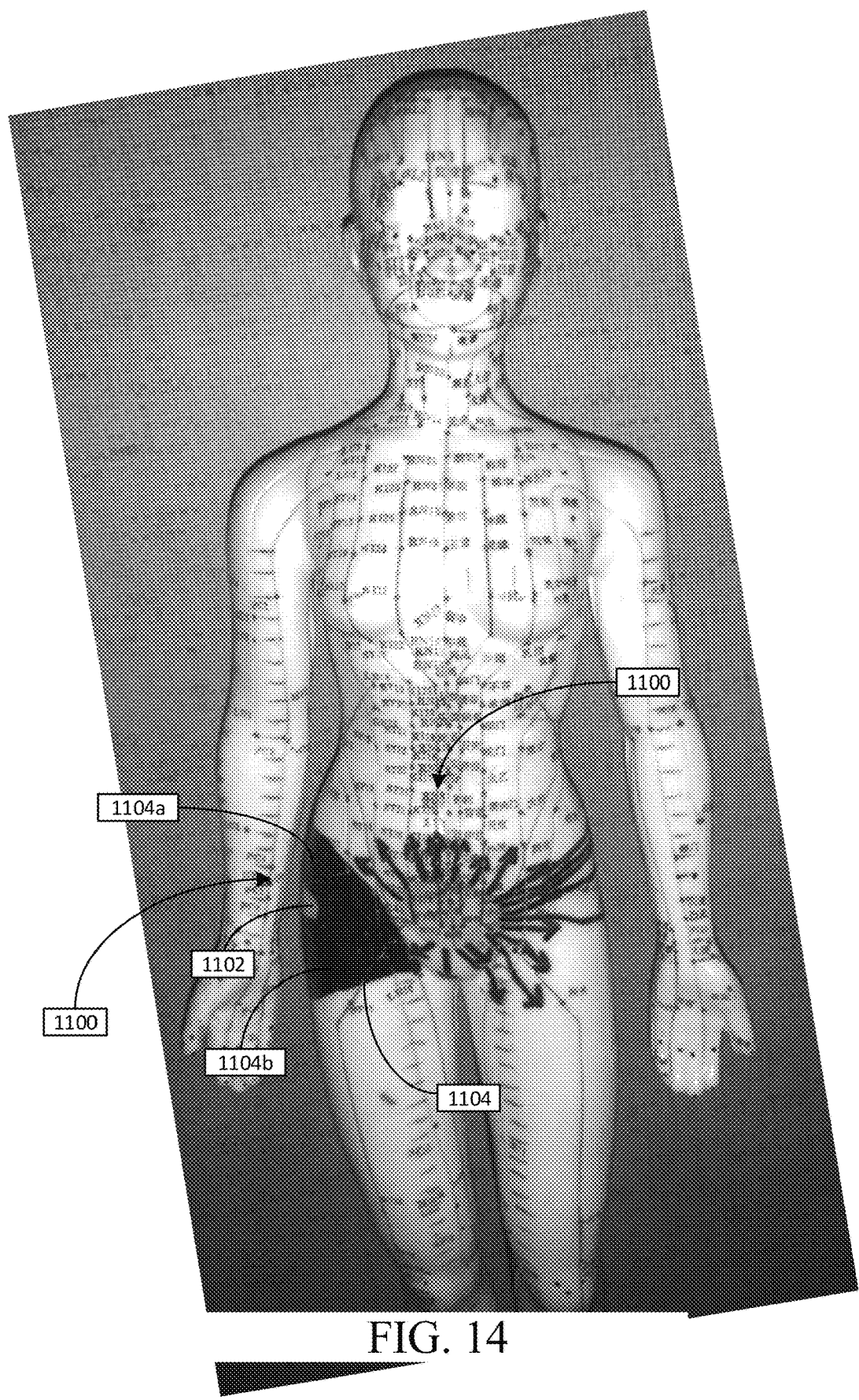
FIG. 14 depicts a front view of on a second patient including example treatment areas.
Figure 15:
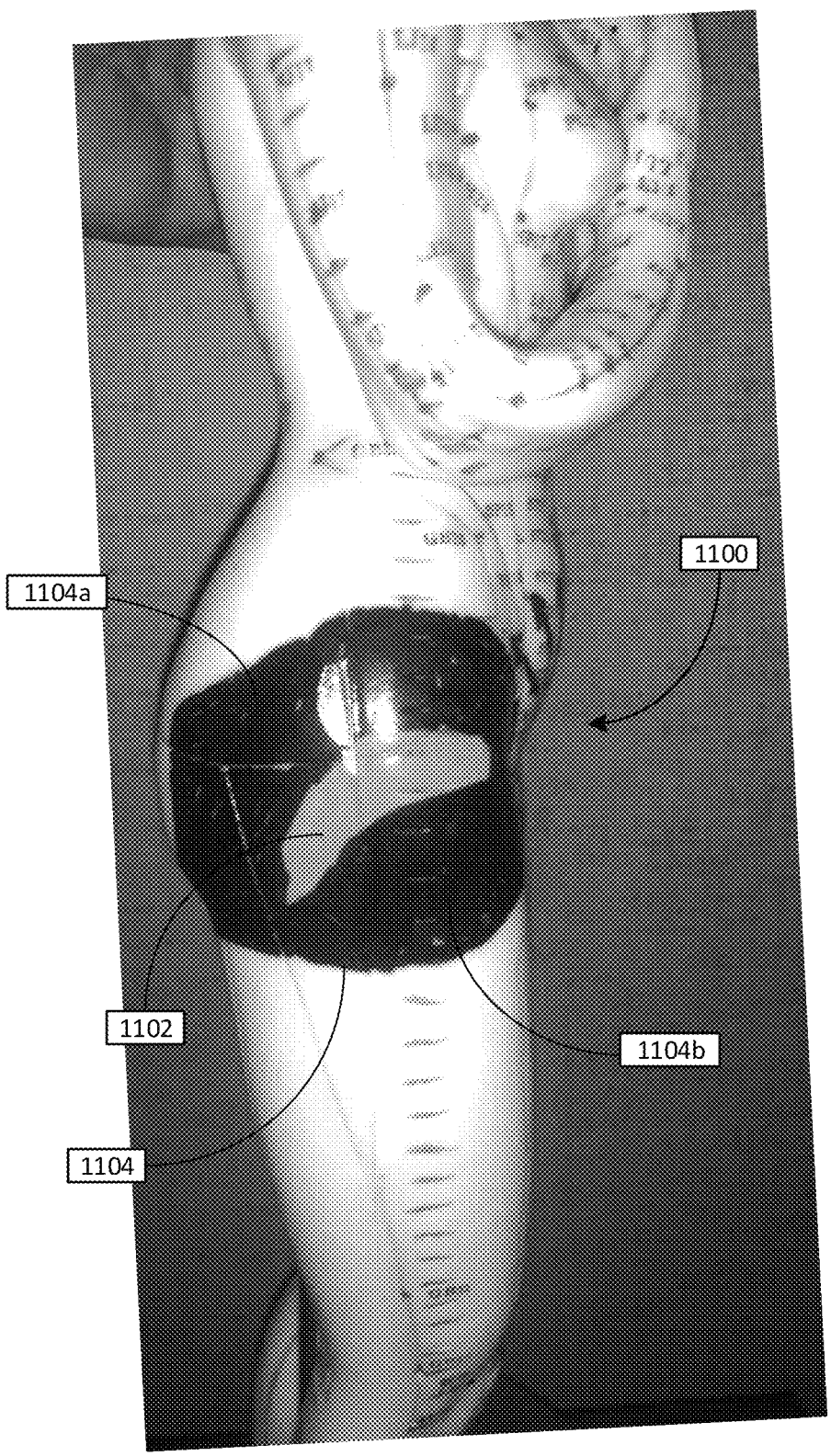
FIG. 15 depicts a side view of the patient of FIG. 14 including example treatment areas.
Figure 16:
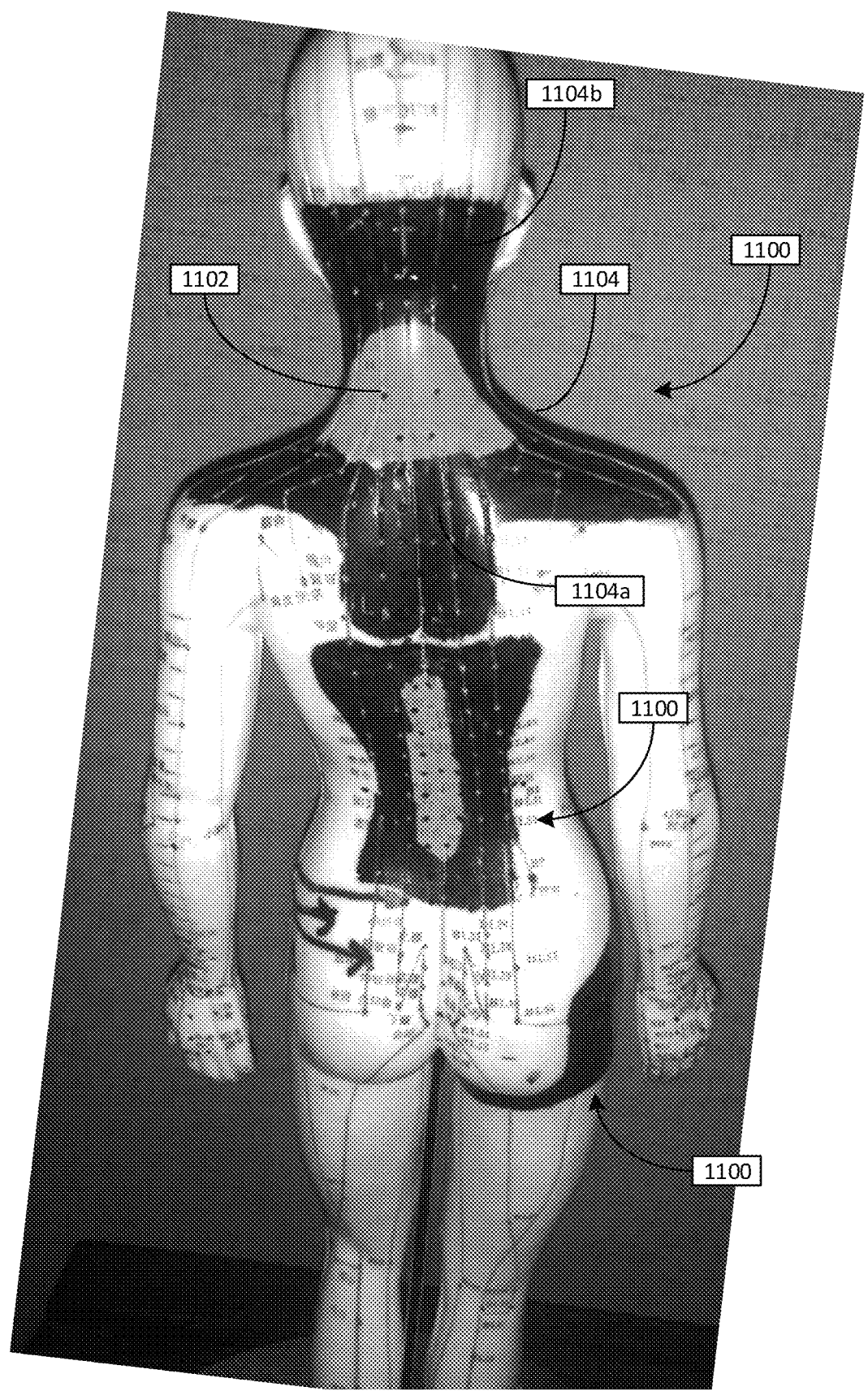
FIG. 16 depicts a back view of the patient of FIG. 14 including example treatment areas.

FIGS. 11-13 show example areas on a first patient that may be treated using the phototherapy device embodiments discussed above. FIGS. 14-16 show different or additional example areas on a second patient (e.g., based on the gender of the second patient) that may be treated using the phototherapy device embodiments discussed above. Each of these areas represents an expanded therapeutic treatment area ("ETTA") 1100, which may be one of the targeted treatment sites discussed herein. Each ETTA 1100 includes a primary treatment zone ("PTZ") 1102 and a secondary treatment zone 1104. Further, each secondary treatment zone may be divided into a proximal secondary treatment zone ("PSTZ") 1104a, or the section of the secondary treatment zone that is closest to the heart, and a distal secondary treatment zone ("DSTZ") 1104b, or the section of the secondary treatment zone that furthest from the heart. When therapy is delivered to the patient using a phototherapy device, the therapy is provided first to the PTZ 1102 and then to the PSTZ 1104a and the DSTZ 1104b. In some embodiments, the therapy delivered to the PTZ 1102 may also differ from the therapy delivered to the PSTZ 1104a and the DSTZ 1104b (e.g., the photons may be delivered at a higher energy to the PTZ 1102), or the therapy between all three zones may differ.

Using an arthritic knee as an example, during a treatment session, photons may be administered to the skin surface into soft tissues into the knee joint, 3 to 4 cm below the joint, and 3 to 4 cm above the joint, with this area representing the PTZ 1102. In addition, the inflamed and in-spasm muscles and ligaments 5 to 12 cm above and below the joint may also receive therapeutic photons during a treatment session. Expanding the treatment area in this way may result in a better and longer-lasting therapeutic response through the delivery of more photons into the tissues, triggering the creation of non-cellular ATP energy, which is a primary and essential ingredient that the body needs to help tissues heal. Additionally, this expanded targeted treatment site may suppress more areas and spots of inflammation and may improve the degree or level of symptom reduction, thereby increasing the positive response to the phototherapy.

Figure 17:
FIG. 17 depicts a side view of a treatment cylinder portion of a phototherapy device in use.
Figure 18:
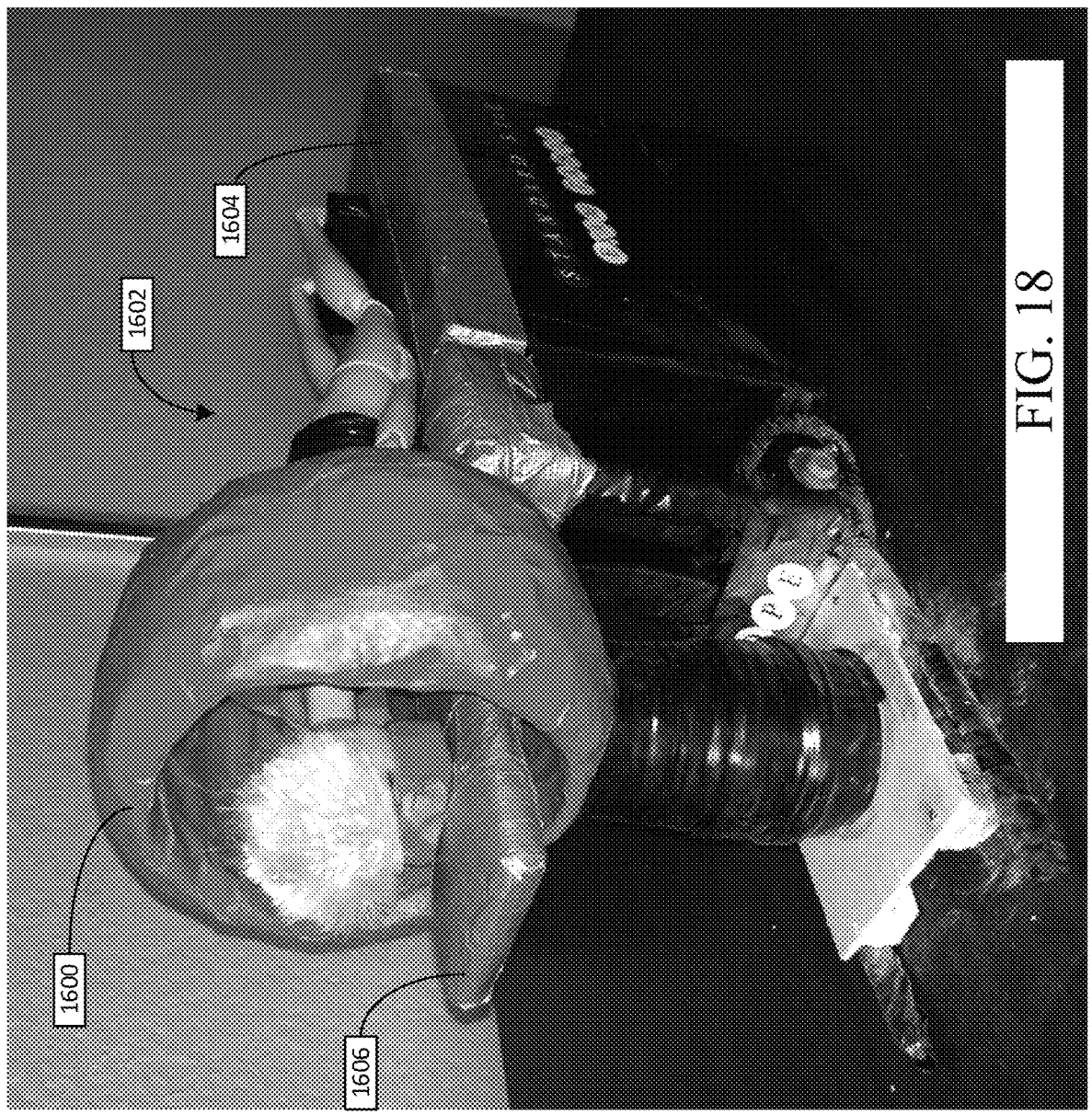
FIG. 18 depicts a side perspective view of the treatment cylinder portion of FIG. 17 in use.

The phototherapy device embodiments may be used in any medically safe and practical way to provide therapy to the targeted treatment sites, such as ETTA 1100 shown in FIGS. 11-16. For example, the phototherapy device may be used as shown in FIGS. 17 and 18. As illustrated in FIG. 17, treatment cylinder 1600 may be used to provide phototherapy to lower back and hip areas of patient 1602. These areas are treated by having patient 1602 lie face down on medical exam table 1604. The patient may rest their head on or into a pillow. The additionally, the patient's pelvic area may be positioned on secondary exam table 1606, which includes a narrower top end such that treatment cylinder 1600 can be placed around secondary exam table 1606 and the patient's lower back and hip areas. The patient's legs may be rested on medical exam table 1604 or secondary exam table 1606 (depending on which direction patient 1602 is facing) or, if medical exam table 1604 and secondary exam table 1606 are not long enough, on another exam table or support. The patient may also be propped with other pillows, such as a pillow provided under the patient's feet, to move the patient into a comfortable position and/or a position that best exposes the targeted treatment site.

As illustrated in FIG. 18, the patient's posterior neck, upper back, and/or posterior-lateral shoulders may also be treated by having patient 1602 lie down face first on medical exam table 1604. Patient 1602 may rest their head on or into a pillow configured to receive the patient's face. Additionally, the pillow may be provided on secondary exam table 1606 with a narrower top end such that treatment cylinder 1600 can be placed around secondary exam table 1606 and the patient's posterior neck, upper back, and/or posterior-lateral shoulders that are exposed by patient 1602 lying down on medical exam table 1604 and secondary exam table 1606. Patient 1602 may also be propped with other pillows, such as a pillow provided under the patient's feet, to move patient 1602 into a comfortable position and/or a position that best exposes the targeted treatment site. A similar position may be used to administer therapy via treatment cylinder 1600 onto the upper and/or mid back and onto and/or into the upper and/or lower chest areas, except that the patient's chest may be provided on the narrow portion of the secondary exam table such that the treatment cylinder can be placed around these back and chest areas.

However, it should be understood that the phototherapy device embodiments described herein may be used to provide phototherapy to a number of portions of patient anatomy. In one example, the patient's knee is treated by having the patient lie down on a medical exam table and place their leg through the treatment cylinder such that the treatment cylinder can target phototherapy to the knee. The patient may be provided with a secondary exam table or support for resting their other leg and feet. Additionally, the patient's leg being treated may be propped up with a pillow as needed to ensure that the patient's knee is in an optimal location within the treatment cylinder.

In another example, the patient's face, forehead, jaw, front of neck, ears, and/or side of head are treated by having the patient lie down on a medical exam table. The patient's head may be positioned on a secondary exam table with a narrower top end such that the treatment cylinder can be placed around the secondary exam table and the patient's head. Additionally, the patient may be propped with pillows, such as a pillow under the patient's head and a pillow under the patient's knees, to move the patient into a comfortable position and/or a position that best exposes the targeted treatment site.

In another example, the patient's lower torso is treated by having the patient stand and placing a treatment globe over the patient's lower torso such that the patient's legs extend below a lower opening of the treatment globe and the patients head and upper torso extend above an upper opening of the treatment globe. A similar procedure may be used to treat the patient's upper torso by having the patient stand or kneel and placing a treatment globe over the patient's lower torso. The gap between the upper opening and the patient's anatomy may be covered with a cap or other covering to prevent photons from escaping from the treatment globe.

In another example, the patient's arm is treated by having the patient sit and placing a treatment globe over the patient's arm. A cap or other covering may be placed between the opening(s) through which the patient's arm is inserted and the patient's anatomy to prevent photons from escaping from the treatment globe. A cap or other covering may also be placed over the entirety of the opening opposite from where the patient's arm is inserted if the patient's arm does not extend through the treatment globe (e.g., the patient's arm is contained entirely within the treatment globe).

Figure 20:
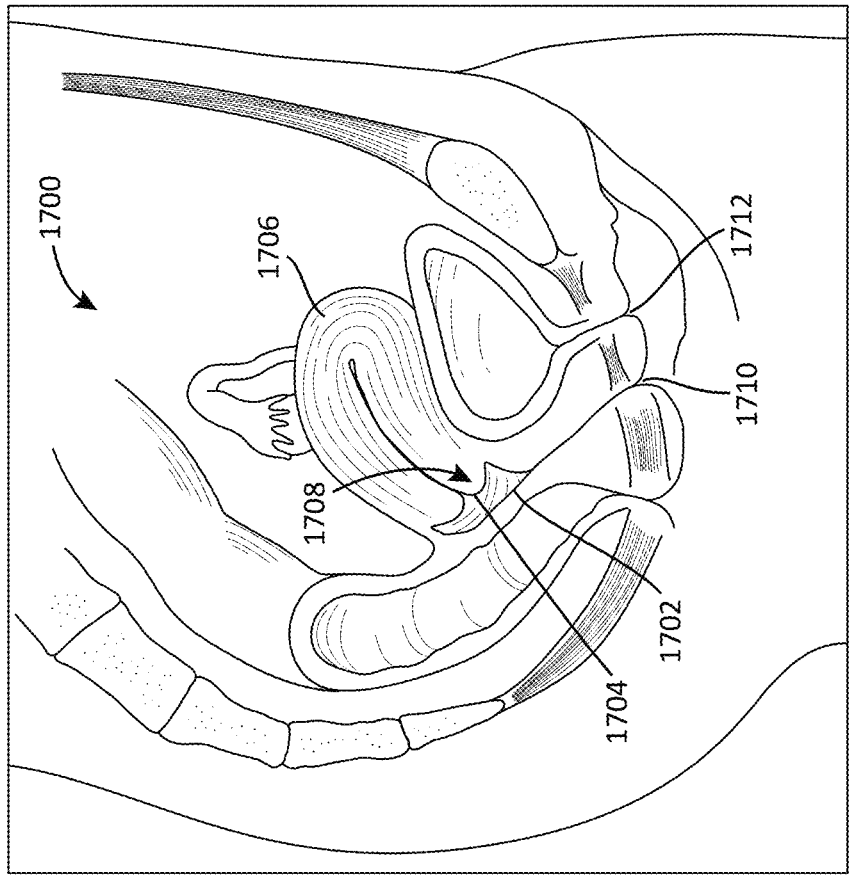
FIG. 20 depicts a front view of the treatment area of FIG. 19 with respect to the pelvic region of the female patient.
Figure 19:
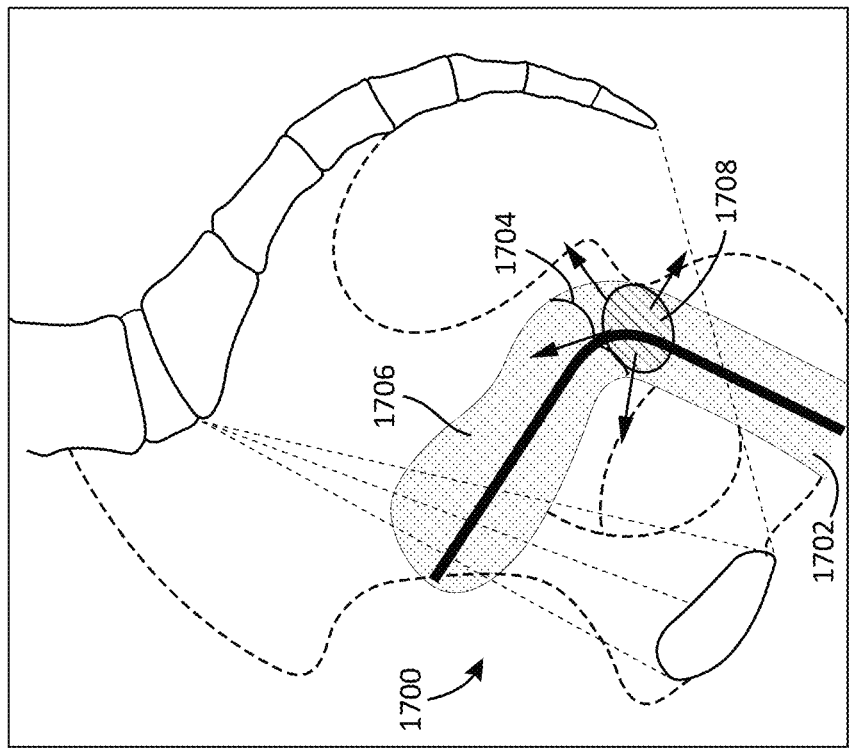
FIG. 19 depicts a side view of a treatment area with respect to a pelvic region of a female patient.
Figure 21:
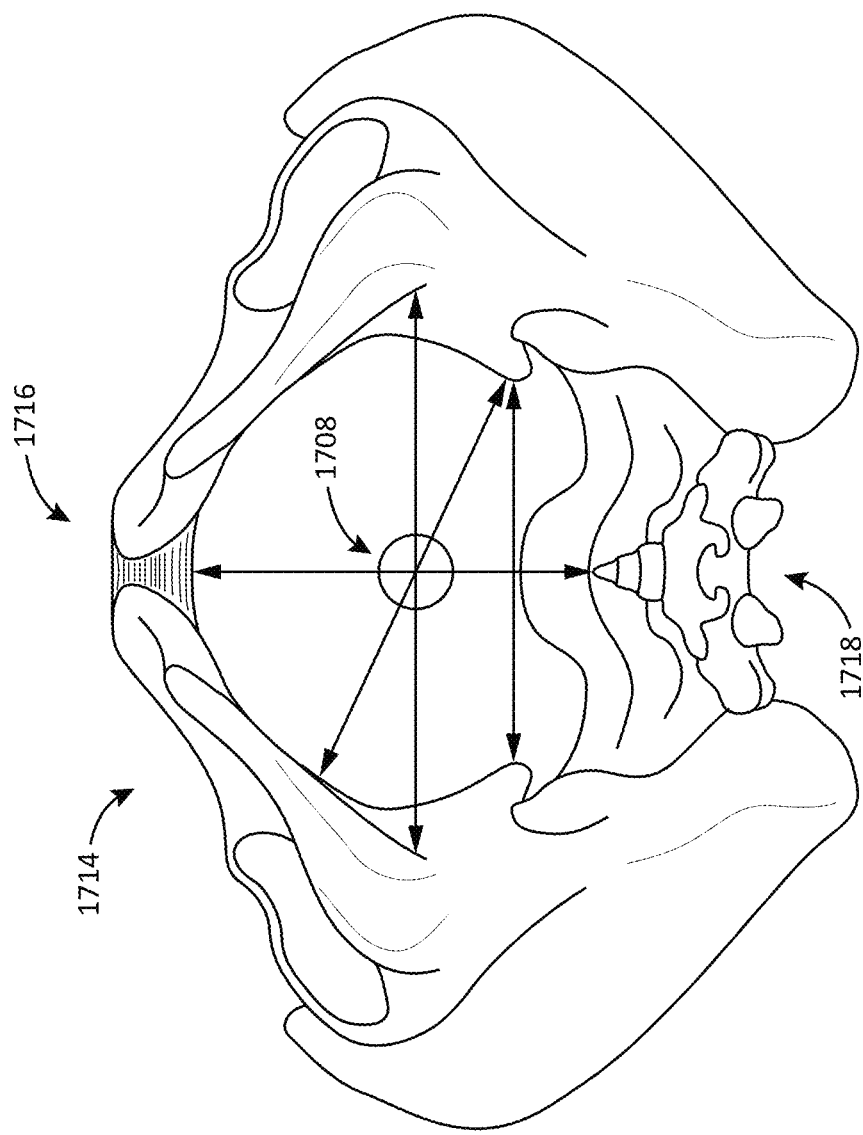
FIG. 21 depicts a top view of the treatment area of FIG. 19 with respect to pelvic bones of the female patient.

Additionally, FIGS. 19-21 illustrate areas of a female patient's anatomy that may be treated using a probe embodiment, such as any of the probe embodiments described above. Referring to FIG. 19 (which shows female anatomy from the side) and FIG. 20 (which shows female anatomy from the front), pelvic region 1700 of a female patient includes vagina 1702, cervix 1704, and uterus 1706. With reference to FIG. 20, vaginal opening 1710 and urethral opening 1712 may also be observed. In various arrangements, a probe may be inserted into vagina 1702 until the tip is in area 1708 near cervix 1704. If the probe is being used to deliver phototherapy to deep pelvic structures, the operator may manipulate the probe within vagina 1702 such that the probe moves the vaginal wall anteriorly, posteriorly, laterally to the right, and laterally to the left (e.g., 2.0-2.5 cm in any of these directions) to better position the probe to deliver therapy to the pelvic structures. In this way, phototherapy may be delivered to various pelvic structures (e.g., through the vaginal wall, which may be approximately 0.3 to 0.5 cm, the rectal wall, which may be approximately 0.3 cm, and/or the bladder wall, which may be 0.3 to 0.35 cm). Similarly, FIG. 21 shows pelvic bones 1714 with anterior side 1716 (e.g., leading to the pubic arch) and posterior side 1718 (e.g., leading to the coccyx). Treatment area 1708 with respect to pelvic bones 1714 is accordingly also shown in FIG. 21.

Figure 23:
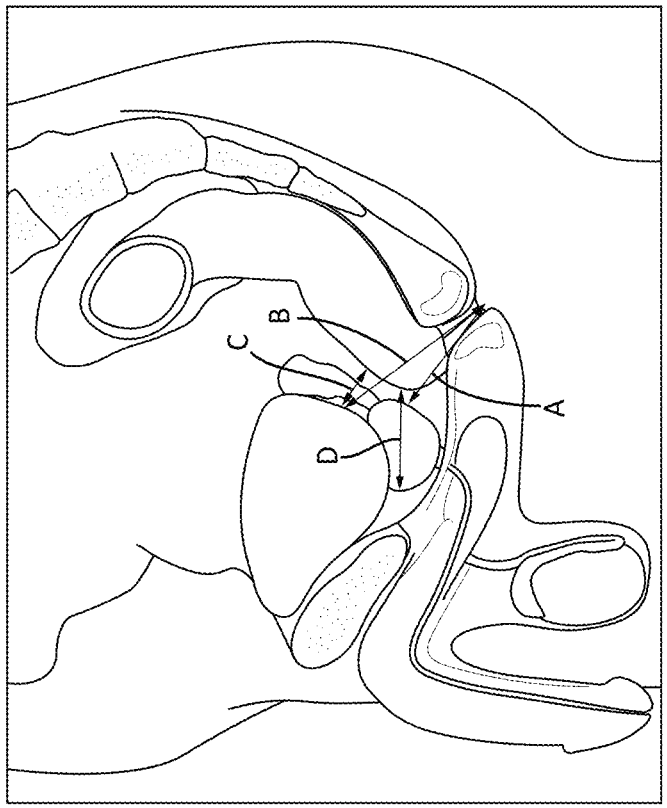
FIG. 23 depicts a side view of pelvic structures of a male patient.
Figure 22:
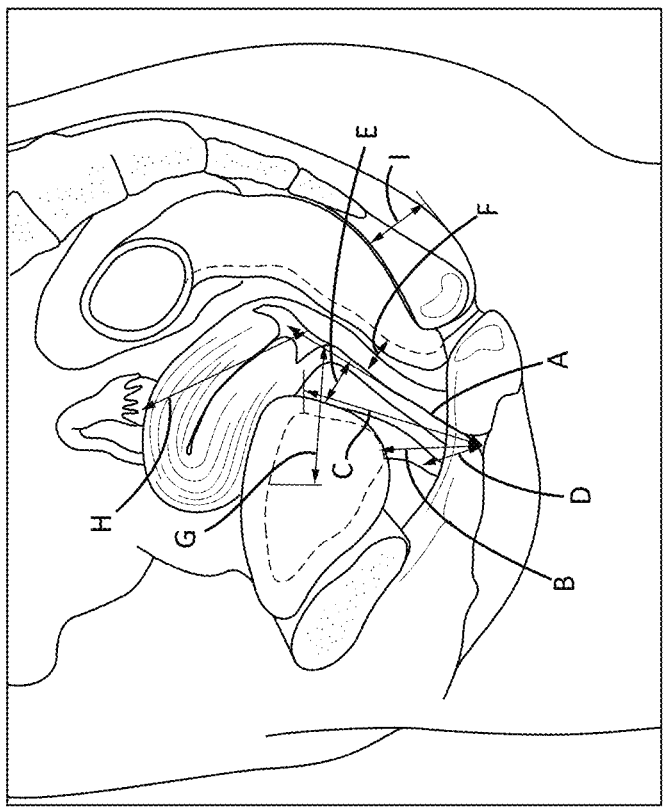
FIG. 22 depicts a side view of pelvic structures of a female patient.

For reference, FIG. 22 illustrates distances between various pelvic structures of a female patient, and FIG. 23 illustrates distances between various pelvic structures of a male patient. Referring first to FIG. 22, in various female patients, distance A between the vaginal opening (introitus) to the cervix or area deep within the vaginal vault (e.g., where a probe tip may be placed during PBMT treatments to deep pelvic organs) may be 8.5 cm±2.0 cm. Distance B from the introitus to the bladder wall base may be 3.7 cm±1.5 cm. Distance C from the introitus to the bladder wall base may be 6.5 cm. Distance d from the introitus to the urethral walls may be 2.4 cm±2.0 cm. Distance E, which represents the thickness between the anterior vaginal mucosal wall to the bladder wall base and to the urethral walls, may be 1.1 cm. Distance F, which may represent the thickness between the posterior vaginal mucosal wall and the rectal wall-rectal mucosa, may be 1.1 cm. Distance g from the anterior vaginal mucosal to the mid-bladder or to anterior bladder wall (e.g., representing the thickness of the soft tissues) may be 2.0 to 4.6 cm. Distance H from the deepest depth of the bladder wall to the ovaries and fallopian tubes and uterine fundus (e.g., representing the thickness of the soft tissues) may be 6.9 cm±3.0 cm. Distance I between the vaginal introitus to the level of pelvic floor muscles may be 2.3 to 3.0 cm.

Referring next to FIG. 23, in various male patients, distance A from the anal external opening to the leading edge of the prostate gland may be 4.3 cm. Distance B from the anal external opening to the bladder wall base may be 6.2 cm. Distance C from the rectal mucosal wall to the leading edge of the bladder wall base may be 1.7 cm. Distance d, which represents the thickness between the rectal mucosal wall to the top edge of the prostate gland, may be 3.0 cm. Distance E, which represents the thickness from the rectal mucosal wall to the leading edge of the prostate gland, may be 0.6 cm.

Figure 24:
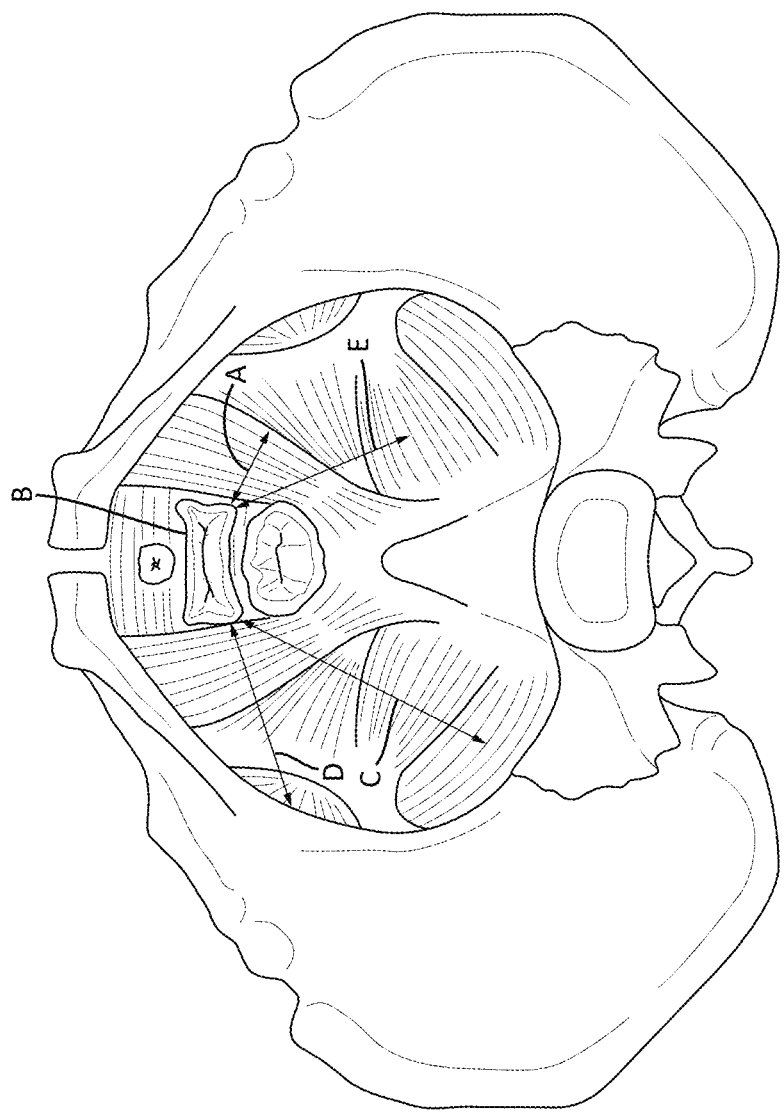
FIG. 24 depicts a top view of pelvic structures of a female patient.

FIG. 24 also illustrates distances between various pelvic structures of a female patient with reference to bone and muscle. As such, in various female patients, Distance A from the vaginal mucosal surface laterally to the deepest edge of the deepest edge of the levator ani muscle and to the obturator muscles that are higher into the pelvis and next to or lateral to the vaginal walls may be 1.8 cm. Distance B from the lateral vaginal mucosa to the leading edge of the levator ani muscle and to the obturator muscle may be 0.7 to 1.0 cm. Distance C from the lateral vaginal mucosa to the piriformis muscle may be 6.5 cm. Distance e from the vaginal mucosa to the obturator internus may be 4.6 cm. Distance E from the vaginal mucosa to the coccygeus muscle may be 4.0 to 5.0 cm. These pelvic for muscles may also be approximately 2.3 to 3.0 cm deep into the pelvis or beyond the vaginal opening (introitus) and beyond the level of the anal opening.

Examples of the Phototherapy Device

Example One. An example of the phototherapy device may be used in treating conditions such as chronic inflammatory prostatitis or interstitial cystitis (e.g., painful bladder and/or irritable bladder muscle). The phototherapy device may include a probe, and the probe could be connected to a handle attached to a rigid or flexible endoscope. The device, the endoscope plus the probe, could be programmed by the user or automatically given the patient's data (e.g., heart rate, blood circulation, etc.). The probe could then be inserted in the lower or upper rectum to treat proctitis or higher into the colon to the sigmoid colon to treat inflammatory diverticulitis or Crohn's Disease and/or ulcerative colitis. The placement of the probe could be performed by a human operator or a robotic operator, as described above.

Adjustments could be made for proper position on all axis and/or vector planes. The pulse of the light could be programmed to provide 1 pulse per 1 picosecond to 1 pulse per 10 minutes, and the time-of-light emission could be set anywhere from 0.01 microsecond to 12 minutes. For example, different pulses could be used to allow for different levels of tissue relaxation, allowing the phototherapy device to administer higher levels of energy without causing tissue damage or tissue overheating. Additionally, the wavelength range for the photobiomodulation therapy could range from near-infrared to far infrared.

The light could then be emitted through portals at the tip of the probe (e.g., on the end or the sides of the probe), as discussed above with reference to FIGS. 8-8E. Direct illumination could be delivered using LEDs, diodes, or other energy-emitting techniques. Optical elements in the probe could change the profile, shape, diffusion, and frequency the beam to tailor the light administered to the patient. The width of the beam could be 0.1 cm to 5 cm. The probe could also be tracked (e.g., by GPS) prior to, during and post treatment to aide in delivering the therapy to specific location(s).

Example Two. An example of the phototherapy device may be used in transpharyngeal phototherapy delivery. This embodiment could be a probe that is inserted into the oral cavity and further into oral-pharyngeal cavity. The probe could be a straight or angled-end probe such that the emitted beam of light is a diffused-beam laser beam that is targeted toward and/or in direct contact with the pharyngeal mucosal surfaces, as well as targeted toward and/or onto the epiglottis to treat acute or chronic epiglottis and/or into the laryngeal orifice to treat diseases like laryngitis. The administered photons from this transphynygeal probe could be directed upward and outward toward the face's cheeks and the undersides of the maxillary sinuses. The delivered photons could also be configured as one or more diffused-beam laser wavelengths for treating diseases like chronic maxillary sinusitis. Further, the administered photons could be directed upward and inward toward the front base of the cranial cavity where the base areas of the frontal lobes of the brain exist and where diseased CNS states like depression, anxiety, concussions, and strokes can originate or arise.

In some embodiments, this transpharyngeal probe's phototherapy (e.g., PBMT) could replace some surgical interventions, chronic antibiotic therapy and/or steroid therapy. Moreover, this transpharyngeal probe could be use as stand-alone therapy or in conjunction with other known therapies. The probe could also be used in conjunction with the same or similar phototherapy delivered or administered via the rotational treatment cylinder transcutaneously.

Furthermore, in some embodiments, the administered photons could be directed more posteriorly and upward or directly to the back of the pharynx or pharyngeal pharynx and onto the upper brainstem, the mid brainstem, and the lower brainstem and the upper spinal column. Delivering phototherapy via this transpharyngeal probe to the brainstem's sleep center or into a brainstem that has suffered a contusion or concussion injury may be more successful in delivering more amounts of photons into these CNS tissues than delivering phototherapy via further-away emitting photon sources (e.g., devices like a transcranially or topically applied low level laser therapy through the forehead's skin and frontal bone's skull bone areas).

This transpharyngeal probe could be connected to a handle or attached to a rigid or flexible endoscope. The device, the endoscope plus probe, could then be manually or automatically programmed upon being given the patient's data (e.g., heart rate, blood circulation, disease state(s), etc.). The probe could be manually inserted and strategically placed into oral cavity and onto surfaces of the pharyngeal pharynx. The actual pointing toward or the positioning of the probe to deliver the emitting photons toward specifics structures, and/or even intracranial structures, could be performed by a human operator or robotic-controlled operator, as discussed above. Further positioning of the probe and refined targeting of tissues could be adjusted on all axis and/or vector planes and coordinates with the guidance of an MRI-interfacing system, ultrasound interfacing guidance, and even by other x-ray guidance-targeting systems like fluoroscopy and/or CT-scanning systems.

The pulse of the light-photons could be programmed to provide 1 pulse per 1 picosecond to 1 pulse per 10 minutes, and the time-of-light emission can be set anywhere from 0.01 microsecond to 12 minutes. For example, different pulses could be used to allow for different levels of tissue relaxation, allowing the phototherapy device to administer higher levels of energy without causing tissue damage or tissue overheating. Additionally, the wavelength range for the photobiomodulation therapy could range from near-infrared to far infrared.

The light could then be emitted through portals or the sides of the probe, as discussed above with reference to FIGS. 8-8E. Direct illumination could be delivered using LEDs, diodes, or other energy-emitting techniques. Optical elements in the probe could change the profile, shape, diffusion, and frequency of the beam to tailor the light administered to the patient. The width of the beam could be 1 mm to more than one 1 cm. The probe could also be tracked (e.g., by GPS) prior to, during, and following the delivery session of the photons to aide in the specific deliver location(s) and to maneuver into and out of the cavity area where the administration was achieved.

In various embodiments, the photon-emitting tip or portals of the probe are not to exceed mucosal tissue-irritating temperatures below 33° C. or above 40 to 41° C. This probe could be cooled using a chilled fluid such as water, a menthol solution, gases like $CO_2$, nitrous oxide, liquid nitrogen, chilled air, etc.

Example Three. An example of the phototherapy device may be used in transurethral phototherapy delivery. This embodiment could include a standalone probe or a probe used in conjunction with another device. The additional device could include a flexible cable, endoscopic device(s), or non-endoscopic device(s) or a rigid or flexible laryngoscope or bronchoscope. This probe could be inserted into the urethral meatus, and phototherapy could be administered into the urethral mucosa, into the urethral soft tissues deeper past the mucosa, and into the tissues supporting the urethra and urethrovesicle junction, as well as into the lower bladder base and the bladder neck. This transurethral probe could be further passed into the bladder to administer phototherapy into the bladder and into structures that are connected to and/or support the blabber, as well as structures near the bladder including the pelvic honey structures and the ligaments and muscles that make up the pelvic floor.

The probe could be a straight or angled-end probe such that the emitted beam is a diffused-beam laser beam that is targeted toward, and/or in direct contact with, the urethral and bladder mucosal surfaces, as well as toward and/or into the ureters that drain urine and which lead to the kidneys.

While these probes are specifically positioned within the urethral lumen and/or within the bladder, the probe's phototherapy-emitting portals or tip(s) could be directed such that photons are targeted toward and into the urethral and the bladder soft tissues. Some of the diseases that could be treated with phototherapy via this transurethral and transvesical probe include acute and chronic urethritis and cystitis, as well as interstitial cystitis and detrusor instability or overactive bladder-causing tissues.

As described above, the probe may be used with an endoscope. The device, the endoscope plus probe, could then be manually or automatically programmed upon being given the patient's data (e.g., heart rate, blood circulation, disease state(s), etc.). The actual pointing and directing of the probe's photon emitting portals and/or tip(s) toward specifics structures could be performed by a human operator or robotic-controlled operator, as discussed above. Further positioning of the probe and refined targeting of tissues could be adjusted on all axis and/or vector planes and coordinates with the guidance of an interfacing system, ultrasound-interfacing guidance, and even by other x-ray guidance-targeting systems like fluoroscopy and/or CT-scanning systems.

The pulse of the light-photons could be programmed to provide 1 pulse per 1 picosecond to 1 pulse per 10 minutes, and the time-of-light emission could be set anywhere from 0.01 microsecond to 12 minutes. For example, different pulses could be used to allow for different levels of tissue relaxation, allowing the phototherapy device to administer higher levels of energy without causing tissue damage or tissue overheating. Additionally, the wavelength range for the photobiomodulation therapy could range from near-infrared to far infrared.

As discussed, the light could be emitted through portals or the sides of the probe, as discussed above with reference to FIGS. 8-8E. Direct illumination could be delivered using LEDs, diodes, or other energy-emitting techniques. Optical elements in the probe could change the profile, shape, diffusion, and frequency of the beam to tailor the light administered to the patient. The width of the beam could be 1 mm to more than one 1 cm. The probe could also be tracked (e.g., by GPS) prior to, during, and following the delivery session of the photons to aide in the delivery to specific location(s) and to maneuver into and out of the cavity area used for the administration of phototherapy.

In various embodiments, the photon-emitting tip or portals of the probe are not to exceed mucosal tissue irritating temperatures below 33° C. or above 40 to 41° C. This probe could be cooled using a chilled fluid such as water, a menthol solution, gases like $CO_2$, nitrous oxide, liquid nitrogen, chilled air, etc.

Example Four. An example of the phototherapy device may be used in translaryngeal and transbronchial phototherapy delivery. A probe could be used with a standalone rigid or flexible cable, endoscopic device(s), or nonendoscopic device(s) or could be a probe that is attachable and detachable to the end of a rigid or flexible laryngoscope or bronchoscope. This probe could be inserted into the mouth (e.g., oral cavity), down the oral pharyngeal cavity, and guided into (e.g., inserted into) the laryngeal lumen (or down through a tracheotomy portal or tube) and in some cases down into the bronchial tree's lumens.

The probe could be a straight or angled-end probe such that the emitted beam is a diffused-beam laser beam that is targeted toward and/or in direct contact with the laryngeal and/or inner bronchial mucosal surfaces as well as toward and/or down near the alveolar sacs within the lung's interstitial and parenchymal tissues.

While the probe is specifically positioned in laryngeal and/or bronchial lumen(s), the phototherapy-emitting portals or tip(s) of the probe could be directed such that photons are targeted toward and into the larynx and/or toward bronchial intralumenal diseases, parenchymal lung tissue diseases, and/or interstitial diseases like chronic pulmonary fibrosis and radiation inflammatory pulmonary fibrosis. Photons may even be targeted toward and into external to pulmonary-lung tissues and toward intrathoracic diseases (e.g., including mediastinal disease states and cardiac diseases like cardiomyopathy or coronary artery diseases and/or pericardial sac diseases like inflammatory pleurisy).

Further, this probe could administer photons from within the larynx or bronchi toward and into the thyroid lobes, parathyroid glands, into the thymus, the esophagus, etc. An intralumen and/or intractability phototherapy probe could deliver photons of one or more diffused-beam laser wavelengths into healthy and/or diseased tissues within the neck, within the thoracic cavity, into the vertebral bodies, toward and into the spinal column and CNS nerve and interstitial tissues, as well as into and around exiting spinal column nerve and nerve roots. Additionally, photons from the intralumenal and/or intracavitary-positioned probe could be directed into rib bones, sternum bones, and ligaments and their surrounding muscles and other soft tissues.

The probe could be connected to a handle or attached to a rigid or flexible endoscope. The device, the endoscope plus probe, could then be manually or automatically programmed based on the patient's data (e.g., heart rate, blood circulation, disease state(s), etc.). The actual pointing and directing of the photon-emitting portals and/or tip(s) of the probe(s) toward specifics structures could be performed by a human operator or robotic-control led operator, as described above. Further positioning of the probe(s) and refined targeting of tissues could be adjusted on all axis and/or vector planes and coordinates with the guidance of an MRI-interfacing system, ultrasound-interfacing guidance, and even by other x-ray guidance-targeting systems like fluoroscopy and/or CT-scanning systems.

The pulse of the light-photons could be programmed to provide 1 pulse per 1 picosecond to 1 pulse per 10 minutes, and the time-of-light emission can be set anywhere from 0.01 microsecond to 12 minutes. For example, different pulses could be used to allow for different levels of tissue relaxation, allowing the phototherapy device to administer higher levels of energy without causing tissue damage or tissue overheating. The wavelength range for the photobiomodulation therapy could range from near-infrared to far infrared.

As described above, the light could be emitted through portals or the sides of the probe, as discussed above with reference to FIGS. 8-8F Direct illumination could be delivered using LEDs, diodes, or other energy-emitting techniques. Optical elements in the probe could change the profile, shape, diffusion, and frequency of the beam to tailor the light administered to the patient. The width of the beam could be 1 mm to more than one 1 cm. The probe could also be tracked (e.g., by OPS) prior to, during, and following the delivery session of the photons to aide in delivering the therapy to specific location(s) and to maneuver into and out of the cavity area used for the administration of phototherapy.

In various embodiments, the photon-emitting tip or portals of the probe are not to exceed mucosal tissue irritating temperatures below 33° C. or above 40 to 41° C. This probe could be cooled using a chilled fluid such as water, a menthol solution, gases like $CO_2$, nitrous oxide, liquid nitrogen, chilled air, etc.

This transpharyngeal probe's phototherapy (e.g., PBMT) could replace some surgical interventions, chronic antibiotic therapy, and/or steroid therapy. Moreover, this transpharyngeal probe could be use as standalone therapy or in conjunction with other known therapies. The probe could be also used in conjunction with the same or similar phototherapy delivered or administered via the rotational treatment cylinder transcutaneously.

Example Five. A treatment cylinder can be used to treat inflammation and/or torn tissue in the knee. The following are examples of parameters of the treatment cylinder and/or therapy parameters provided by the treatment cylinder:

90 W, 810 nm diode; DLCR rotates to administer 9 $J/cm^2$ into PSTZ;
90 W, 810 nm diode; DLCR rotates to administer 9 $J/cm^2$ into PTZ;
90 W, 810 nm diode; DLCR rotates to administer 9 $J/cm^2$ into DSTZ;
180 W, 980 nm diode; DLCR rotates to administer 5 $J/cm^2$ into PSTZ;
180 W. 980 nm diode; DLCR rotates to administer 5 $J/cm^2$ into PIZ;
180 W, 980 inn diode; DLCR rotates to administer 5 $J/cm^2$ into DSTZ;
180 W, 905 nm diode; DLCR rotates to administer 4 $J/cm^2$ into PSTZ;
180 W, 905 nm diode; DLCR rotates to administer 4 $J/cm^2$ into PIZ; and
180 W, 905 nm diode; DLCR rotates to administer 4 $J/cm^2$ into DSTZ.

Example Six. An example of the phototherapy device may be used in phototherapy delivery on a knee. A combination of wavelengths and wattage could be used independently or jointly to deliver treatment using a treatment cylinder embodiment. In one example, a three 70 W diode set (e.g., S3D) of 980 nm is used to treat the PSTZ of the knee at 50% power while another three 35 W diode set (e.g., S3D) of 810 nm is simultaneously administering therapy at 75% power onto the DSTZ of the knee. In another example, a three 70 W diode set (e.g., S3D) of 980 nm is used to treat the PSTZ of the knee at 50% power while another three 70 W diode set (e.g., S3D) of 980 nm is simultaneously administering PBMT at 50% power onto the DSTZ of the knee. In another example, a diode set of 70-80 W/980 nm is used to treat the PSTZ of the knee at 33% Power while another diode set of 35 W/810 nm is simultaneously administering therapy at 50% Power onto the DSTZ of the knee and while still another diode set of 35 W1605-650 nm is administering PB TT at 35% Power (e.g., onto the PIZ).

In various embodiments, the frequency of the administration of the phototherapy is in according with the blood flow direction. For example, therapy is administered such that photons are delivered downstream before photons are delivered upstream, which avoids causing an increase in temperature of the treatment site that would negatively affect the photon penetration depth into the targeted tissues.

Example Seven. An example of the phototherapy device may be used in transauricular phototherapy delivery. An example of a transauricular phototherapy delivery probe could be a probe configured to transverse the external ear canal to deliver diffused-beam laser photons and low level laser therapy into inflamed tissues, diseased tissues, and/or infected tissues such as external otitis media (which involves the auditory canal) and internal otitis (within the inner ear) instead of administering or prescribing steroids and/or antibiotics. A transauricular probe could better deliver higher levels of low intensity and high intensity photons than a delivery system external to the ear canal, thus possibly enhancing potential therapeutic effects.

In addition, the internal ear structures, like the cochlea, that also are disease-prone could possibly benefit patients with tinnitus (ringing in the ears) or vertigo. Photons from transcranial or topically-applied low level laser therapy will result in fewer photons being delivered to the inner ear structures due to the depth that these structures lie within the skull and because more photons are blocked by the dense skull bones, thus reducing the number of applied photons that reach the inner ear. Using a transauricular probe could allow the photon-emitting source to be placed closer to these inner ear structures, allowing the photons to be applied with less bone mass to block photons from reaching the treatment site compared to transcranially-topically applied photons.

The transauricular probe could be connected to a handle or attached to a rigid or flexible endoscope. The device, the endoscope plus probe, could then be programmed by the user or automatically programmed based on the patient's data (e.g., heart rate, blood circulation, etc.). The probe could be manually inserted into the first 1 to 2 cm into the auricular canal, pointing the emitted photons toward specific external and internal ear structures and even intracranial structures, by a human operator or robotic operator, as described above. Further positioning of the probe and refined targeting of tissues could be adjusted on all axis and/or vector planes and coordinates with MRI guidance, ultrasound guidance, fluoroscopy x-rays, etc.

The pulse of the light-photons could be programmed to provide 1 pulse per 1 picosecond to 1 pulse per 10 minutes, and the time-of-light emission can be set anywhere from 0.01 microsecond to 12 minutes. For example, different pulses could be used to allow for different levels of tissue relaxation, allowing the phototherapy device to administer higher levels of energy without causing tissue damage or tissue overheating. The wavelength range for the photobiomodulation therapy could range from near-infrared to far infrared.

The light could be emitted through portals or the sides of the probe, as described above with reference to FIGS. 8-8E. Direct illumination could be delivered using LEDs, diodes, or other energy-emitting techniques. Optical elements in the probe could change the profile, shape, diffusion, and frequency of the beam to tailor the light administered to the patient. The width of the beam could be 1 mm to more than one 1 cm. The probe could also be tracked (e.g., by GPS) prior to, during, and post treatment to aide in the delivering the therapy to specific location(s).

In various embodiments, the photon-emitting tip or portals of the probe are not to exceed a temperature between 37 to 45° C. This probe could be cooled using a chilled fluid such as water, a menthol solution, gases like $CO_2$, nitrous oxide, liquid nitrogen, chilled air, etc.

Example Eight. An example of the phototherapy device may be used in transesophageal, transgastric, and/or transduodenal phototherapy delivery. For example, a probe could be applied down into the esophagus, stomach, and intestinal structures such as the duodenum, either separately or incorporated with or within a tube (e.g., a percutaneous endoscopic gastronomy ("PEG") tube or a jejunostomy tube ("J-tube")), to treat and/or prevent gastritis or esophagitis. Additionally, the probe could be placed short-term or long-term in the patient.

The probe could be used to apply phototherapy in a continuous mode, in a pulsed mode, in a micropulsed mode, and/or in a superpulsed mode. The therapy could last for minutes to days at a low level of power, such as on the 0.1 mW range, 1.0 mW range, 10 mW range, 100 mW range, or 1000 mW range. For intermittent phototherapy, each treatment session could last for less than a second, for a second or more, or for several minutes or more. Additionally, the frequency of therapy could be once every several seconds, once every one or more minutes, once an hour, once a day, or several times a day. The probe could also be used with or include any of the probe features described above (e.g., a cooling structure).

Figure 25:
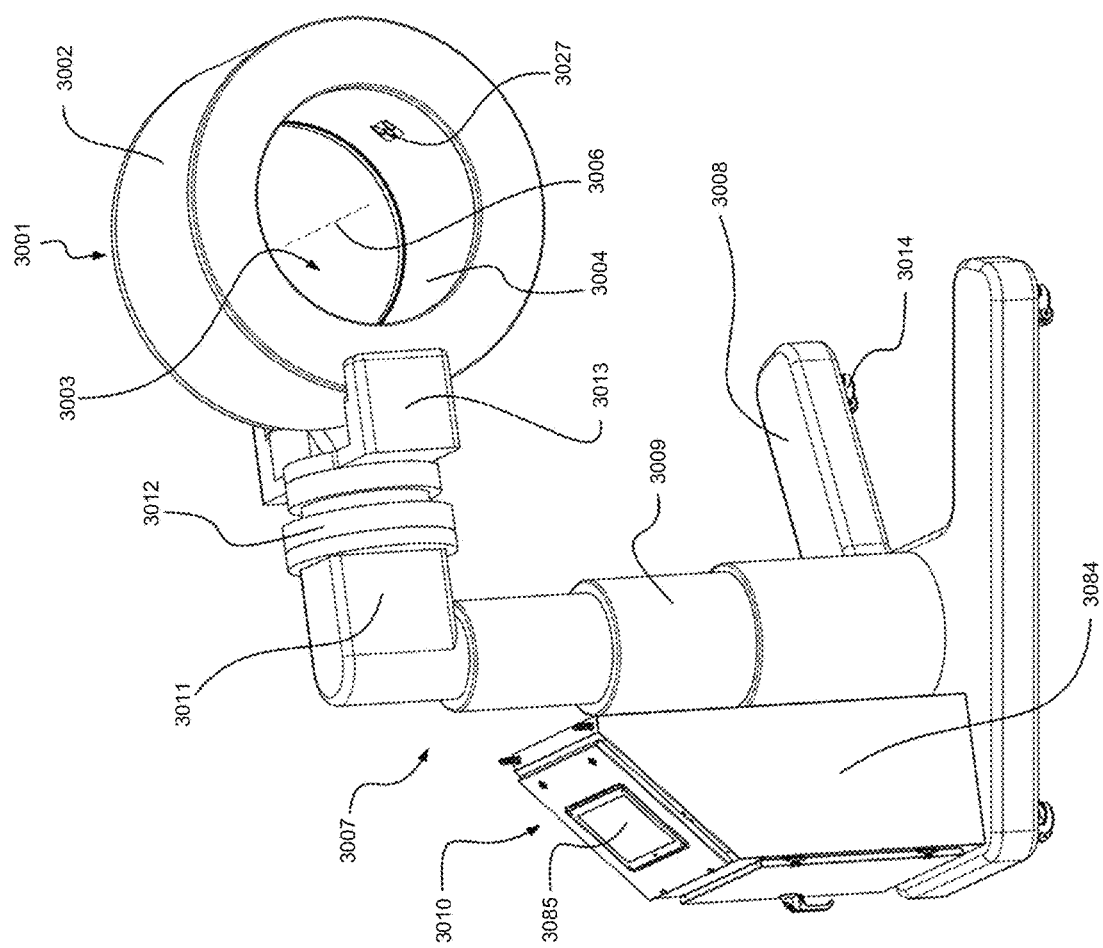
FIG. 25 depicts a perspective view of another embodiment of a treatment cylinder device for the application of photobiomodulation therapy (PBMT).

Referring now to the drawings and further detailed example embodiments, FIG. 25 depicts another embodiment of a treatment cylinder ("TC") device 3001 of the present disclosure for the delivery of PBMT. The device includes a hollow structure 3002 characterized by a bore of any geometric shape with at least one open end 3003 capable of accepting a portion of patient anatomy. For example, in some instances, the hollow structure may have a circular cross-section. Within the hollow structure 3002 resides a rotatable member 3004 which, when directed by an operator, manually or utilizing semi- or fully-automated routines, may rotate around an axis 3006 (depicted by the dashed line) extending through the hollow structure 3002. The axis 3006 may be aligned with the patient anatomy such that the rotatable member 3004 can fully and freely (e.g., without interference) rotate 360 degrees around the inserted patient anatomy.

The axis 3006 of the rotatable member 3004 may or may not be located at the center of the hollow structure 3002. Within the hollow structure 3002, integrated within the apparatus which constitutes the rotatable member 3004, is a coherent light generator ("CLG") which is optically connected by means of one or more optomechanical or optoelectrical components such that light from the CLG is emitted from the coherent light emission optics ("CLEO") 3027 located at the interior circumferential surface of the rotatable member 3004 within the hollow structure 3002. The CLEO 3027 includes a plurality of lenses arranged such that the resultant output is one or more parallel collimated beams of light oriented orthogonal to the patient anatomy. The CLEO 3027 in conjunction with the prescribed rotation of the rotatable member 3004 within the hollow structure 3002 facilitates the application of PBMT light delivery from a locus of precise angles circumferential to the surface of the volume of tissues within the patient anatomy inserted into the open end 3003 of the TC 3001.

Referring further to the embodiment in FIG. 25, the TC 3001 is elevated off of the floor wherever the device is located by a support structure 3007. The support structure 3007 is itself an apparatus comprising a base 3008, a post 3009, control electronics 3010, an elbow 3011, a rotatable knuckle 3012, and a TC mounting interface 3013. The base 3008 is a sturdy structural component or assembly which provides a suitable foundation for the post 3009 and a mounting location for the control electronics 3010. The base further supports device mobility by means of rolling elements 3014 (e.g., casters). The post 3009 extends vertically from the base 3008 to a suitable elevation such that the portion of patient anatomy to be treated can be inserted into the open end 3003 of the treatment cylinder 3001 with the minimum possible patient effort and inconvenience. The rotatable knuckle 3012 further supports minimizing patient impact by facilitating rotation of the TC 3001 to adjust the angle and position of the open end 3003. The elbow 3011 and TC mounting interface 3013 are independent apparatuses, which provide interfaces between the top of the post 3009 and the rotatable knuckle 3012 then between the rotatable knuckle 3012 and the TC 3001 respectively. These apparatuses structurally mount and electronically connect the TC 3001 to the support structure 3007 and control electronics 3010. In the illustrated embodiment the control electronics 3010 apparatus is depicted as an electronics cabinet 3084 with integrated human machine interface ("HMI") 3085.

Figure 26:
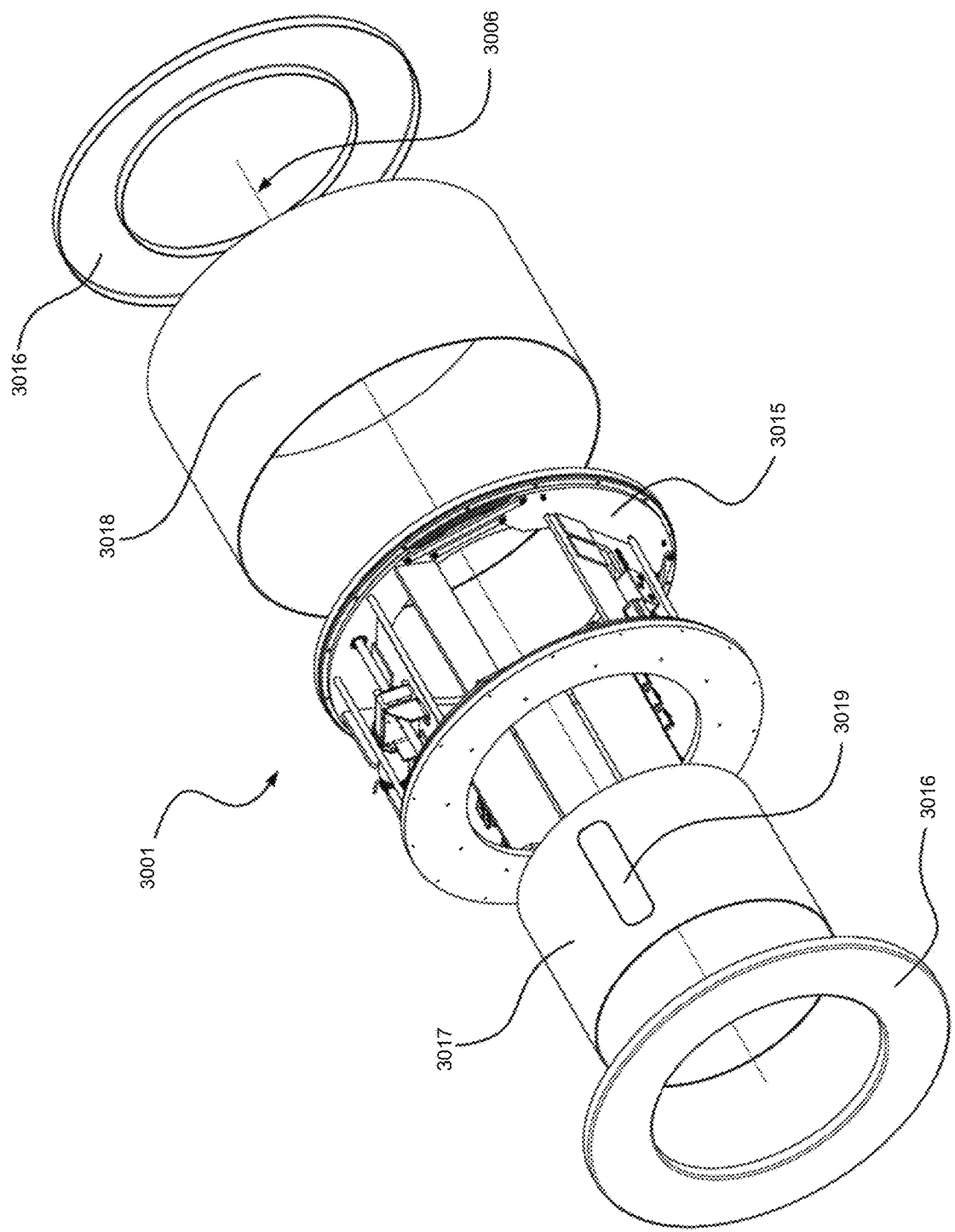
FIG. 26 depicts a perspective exploded view of a treatment cylinder apparatus of the treatment cylinder device shown in FIG. 25, illustrating internal mechanisms of the treatment cylinder apparatus and associated cosmetic and protective enclosures.

Referring now to FIG. 26 the treatment cylinder 3001 is depicted independently of the support structure 3007 shown in FIG. 25. FIG. 26 depicts an exploded perspective view of the TC 3001 along its axis 3006 exposing the TC internals 3015, which may be a complex apparatus for the implementation and application of PBMT by a device as described herein. The TC internals 3015 are enclosed within covers to provide a desirable aesthetic and protect the operator and patient from hazards present within the TC internals 3015. It is to be understood that the implementation and design of system covers have a multitude of potential industrial design configurations.

For the purposes of this disclosure, and as illustrated in FIG. 26, exterior end member(s) 3016, interior surface member 3017, and exterior surface member 3018 may collectively be referred to as "covers." The interior surface member 3017 and exterior surface member 3018 are removably attached to either stationary structural elements of the hollow structure 3002 or to the rotatable member 3004 as depicted in FIG. 25. The exterior end members 3016 are removably attached from the TC 3001 and serve to fully enclose the TC internals 3015 and cover any gaps or pinch points between the stationary hollow structure 3002 and rotatable member 3004 of the TC 3001 depicted in FIG. 25. Referring again to FIG. 25 the CLEO 3027 is exposed through an optical opening 3019 in the interior surface member 3017 as illustrated in FIG. 26.

Figure 27:
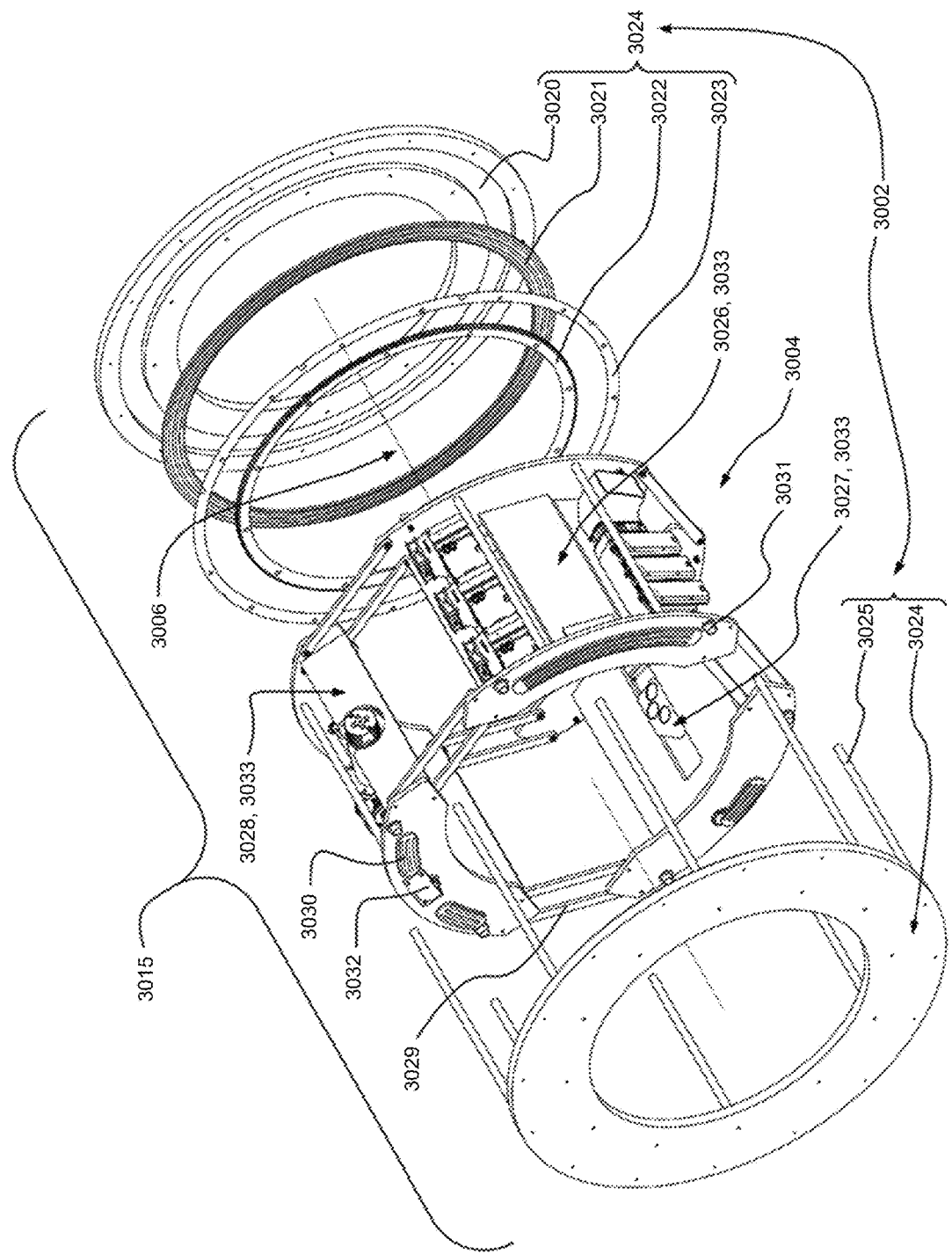
FIG. 27 depicts a perspective exploded view of the internal mechanisms of the treatment cylinder apparatus shown in FIG. 26, illustrating the composition and configuration of a hollow structure and rotatable member of the treatment cylinder apparatus.

A closer look at the example embodiment of the TC internals 3015 is depicted in FIG. 27. The TC internals 3015 are the physical assembly of the hollow structure 3002, which interfaces with the support structure 3007 and the apparatus of the rotatable member 3004 within the hollow structure 3002 illustrated in FIG. 25. The hollow structure 3002 as depicted in FIG. 27 as a cylindrical assembly characterized by an end apparatus 3024 on either side of the rotatable member 3004 connected by a plurality of lateral support(s) 3025, which connect the structure end plates 3020 on the outermost ends of the of the TC internals 3015. The lateral support(s) 3025 are illustrated as simple rods for the purposes of this disclosure. However, a lateral support 3025 can be implemented in a multitude of configurations including ridged members, static assemblies, kinematic mechanisms for adjustment or dynamic load management, and tension members like a cable to provide counter force where applicable. The end apparatus 3024 includes the structure end plate 3020 with a slip ring 3021, fixed gear 3022, and carrier ring 3023. In addition to serving as a sturdy structure for the rotatable member 3004 the apparatus of the hollow structure 3002 integrates the essential electrical connections and physical mechanisms required for the execution of PBMT utilizing the device of this disclosure.

The rotatable member 3004 includes an apparatus of sub-systems including but not limited to; the coherent light generator ("CLG") 3026, the coherent light emission optics ("CLEO") 3027 for the delivery of PBMT, and the rotational drive mechanism 3028 mechanism and/or suitable interfaces for a drive system not located within the TC internals 3015. In the embodiment illustrated in FIG. 27, each sub-system is an independent apparatus referred to as a "carriage" 3033. The various carriages 3033 are interconnected by a plurality of removable links 3029 between each sub-system carriage 3033 of which there is one for each sub-system 3026, 3027, and 3028. The removable interconnectedness of the carriages 3033 facilitates simplified assembly and serviceability of the system. However, the illustrated embodiment is provided as an example, and it is to be understood that the particular implementation of the rotatable member 3004 has a multitude of variations of the structure and layout of the respective elements within each sub-system carriage 3033 for the CLG 3026, CLEO 3027, and rotational drive mechanism 3028, as well as within the rotatable member 3004. One such alternative embodiment may eliminate the links 3029 between the carriages 3033 and utilizes a unified structure as a single carriage 3033 for the construction of the rotatable member 3004 to include the CLG 3026, CLEO 3027, and rotational drive mechanism 3028 mechanism and/or interfaces. For the purposes of this disclosure the CLG 3026, CLEO 3027, and rotational drive mechanism 3028 will be defined individually to illustrate the elements within each, independently as an individual carriage 3033, collectively as carriages 3033, or alternatively as the rotatable member 3004 to illustrate the interfaces between the rotatable member 3004 and the hollow structure 3002.

Continuing in reference to FIG. 27 the end apparatus 3024 includes a slip ring 3021 attached to the exterior end member 3016 of the hollow structure 3002. The slip ring 3021 is characterized by a plurality of independent electrically isolated circular traces suitable for the associated power carrying requirements. The slip ring 3021 may interface with a slip ring contact 3030 mounted to any or all carriages 3033, such that the power and/or logic and control signals for the entire rotatable member 3004 or each carriage 3033 respectively, may be reliably and robustly connected between the rotatable member 3004 and the control electronics 3010 depicted in FIG. 25. The slip ring contact 3030 is a component or assembly with a characteristic form similar to that of the slip ring 3021 such that when the rotatable member 3004 is rotating within the hollow structure 3002 the slip ring contact 3030 is perpetually electrically connected to the slip ring 3021. There may be a single slip ring contact 3030 or a plurality of contacts 3030 as illustrated in FIG. 27. Further, the slip ring contact 3030 has a plurality of independent electrically isolated circular or semi-circular traces oriented such that they interface with a mating trace radially over the entire circumference of the slip ring 3021 along the prescribed axis 3006 of rotation of the rotatable member 3004. The traces are defined as a conductive path on or adjacent to the surface of the slip ring 3021 and slip ring contact 3030 where the surface and fundamental structure of the slip ring 3021 and contact 3030 is non-conductive resulting in the electrically isolated conductive paths for transfer of electrical power and signals between the slip ring 3021 and slip ring contact(s) 3030.

The rotatable member 3004 is suspended within the hollow structure 3002 by a plurality of roller elements 3031 removably and adjustably secured to each end of the carriages 3033, which are included on the rotatable member 3004, such that the circumferential surface of the each roller element 3031 is tangent to the circumferential surface of the inside diameter and/or outside diameter of the carrier ring 3023 component of the end apparatus 3024 on both ends of the hollow structure 3002 as illustrated in FIG. 27. The roller elements 3031 are distributed along the circumferential perimeter of the rotatable member 3004 such that all roller elements 3031 are in perpetual contact with the mating surface of the carrier ring 3023 on both end apparatus 3024 of the hollow structure 3002 resulting in the suspension of the rotatable member 3004 within the hollow structure 3002.

Additional roller elements 3031 may be utilized with the non-gear toothed side of fixed gear 3022 on each end apparatus 3024 in like alignment as described with respect to the carrier ring 3023 to provide additional contact area and load bearing support or stability of the rotatable member 3004 within the hollow structure 3002. Each roller element 3031 is independently, or as part of a mechanism comprising one or more roller elements 3031, adjustable along the radial distance of the rotatable member 3004, where the center reference is defined by the axis 3006 of the rotatable member 3004. The radial adjustment of the distance of each roller element 3031 from the central axis 3006 of the rotatable member 3004 allows for fine tune alignment of the rotatable member 3004 within the hollow structure 3002 and setting of a desirable preload force between the roller elements 3031 and the carrier ring 3023 to provide, in some implementations, optimized rotational performance of the rotatable member 3004. In some instances, optimized rotation is characterized by smooth balanced movement free of interference, vibrations, or other motion degrading factors including but not limited to friction and noise.

The motion characterized above is between the rotatable member 3004 and the hollow structure 3002. A rotational drive mechanism 3028 system in the embodiment illustrated in FIG. 27 is a sub system within the rotatable member 3004. A drive gear 3032, driven by a motor or other means of converting electrical current into rotational motion within the rotational drive mechanism 3028, is in mesh with the teeth on fixed gear 3022 mounted to structure end plate 3020 within the end apparatus 3024 on both ends of the hollow structure 3002.

Figure 28:
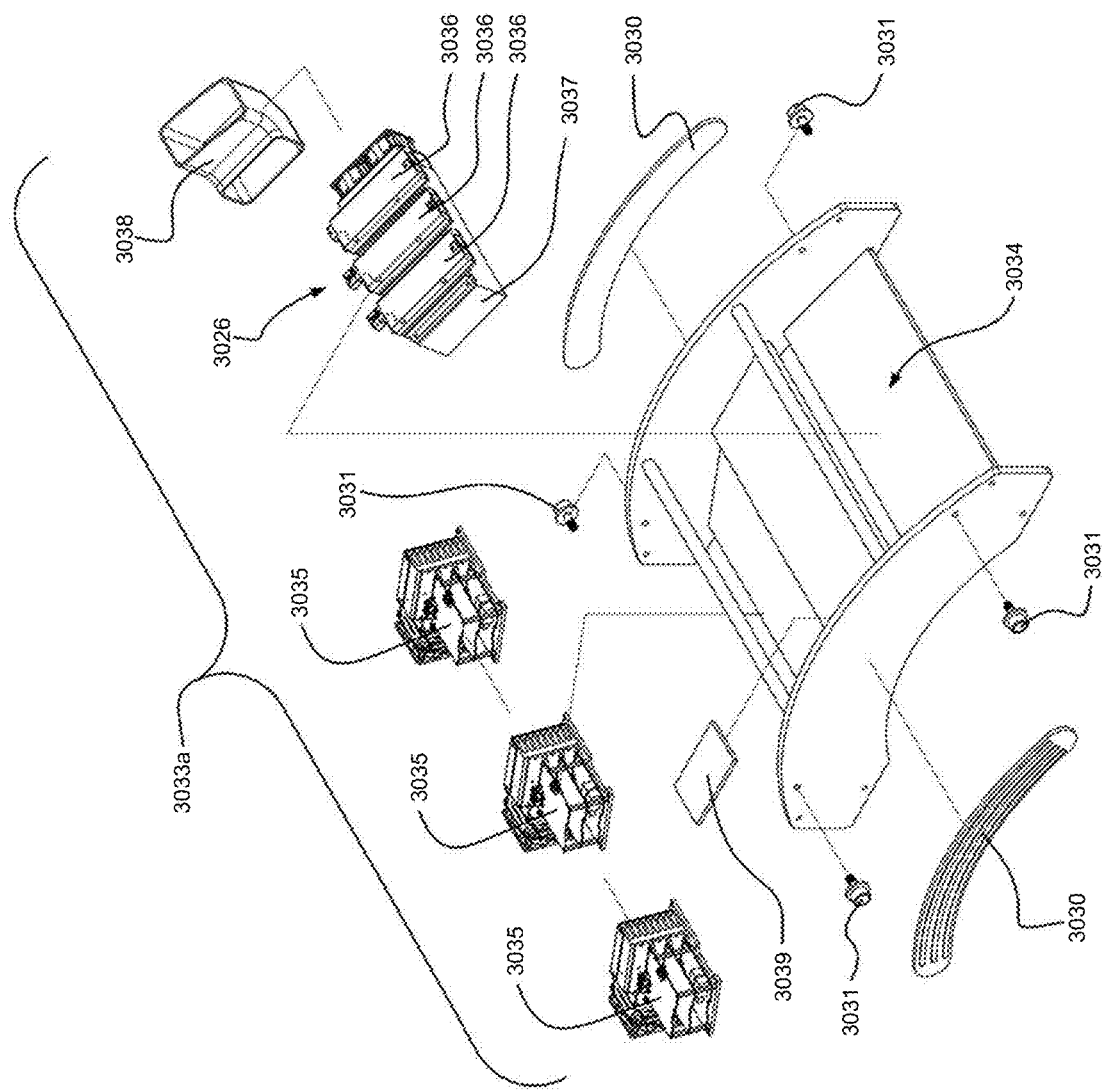
FIG. 28 depicts a perspective exploded view of an embodiment of a coherent light generator carriage apparatus integrated within the internal mechanisms of the treatment cylinder apparatus shown in FIG. 27.

Referring now to FIG. 28, the apparatus of the coherent light generator ("CLG") 3026 on a CLG carriage 3033a is shown in an exploded view to illustrate the elements of the CLG 3026. The CLG carriage 3033a has a unique carriage structure 3034 which serves as the physical mounting apparatus for the CLG 3026 and associated system elements. The unique carriage structure 3034 includes slip ring contact(s) 3030, roller element(s) 3031, CLG control kit(s) 3035, air duct 3038, and a printed circuit board ("PCB") 3039. The carriage structure 3034 for the CLG carriage 3033a is a ridged body structure either formed as a unified component or assembled from a plurality of individual components such that the resulting carriage structure 3034 has the necessary features and characteristics for interfacing the CLG 3026 with the rest of the system of the present disclosure. The CLG 3026 may include a plurality of diode lasers 3036 mounted to a cooling module 3037. The air duct 3038 depicted may be removably attached to one end of the cooling module 3037 to control flow of air into and through the module for improved cooling and system performance. The CLG control kit 3035 represents the specialized power and control electronics required to drive the diode laser(s) 3036 and associated cooling module 3037. In the illustrated embodiment, three (3) CLG control kits 3035 are depicted, one for each of the diode lasers 3036 shown. However, in other embodiments, there may be more or less than three CLG control kits 3035, depending on the number of diode lasers 3036. Each diode laser 3036 may be independently controllable and capable of producing one or more wavelengths of coherent light in continuous and/or pulse modes. The cooling module 3037 may include a thermoelectric interface between each diode laser 3036 and a heat sink (visible element of the cooling module 3037) with integrated fans on the end where the air duct 3038 is located. The PCB 3039 illustrated is representative of the intermediate electronics which facilitate electrical power transfer and communications between the slip ring contact 3030 and CLG control kit(s) 3035 to the device control electronics 3010 illustrated in FIG. 25.

Figure 29:
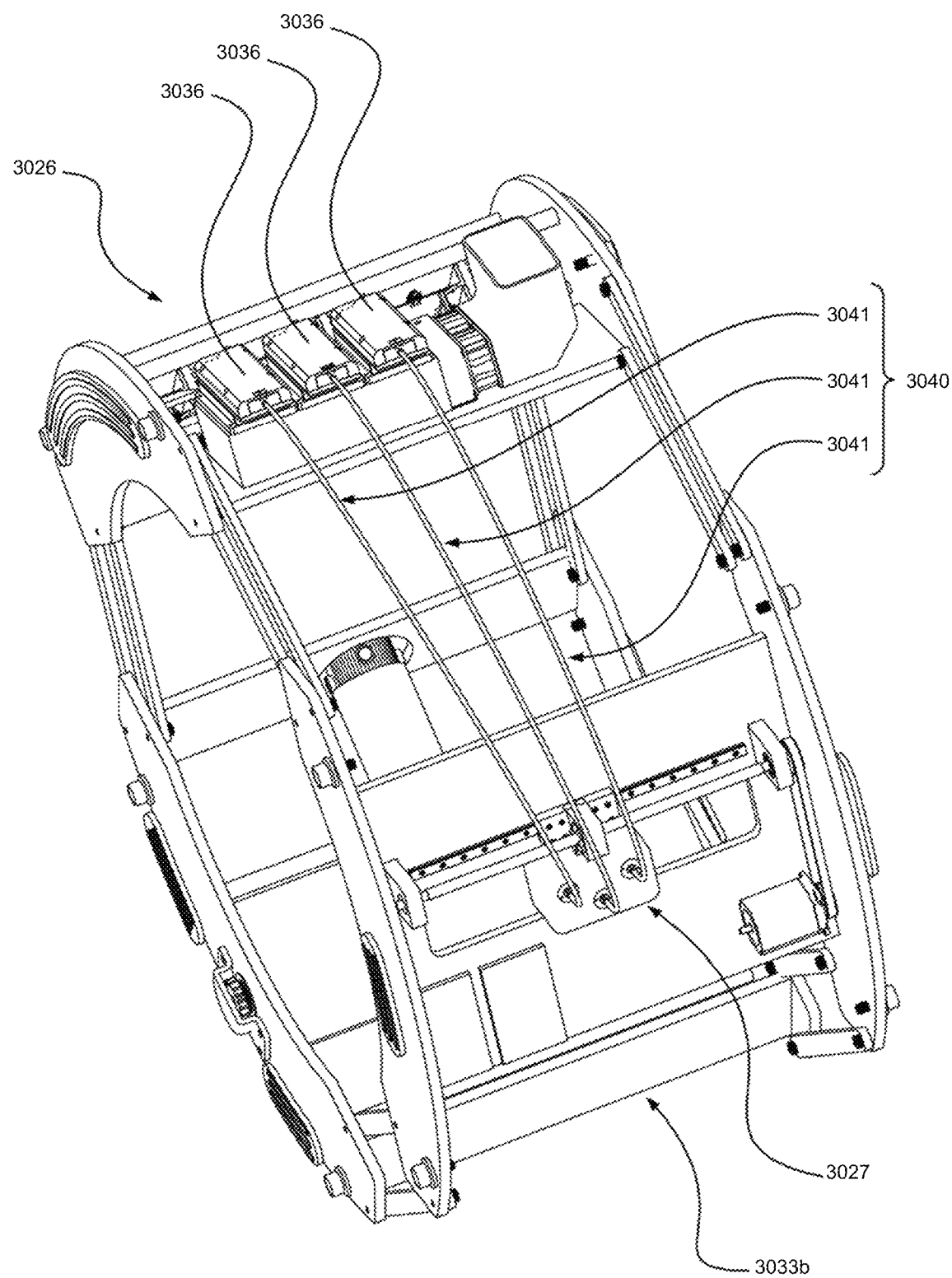
FIG. 29 depicts another perspective view of the internal mechanisms of the treatment cylinder shown in FIG. 27, illustrating example transmission optics between a coherent light generator and the coherent light emitting optics.

The output of the CLG 3026 is delivered to the CLEO 3027 by means of a plurality of optical light tubes or a series of optically-connected opto-electromechanical components henceforth referred to as the transmission optics 3040 illustrated in the perspective view of the rotatable member 3004 depicted in FIG. 29 as a plurality of fiber optic cables ("FOC") 3041. The embodiment depicted in FIG. 29 includes a single FOC 3041 between the output of each diode laser 3036 and the CLEO 3027 within the CLEO Carriage 3033b collectively referred to as the transmission optics 3040. Additional embodiments of the transmission optics 3040 and associated detailed embodiments are described herein.

Figure 30:
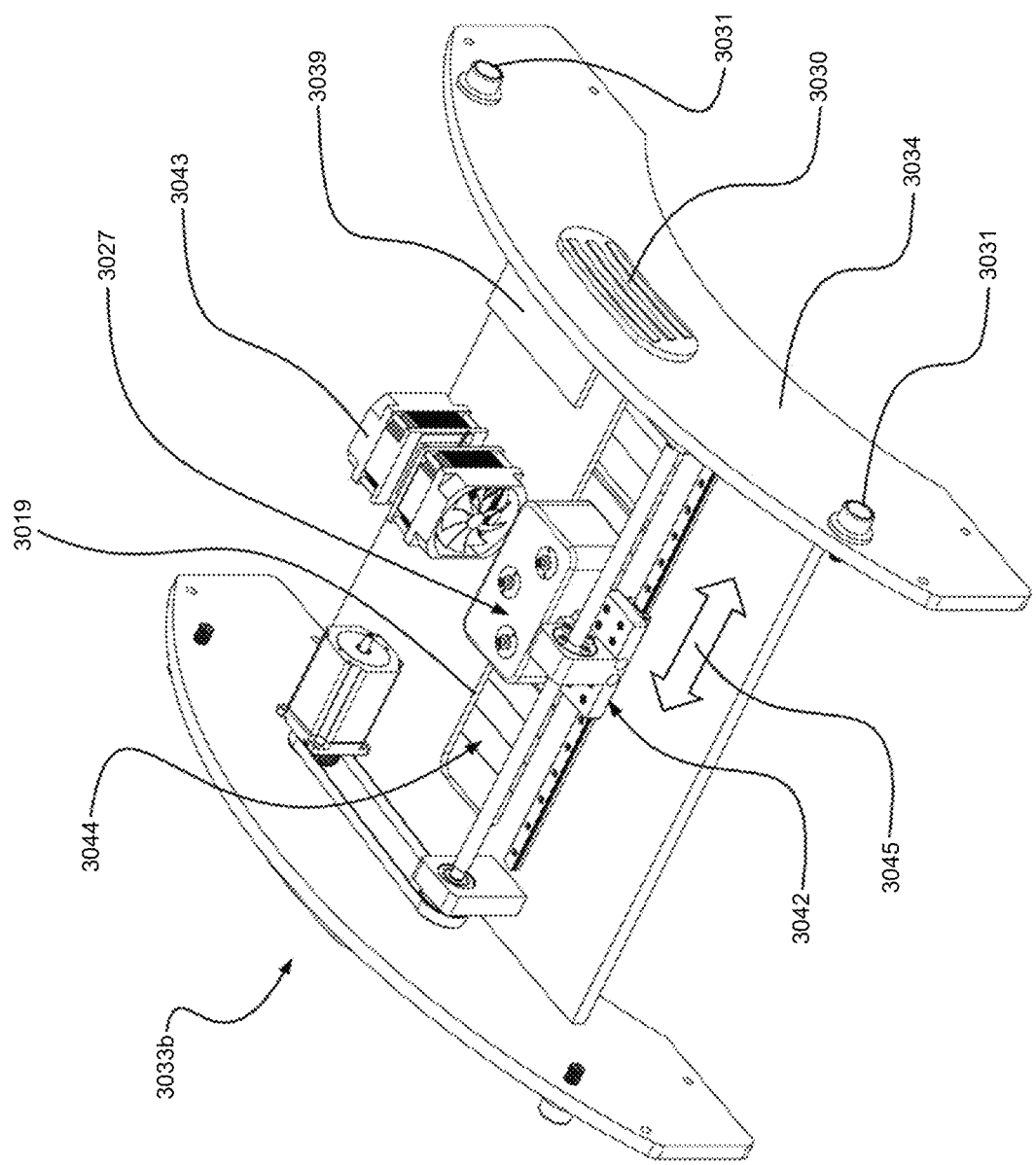
FIG. 30 depicts a perspective view of an embodiment of a coherent light emission optics carriage for integration within the internal mechanisms of the treatment cylinder apparatus shown in FIG. 27.

Referring now to FIG. 30, a perspective view of a CLEO carriage 3033b illustrates the CLEO 3027 and ancillary systems and components including the translation stage 3042, optics cooler 3043, and PCB 3039. The carriage structure 3034 of the CLEO carriage 3033b may be a unified body or assembly of components suitable for mounting the CLEO 3027 and ancillary systems identified herein. Core components including roller element(s) 3031 and slip ring contact 3030 are located on either or both ends of the carriage structure 3034 for interfacing with the end apparatus 3024 of the hollow structure 3002 as depicted in FIG. 27.

Continuing in reference to FIG. 30, the CLEO 3027 is mounted to the translation stage 3042 within the CLEO carriage 3033b in order to facilitate the positional adjustment of the CLEO 3027 by the translation stage 3042 as indicated by the arrow representing travel direction 3045. The isolation covers 3044 provides a dynamic interface between the CLEO 3027 and optical opening 3019 in the CLEO carriage 3033b structure 3034 over the entire range of travel of the translation stage 3042. An optics cooler 3043 module is utilized in some embodiments for controlling the temperature of the CLEO 3027 to improve the efficiency and minimize loss of energy due to heat generated within the CLEO 3027 as a result of the coherent light delivered by the CLG 3026 via the transmission optics 3040 as illustrated in FIG. 29 for the application of PBMT. The PCB 3039 serves as a medial electrical and control interface between the electromechanical elements of the CLEO carriage 3033b and the device control electronics 3010 shown in FIG. 25.

Figure 31:
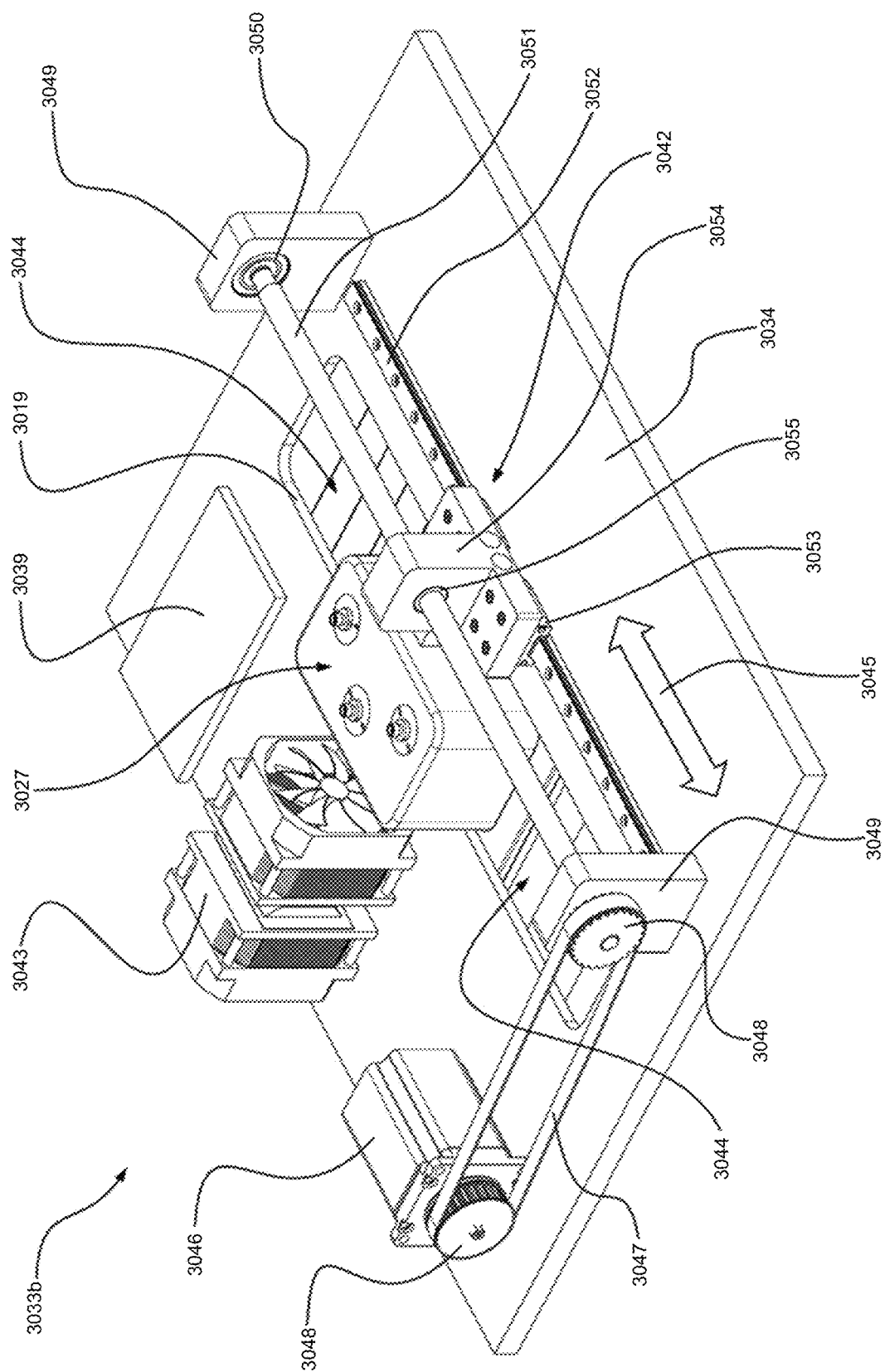
FIG. 31 depicts another perspective detail view of the coherent light emission optics carriage shown in FIG. 30.

FIG. 31 provides a detailed perspective view of the CLEO carriage 3033b with various elements of the carriage structure 3034 and ancillary components not shown in order to clearly depict details of the CLEO 3027, translation stage 3042, and isolation cover 3044. The coherent light emission optics ("CLEO") 3027 is an apparatus including a plurality of lenses and/or collimators configured to alter at least one aspect of the coherent light produced by the CLG 3026. The CLEO 3027 is supported by a mount interface 3054 removably attached to a plurality of linear carriages 3053 assembled on a linear rail 3052 secured to the carriage structure 3034. The CLEO 3027 can, when directed by an operator, be moved side to side across the width of the optical opening 3019 of the carriage structure 3034 in the travel direction 3045 indicated by the arrow shown in FIG. 31. The linear translation of the CLEO 3027 is facilitated by the conversion of electrical energy to rotational motion by a linear drive motor 3046 mechanically connected to a lead screw 3051 by a plurality of motion components. As illustrated, the plurality of motion components may include pulleys 3048 rotatably coupled to each of the linear drive motor 3046 and the lead screw 3051 with a belt 3047 arranged between and rotatably coupling the pulleys 3048. The lead screw 3051 is supported on each end by a shaft support 3049 with a bearing 3050 mounted to the carriage structure 3034. The rotational motion of the linear drive motor 3046 is converted to linear motion of the CLEO 3027 in the travel direction 3045 by a lead nut 3055 within the apparatus of the mount interface 3054, where the thread profile of the lead screw 3051 matches the thread profile of the lead nut 3055.

The CLEO 3027 passes at least partially through the optical opening 3019 in the carriage structure 3034, such that the light emitted from the CLEO 3027 may fall incident upon patient anatomy within the hollow structure 3002 of the TC device 3001 depicted in FIG. 25 during operation. The optical opening 3019 is sufficiently sized to allow unobstructed passage of the CLEO 3027 through the carriage structure 3034 of the full range of travel. To facilitate linear travel of the CLEO 3027 as defined, the resultant opening would leave the device internals exposed to contaminants and user or patient interference. The isolation cover 3044 is an apparatus which dynamically moves with the translation stage 3042 maintaining a cover between the CLEO 3027 and the carriage structure 3034, such that the optical opening 3019 is fully closed between the TC internals 3015 and the inside of hollow structure 3002, shown in FIG. 27, thereby preventing dust or foreign object intrusion over the full range of travel of the CLEO 3027 in the travel direction 3045 of the translation stage 3042. The isolation cover 3044 includes a plurality of closely fitting sliding members which overlap each other providing expanding or contracting telescopic motion between the sliding members of the isolation cover as is commonly implemented on industrial machines and other equipment known in the art as way covers.

Figure 32:
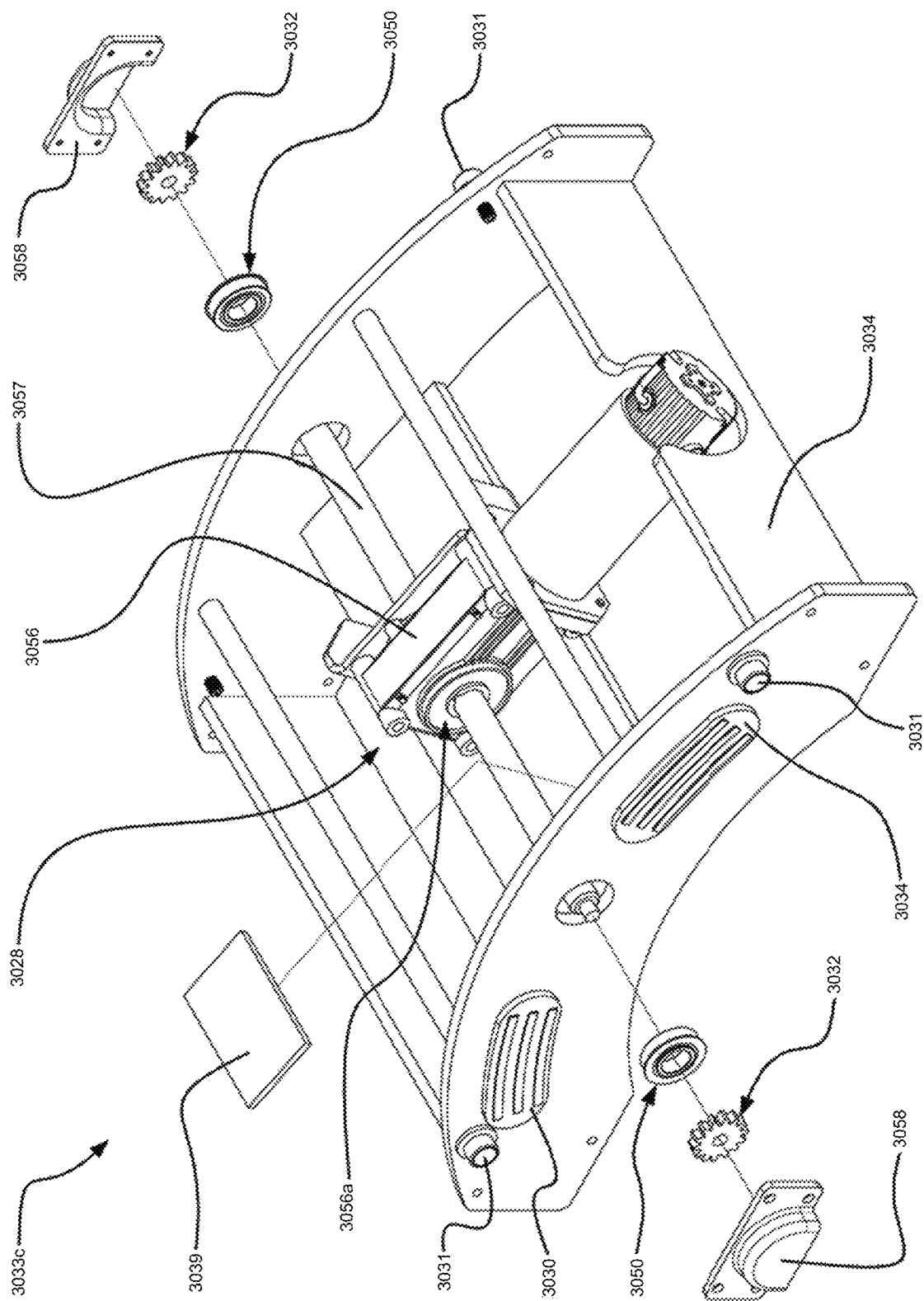
FIG. 32 depicts a partially exploded perspective view of an embodiment of the rotatable drive carriage for integration within the internal mechanisms of the treatment cylinder apparatus shown in FIG. 27.

Referring now to FIG. 32 a partially exploded perspective view of the illustrative embodiment of the rotational drive mechanism 3028 system is shown for the movement of the rotatable member 3004 about the axis 3006 through the open end 3003 of the TC 3001 as illustrated in FIG. 25. The rotational drive mechanism 3028 of the illustrative embodiment is characterized by a sufficiently-sized rotation drive motor 3056 (illustrated as a gear head motor) robustly mounted to the structure 3034 of the rotational drive carriage 3033*c*. A drive shaft 3057 is connected to the output 3056*a* of the rotation drive motor 3056, a through bore in the illustrative embodiment, such that the output torque of the rotation drive motor 3056 is transferred to the drive shaft 3057, thereby transferring the rotational motion through bearings 3050 mounted to the carriage structure 3034 to a drive gear 3032 on each end of the drive shaft 3057. The drive gear 3032 is located outside the carriage structure 3034, such that in the combined apparatus of the rotatable member 3004 within the hollow structure 3002, the teeth on the drive gear 3032 are in mesh with the teeth of the fixed gear 3022 on the end apparatus 3024 of the hollow structure 3002 of the TC internals 3015 depicted in FIG. 27. A gear cover 3058 is removably attached to the carriage structure 3034 over the drive gear 3032 as a protective measure to both prevent accidental interference of the drive gear 3032 and to electrically isolate the rotational drive mechanism 3028 system from the slip ring 3021 within the end apparatus 3024 of the hollow structure 3002 depicted in FIG. 27. Optional printed circuit board 3039 or a plurality of electrical components facilitate electrical power transfer from one or more slip ring contact(s) 3030 to the rotation drive motor 3056 and communication and control of the rotational drive mechanism 3028. The roller elements 3031 integrated in the apparatus of the carriage structure 3034 are located and oriented such that they align with the carrier ring 3023 on each end apparatus 3024 of the hollow structure 3002 illustrated in FIG. 27.

Figure 33:
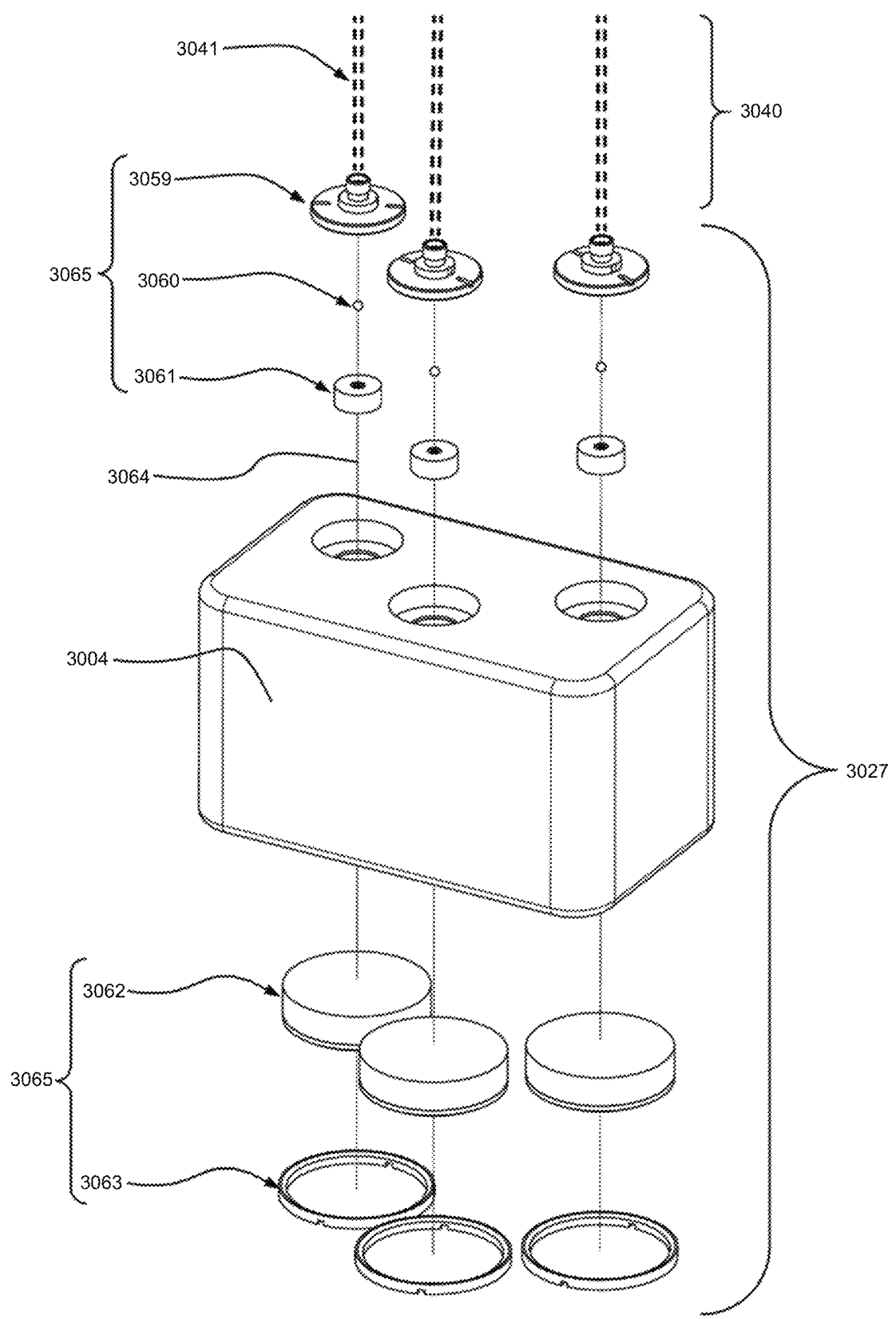
FIG. 33 depicts an exploded perspective view of internal components of the coherent light emission optics apparatus embodiment shown in FIG. 31, illustrating a plurality of optical sets.

A closer look at the coherent light emission optics ("CLEO") 3027 is depicted by the exploded view in FIG. 33. The CLEO 3027 is an optomechanical apparatus comprising a plurality of lenses and the essential hardware to diffuse, focus, or collimate the coherent light to be emitted by the CLEO 3027. The CLEO 3027 may also alter the optical path of the coherent light in some embodiments for orientation with respect to the rotary axis 3006 of the TC 3001 depicted in FIG. 25, whereby the optical box 3005 is the exposed housing of the CLEO 3027 presented to the patient within the TC device. The CLEO 3027 of the embodiment illustrated in FIG. 33 includes the optical box ("OB") 3005 and a plurality of optical set(s) 3065 comprising optical and mechanical elements including fiber port(s) 3059, ball lens(es) 3060, ball lens holder(s) 3061, collimating lens(es) 3062, and lens retainer(s) 3063 aligned within the apparatus of the CLEO 3027 such that each optical set 3065 is oriented coaxially on the respective optical axis 3064 through the optical box 3005 for a given optical set 3065.

The coherent light emitted by the CLG 3026 enters the CLEO 3027 at a fiber port 3059 via the transmission optics 3040, illustrated in FIG. 29 as fiber optic cables 3041. The fiber port 3059 is a specialized adapter interface for a physical connection between the incoming transmission optics 3040 and the physical apparatus of the optical box 3005 whereby the coherent light is free to pass from the CLG 3026 through the fiber optic cable(s) 3041 of the transmission optics 3040 and fiber port 3059 into the optical box 3005 unobstructed by component geometry. Coherent light entering the CLEO 3027 in the illustrative embodiment travels along the optical axis 3064 through a ball lens 3060 installed in a ball lens holder 3061, which is retained within the apparatus of the optical box 3005. The alignment of the ball lens 3060 within the apparatus of the CLEO 3027 is such that the incident coherent light from the fiber port 3059 is concentric to the optical axis 3064 of the ball lens 3060 at a specific distance from a surface of the ball lens 3060 where the coherent light departure angle from the transmission optics 3040 may be optimized for the ball lens 3060 design focal length. The ball lens 3060 increases the light dispersion rate such that the desired collimating lens 3062 beam diameter can be achieved in a shorter focal distance than if the ball lens 3060 is omitted. A potential tradeoff for using a ball lens 3060 to reduce the CLEO 3027 size may be increased heat generation and a reduction in the transmission efficiency of the coherent light generated by the CLG 3026. The collimating lens 3062 of the embodiment illustrated in FIG. 33 is an achromatic doublet, commonly used for collimating light applications, located at the optimized distance for the combined effective focal length of the ball lens 3060 and collimating lens 3062 utilized in the apparatus of the CLEO 3027. The collimating lens(es) 3062 are removably mounted within the apparatus of the optical box 3005 by lens retainer(s) 3063 illustrated as a treaded ring, commonly used in lens retaining applications, such that the collimating lens 3062 is concentric to its respective optical axis 3064.

Figure 34:
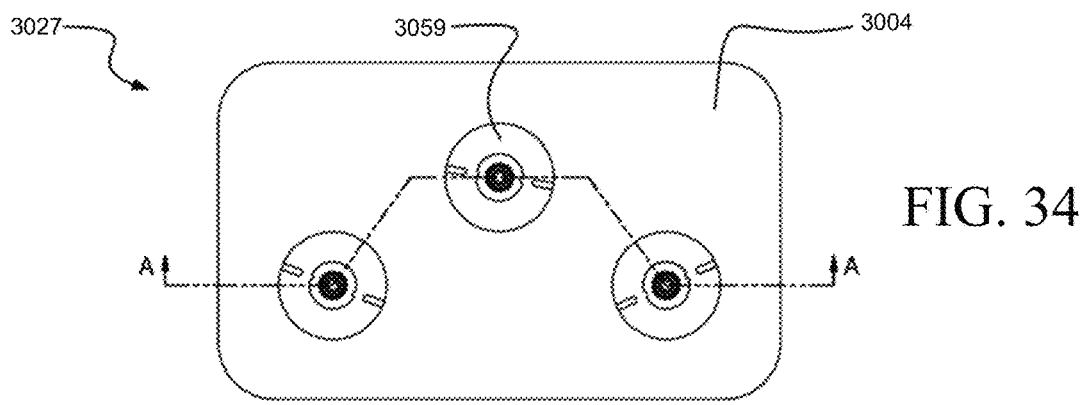
FIG. 34 depicts a top view of the coherent light emission optics assembly shown in FIG. 33.
Figure 35:
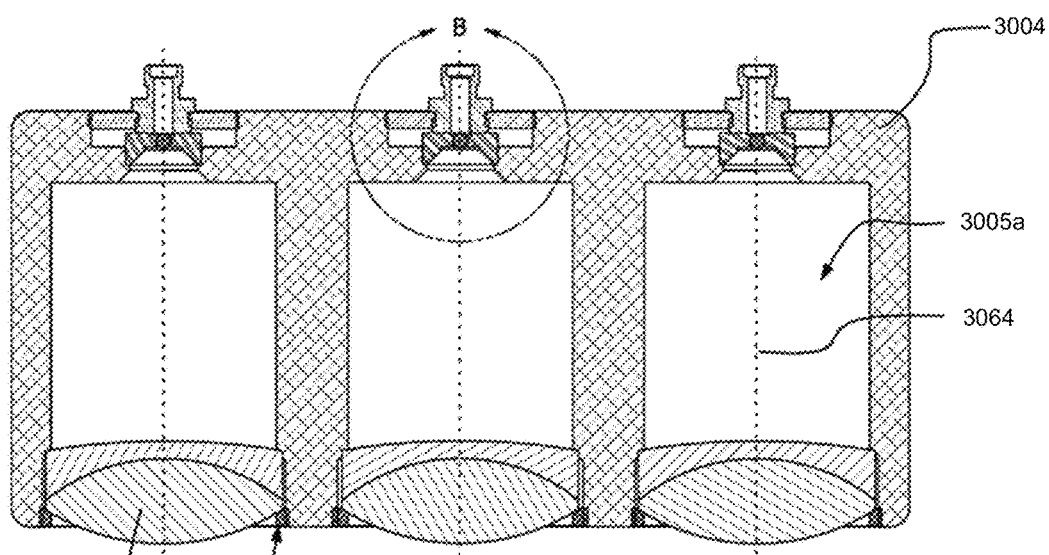
FIG. 35 depicts a segmented section view of the coherent light emission optics assembly of FIG. 34, shown from the perspective of line A-A in FIG. 34.
Figure 36:
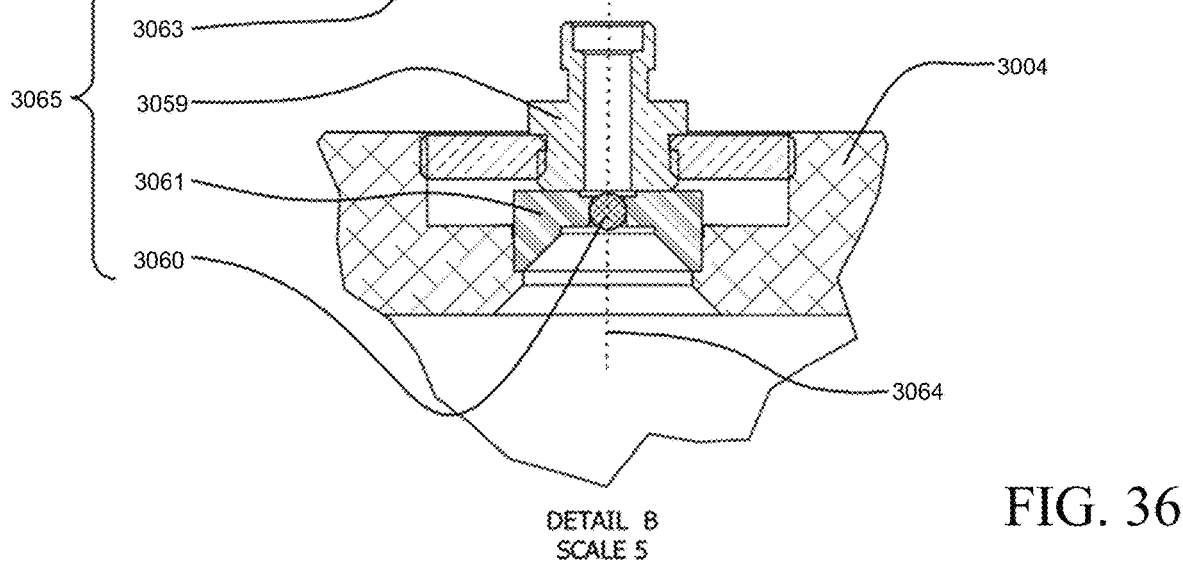
FIG. 36 depicts a detail view of the segmented section view of the coherent light emissions optics assembly of FIG. 35, shown from the perspective of detail line B in FIG. 35.

FIG. 34-36 depict a top view of the CLEO 3027 (FIG. 34) with a projected section view (FIG. 35) illustrating the internal components within the assembled apparatus of the CLEO 3027 taken along the depicted section line ("A-A") and a detail view (FIG. 36) showing area ("B") illustrating the optical box 3005 mounted fiber port 3059 with ball lens 3060 installed within the ball lens holder 3061.

FIG. 35 illustrates the internal geometry of the optical box 3005, where an open bore 3005*a* is located such that there is no obstruction of coherent light along the optical axis 3064 for each of a plurality of coherent light emission optical set(s) 3065. Light emitted from the CLG 3026 enters the CLEO 3027 at the fiber port 3059 from the transmission optics 3040 as illustrated in FIG. 33. The coherent light exiting the FOC(s) 3041 of the transmission optics 3040 at the fiber port 3059 enters the optical box 3005 and passes through the ball lens 3060 diverging the light such that the projected cross-section of light increases in diameter as the distance from the ball lens 3060 increases. The divergent coherent light is collimated by the collimating lens 3062 near the open end of the open bore 3005*a* of the optical box 3005 for each optical set 3065 within the apparatus of the CLEO 3027. The open bore 3005*a* of the optical box 3005 is illustrated as a plurality of discrete pockets of sufficient size and shape to accept and locate the collimating lens 3062 concentric to the optical axis 3064 at a specific distance suitable for the focal lengths of the ball lens 3060 and collimating lens 3062. The optical box 3005 may be a single component with open bore 3005*a* characterized as a plurality of pockets depicted in the illustrated embodiment or an apparatus with a plurality of components which when assembled function as outlined herein. Similarly the fiber port 3059 and lens retainer 3063 may take a multitude of forms suitable to the specific functional characteristics of the embodied transmission optics 3040 and optical box 3005 design.

Figure 37:
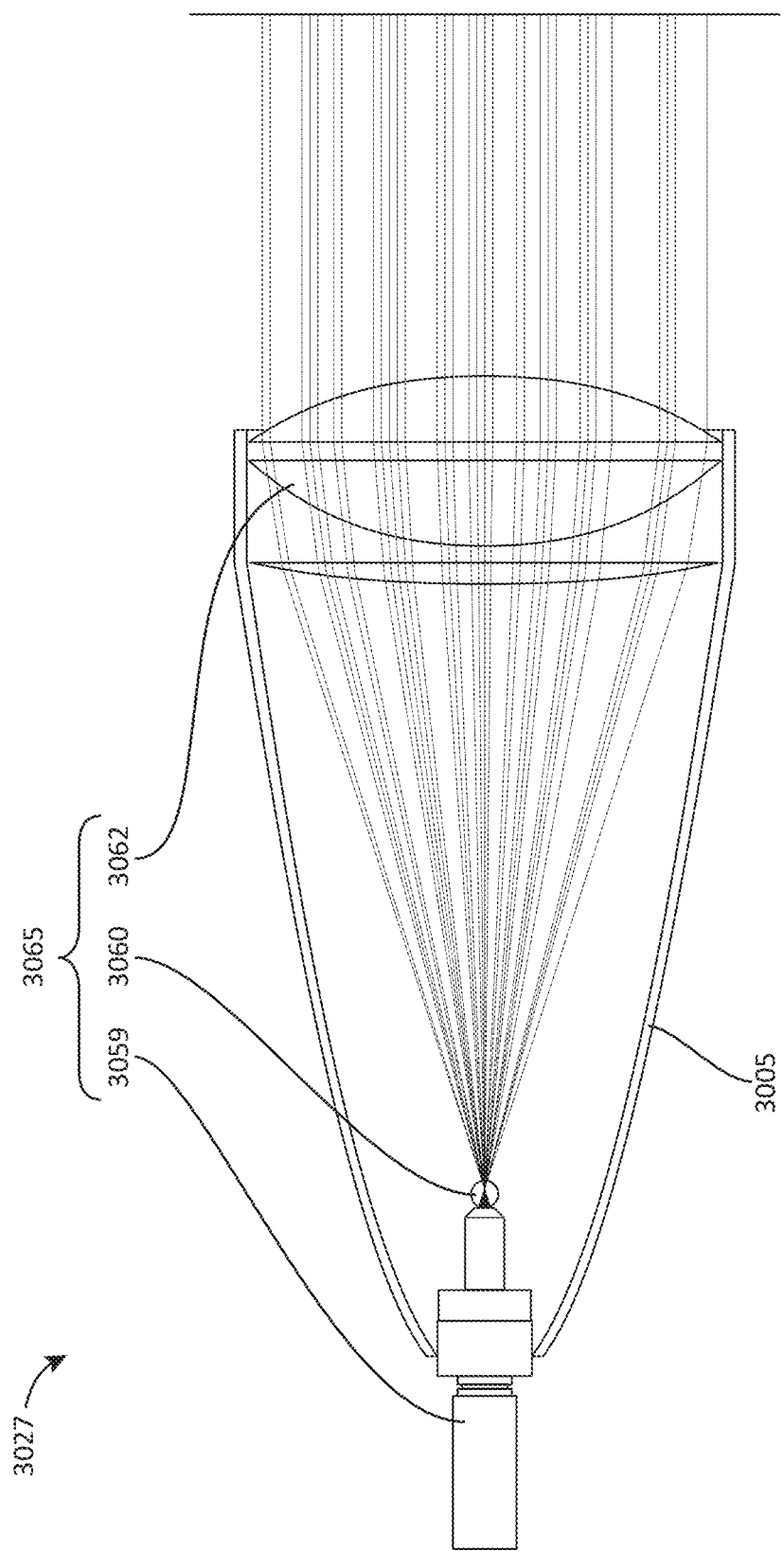
FIG. 37 depicts a light ray tracing diagram of a representative embodiment of one optic set within the coherent light emission optics shown in FIG. 33 illustrating the path of coherent light traveling through the ball lens and collimating lens.

The optical path of the coherent light generated by the CLG 3026 through the CLEO 3027 is illustrated in the ray diagram for a single optical set 3065 in FIG. 37. The optical box 3005 is depicted in FIG. 37 as a simple shell body with mounted fiber port 3059 ball lens 3060 and collimating lens 3062 shown. Note that the ball lens holder 3061 and lens retainer 3063 elements of a complete optical set 3065 illustrated in FIGS. 34-36 are not shown in the ray diagram of FIG. 37 and may not be required in some embodiments. The characteristic dimensions illustrated are provided as an example and are not intended to limit or otherwise confining the scope of this disclosure and the embodiments defined herein. As previously discussed, the ball lens 3060 is optional and may be omitted resulting in an increased overall fiber tip to outside achromatic surface distance over the distance shown in FIG. 37 with the ball lens 3060. Alternate designs for the ball lens 3060, collimating lens 3062, and associated optomechanical elements will dictate the size and arrangements of the optical box 3005 and associated elements of the apparatus of the CLEO 3027.

Figure 38:
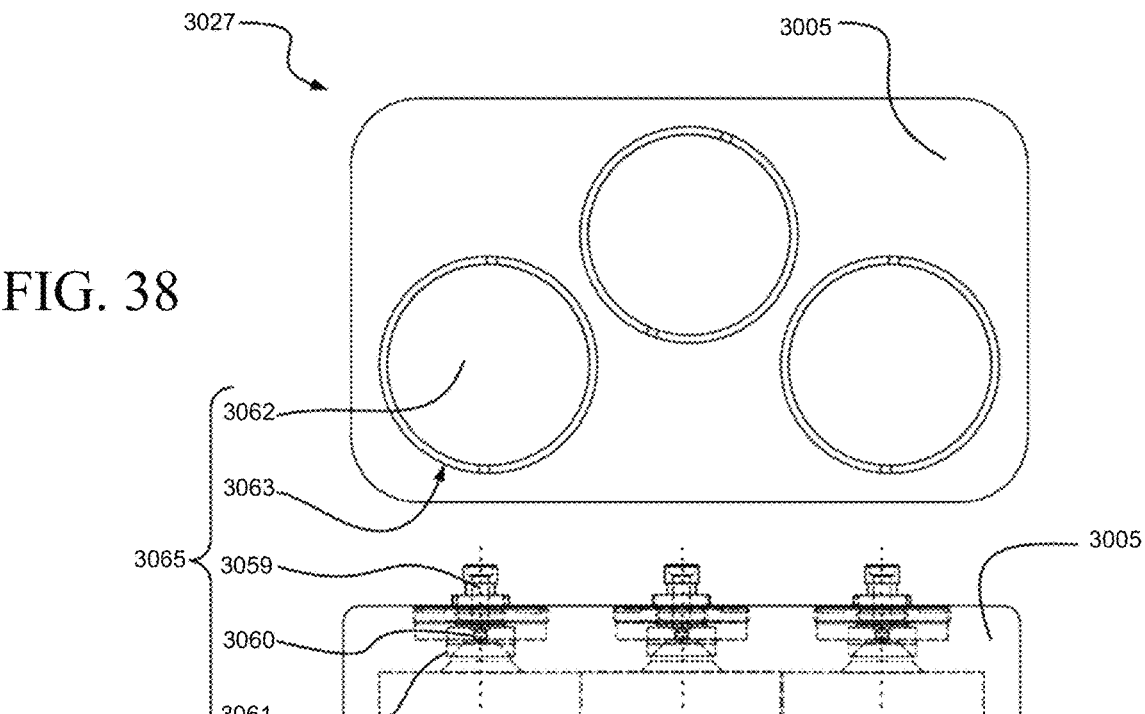
FIG. 38 depicts a bottom view of the collimating lens arrangement of the coherent light emission optics of FIG. 33.
Figure 39:
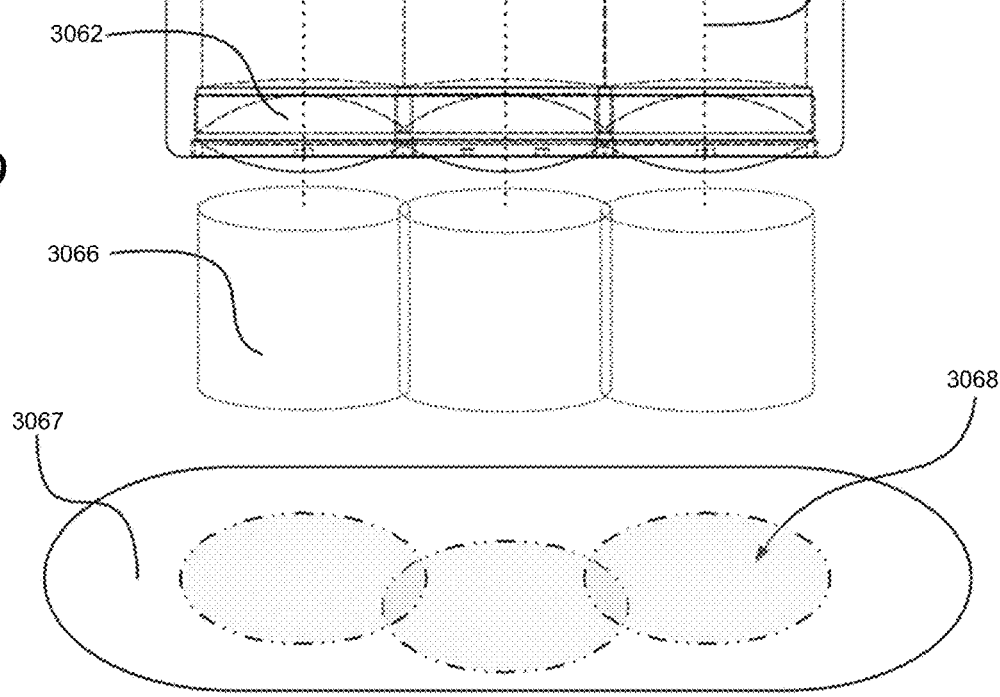
FIG. 39 depicts a side view of the collimating lens arrangement of the coherent light emission optics of FIG. 33, shown with a representative illustration of coherent collimated light emitted by the coherent light emission optics and the resulting treatment area on a target surface where the PBMT is being applied.

Another view of the CLEO 3027 shown in FIGS. 38 and 39 illustrates the configuration of a plurality of optical sets 3065 within the optical box 3005 such that the coherent collimated light ("CCL") 3066 beams emitted from each optical set 3065 overlap resulting in one contiguous beam of CCL 3066 from the CLEO 3027. The CLEO 3027 of the illustrated embodiment in FIGS. 38 and 39 includes three (3) optical sets 3065, each on an independent optical axis 3064 aligned parallel and adjacent to each other so that the area of the CCL 3066 projected upon the target surface 3067 constitutes the treatment area 3068. The treatment area 3068 receives the CCL 3066 energy generated by the CLG 3026. The linear motion of the CLEO 3027 by the translation stage 3042 combined with the rotation of the rotatable member 3004 results in the treatment area 3068 of CCL 3066 incident upon the target surface 3067 to scan across the circumference of the treatment area 3068 over the span of travel of the translation stage 3042. In some embodiments, a plurality of treatment areas 3068 covering a larger area of the target surface 3067 or by multiple CLEO 3027 illuminating more than one non-contiguous treatment area 3068 on the target surface 3067.

Figure 40:
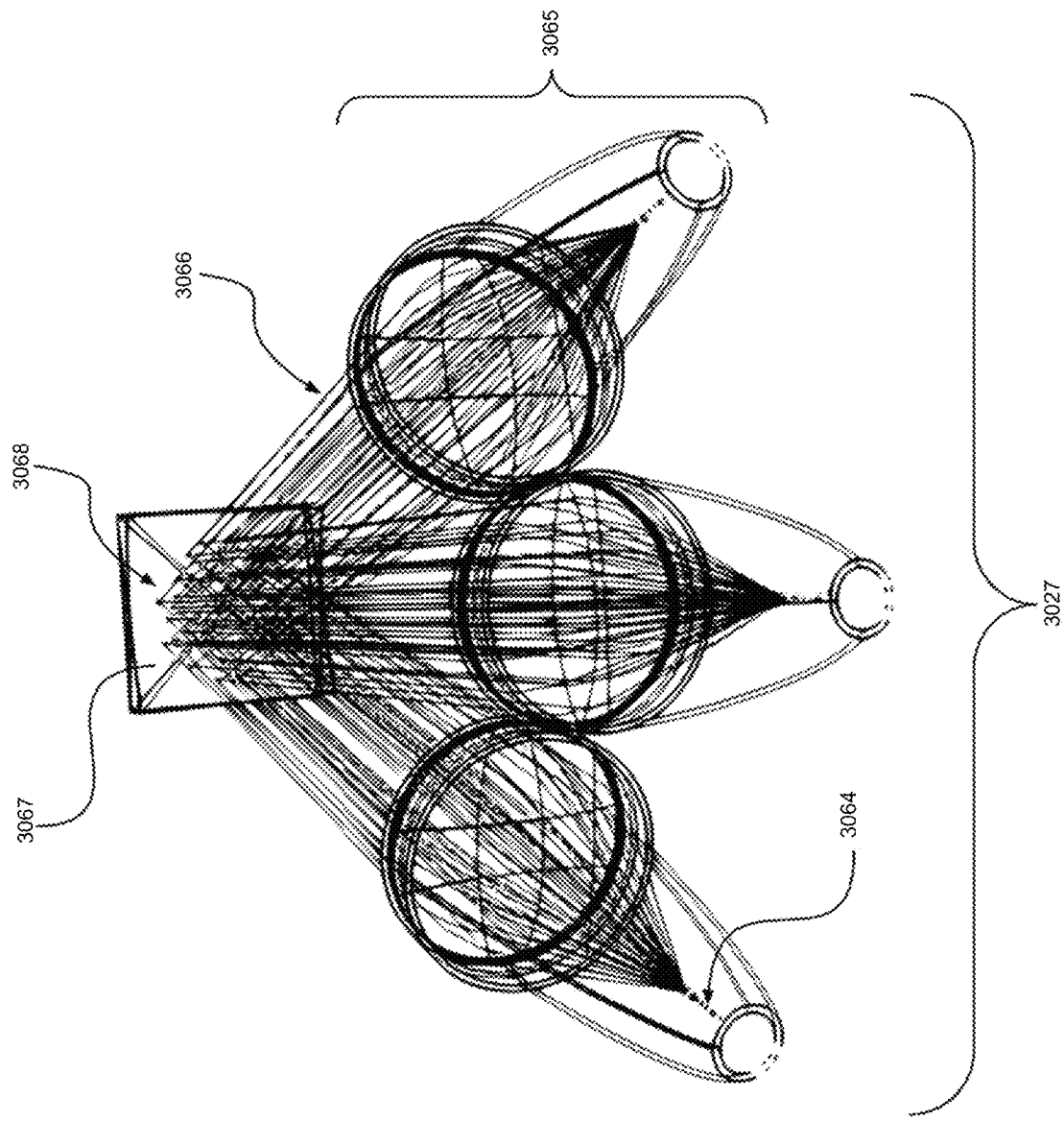
FIG. 40 depicts another example embodiment of the coherent light emission optics shown in FIG. 33 having intersecting coherent collimated light beams emitted illustrated by light ray tracing diagrams of a plurality of optical sets.

In some embodiments, as illustrated in FIG. 40, the CCL 3066 emitted from each optical set 3065 of the CLEO 3027 may be incident upon a common treatment area 3068. The optical axis 3064 of each optical set 3065 may oriented such that they intersect on the target surface 3067. In some embodiments, the incident angle of the CCL 3066 optical axis 3064 is adjustable along one or more degrees of freedom with respect to the target surface 3067 and/or between optical sets 3065 changing number and or size of the treatment area(s) 3068.

Figure 41:
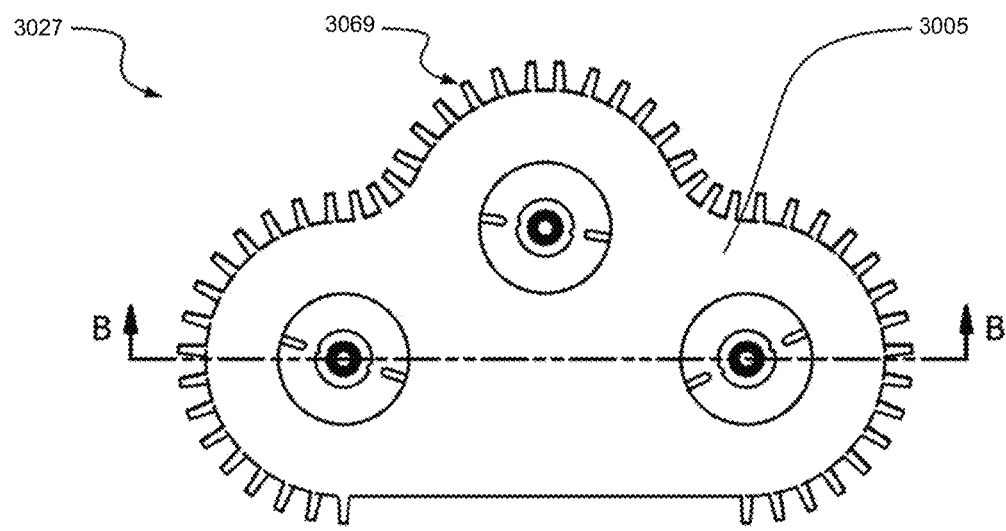
FIG. 41 depicts a top view of another example embodiment of the coherent light emission optics apparatus shown in FIG. 33.
Figure 42:
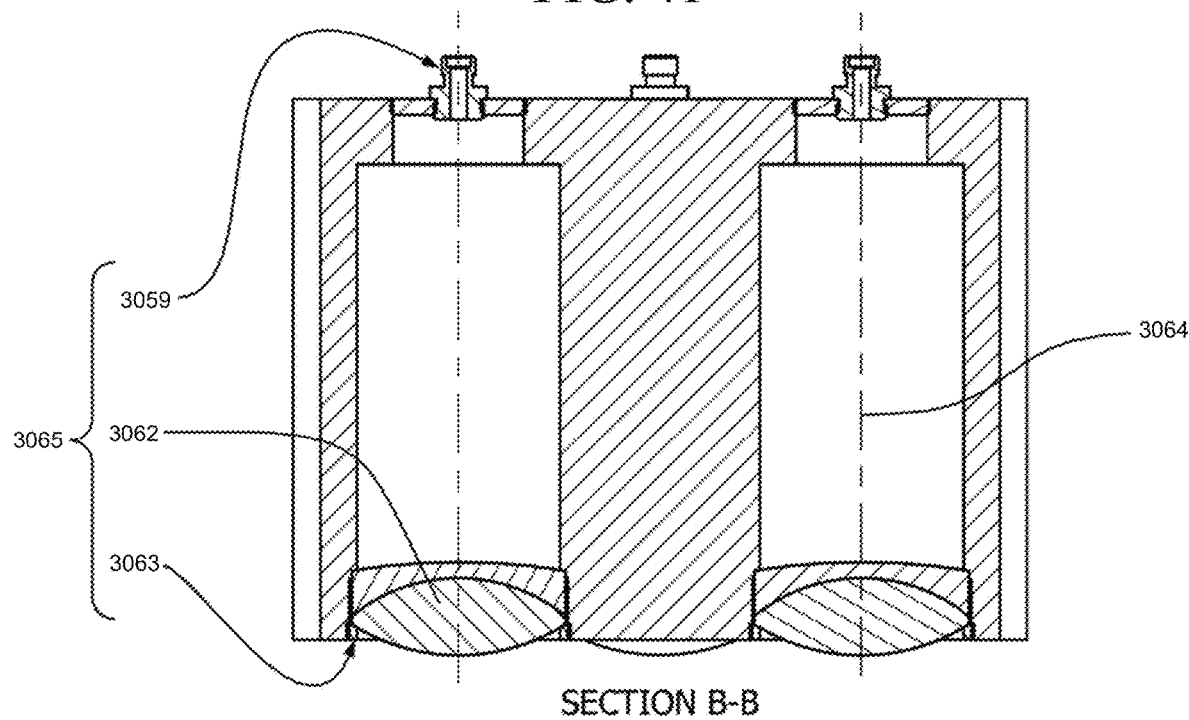
FIG. 42 depicts a section view of the coherent light emission optics apparatus of FIG. 41, shown from the perspective of line B-B in FIG. 41 and illustrating the omission of a ball lens and the addition of cooling fins to the optical box.

Referring now to FIGS. 41 and 42, another possible embodiment of the CLEO 3027 is illustrated, including a top view (FIG. 41) and a section view (FIG. 42) taken along line ("B-B") of FIG. 41. In this possible embodiment, the optical box 3005 includes cooling fins 3069 protruding from the entire surface or a subset of the surface of the optical box 3005. The addition of cooling fins 3069 improves heat transfer from the CLEO 3027 through the optical box 3005 to accelerate or increase the overall cooling efficiency of the optics cooler 3043, depicted in FIG. 31 as a thermoelectric module with fans for forced convection cooling of the exterior surfaces of the optical box 3005. Also note the illustrated embodiment in FIGS. 41 and 42 omits the ball lens 3060 and ball lens holder 3061 previously depicted in FIG. 33-39. It will be appreciated that a similar embodiment including the cooling fins 3069, the ball lens 3060, and/or the ball lens holder 3061 may be utilized. Further, in some other embodiments, the optics cooler 3043 may duct cooled or super cooled air, $CO_2$, or any other suitable coolant media via tubes directly into and out of the optical box where the cooling of the CLEO 3027 is the result of direct air flow cooling of the optical elements of each optical set 3065 within the optical box 3005. As used herein, the term "coolant media" may refer to a gas or, in some instances, a liquid, that is used to cool the various components of the devices of the present disclosure.

Referring now to FIGS. 61 and 62, an alternative illustrative embodiment of the CLEO carriage 3033*b* is depicted with an optics cooler 3043 attached to the optical box 3005 of the CLEO 3027. The optics cooler 3043 depicted utilizes a thermoelectric element with the cold side conductively cooling the apparatus of the CLEO 3027 with a fan on the hot side drawing heat away from the CLEO 3027 to be vented from the system.

Figure 63:
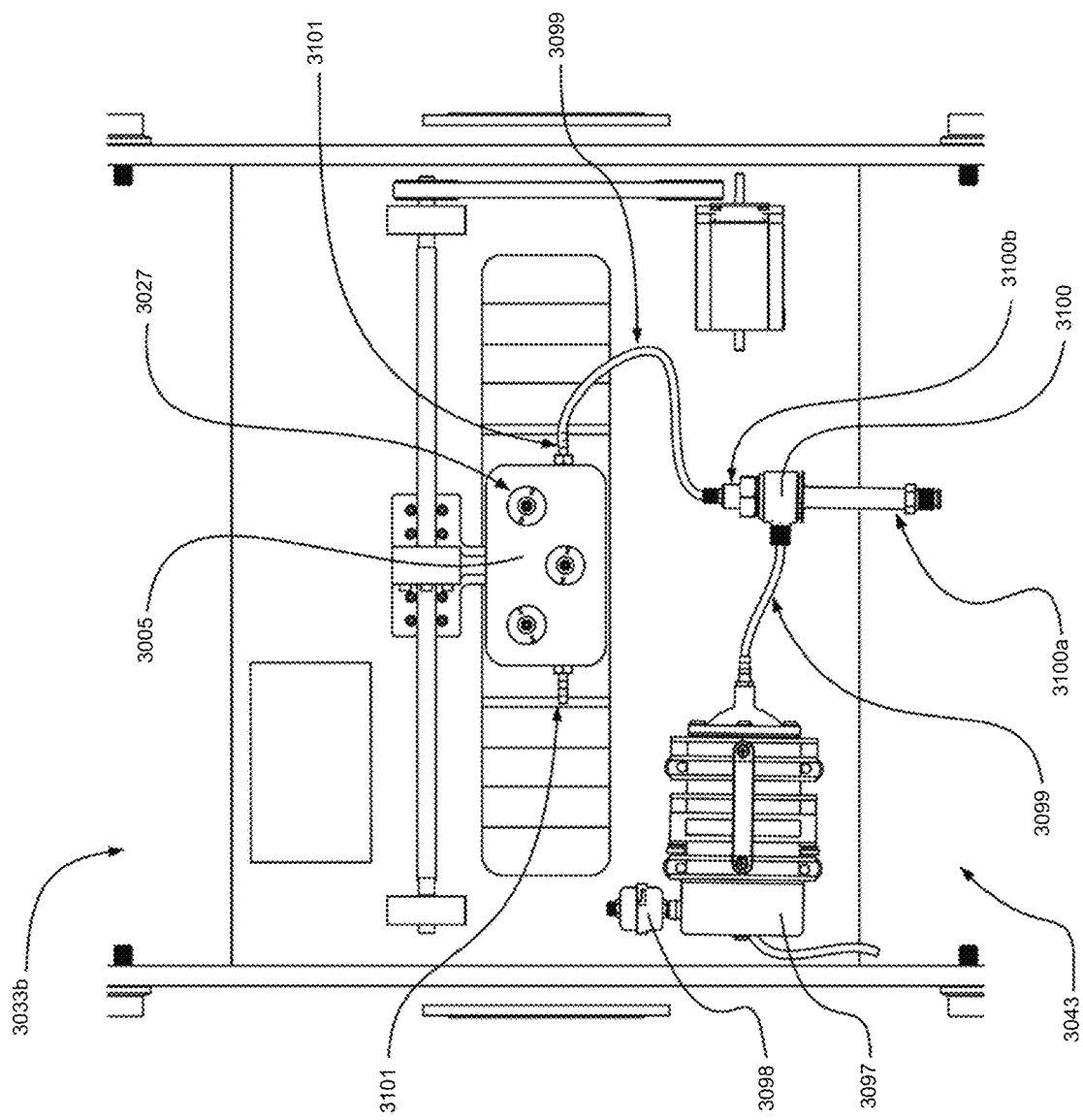
FIG. 63 depicts a top view of the of an illustrative embodiment of the coherent light emission optics carriage with another possible embodiment of the optics cooler utilizing an air compressor and vortex cooler to deliver cooled air into the optical box.

Another alternative illustrative embodiment of the CLEO carriage 3033*b* is depicted in FIG. 63. This embodiment includes an optics cooler 3043 employing an alternative cooling scheme utilizing compressed air from an air compressor 3097 and a vortex tube 3100 to deliver cooled air into the CLEO 3027 for direct cooling of the optical elements and/or the physical structure of the optical box 3005.

A vortex tube 3100 is a device that spins compressed air through the body of the vortex tube 3100 towards the hot side 3100*a* where some air escapes through a valve or orifice and the remaining air is forced towards the cold side 3100*b* resulting in kinetic energy in the form of heat to be transferred to the incoming compressed air and cooled air exits the vortex tube 3100 at the cold side 3100*b*. Cooled air exiting the vortex tube 3100 can be up to 100° F. below the inlet air temperature generated by the air compressor 3097. Pneumatic tubing 3099 facilitates the transfer of compressed air from the air compressor 3097 to the vortex tube 3100 and from the cold side 3100*b* of the vortex tube 3100 to a pneumatic fitting 3101 attached to the optical box 3005 of the CLEO 3027 apparatus.

Cooled air is circulated through cooling channels through the apparatus of the CLEO 3027 or directly through the open bore 3051*a* of each optical set 3065 within the optical box 3005 as depicted in FIGS. 34-36 and is vented out of the CLEO 3027 at a pneumatic fitting 3101 on the opposing side of the optical box 3005 functioning as an outlet port. Ambient air entering the air compressor 3097 passes thought an air treatment element 3098 which filters and/or dries incoming air. The air treatment element removes all dust, particulates, or potential contaminants from the air and/or dries the air to remove all moisture prior to entering the CLEO 3027 where external contamination and moisture may detrimentally impact performance of the device for the application of PBMT. In some embodiments the air treatment elements may be one element with integrated functions or a plurality of elements to independently filter and dry the air. Further, in some embodiments additional pneumatic devices including but not limited to air driers, pressure regulators, and control valves may be inserted within the optics cooler 3043 apparatus as depicted in FIG. 63 in order to dry, regulate, control flow, or otherwise optimize the performance of the CLEO 3027 by regulating the temperature of the optical elements and preserving the environment within the CLEO 3027. In some embodiments temperature sensor(s) may be integrated within the apparatus of the CLEO 3027 to monitor operating temperature and optics cooler 3043 apparatus performance.

Figures 43, 44:
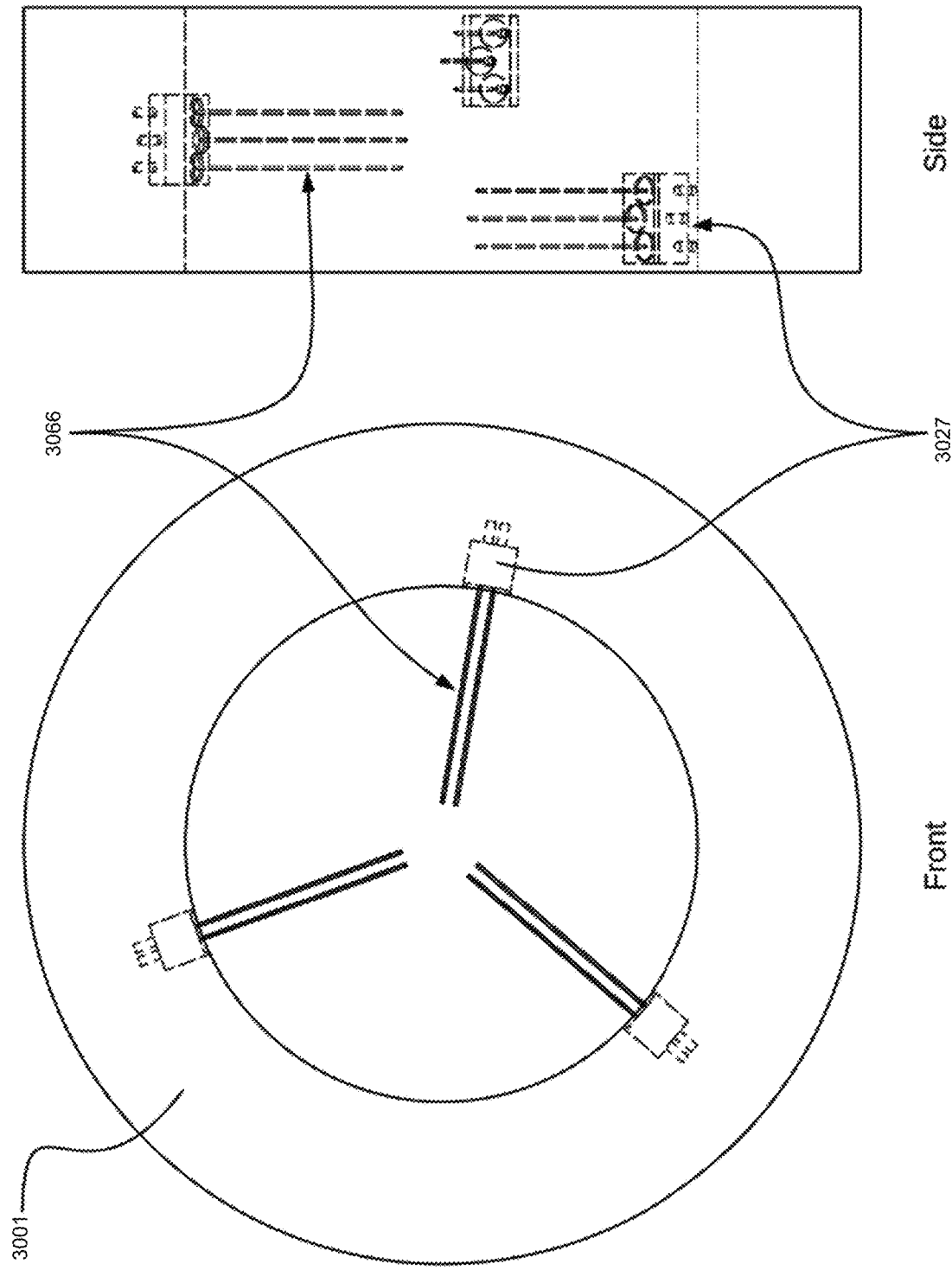
FIG. 43 depicts a front view of another embodiment of an example treatment cylinder device illustrating a plurality of coherent light emission optics apparatuses distributed around the circumference.
FIG. 44 depicts a side view of the treatment cylinder device of FIG. 43, illustrating the plurality of coherent light emission optics apparatuses distributed across the length of the rotatable member within the hollow structure, such that even and distributed continuous or selectable PBMT may be applied.

FIGS. 43 and 44 depict simplified front (FIG. 43) and side (FIG. 44) projection views of another embodiment of the TC 3001 incorporating a plurality of CLEO 3027 apparatuses distributed around the circumference of the rotatable member as seen in the "front" view, such that the CCL 3066 of each CLEO 3027 is incident upon a different treatment area 3068 of the target surface 3067 as illustrated in FIGS. 38 and 39. In some embodiment, the plurality of CLEO 3027 may also be distributed across the width (or the axial length) of the TC 3001, as illustrated in FIG. 44, such that the entire target surface 3067 within the TC 3001 receives PBMT from the CCL 3066 of each CLEO 3027 during each complete rotation of the rotatable member 3004 within the TC 3001 as illustrated in FIG. 25.

Figures 45, 46:
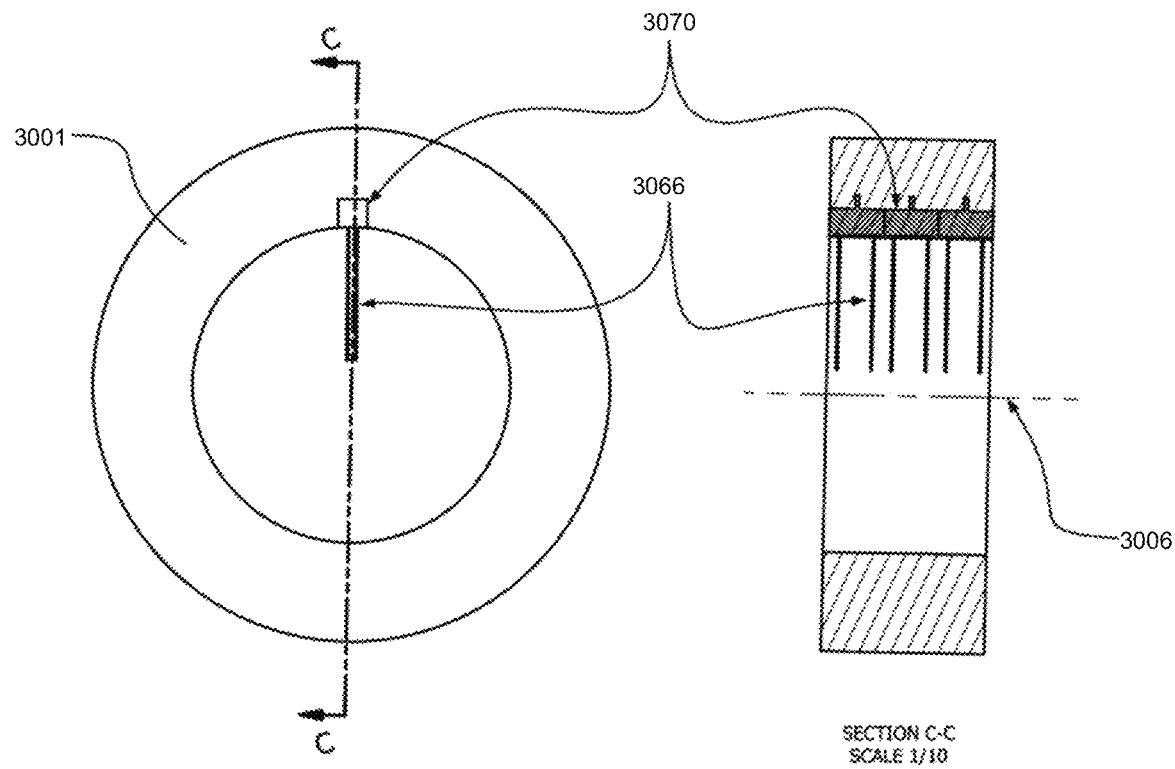
FIG. 45 depicts a front view of another embodiment of an example treatment cylinder device illustrating a plurality of coherent light emission optics apparatuses aligned linearly such that the arrangement of a plurality of coherent light emission optics forms a coherent light emission rail.
FIG. 46 depicts a side view of the treatment cylinder device of FIG. 45.
Figure 47:
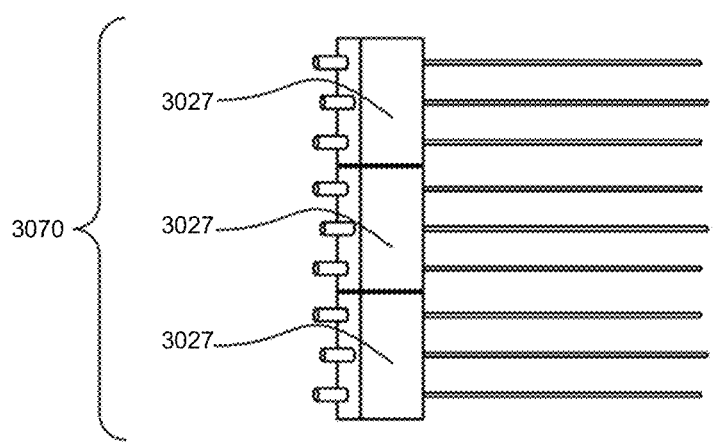
FIG. 47 depicts a side view of the coherent light emission rail formed by the plurality of coherent light emission optics of FIG. 45.

Some embodiments of the TC 3001 device, as illustrated in FIGS. 45-47, may utilize a coherent light emission rail ("CLER") 3070 including a plurality of similar or equivalent CLEO 3027 apparatuses configured in alignment such that the CCLs 3066 emitted from each CLEO 3027 of the CLER 3070 together apply PBMT to a larger section of patient anatomy within the TC 3001 on the axis 3006 of the rotatable member. The CLER 3070 may thus be characterized as a one or more-dimensional array of CLEO 3027 within the apparatus of the rotatable member of the TC 3001 device oriented such that the CCL 3066 emitted from the CLER 3070 is incident upon a larger area of patient anatomy simultaneously. Further possible embodiments include a multitude of configurations of CLEO 3027 in a plurality of orientations with respect to the axis 3006 of the TC 3001 utilizing one or more CLEO 3027 independently or within one or more CLER 3070. Some embodiments discussed further in the following disclosures utilize optical, optomechanical, and optoelectrical components and assemblies to further refine the application of PBMT to a patients anatomy by selectively applying various wavelengths of coherent light generated by one or more CLG to any number of CLEO 3027 and/or CLER 3070 within the TC 3001 device in order to achieve the desired PBMT treatment scheme.

Figure 48:
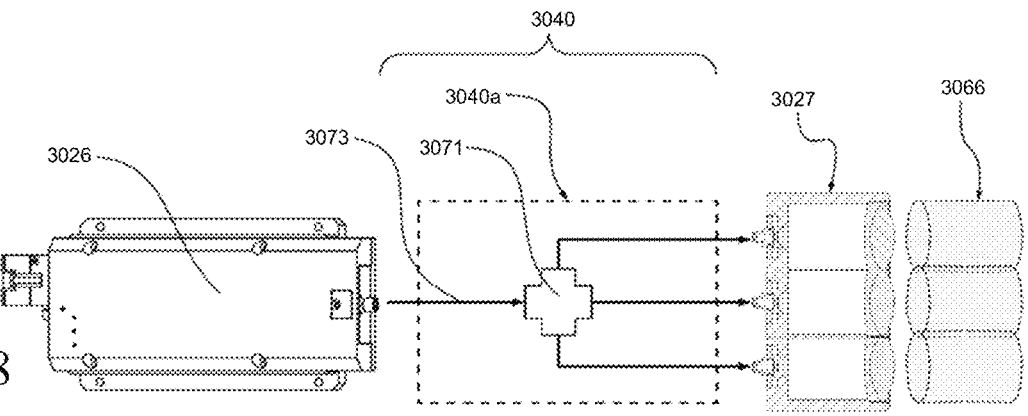
FIG. 48 depicts a schematic embodiment of one possible arrangement of transmission optics between the coherent light generator and the coherent light emission optics apparatus shown in FIG. 29, illustrating the integration of a beam splitting device.
Figure 49:
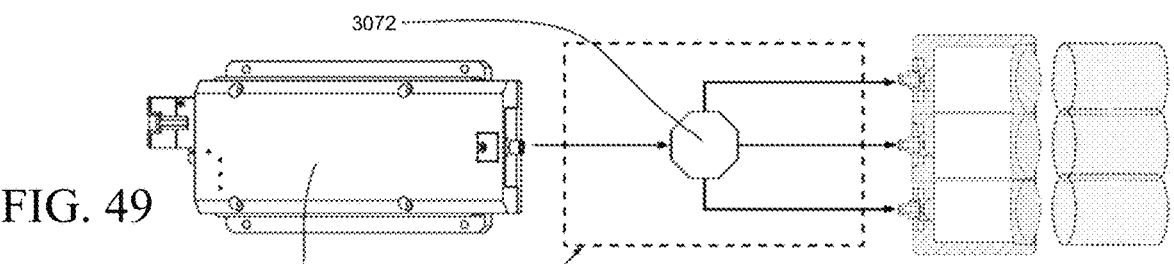
FIG. 49 depicts a schematic embodiment of another possible arrangement of transmission optics between the coherent light generator and the coherent light emission optics apparatus shown in FIG. 29, illustrating the integration of a beam steering device.
Figure 50:
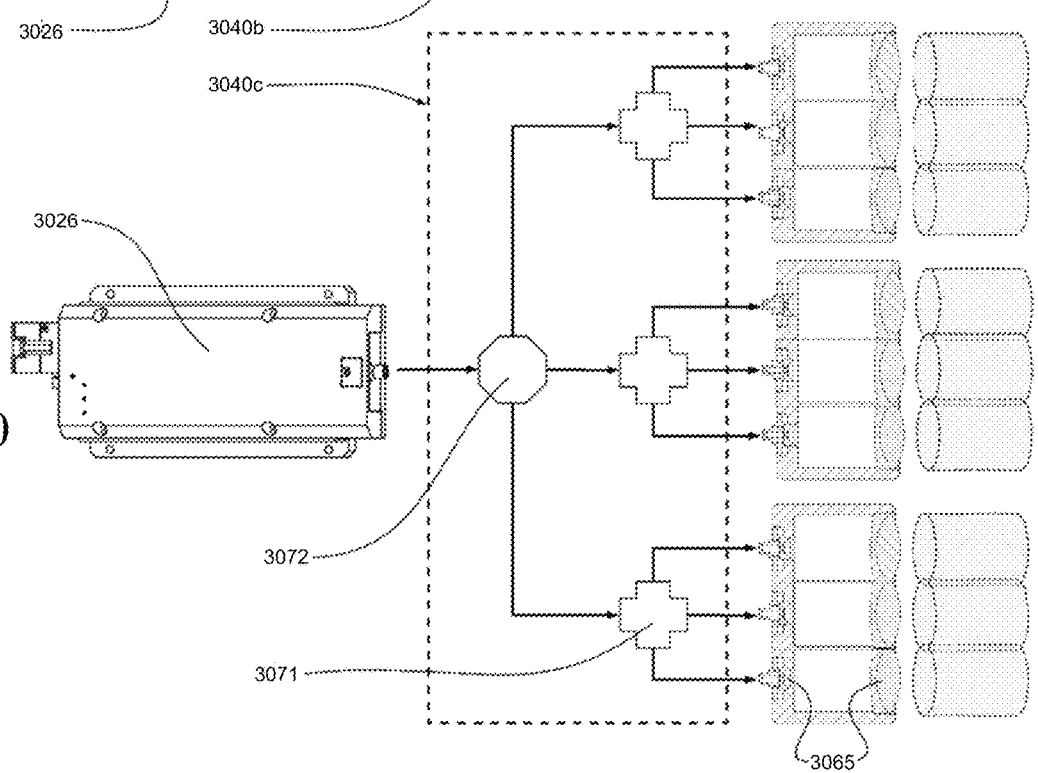
FIG. 50 depicts a schematic embodiment of another possible arrangement of transmission optics between the coherent light generator and a plurality of coherent light emission optics apparatuses shown in FIG. 29, illustrating the integration of beam splitting and beam steering devices.

Some embodiments of a device for the application of PBMT include transmission optics 3040 which alter the path or characteristics of the coherent light generated by the CLG 3026 prior to its delivery to one or more CLEO 3027. The diagrams in FIGS. 48-50 illustrate some possible embodiments of basic optical schematics for transmission optics 3040 in a simple system with one (1) CLG 3026 and one or more CLEO 3027. The transmission optics 3040 embodiments 3040*a*, 3040*b*, 3040*c*, utilize one or more optical, optomechanical, and/or optoelectrical elements to direct, multiply, modify, and deliver coherent light from a CLG 3026 to one or more CLEO 3027 either simultaneously or selectively. The coherent light beam 3073 generated by the CLG 3026 is a vector illustrated as lines with arrows in the direction the beam 3073 is traveling into or out of the apparatus of and elements within the transmission optics 3040. The coherent light beam 3073 may be transmitted through air, fiber optic cables, or other suitable means of transmission of the coherent light beam 3073 from the CLG 3026 to and through the transmission optics 3040 including between elements within the apparatus of the transmission optics 3040 and the input of any number of CLEO 3027 for delivery of CCL 3066 to a patient for the application of PBMT.

In sample configuration transmission optics 3040*a* shown in FIG. 48, a beam splitting device 3071 is incorporated to multiply the coherent light beam 3073 generated by the CLG 3026 one or more times resulting in a plurality of coherent light beams 3073 proportionally split according to the characteristics of the beam splitting optical element(s) utilized within the beam splitting device 3071. A beam splitter is a standard optical element utilized in a wide variety of optical systems which divides a beam of light into two. Beam splitters are commonly formed by prisms and mirrors in conjunction with specialized coatings and/or materials with variable refractive indices that cause incident light to be partially transmitted and partially reflected resulting in two distinct beams. The proportion of the incident light transmitted and reflected to each of the output beams is the split ratio, which may be variable and tunable according to the composition of the beam splitting element. In the illustrative embodiment of the sample configuration of transmission optics 3040*a*, the addition of beam splitter(s) 3071 makes possible the delivery of coherent light from one CLG 3026 to a plurality of optical sets 3065 within the apparatus of the CLEO 3027. The number of beam splitting elements and split ratio between each beam splitting element within the beam splitting device 3071 is dependent on the desired characteristics of the CCL 3066 delivered from one or more optical sets 3065 within one or more CLEO 3027.

Continuing in reference to FIG. 49, the sample configuration of transmission optics 3040*b* replaces the beam splitting device 3071 shown in the sample configuration of transmission optics 3040*a* with a beam steering device 3072. A beam steering device 3072 is generally characterized as an apparatus in which an input beam 3073 is redirected to one fixed output or a plurality of selectable outputs with respect to the input beam vector direction by changing the refractive index of the medium the beam is traveling through using lenses or prisms or by reflecting the beam using a mirror or detraction grating. In the most basic case, a mirror is a beam steering device 3072 which reflects an incident beam 90 degrees off the surface. In a more advanced implementation and galvanometer mechanism is a beam steering device 3072 which can make precision mirror movements across multiple degrees of freedom providing precise directional control of a coherent light beam. A beam steering device 3072 within the apparatus of the transmission optics 3040 enables a user to select which CLEO 3027 or optical set 3065 to deliver the coherent light beam 3073 from the CLG 3026 to for the generation of CCL 3066 for the application of PBMT. Alternatively, a beam steering device which is capable of fast precision switching like a galvanometer can scan between a plurality of optical sets 3065 within one or more CLEO 3027 such that the application of PBMT perceived as pulsing preventing continuous exposure to CCL 3066 from a single optical set 3065 for an extended period of time.

The sample configuration of transmission optics 3040c illustrates a possible combination of beam steering device 3072 and a plurality of beam splitting devices 3071 each delivering a coherent light beam 3073 to optical set(s) within a CLEO 3027. In the illustrated combination sample configuration of transmission optics 3040c, the beam steering device 3072 directs the coherent light beam 3073 from the CLG 3026 to one of the beam splitting devices 3071. This configuration would enable to application of PBMT from each CLEO 3027 according to the desired treatment scheme then allow switching to another CLEO 3027. The TC 3001 alternate embodiment detailed in FIGS. 43 and 44 is an example embodiment for the implementation of the transmission optics 3040c shown in FIG. 50. It is to be understood that the CCL 3066 delivered from each optical set 3065 of a given CLEO 3027 may or may not be identical to the CCL 3066 emitted from another optical set 3065 within the same or another CLEO 3027. Further it is to be understood that any optical set 3065 may or may not emit CCL 3066 during some or all PBMT treatment schemes depending on the combined apparatus of the transmission optics 3040, and associated operating parameters of the treatment cylinder device for the application of precision photobiomodulation therapy.

Figure 51:
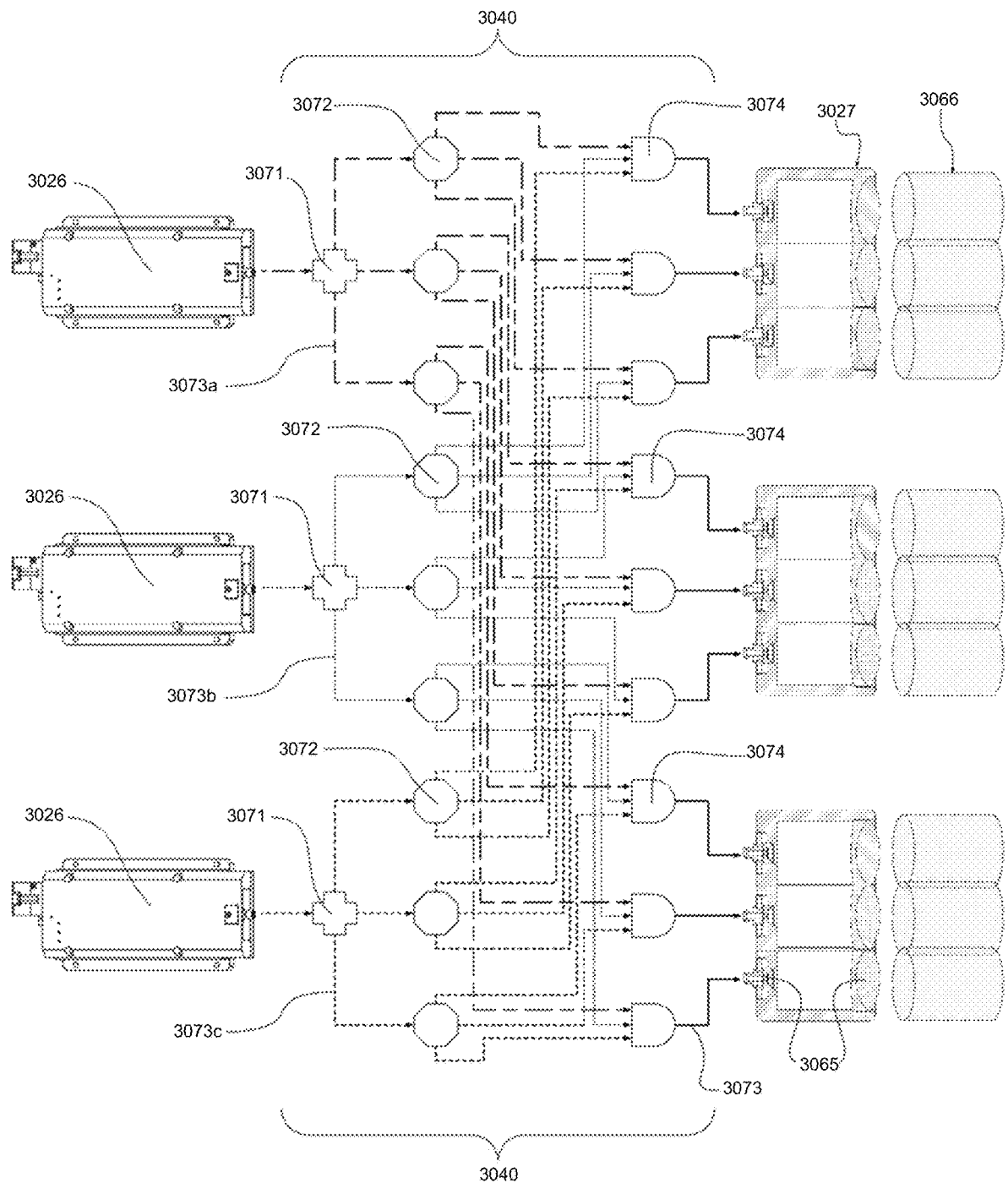
FIG. 51 depicts a complex schematic representative embodiment of another possible arrangement of transmission optics for a system comprising a plurality of the coherent light generators and coherent light emission optics apparatuses shown in FIG. 29, illustrating the integration of beam splitting, beam steering, and beam combining devices.

Referring now to FIG. 51 a more complex transmission optics 3040 schematic is laid out illustrating a system with a plurality of CLG(s) 3026 and CLEO(s) 3027 where each CLG 3026 generates a coherent light beam 3073 of a different wavelength 3073a, 3073b, and 3073c denoted by lines with different patterns. The transmission optics 3040 of the illustrative embodiment utilizes previously defined beam splitter device(s) 3071 and beam steering device(s) 3072 in conjunction with beam combining device(s) 3074 to selectively deliver all available wavelengths of coherent light generated by any given CLG 3026 to any and/or all optical sets 3065 within any and/or all CLEO(s) 3027 configured to receive coherent light from the CLG 3026 by the transmission optics 3040. The beam combining device 3074 is an apparatus which, converse to the beam splitting device 3071, accepts multiple input beams of coherent light and outputs a single beam of coherent light where the resultant beam characteristics are that of the combined characteristics of all input beams. This and all reasonably foreseeable combinations of beam splitter device(s) 3071, beam steering device(s) 3072, and beam combining devices 3074 in addition to the multitude of CLEO 3027 configurations provide a myriad of embodiments and possible treatment schemes for the specialized delivery and targeted application of PBMT.

The optical devices of the transmission optics embodiments illustrated in FIGS. 48-51 represent methods and general apparatuses of a beam splitting device 3071, a beam steering device 3072, and a beam combining device 3074 each independently achievable under a multitude of design configurations. The following detailed embodiments represent various embodiments of simplified apparatuses for each device defined herein for the control and delivery of coherent light generated by one or more CLG 3026 via the transmission optics 3040 to one or more CLEO 3027 for the application of PBMT by the treatment cylinder device of the present disclosure. Further, the transmission optics 3040 will in some embodiments include other optical elements including: mirrors, prisms, lenses, filters, etc. which as an apparatus, with or without specialized devices, change the direction, shape, intensity, number, and characteristics of coherent light carried by the transmission optics 3040 between the CLG 3026 and CLEO 3027.

Referring now to FIGS. 52 and 53, a beam splitting device 3071 is illustrated according to one possible embodiment. As best illustrated in FIG. 53, the beam splitting device 3071 includes a single incoming optical port 3075 where a coherent light beam 3073 enters the apparatus of the beam splitting device 3071. The coherent light beam 3073 interfaces with the first beam splitting element 3076 located and oriented such that the light incident light enters the beam splitting element 3076 at an optimized angle (typically 45 degrees) splitting the coherent light beam 3073 into two beams whereby one beam is transmitted through the beam splitting element 3076 and the other reflected off the surface of the beam splitting element 3076. The beam splitting device 3071 may include one or more beam splitting elements(s) 3076 in any arrangement necessary to produce the desired number of coherent light beams 3073 exiting a plurality of optical ports 3075 within the apparatus of the beam splitting device 3071. The apparatus of the beam splitting device 3071 may in some embodiments include one or more mirror(s) 3079 to change the direction of a beam to facilitate form and function of the beam splitting device 3071. Additionally, the apparatus of the beam splitting device 3071 may in some embodiments utilize a port adjustment mechanism 3077 integrated within the optical port 3075 as illustrated or independently to allow for fine adjustment of the optical port 3075 alignment with respect to one or more degrees of freedom within the apparatus of the beam splitting device 3071. Each beam splitting element 3076 is retained in an optic mount 3078 suitable for the beam splitting element 3076 used, which in some embodiments provides additional kinematic adjustment of the beam splitting element 3076 to fine tune alignment. Further, each beam splitting element 3076 may vary between and within some embodiments according to the desired coherent light beam 3073 characteristics for each coherent light beam 3073 exiting the beam splitting device 3071. The materials and composition of the substrate and coatings applied to each beam splitting element 3076 dictate the ratio of the incident beam transmitted and reflected by the beam splitting element 3076. Common split ratios include 70:30 and 50:50 transmitted and reflected light respectively. In the illustrated embodiment shown in FIGS. 52 and 53 assuming the desired output for each of the three coherent light beams 3073 exiting the beam splitting device 3071 is for each to be approximately one-third (⅓) of the energy of the input beam then the first beam splitting element 3076 would need to have a 33:67 split ratio followed by a beam splitting element 3076 with a 50:50 split ratio to split the 67% reflected beam from the first beam splitting element 3076 resulting in three approximately equal beams each having approximately 33% of the energy of the coherent light beam 3073 at the inlet of the beam splitting device 3071.

Figure 54:
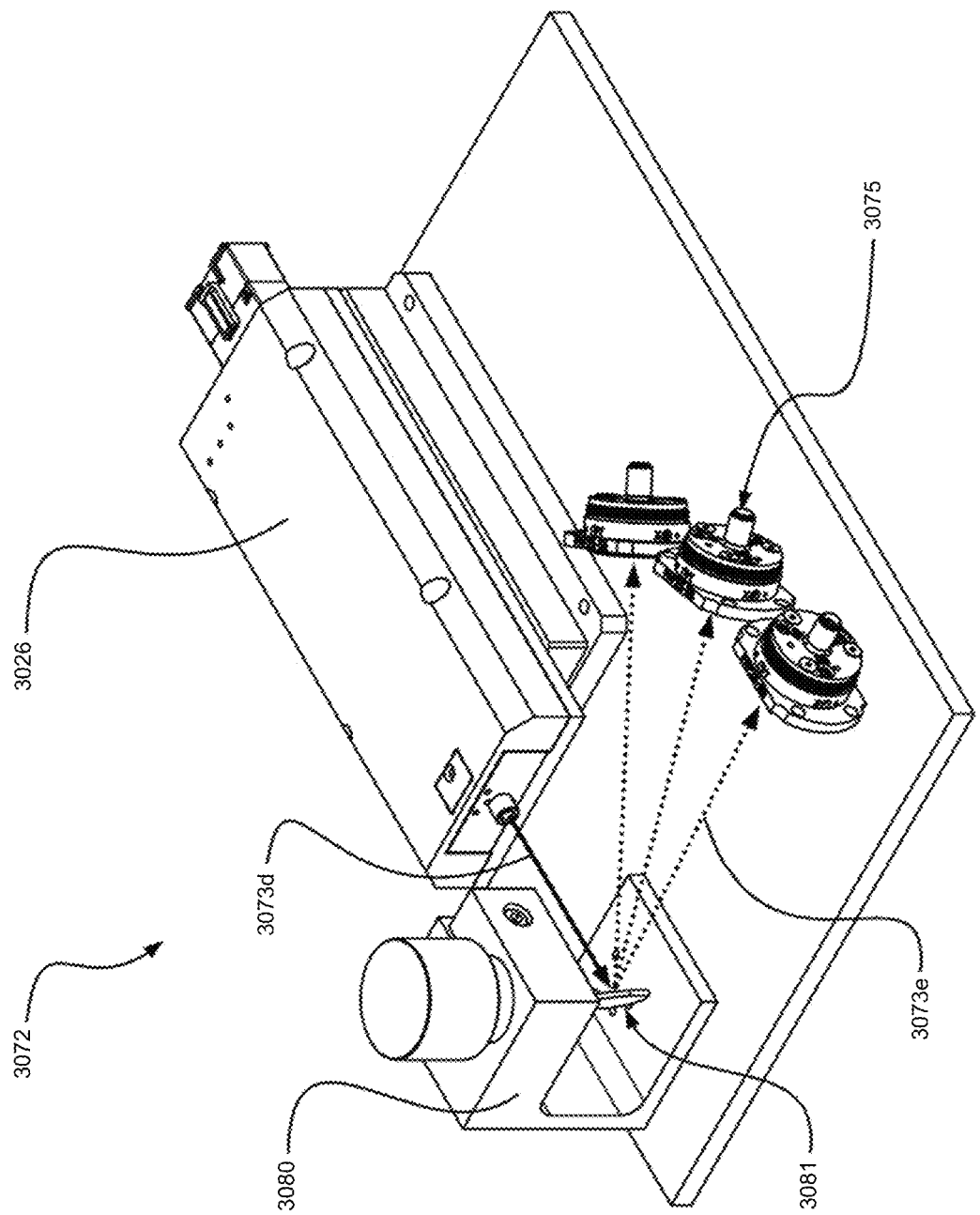
FIG. 54 depicts a perspective view of a simplified representative embodiment of the beam steering device shown in FIGS. 49 and 50, illustrating the associated components and their configuration with the path of light through the device.

Referring now to FIG. 54 a simplified beam steering device 3072 apparatus is shown in a perspective view with one CLG 3026 representing the incident coherent light beam 3073d source and a mirror galvanometer 3080 which reflects the incident coherent light beam 3073d to one of a plurality of optical ports 3075. A coherent light beam 3073d is incident upon the mirror galvanometer 3080 mirror 3081 and is reflected to a precisely controllable angular locus within the range of travel of the mirror galvanometer 3080 such that the reflected coherent light beam 3073e is directed at a desirable target illustrated by an optical port 3075. In some embodiments the source of the incident coherent light beam 3073d is an optical port 3075 or other optical element between the CLG 3026, or in some embodiments a plurality of CLG 3026, and the mirror galvanometer 3080. In some embodiments the reflected coherent light beam 3073e is directed towards other optical elements and/or devices which may further alter the lights path and characteristics.

Figure 55:
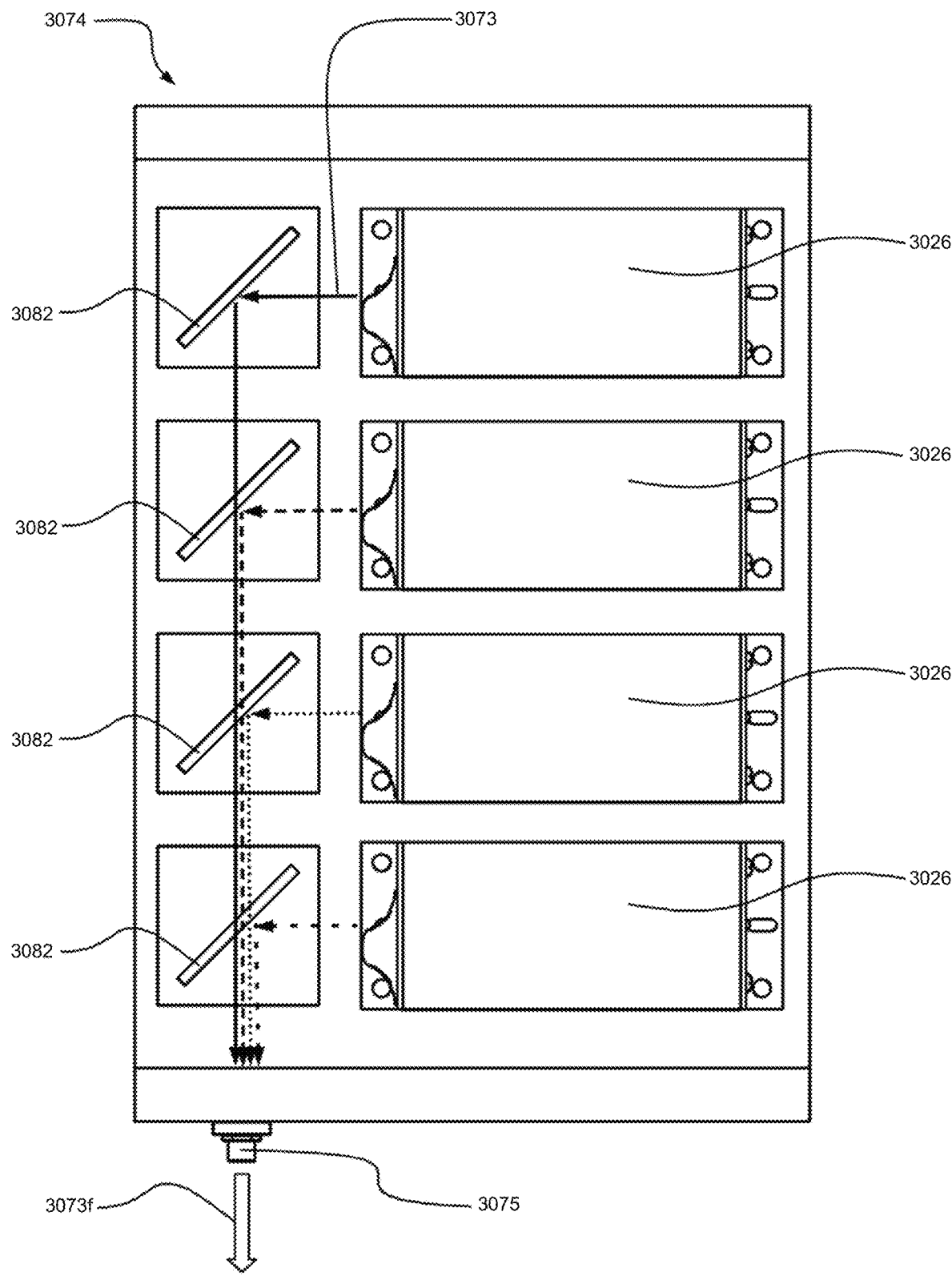
FIG. 55 depicts a top view of a representative embodiment of the beam combining device shown in FIG. 51, illustrating the associated components and their configuration with the path of light through the device.

Referring now to FIG. 55 a top down view of an embodiment of a beam combining device 3074 is illustrated. The beam combining device 3074 includes a plurality of coherent light generators 3026 and a plurality of dichroic mirrors 3082 which facilitate the coherent light beams 3073 generated by each CLG 3026 being aligned and emitted from the beam combining device 3074 as a combined coherent light beam 3073f. A dichroic mirror 3082 is a specialized filter which allows selective reflectance and transmittance based on the wavelength of light such that the coherent light beam 3073 generated by each CLG 3026 is reflected then transmitted through subsequent dichroic mirror(s) 3081, where the beams align and are emitted from the beam combine device 3074 as a combined coherent light beam 3073f from the optical port 3075. In some embodiments the wavelength of coherent light generated by each CLG 3026 is different, producing a combined coherent light beam 3073f with a plurality of wavelengths of light. In some embodiments a coherent light beam 3073 enters the beam combining device 3074 from one or more coherent light generators 3026 external to the beam combining device 3074 via one or more optical ports. Other embodiments utilize a plurality or mirrors and lenses to direct and focus light from multiple sources to produce a single combined coherent light beam 3073f.

The optical ports defined in these disclosures are illustrated in several figures as interfaces for fiber optic cables. In some embodiments the optical port may be an opening through which a beam can travel through air or a multitude of other optical elements including the CLEO. The optical port and fiber port of the CLEO embodiments are intended as representative features at the inlet or outlet of a discrete optical system through which light travels. In some embodiments no fiber or optical ports are required.

Continuing with the present disclosure, some alternative embodiments of the design, layout, configuration, and orientation of the TC device 3001 and associated elements detailed herein through these disclosures and associated figures FIG. 25 through FIG. 32.

Figure 56:
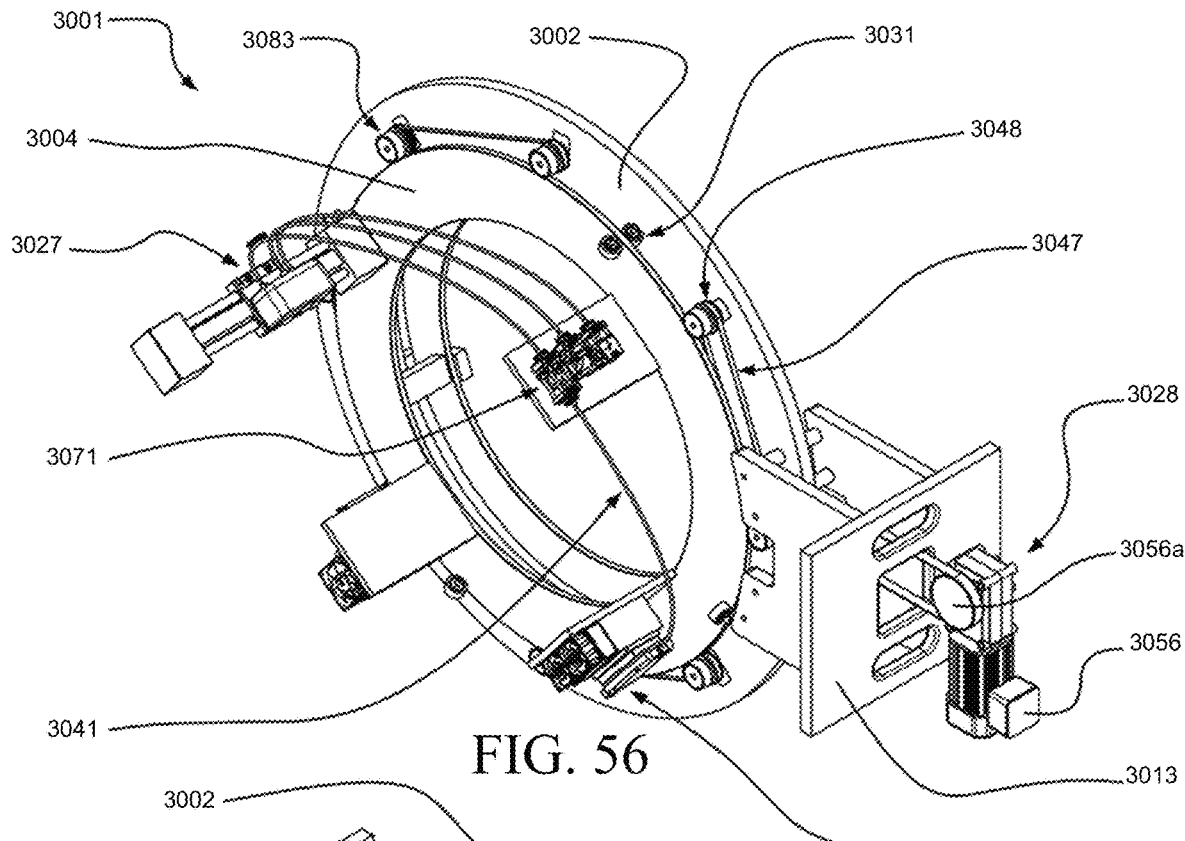
FIG. 56 depicts a front, top, right perspective view of another embodiment of the treatment cylinder device rotation drive mechanism shown in FIG. 27, illustrating another possible construction of the hollow structure and rotatable member, as well as another possible drive mechanism with a rotation drive motor mounted externally to the rotatable member.
Figure 57:
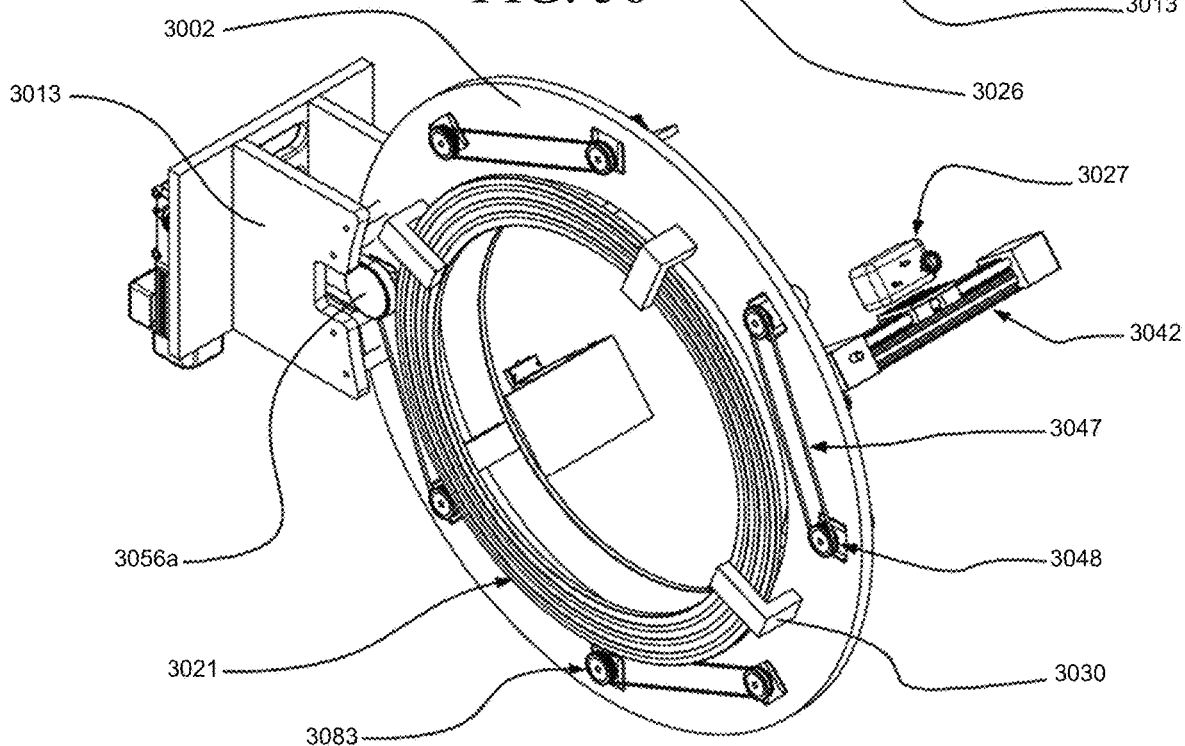
FIG. 57 depicts a rear, top, left perspective view of the treatment cylinder device rotation drive mechanism shown in FIG. 56.

Referring now to FIGS. 56 and 57, various perspective views illustrate an additional embodiment of the device for the application of PBMT in which the rotational drive mechanism 3028 system is powered by a rotation drive motor 3056 external to the rotatable member 3004. In some embodiments the rotatable member 3004 is suspended from the hollow structure 3002 by a plurality of roller elements 3031 and drive rollers 3083. The drive rollers 3083 are all interconnected by a series of belts 3047 and pulleys 3048 spanning subsections of the circumference of the hollow structure 3002 such that there is no obstruction of the opening through the hollow structure 3002 around which the rotatable member 3004 rotates. The drive rollers 3083 are all driven simultaneously by the rotation drive motor 3056 kinematically connected to the series of belts 3047 and pulleys 3048. The plurality of points where the drive rollers 3083 contact the supported surface of the rotatable member 3004 facilitates smooth quiet power transfer from the rotation drive motor 3056 to the rotatable member 3004.

In the illustrative embodiment of FIGS. 56 and 57 the hollow structure is rigidly attached to the TC mounting interface 3013 with the rotation drive motor 3056 output 3056a to pass through the TC mounting interface 3013 to connect with the series of drive rollers 3083. In the illustrative embodiments of FIGS. 56 and 57 the optical system includes one (1) CLG 3026, a beam splitting device 3071 and one (1) CLEO 3027, mounted to a translation stage 3042, which receives coherent light via fiber optic cables 3041. In some embodiments, specifically as illustrated in FIGS. 56 and 57, power required for devices within the apparatus of the rotatable member 3004 is received by a slip ring 3021 from a plurality of slip ring contacts 3030, where the slip ring 3021 is rigidly secured to and supported by the rotatable member 3004 and the slip ring contact 3030 is integrated within the apparatus of the hollow structure 3002 such that there is continuous electrical energy delivered to the rotatable member 3004 throughout the entire range of travel of the rotatable member 3004. In some embodiments the rotatable member 3004 may be supported by a plurality of roller elements 3031 and driven by a single drive roller 3083 kinematically connected to the rotation drive motor 3056 output 3056a.

Figure 58:
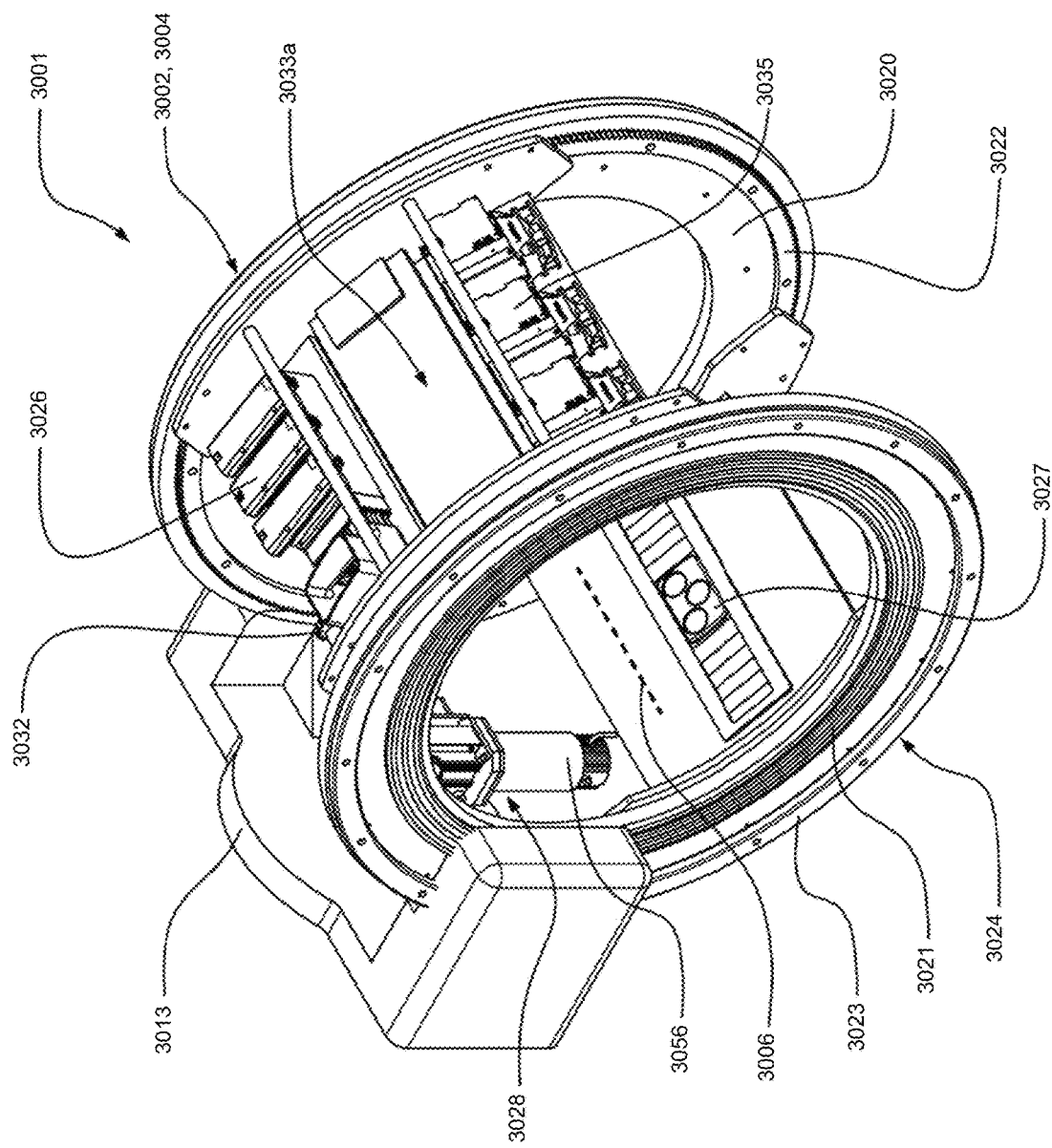
FIG. 58 depicts a perspective view of another embodiment of the treatment cylinder device rotation drive mechanism shown in FIG. 27, illustrating another possible construction of the hollow structure wherein the hollow structure is also the rotatable member driven and supported by the apparatus of the treatment cylinder mounting interface shown in FIG. 25.

In the alternate illustrative embodiment of the TC 3001 device for the application of PBMT illustrated by the perspective view in FIG. 58, the hollow structure 3002 is formed by the rotatable member 3004, such that the rotatable member 3004 is kinematically and electrically connected directly to the TC mounting interface 3013. The rotatable member 3004 includes the structural and operational elements of the CLG carriage 3033a and the CLEO carriage 3033b rigidly fastened to the end apparatus 3024 of the hollow structure 3002 resulting in a single unified apparatus. The carrier ring 3023 and slip ring 3021 are located on the exterior surfaces of the structure end plate 3020 of each end apparatus 3024, such that they interface with roller elements and slip ring contacts within the apparatus of the TC mounting interface 3013. The combined unified hollow structure 3002 and rotatable member 3004 are supported from the TC mounting interface 3013 by a plurality of roller elements which contact a plurality of points on any or all surfaces of the carrier ring 3023 on each end apparatus 3024 such that the hollow structure 3002 and rotatable member 3004 are fully supported in any operational orientation of the TC device 3001 while being able to freely rotate around the axis 3006 of the rotatable member 3004.

Further, the electrical energy required by one or more CLG 3026 and associated CLG control kit(s) 3035 in addition to the power required for the transmission optics and translation stage between the CLG 3026 and CLEO 3027 may be conducted by slip ring contact(s) within the apparatus of the TC mounting interface 3013. In some embodiments the rotational drive mechanism 3028 is significantly like the rotational drive mechanism 3028 illustrated in FIG. 27 and FIG. 32 except the rotation drive motor 3056 is affixed to the TC mounting interface 3013. In the illustrative embodiment of FIG. 58, the drive gear 3032 on each end of the drive shaft meshed or otherwise engaged with the fixed gear 3022 on the inside of each end apparatus 3024 such that the rotation of the drive gears 3032 by the rotation drive motor 3056 of the rotational drive mechanism 3028 induce rotation of the rotatable member 3004.

Figure 59:
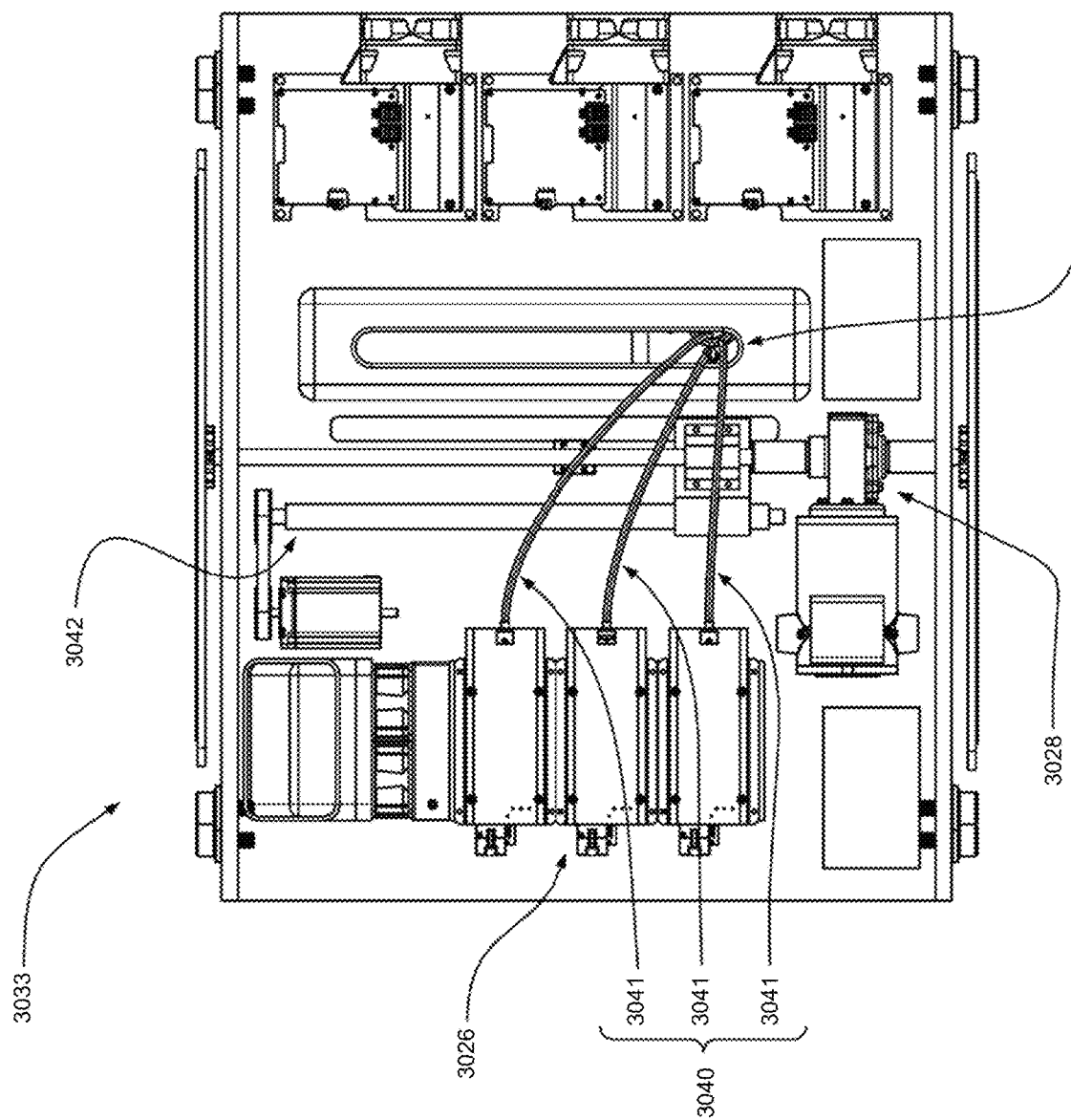
FIG. 59 depicts a top view of another embodiment of the configuration of the rotatable member and treatment cylinder internal components shown in FIG. 27, illustrating the combination of the coherent light generator, coherent light emission optics, and rotational drive system within a unified apparatus.

In some embodiments the carriages 3033 illustrated in FIG. 27 are combined into one unified apparatus illustrated by the carriage 3033 shown in FIG. 59. The unified carriage 3033 includes the essential elements of the CLG 3026, CLEO 3027 with translation stage 3042 and associated transmission optics 3040 illustrated as a plurality of FOCs 3041, and the rotational drive mechanism 3028. The integrated systems of the combined carriage 3033 apparatus illustrated in FIG. 59 are significantly similar in form and function to the systems detailed for the CLG carriage 3033a, CLEO carriage 3033b and rotational drive carriage 3033c illustrated in detail in figures FIG. 28, FIG. 30/FIG. 31 and FIG. 32 respectively. However, the contents of the apparatus and specifications of associated components are fit within the apparatus of the carriage 3033 in a way suitable to their re-configured layout.

For the purpose of clarity and simplicity the embodiments illustrated in FIGS. 56-59 are shown without interior or exterior surface members commonly referred to as covers or enclosures so that the internal features are visible. It is to be understood that in practice the device would include suitable covers for the specific design characteristics of the implemented embodiments like those illustrated in FIG. 26.

Figure 60:
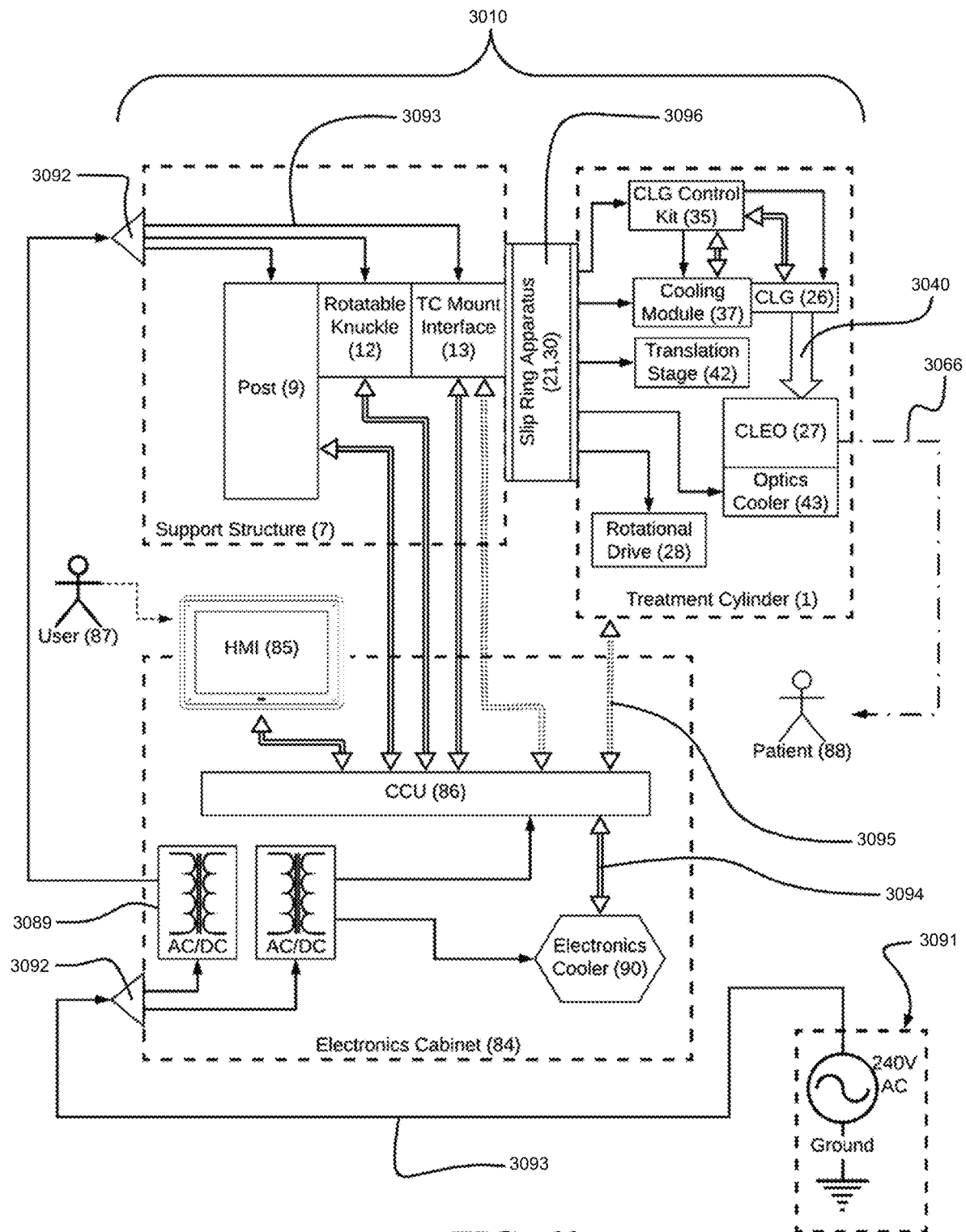
FIG. 60 depicts a schematic representation of the overall system architecture and control electronics shown in FIG. 25, illustrating system inputs and outputs from user instructions to the delivery of PBMT to a patient.

Referring now to the schematic diagram in FIG. 60 depicting the elements and configuration of the control electronics 3010 illustrated by an electronics cabinet 3084 with the integrated human machine interface ("HMI") 3085 of FIG. 25, which facilitate the operation of the treatment cylinder 3001 and the manipulation of the support structure 3007 to allow for the application of the PBMT of the present disclosure. For the purposes of this disclosure the complete contents of the control electronics 3010 depicted in FIG. 60 are contained within the electronics cabinet 3084 and all user operation of the device is conducted via the HMI 3085. However, it is to be understood that the implementation of the electronics architecture and associated computer control schemes have a myriad of embodiments which may include in some instances a plurality of electronics cabinets 3084 used in conjunction with one or more HMI 3085 that may or may not be integrated as a part of the support structure 3007 as illustrated in FIG. 25, or as standalone modules located in near proximity to the device such that sufficient mechanical and electrical connections can be made.

Further, the HMI 3085 may be a single device like a touch screen computer displaying a graphical user interface ("GUI") or a plurality of devices including: buttons, dials, switches, indicators, readouts, and feedback mechanisms for sensors or other monitoring devices utilized throughout the device. The electronics cabinet 3084 includes the computer control unit ("CCU") 3086 which interprets commands from the user 3087 input into the HMI 3085 in conjunction with information provided by sensors and monitoring devices and executes operation of the TC 3001 device to achieve the desired PBMT treatment scheme.

Continuing in reference to FIG. 60, the control electronics 3010 are illustrated by the electronics cabinet 3084 and an array of interconnected system elements with lines representing electrical power and communication into and out of the electronics cabinet 3084 between the interconnected systems of the support structure 3007 and TC 3001 device. The unidirectional solid lines represent electrical lines 3093 where electricity flows in the direction of the filled arrow. Electrical energy transfer from the support structure 3007 TC mounting interface 3013 to the treatment cylinder 3001 is via the slip ring apparatus which includes the slip ring(s) 3021 and slip ring contact(s) 3030. The double solid lines with unfilled arrows on both ends represent data and communication between the CCU 3086 and core systems within the electronics cabinet 3084 as well as between the electronics cabinet 3084 and support structure 3007/TC 3001. The double dotted lines with an unfilled arrow on both ends represent the TC communication 3095 illustrated in two possible configurations. In some embodiments the systems within the apparatus of the TC 3001 communicate with the CCU 3086 directly via wireless communication. In some embodiments some or all TC communications between the CCU 3086 and TC 3001 are physical connection via communication circuits integrated within the slip ring apparatus 3096. Similarly, communication 3094 between the CCU 3086 and other system elements not within the apparatus of the TC 3001 including the post 3009 and rotatable knuckle 3012 mechanisms or between the CCU 3086 and HMI 3085 could, in some embodiments, be wireless.

The mains supply 3091 represents the source of electricity for the device originating from the facilities of the physical location where the device is intended for use. The mains supply 3091 is illustrated as 220 volts, alternating current, electricity common around the world. Electrical energy from the mains supply 3091 enters the electronics cabinet 3084 via one or more electrical interface(s) 3092 and is distributed within the electronics cabinet 3084 to a plurality of power inverters 3089. The power inverters 3089 convert alternating current ("AC") mains supply 3091 power to direct current ("DC") electrical energy suitable for the electrical circuitry of the control electronics 3010 systems including the electrical apparatuses within the electronics cabinet 3084, support structure 3007 and treatment cylinder 3001. Each power inverter 3089 outputs one or more specific DC voltages appropriate for the intended system(s). Common DC voltages suitable for the devices detailed herein include 3, 5, 9, 12, 24, 48, and 60 volts. The electronic devices within the control electronics 3010 connected systems may in some embodiments receive electrical energy from one or more power inverters 3089 located within the electronics cabinet 3084 as illustrated in FIG. 60 or from supplementary power inverters or power management and distribution devices within the apparatus of electrical interface(s) 3092 or independent devices not illustrated.

Primary device functions are orchestrated by the CCU 3086, the brain of the PBMT device, located within the primary electronics cabinet 3084. The CCU 3086 is generally characterized as a computer with a plurality of circuits and interconnected electronic interfaces and devices running commercially available and/or custom embedded firmware and software programs specifically developed for the implementation of the device design and methods described herein. The HMI 3085 is the interface usable by the user 3087 for the control and operation of the control electronics 3010 systems within the apparatuses of the electronics cabinet 3084, support structure 3007, and treatment cylinder 3001, collectively the control electronics 3010. A user 3087 inputs instruction(s) and/or operating parameter(s) to the HMI 3085, which are transmitted to the CCU 3086 via communication line(s) 3094 where the user 3087 instruction(s) and/or parameter(s) are interpreted, executed and updated. If and when, according to inputs provided by the user 3087, various drive mechanisms and electronics systems need to be energized (turned on) or disengaged (turned off) or in the case of the HMI 3085 itself, updated to reflect the current state of systems, the CCU 3086 transmits the necessary signal(s) via one or more communication line(s) 3094 and/or TC communication line(s) 3095 between the apparatuses of the electronics cabinet 3084, support structure 3007 and TC 3001 as appropriate for the instruction(s) to be received by the subject electronic system within the control electronics 3010 architecture illustrated in FIG. 60. The subject systems which may in some embodiments receive instructions from the CCU 3086 include the post 3009 apparatus, rotatable knuckle 3012 mechanism, TC mounting interface 3013, CLG control kit 3035, CLG 3026, CLEO 3027, rotational drive mechanism 3028, cooling module 3037, transmission optics 3040, translation stage 3042, optics cooler 3043, HMI 3085 and electronics cooler 3090. Additionally, in some embodiments the CLG control kit 3035 is the interface between the CCU 3086 and the CLG 3026 and cooling module 3037 delegating ongoing operational power and task management to the CLG control kit 3035. In some embodiments the CCU 3086 communicates directly with apparatuses within the subject systems or to an intermediate interface like PCB(s) 3039, illustrated in figured FIG. 28, FIG. 30, FIG. 31 and FIG. 32, including circuitry and in some embodiments computing capability to delegate instructions received from the CCU 3086 to the various electrical devices and apparatuses of the control electronics 3010 interconnected systems.

Continuing in reference to FIG. 60, under normal operating conditions the CCU 3086 is continuously monitoring user 3087 inputs to the HMI 3085 and feedback information from the network of interconnected sensors and monitoring devices within the apparatuses of the control electronics 3010 architecture including the electronics cabinet 3084, support structure 3007 and TC 3001. Sensors and monitoring devices provide essential operating information from device systems to the CCU 3086 for precision control of all functions. Common sensors and monitoring devices include switches, encoders, temperature sensors, photo sensors, proximity sensors, infrared and ultrasonic devices, and cameras. These monitoring devices provide specific and targeted information about the sub-system or apparatus the sensor is used in association with. Each sensor has a specific operating range and feedback mechanism for reporting the relative information associated with the sensor back to the CCU 3086 via communication line(s) 3094 or TC communication line(s) 3095. For motors and kinematic systems encoders provide stepwise feedback with fine resolution over a long range indicating the location, direction, and speed of travel of a motor or kinematic system relative to an index or home position. The home position or other indexing and locating parameters of a device or apparatus can be denoted by a feature which triggers a sensor when the travel reaches a designated position providing a known reference location. Temperature sensors are utilized throughout the device of the present disclosure in both custom apparatuses like the CLEO 3027 and OEM modules including the coherent light generator 3026. Temperature sensors in the optical and electronic systems tell the CCU 3086 when to engage and at what level to set cooling devices including the CLG 3026 cooling module 3037, optics cooler 3043 and electronics cooler 3090.

Throughout these disclosures the illustrations and detailed embodiments omit some monitoring devices and feedback mechanisms integrated in the apparatuses and embodiments. Many such devices are known, and a skilled person would appreciate that such devices could be utilized and integrated with the illustrated embodiments in various implementations. All such implementations are contemplated within the scope of the present disclosure. Similarly, nuts, bolts, screws, common hardware and other commercially available off the shelf products not fundamental to the detailed embodiments are not explicitly identified and defined. These components and assemblies are assumed and understood to be part of good design and implementation of the mechanisms employed by various embodiments of the present disclosure such that they support manufacturability, assembly, and maintenance. In some embodiments sensors within the apparatus of the TC 3001 may collect and provide feedback to the CCU 3086 about the patient 3088 anatomy before, during, and after treatment. Patient 3088 feedback may include skin surface temperature, machine vision for identification of patient anatomy and analysis of treatment efficacy through automated evaluation of the patient anatomy and penetration of the CCL 3066 emitted by the CLEO 3027 to target tissue layers beneath the patient's 88 skin surface. The sensor and monitoring information collected by the CCU 3086 is used to optimize and automate the precision application of PBMT by the TC 3001 device of the present disclosure.

The apparatuses of the combined TC 3001 devices have been comprehensively illustrated and various reasonably conceivable embodiments are detailed in conjunction with operational characteristics of the device for the application of PBMT by the present disclosure. The specific and detailed embodiments of the post 3009 apparatus and rotatable knuckle 3012 are not essential to the TC 3001 device for the application of PBMT. The post 3009 apparatus is represented as a cylindrical telescoping lift which is a standard mechanical apparatus with a multitude of commercially available OEM solutions including: power screw jacks, scissor lifts, lifting columns, hydraulic jacks, and other kinematic systems with manually, electrically, or hydraulically driven mechanisms for adjustable elevation control.

Similarly, the rotatable knuckle 3012 is represented as a cylindrical mechanism which facilitates partial or complete rotation of the TC 3001 about an axis perpendicular or a desirable angle with respect to the post 3009 such that the TC 3001 is in an ideal orientation for the application of PBMT to a patient 3088. Common commercially available and custom rotation stages frequently actuated by a worm gear mechanism would be well suited to the apparatus of the rotatable knuckle 3012. Similarly, manual adjustment with a locking mechanism to prevent unintended movement of the rotatable knuckle 3012 would be easily implemented with two sliding plates between the post 3009 and TC mounting interface 3013 supported on a common axis via bearing or other load bearing component with a plurality of screws, cam locking mechanisms or other fasteners to secure the rotatable knuckle 3012 in the desired orientation.

Figure 64:
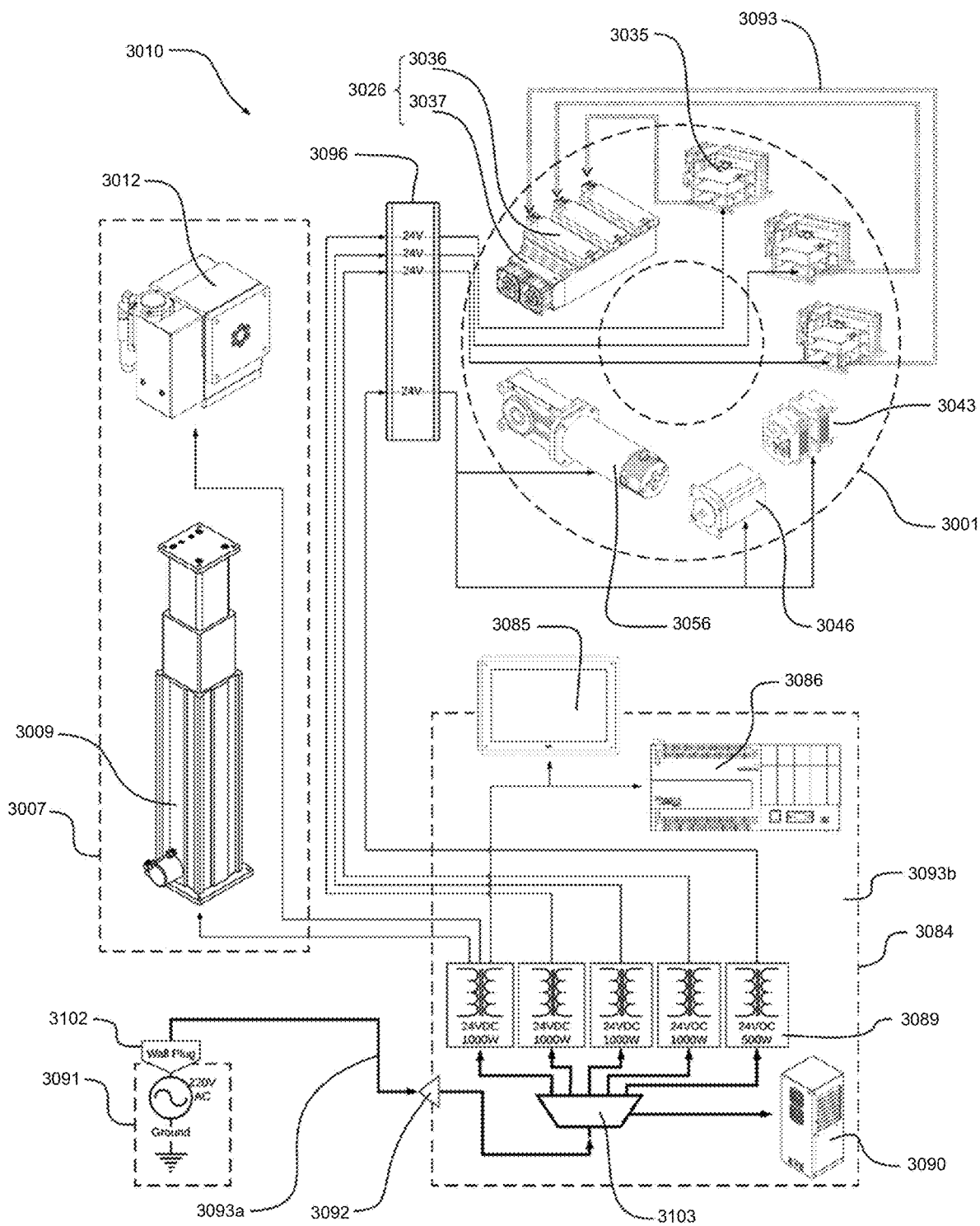
FIG. 64 depicts a schematic representation of an example embodiment of the device control electronics and associated electrical energy management and distribution methods used to operate the treatment cylinder of FIG. 25, shown with illustrative embodiments for the implementation of various electrical and electro-mechanical devices.

Referring now to the diagram of the control electronics 3010 integrated electrical systems illustrated in FIG. 64, an example embodiment of the primary electronic and electromechanical devices is shown with their associated power characteristics. The example embodiment depicted includes the electronics cabinet 3084, support structure 3007 and treatment cylinder 3001 with all associated sub-systems, devices, and apparatuses including the slip ring apparatus 3096 which facilitates electrical power transmission to the electrical systems within the rotatable member 3004 of the TC 3001. Under full load operating conditions, the illustrated electrical systems will adequately deliver the necessary power without degradation in performance. The example devices illustrated represent an exemplary implementation suitable for real world application of PBMT by the device of the present disclosure.

In the example embodiment of the TC 3001 device for the application of PBMT, the mains supply 3091 may require a single 220 volt ("V") alternating current ("AC") collectively ("VAC") source connection. The mains supply 3091 electrical energy is communicated through a wall plug 3102 and through 220 VAC electrical line 3093a (depicted as a line with heavy line weight) to electrical interface 3092 at the electronics cabinet 3084 where the mains supply 3091 energy enters the control electronics 3010. Inside the control electronics, 220 VAC from the electrical interface 3092 inside the electronics cabinet 3084 is connected via electrical line 3093a, first to a distribution block 3103 then to a plurality of power inverters 3089, which convert AC to direct current ("DC") collectively ("VDC") suitable for connected electrical systems. The distribution block 3103 is a specific type of electrical interface 3092 which facilitates splitting one electrical input to more than one equal output. The mains supply 3091 representative voltage of 220 VAC is characteristic of the nominal acceptable voltage normally between 215 to 240 VAC. Similarly, the power inverters 3089 can typically accept an input between 90 and 360 VAC.

The output of each electrical inverter 3089 is DC electrical energy transmitted via DC electrical lines 3093b (depicted as a thin solid line) to the distributed electrical systems within the apparatuses of the electronics cabinet 3084, support structure 3007 and treatment cylinder 3001. The plurality of 220 VDC power inverters 3089 each generate different DC output voltages and/or have a current capacity suitable for interconnected systems. The following descriptions outline the example devices and associated electrical connections integrated within the apparatus of the control electronics 3010 which derive their energy from power inverters 3089 connected to 220 VDC mains supply 3091.

One 24 VDC power inverter 3089 with 1000 watt ("W") power output powers the CCU 3086 and the HMI 3085 within the electronics cabinet 3084 and the apparatuses of the support structure 3007. The CCU 3086 is depicted as a programmable logic controller ("PLC") commonplace in industrial and commercial automation. Similarly, the HMI 3085 is depicted as a touch screen user interface commercially available for integration into custom devices and electronic systems like the device of the present disclosure. In the example embodiment depicted in FIG. 64 the support structure 3007 is depicted as comprising a post 3009 implemented as a lifting column and a rotatable knuckle 3012 implemented as an electro-mechanical apparatus which interfaces directly to the post 3009 with the rotational axis of the rotatable knuckle 3012 orthogonal to the post 3009 integrating the elbow 3011 previously depicted in FIG. 25.

The TC 3001 kinematic and support systems comprising the rotation drive motor 3056, linear drive motor 3046 and the optics cooler 3043 are powered by a common power inverter 3089 with a 24 VDC output rated for 500 W power capable of driving the connected systems at peak output simultaneously.

The three remaining 220 VAC to VDC power inverters 3089 are in electrical communication via the slip ring apparatus 3096 with the CLG 3026, CLG control kits 3035 and cooling module 3037. Each laser module includes a CLG control kit 3035, a set of multiple specialized PCBs with multiple inputs and outputs for power regulation and operational control of the CLG 3026, the diode laser 3036 and cooling module 3037. A dedicated AC/DC power inverter 3089 delivers electrical energy to the CLG control kit 3035 for each of the three integrated laser modules. Each CLG control kit 3035 delivers regulated power via electrical lines 3093 to its respective CLG 3026 diode laser 3036 and cooling module 3037.

Power to the electronics cooler 3090 is 220 VAC directly from the distribution block 3103 and does not require additional power inversion outside the device. The electronics cooler 3090 is illustrated as a self-contained air conditioner unit, commercially available in a multitude of sizes for electronics cooling applications like the device of the present disclosure.

The example embodiment depicted in FIG. 64 illustrates an exemplary mode implementation of the device for the application of PBMT. Additional embodiments and implementations of the device design and methods detailed herein do exist. The various illustrated embodiments provided herein (with specific reference to FIGS. 25-64) are intended to demonstrate the many ways the TC 3001 device of the present disclosure can be realized in practice. These disclosures are in no way limiting or otherwise intended to confine the scope of the disclosure. There are in theory innumerable iterative embodiments of the designs and methods detailed herein, and all such alternatives are contemplated within the scope of the present disclosure.

Figure 65:
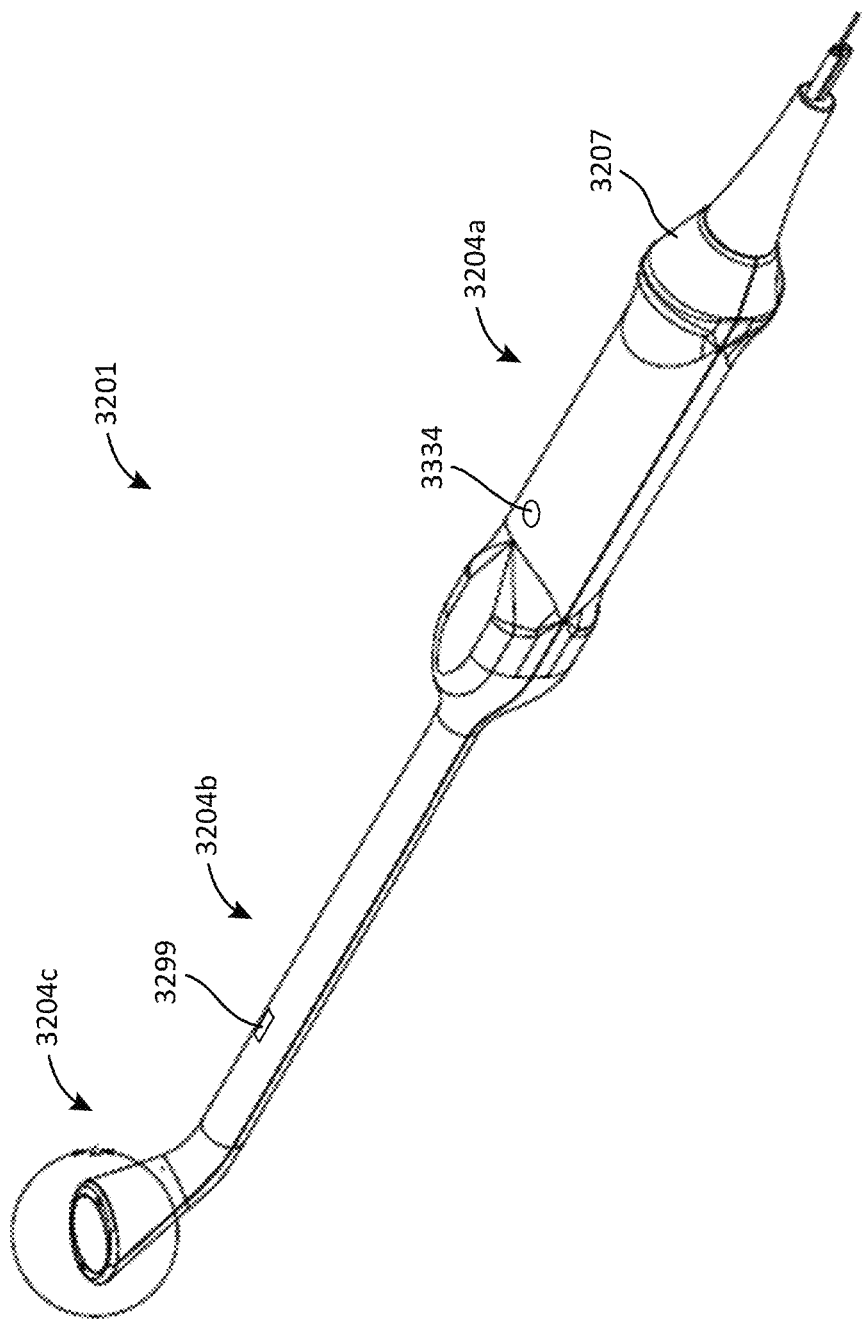
FIG. 65 depicts a perspective view of a handheld probe device for use with a phototherapy system.
Figure 66:
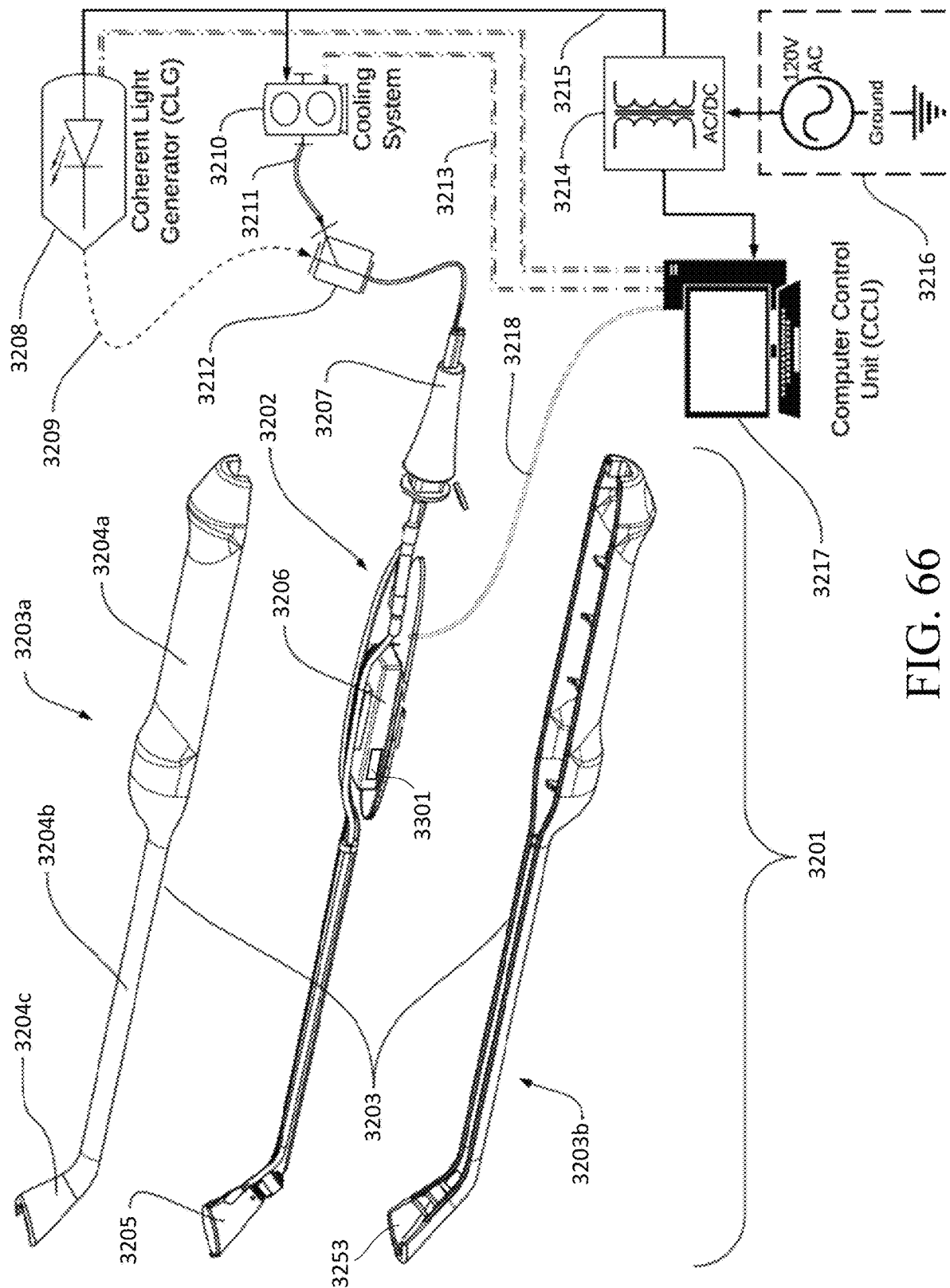
FIG. 66 depicts a schematic representation of a phototherapy system including the handheld probe device of FIG. 65 shown in a partially exploded view.

Referring now to FIGS. 65 and 66 generally, a handheld probe device 3201 and associated phototherapy system 3200 for providing phototherapy as discussed herein. The phototherapy system 3200 includes the handheld probe device 3201, a coherent light generator ("CLG") 3208, a cooling system 3210, a power source 3216, and a computer control unit ("CCU") 3217. The handheld probe device 3201 is configured to receive coherent light generated by the CLG 3208 via a fiber optic cable ("FOC") 3209. The handheld probe device 3201 is further configured to receive a coolant media from the cooling system 3210 via coolant supply tubing 3211.

The handheld probe device 3201, the CLG 3208, and the cooling system 3210 are each in communication with the CCU 3217, which is configured to control operation of each of the various components of the phototherapy system 3200, as will be described in detail below. For example, the CLG 3208 and the cooling system 3210 may be communicably coupled to the CCU 3217 via wired and/or wireless connections 3213. The handheld probe device 3201 may be communicably coupled to the CCU 3217 via a wireless connection 3218. Although the CCU 3217 is depicted as a traditional computer, in some instances the CCU 3217 may be implemented using a programmable logic controller (PLC) or other embedded systems.

The CLG 3208, the cooling system 3210, and the CCU 3217 are each configured to receive power from the power source 3216 through an AC/DC power inverter 3214 via electrical wires 3215. The power source 3216 may be a standard 120 VAC power source provided by the facility or other source of power where the phototherapy system 3200 is to be used. The handheld probe device 3201 may be powered by a rechargeable battery incorporated into the control electronics 3206 that is configured to receive power via an inductive charger that provides power to a receiving coil also incorporated within the control electronics 3206. In some other instances, the handheld probe device 3201 may alternatively receive power for the rechargeable battery via a plug-in electrical source. In yet some other instances, the handheld probe device 3201 may alternatively be externally powered (e.g., via the power source 3216).

As illustrated in FIG. 66, the handheld probe device 3201 includes a handle 3204a, a shaft 3204b, and a distal end or probe tip 3204c. The handheld probe device 3201 further includes an external enclosure 3203 and an internal apparatus 3202. The external enclosure 3203 includes a top portion 3203a and a bottom portion 3203b. The external enclosure 3203 may be made of a plastic material, tempered glass, stainless steel, or any other suitable material. In some instances, the probe tip 3204c and the shaft 3204b may be coated or manufactured using a self-lubricating material, configured to allow for a physician to more easily and comfortably (for the patient) insert the probe tip 3204c and the shaft 3204b into various patient cavities (e.g., the vaginal and/or rectal cavity) to administer treatment.

The top portion 3203a and the bottom portion 3203b are configured to envelop and protect the internal apparatus 3202 of the handheld probe device 3201. The top portion 3203a and the bottom portion 3203b are further configured to be coupled together around the internal apparatus 3202 using any suitable coupling methods. For example, the top portion 3203a and the bottom portion 3203b may be adhered, welded or plastic-welded (depending on the material), fastened, or otherwise secure to each other around the internal apparatus 3202 to form the handheld probe device 3201.

Figure 67:
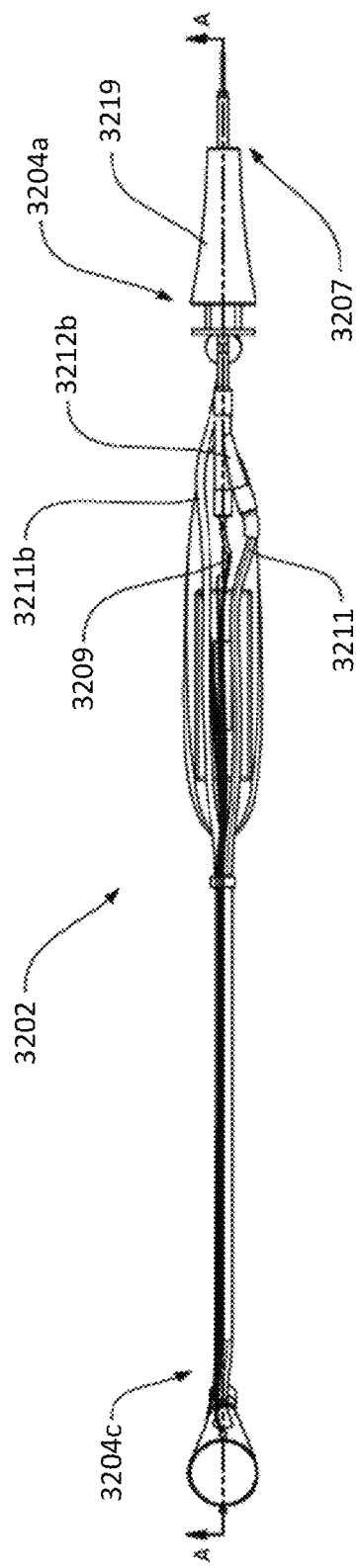
FIG. 67 depicts a top view of internal components of the handheld probe device of FIG. 65.
Figure 68:
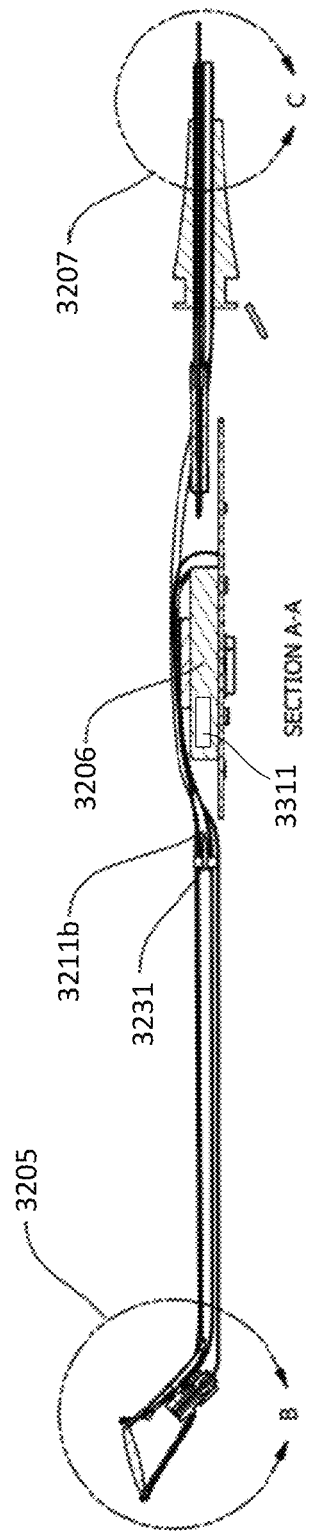
FIG. 68 depicts a section view of the internal components of the handheld probe device of FIG. 67, taken along line A-A in FIG. 67.
Figure 69:
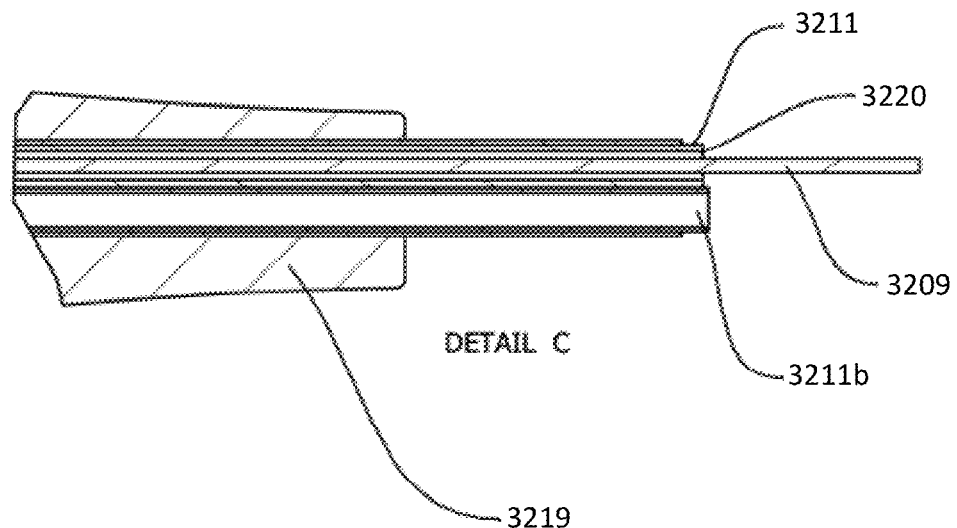
FIG. 69 depicts a detailed view of an external interface of the handheld probe device of FIG. 68, showing the components within the area enclosed by callout "C" in FIG. 68.

As illustrated in FIGS. 66-68, the internal apparatus 3202 includes an optical box 3205, control electronics 3206 (shown in FIG. 66), an external interface 3207, the FOC 3209, coolant supply tubing 3211, and coolant vent tubing 3211b. In some instances, the FOC 3209 and coolant supply tubing 3211 are combined via a wye junction 3212 (shown in FIG. 66) prior to entering the handheld probe device 3201 via the external interface 3207. In these cases, the FOC 3209, the coolant supply tubing 3211, and the coolant vent tubing 3211b may each be routed into or out of the handheld probe device 3201 via a strain relief component 3219 of the external interface 3207, with the FOC 3209 being arranged coaxially within the coolant supply tubing 3211 (as shown in FIG. 69). The strain relief component 3219 is configured to both protect the tubing 3211, 3211b and seal the handheld probe device 3201 from the external environment during use.

In these instances, there is an annular gap 3220 (shown in FIG. 69) surrounding the FOC 3209 within the coolant supply tubing 3211 to allow for coolant to flow through the coolant supply tubing 3211 around the FOC 3209. Further, the FOC 3209 and coolant supply tubing 3211 are subsequently separated by an internal wye junction 3212b within the handheld probe device 3201. In some instances, the FOC 3209 and coolant supply tubing 3211 are provided to the handheld probe device 3201 separately. In either case, the FOC 3209 and coolant supply tubing 3211 are routed within the handheld probe device 3201 from the external interface 3207 to the optical box 3205, and the coolant vent tubing 3211b is routed within the handheld probe device 3201 from the optical box 3205 out of the external interface 3207. In yet some other instances, the coolant supply tubing 3211 may run coaxially with the FOC 3209 all the way into the probe tip 3204c. In these instances, a coolant inlet (similar to coolant inlet 3221 discussed below) may be provided around the FOC 3209 within the probe tip 3204c for feeding coolant media into the optical box 3205.

Figure 70A:
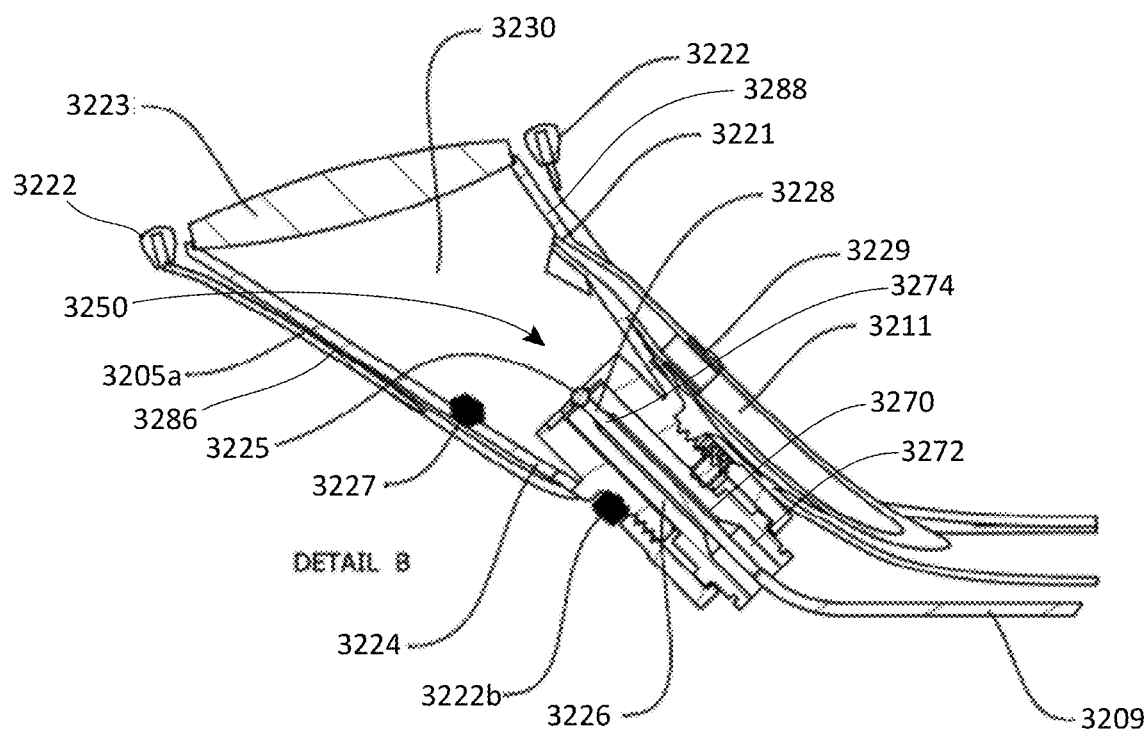
FIG. 70A depicts a detailed view of a probe tip and associated optic assembly features of the handheld probe device of FIG. 68, showing the components within the area enclosed by callout "B" in FIG. 68.

Referring now to FIG. 70A, the optical box 3205 includes an emission lens 3223, a hollow reflection portion 3205a, a lens retention cap 3250, a diffusing lens 3225, and a FOC retention apparatus 3226. In some instances, the emission lens 3223 may be held in place on the top of the optical box 3205 by a retention flange 3253 formed by the distal end of the external enclosure 3203 (shown in FIGS. 66 and 72).

Figure 70B:
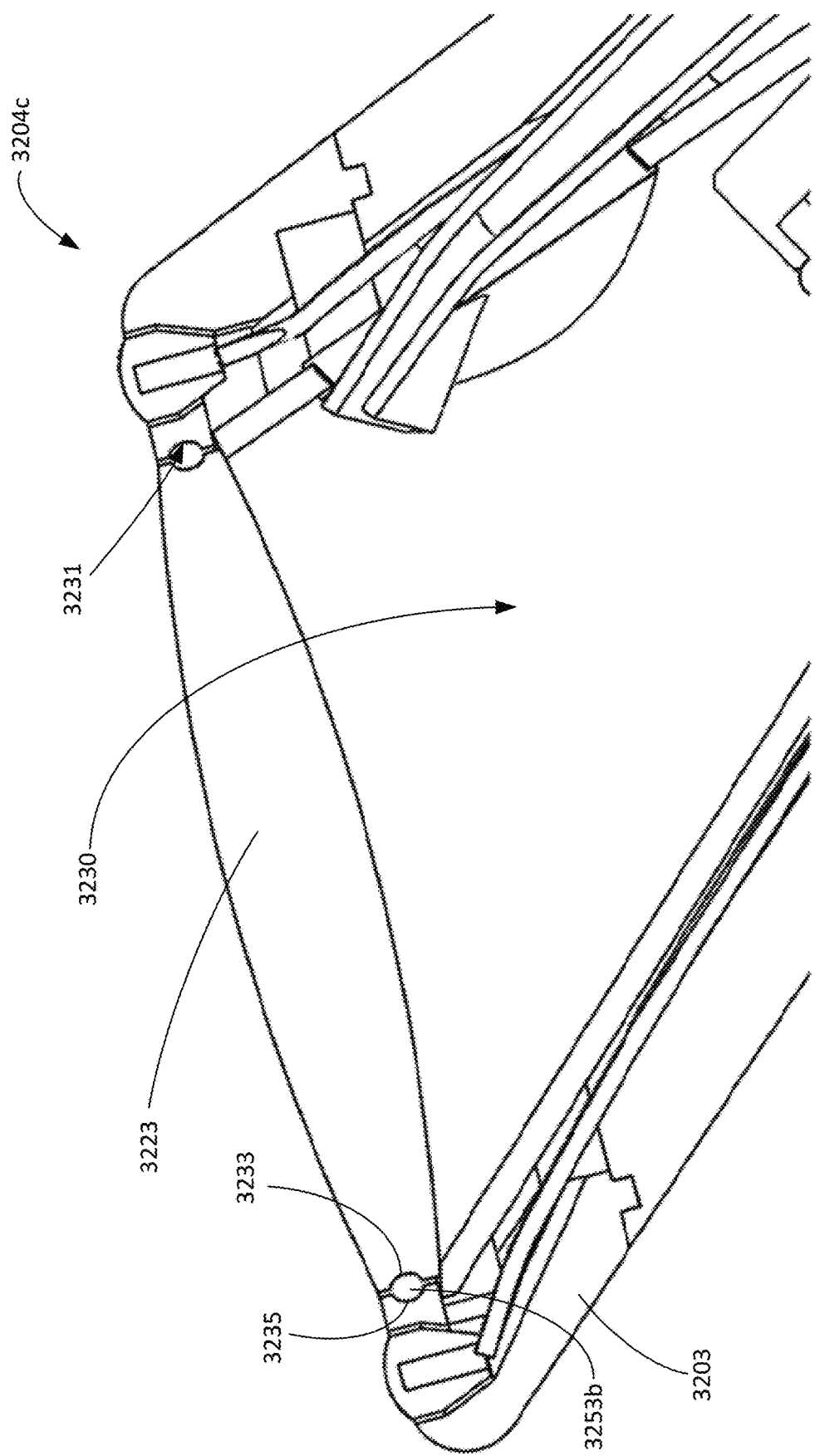
FIG. 70B depicts a detailed view of the probe tip of FIG. 70A, shown with an external enclosure having a sealing ring.
Figure 71:
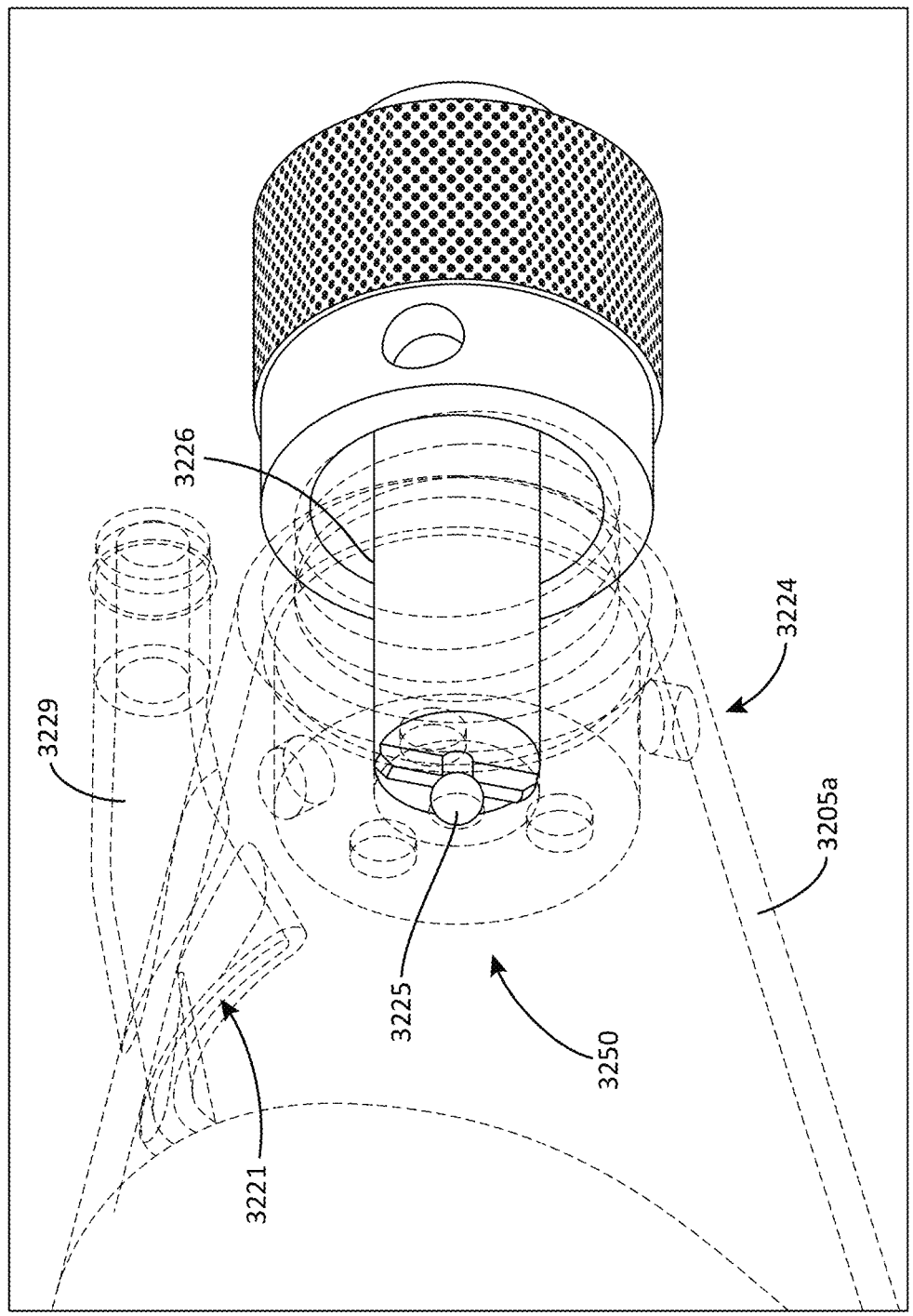
FIG. 71 depicts a perspective view of the probe head portion, shown with various internal components illustrated with hidden lines.

In some instances, as illustrated in FIG. 70B, the emission lens 3223 may be held in place within an emission lens receiving aperture 3231 at the distal end of the external enclosure 3203 via a sealing ring 3253b. In some instances, the sealing ring 3253b may be made of an epoxy material applied between the emission lens 3223 and the emission lens receiving aperture 3231 during assembly. In some other instances, the sealing ring 3253b may be made of other materials. The sealing ring 3253b is disposed between the emission lens 3223 and the emission lens receiving aperture 3231 and extends circumferentially around the emission lens 3223. The sealing ring 3253b provides an impervious seal between the external enclosure 3203 and the emission lens 3223. As such, the probe tip 3204c may be a single "seamless" and enclosed compartment that is configured to prevent fluid and/or gas to be transferred between a cavity 3230 formed within the optical box 3205 and the external environment surrounding the probe tip 3204c during use.

In some instances, the emission lens 3223 may include a lens retention groove 3233 extending circumferentially around a radially-outward facing surface of the emission lens 3223 and the emission lens retention aperture 3231 similarly may include an aperture retention groove 3235 extending circumferentially around a radially-inward facing surface of the emission lens retention aperture 3231. Accordingly, in the case that the sealing ring 3253b is made of the epoxy material described above, when the sealing ring 3253b is added to the probe tip 3204c during assembly, the epoxy flows into the lens retention groove 3233 and the aperture retention groove 3235. Thus, in addition to providing an impervious seal between the emission lens 3223 and the emission lens receiving aperture 3231, once the epoxy sets, the sealing ring 3253b disposed within the lens retention groove 3233 and the aperture retention groove 3235 fixes the emission lens 3223 with respect to the emission lens receiving aperture 3231 within the emission lens receiving aperture 3231.

As shown, the emission lens 3223 is configured to collimate diffracted light emitted through the diffusing lens 3225. The emission lens 3223 may include a generally circular double convex lens configured to serve as an optical window on the probe tip 3204c. However, in some instances, the emission lens 3223 may define other shapes. For example, instead of a circular lens, the emission lens 3223 may be elliptical, oblong, trapezoidal, rectangular, triangular, tear drop shaped, or any other suitable shape. Further, instead of a double convex lens, various other lens types may be used. For example, the emission lens 3223 may be a meniscus or concave-convex lens (as shown in FIG. 82), a beveled-edge planar-planar lens (as shown in FIG. 83), a planar window or planar-planar lens (as shown in FIG. 84), a plano-convex lens (a lens that is planar on one side and convex on the other), or any other suitable lens shape.

In some instances, the emission lens 3223 may be a single glass lens, a double glass lens, a tempered glass lens, an acrylic lens, a resin-based lens, a sapphire lens, a diamond lens, a lens formed of a composite of translucent materials, or any other suitable material for transmitting light therethrough. In some instances, the emission lens may be between 0.5 cm and 4 cm in diameter. In some instances, the emission lens 3223 may be approximately 2 cm in diameter.

As will be further described below, the emission lens 3223 is angled with respect to a light emission path of light emitted through the FOC 3209 and diffusing lens 3225, which allows for both a reduction in the overall length of the optical box 3205 and a non-Gaussian light beam distribution. For example, the emission lens 3223 may be angled between 0 degrees (i.e., perpendicular to the light emission central axis) and 45 degrees away from perpendicular to a light emission central axis 3251 of the optical box 3205. In some instances, the emission lens 3223 may be angled approximately 30 degrees away from perpendicular to the light emission central axis 3251 of the optical box 3205. In these instances, during a treatment session, the emission lens 3223 may generally be angled approximately 15 degrees from a tissue surface being treated (e.g., the vaginal wall, the wall of the rectal cavity). This angulation allows for the emission lens 3223 (and also the probe tip 3204c) to more easily glide over the tissue surface. Accordingly, having the emission lens 3223 tilted with respect to the tissue surface during treatment provides an ergonomic benefit for the physician, while also reducing the likelihood of damaging the treated tissue surface.

Furthermore, in some instances, an outer surface of the emission lens 3223 may be coated to provide various additional protections and/or benefits during use. For example, the outer surface of the emission lens 3223 may be coated in a diamond-like coating to prevent wear and/or damage to the emission lens 3223. Alternatively or additionally, the outer surface of the emission lens 3223 may be coated in a self-lubricating coating to reduce friction between the outer surface of the emission lens 3223 and the tissue surface being treated during use.

Figure 76:
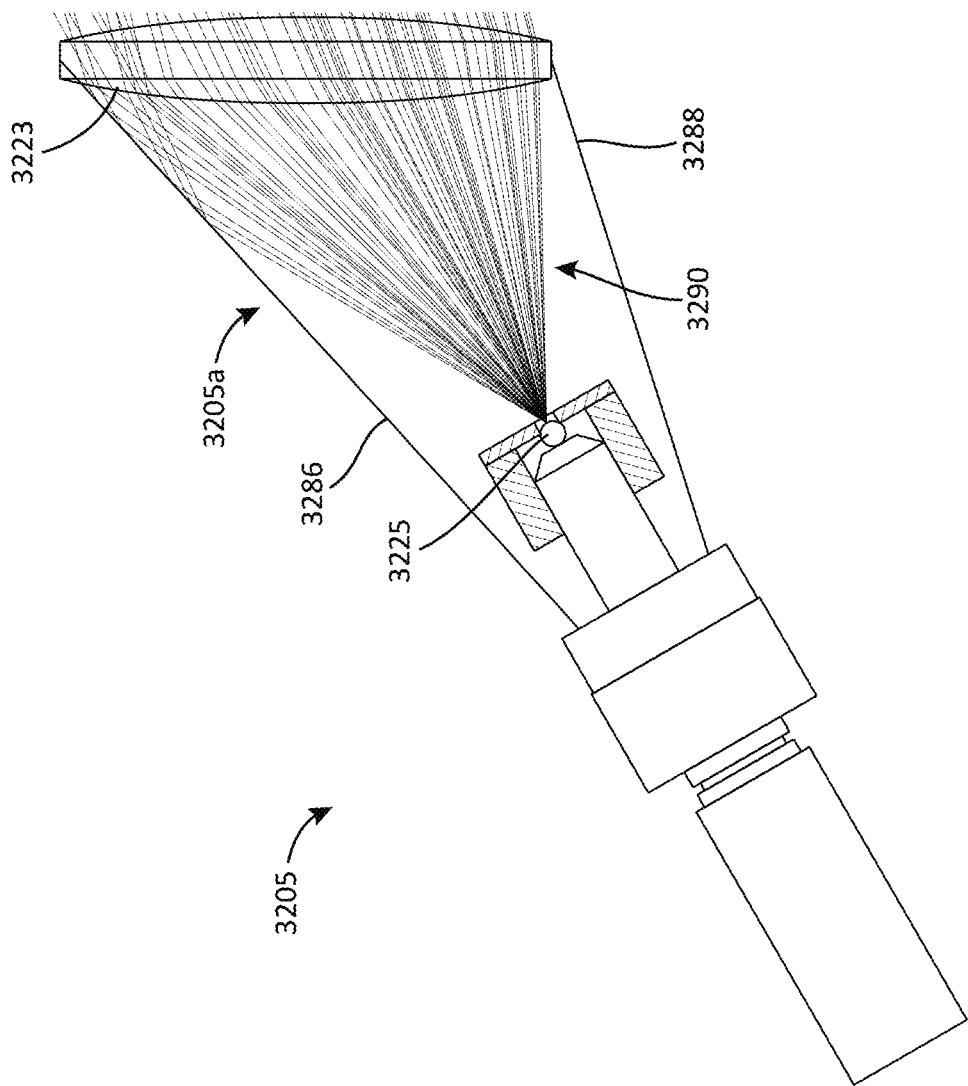
FIG. 76 depicts a schematic representation of various ray tracings emitted using the optical box of the handheld probe device of FIG. 65.

Referring now to FIGS. 70a-72, the hollow reflection portion 3205a has a reflective inner surface 3256 (shown in FIG. 72), a coolant inlet 3221, and a plurality of coolant outlets 3224. In the exemplary embodiment shown in FIGS. 70a-72, the hollow reflection portion 3205a defines a generally hollow conical shape. However, in some other instances, the hollow reflection portion 3205a may define other generally hollow shapes. For example, the hollow reflection portion 3205a could define a generally hollow pyramidal shape or any other suitable shape. The hollow reflection portion 3205a further includes a distal side 3286 and a proximal side 3288. As illustrated, the distal side 3286 is longer than the proximal side 3288 to allow for the emission lens 3223 to be angled with respect to the light emission path of the light emitted through the FOC 3209 and diffusing lens 3225, such that some of the light emitted from the diffusing lens 3225 is reflected off of the distal side 3286 (as shown in FIG. 76).

Figure 87:
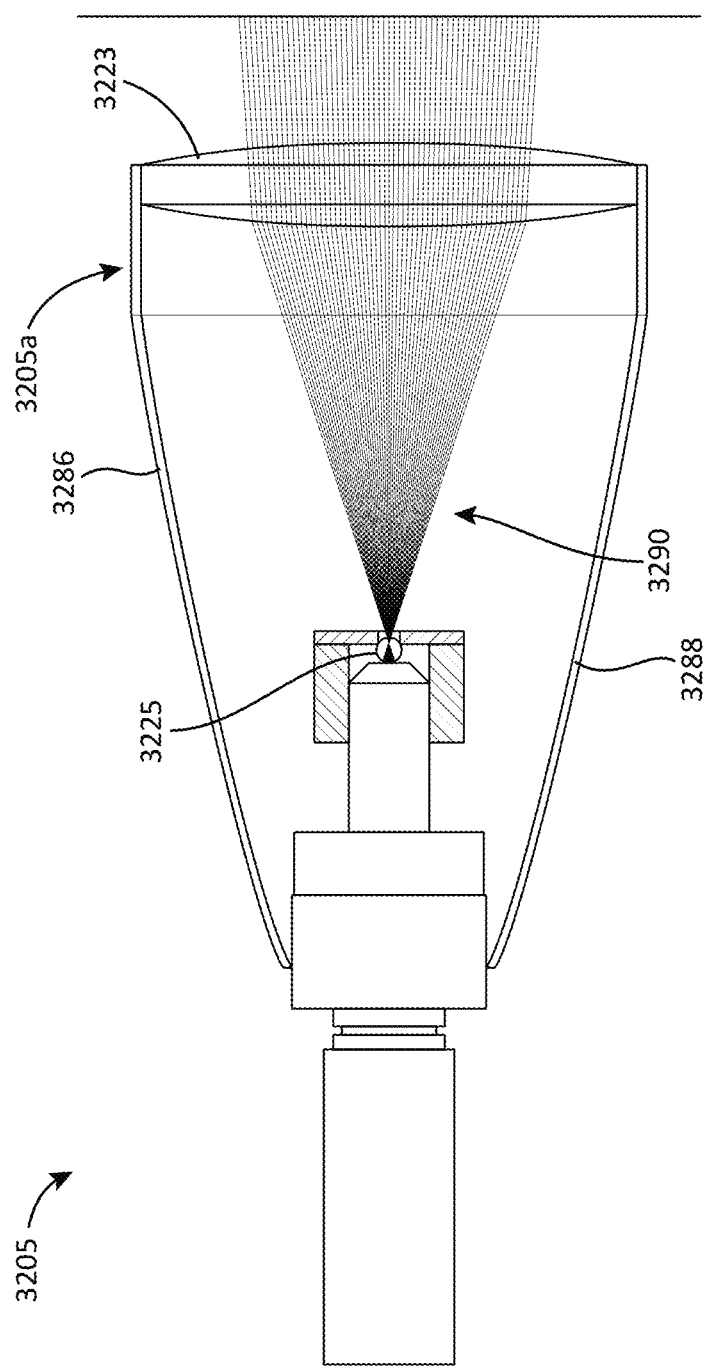
FIG. 87 depicts a schematic representation of an alternative optical box arrangement for a handheld probe device.
Figure 92:
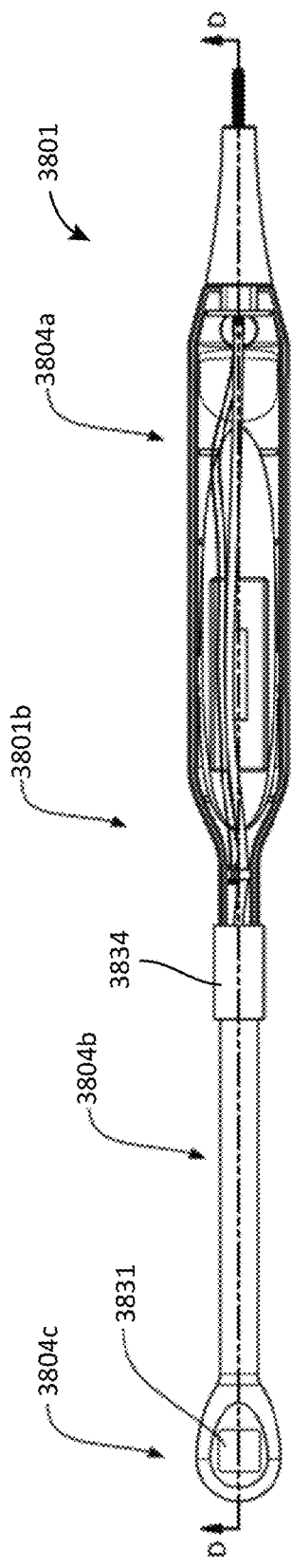
FIG. 92 depicts a top view of the partially disposable handheld probe device of FIG. 88, shown with another disposable probe tip.
Figure 93:
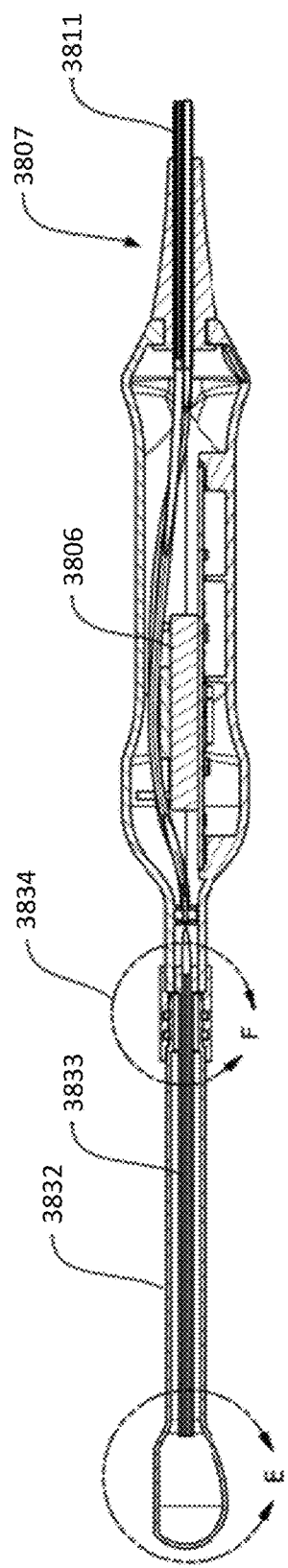
FIG. 93 depicts a sectional view of the partially disposable handheld probe device of FIG. 92, taken along line D-D.
Figure 94:
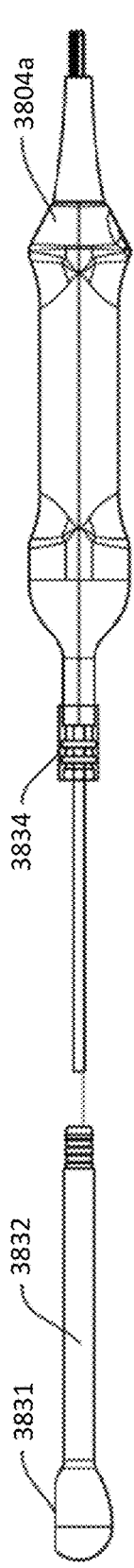
FIG. 94 depicts a partially exploded view of the partially disposable handheld probe device of FIG. 93.

It should be appreciated that, in some instances, the distal side 3286 may be the same length as the proximal side 3288, such that the emission lens 3223 is not angled with respect to the light emission path of the light emitted through the FOC 3209 and diffusing lens 3225 (shown in FIG. 87).

The reflective inner surface 3256 is made of or coated by a reflective material. For example, in some instances, the reflective inner surface 3256 is formed by a polished metal, such as steel, stainless steel, aluminum, or any other suitable metal material. In some instances, the metal material may be electro-polished by using an electrochemical method where electricity used in conjunction with a particular fluid to remove microscopic peaks on the reflective inner surface 3256. In some instances, the reflective inner surface 3256 may be polished using 14,000 grit diamond paste for final polishing.

In some instances, the reflective inner surface 3256 may have a reflective coating applied thereto. For example, the reflective inner surface 3256 may be electroplated, for example, using chrome plating. Accordingly, the hollow reflection portion 3205a may be made of a plastic or resin and the reflective inner surface 3256 may be an electroplated chrome or other highly reflective substance. In some instances, the reflective inner surface 3256 may be made of various other materials, such as, for example, gold, mirrored glass, or a mirrored transparent acrylic material. In some other instances, the reflective inner surface 3256 may further be formed to be diffusive to aid in the diffusion of the emitted coherent light beam. For example, the reflective inner surface 3256 may be sandblasted to create a diffusive surface.

Figure 72:
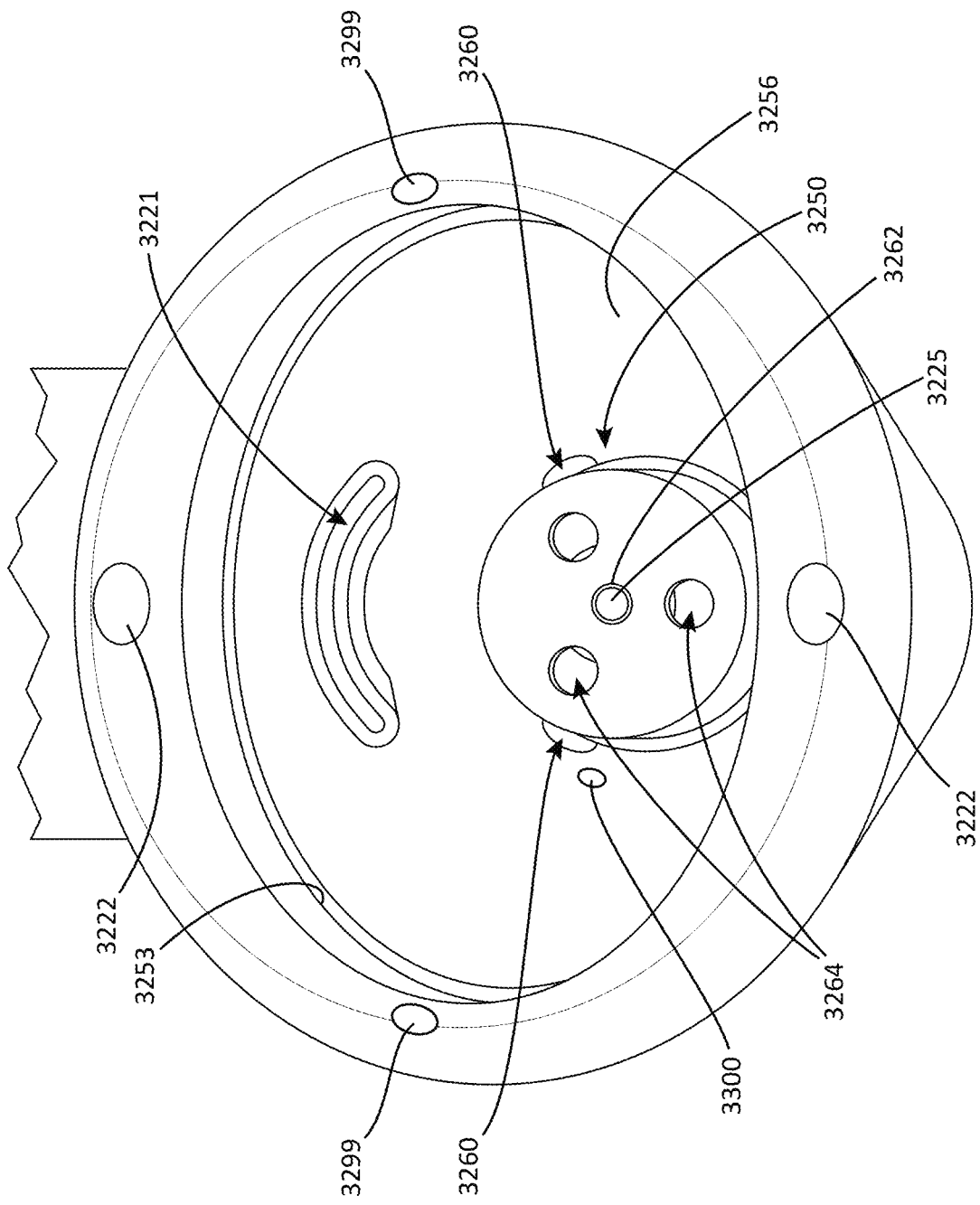
FIG. 72 depicts a top perspective view of the probe head portion, shown without the emission lens and illustrating the internal surface of the optical box.

Referring to FIG. 72, the coolant inlet 3221 defines a generally arc shaped aperture. The coolant inlet 3221 is fluidly coupled to the coolant supply tubing 3211 via a barb or other fitting 3229 (shown in FIG. 70A) to receive a coolant media, as will be described below. The arc shaped aperture defined by the coolant inlet 3221 effectively fans out or spreads out the coolant media upon entry into the hollow reflection portion 3205a to allow for increased dispersion of the coolant media, thereby improving the overall cooling efficiency of the coolant media. The plurality of coolant outlets 3224 are disposed around the circumference of the hollow reflection portion 3205a, proximate a base of the hollow reflection portion 3205a. Each coolant outlet 3224 defines a generally circular aperture. The coolant outlets 3224 are fluidly coupled to the coolant vent tubing 3211b (i.e., coupled so as to allow coolant media to flow therebetween) to allow coolant received through the coolant inlet 3221 to vent out of the optical box 3205, as will be described below.

Referring now to FIGS. 70a-74, the diffusing lens 3225 is held in place against a fiber end 3228 of the FOC 3209 by the lens retention cap 3250. The diffusing lens 3225 is configured to transmit coherent light emitted by the FOC 3209 and to widen a beam received from the FOC 3209 as it travels into the optical box 3205, and eventually through the emission lens 3223 to treat the patient. Accordingly, the diffusing lens 3225 is arranged and held in place by the lens retention cap 3250 and the FOC retention apparatus 3226 in a concentric orientation with the FOC 3209.

Figure 79:
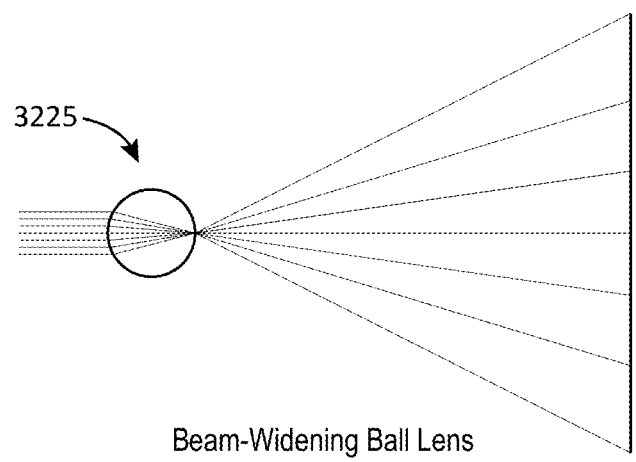
FIG. 79 depicts an example ray tracing of coherent light being directed into a single ball lens.

The diffusing lens 3225 of the illustrated embodiment is a 1 mm diameter sapphire ball diffusing micro-lens. The ball diffusing micro-lens is configured to widen the coherent light beam from the FOC 3209, which may be emitted with a numerical aperture of approximately 0.22, to cover a 2 cm-2.5 cm area within an optical distance of between 1.85 cm and 2 cm. Widening the beam within the shortest optical distance possible is particularly important due to size constraints of the cavities of various tissues and/or structures to be treated using the handheld probe device 3201 (e.g., the vaginal cavity, the rectal cavity). For example, widening the beam within the shortest optical distance possible may be particularly important when a physician is attempting to direct the beam into specific structures within the pelvis from within the vaginal cavity. An example illustration of the beam widening provided by the ball diffusing micro-lens is shown in FIG. 79.

Figure 80:
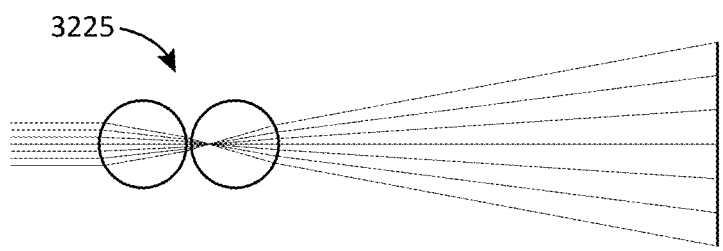
FIG. 80 depicts an example ray tracing of coherent light being directed into a dual ball lens configuration.
Figure 81:
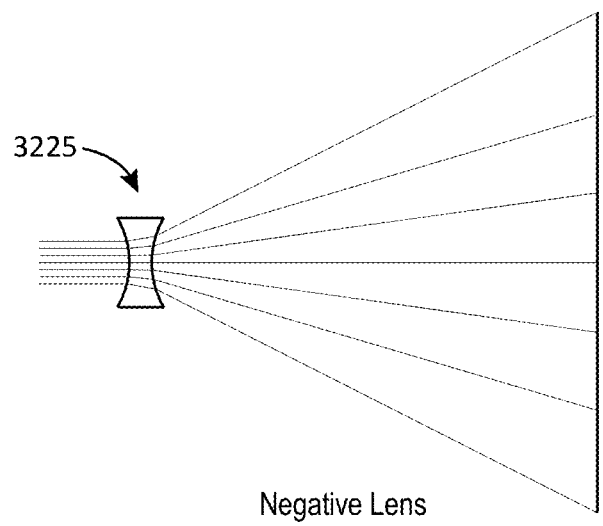
FIG. 81 depicts an example ray tracing of coherent light being directed into a dual-concave lens.

It should be appreciated that, in some instances, the diffusing lens 3225 may be sized differently, shaped differently, or made of a different material as necessary for a given application. For example, in some instances, the diffusing lens may be a ball lens having a smaller or larger diameter than 1 mm as desired for a given application. Further, in some instances, the diffusing lens 3225 may include two or more ball lenses cascaded in a row to achieve the beam widening (shown in FIG. 80). In some instances, the diffusing lens 3225 may include another type of positive lens, such as an Axicon lens, an aspherical lens, a Powell lens, any of these lenses in tandem, or any other suitable positive lens or arrangement of positive lenses. Furthermore, in some instances, diffusing lens may include a negative lens, such as a plano-concave lens, a concave-concave lens (shown in FIG. 81), or any other suitable negative lens or arrangement of negative lenses. In yet some other instances, the diffusing lens 3225 may be an individually sculpted lens created to obtain a desired beam profile.

Additionally, the diffusing lens 3225 may be made of a variety of materials. For example, instead of sapphire, the diffusing lens 3225 could be made of a diamond or diamond-like material, a glass material, a tempered glass material, an acrylic material, or any other suitable material. In some instances, the diffusing lens 3225 may further be coated with a single or multi-layered anti-reflection coating. In some instances, the single or multi-layered anti-reflection coating may reduce reflection on the surface of the diffusing lens 3225 from approximately 4% to approximately 0.4%.

Figure 73:
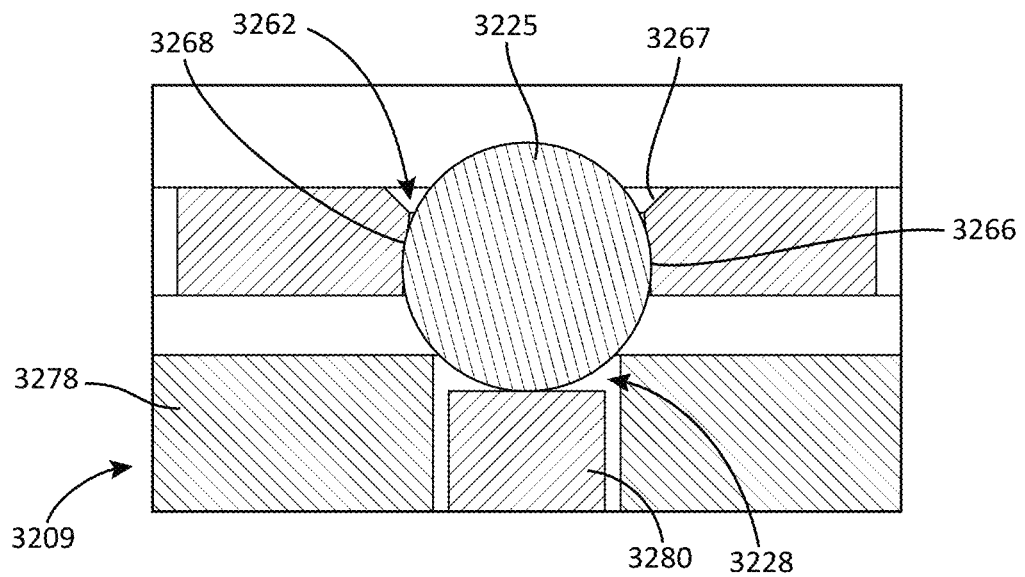
FIG. 73 depicts a sectional detail view of a ball lens cap configuration for implementation in the handheld probe device of FIG. 65.
Figure 74:
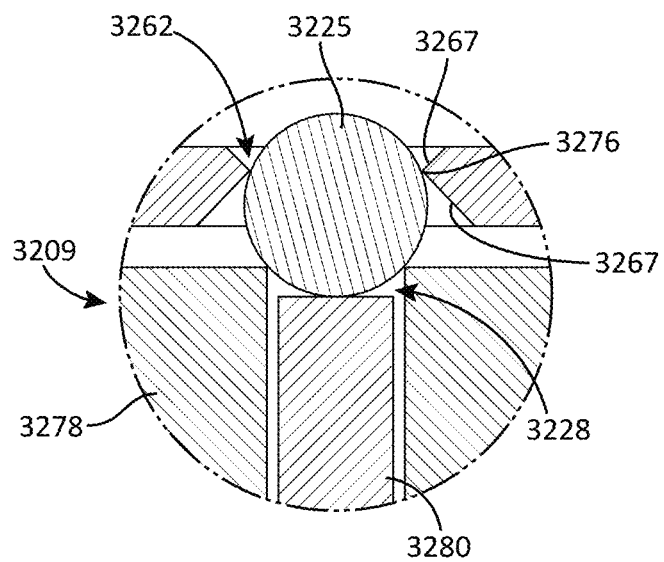
FIG. 74 depicts a section detail view of another ball lens cap configuration for implementation in the handheld probe device of FIG. 65.

The lens retention cap 3250 is configured to secure or nest the diffusing lens 3225 against the fiber end 3228 of the FOC 3209. As best illustrated in FIG. 72, the lens retention cap 3250 includes a lens retention aperture 3262 and a plurality of cooling apertures 3264. The lens retention aperture 3262 is shaped to receive and retain the diffusing lens 3225. As shown in FIGS. 73 and 74, the lens retention aperture 3262 can have a variety of shapes for retaining the diffusing lens 3225.

Referring specifically to FIG. 73, in some instances, the lens retention aperture 3262 includes a cylindrical bore portion 3266, a curved retention lip 3268, and an external chamfer 3267. The cylindrical bore portion 3266 may be sized according to the size of the diffusing lens 3225. For example, in the illustrated embodiment shown in FIG. 73, the diffusing lens 3225 is a 1 mm ball lens and the diameter of the cylindrical bore portion 3266 is approximately 1 mm to allow for the insertion of the 1 mm ball lens. The curved retention lip 3268 curves slightly inward and is shaped according to the radius of curvature of the diffusing lens 3225. That is, the curved retention lip 3268 curves inward at the same radius of curvature as the 1 mm ball lens. As such, the ball lens is effectively in contact with the curved retention lip 3268, which aids in preventing heat buildup during operation. Further, because the curved retention lip 3268 curves inwardly from the cylindrical bore portion 3266, and the cylindrical bore portion 3266 is sized according to the size of the diffusing lens, an innermost annular edge of the curved retention lip 3268 is smaller than the diffusing lens 3225. For example, if the diffusing lens 3225 is a ball lens that is 1 mm in diameter, the annular edge of the curved retention lip 3268 may have a diameter that is approximately 0.95 mm. Accordingly, the curved retention lip 3268 prevents the diffusing lens 3225 from "popping" through the lens retention aperture 3262. The external chamfer 3267 is an annular chamfer around the circumference of the external end of the lens retention aperture 3262. The external chamfer 3267 is angled and sized to provide a clear path for the light beam emitted through the diffusing lens.

Referring now to FIG. 74, in some instances, the lens retention aperture 3262 includes the external chamfer 3267 and an internal chamfer 3269. The external chamfer 3267 in these instances is similarly angled and sized to provide a clear path for the light beam emitted through the diffusing lens. The internal chamfer 3269 is similarly an annular chamfer around the internal end of the lens retention aperture 3262, and is configured to retain or nest the diffusing lens into the lens retention aperture 3262. The external chamfer 3267 and the internal chamfer 3269 meet at an annular edge 3276 that is sized to be slightly smaller in diameter than the diameter of the diffusing lens 3225. For example, if the diffusing lens 3225 is a ball lens that is 1 mm in diameter, the annular edge 3276 may have a diameter that is approximately 0.95 mm. Accordingly, the diffusing lens 3225 is similarly prevented from "popping" through the lens retention aperture 3262 by the annular edge 3276.

In either of the aforementioned configurations, the surfaces of the lens retention aperture 3262 may further be coated in a reflective coating to reduce heat buildup within the lens retention cap 3250. Accordingly, any incidental light shined or reflected onto the surfaces of the lens retention aperture 3262 would likely be transmitted back through the diffusing lens 3225, into the hollow reflection portion 3205a, and ultimately through the emission lens 3223 to the treatment area.

Referring again to FIGS. 71 and 72, the plurality of cooling apertures 3264 are configured to permit coolant received within the optical box 3205 to enter into the lens retention cap 3250 to cool the diffusing lens 3225, the fiber end 3228 of the FOC 3209, and the various surfaces of the lens retention cap. As illustrated, the plurality of cooling apertures 3264 are arranged circumferentially around the lens retention aperture 3262 and define generally circular apertures. In some instances, the plurality of cooling apertures 3264 may be arranged differently and/or define various other shapes. For example, in some instances, the plurality of cooling apertures 3264 may be arranged non-circumferentially (all or most could be shifted to one side of the lens retention cap 3250. Further, in some instances, the plurality of cooling apertures 3264 may define arc-like shapes (similar to the coolant inlet 3221 of the hollow reflection portion 3205a), oval shapes, oblong shapes, triangular shapes, rectangular shapes, trapezoidal shapes, or any other suitable shapes.

In some instances, the lens retention cap 3250 may be a separate component from the FOC retention apparatus 3226 that is coupled to the FOC retention apparatus 3226 using any suitable mechanical coupling method. For example, the lens retention cap 3250 may be threadably coupled to, adhered to, interference fit onto, or otherwise mechanically coupled to the FOC retention apparatus 3226. In some other instances, the lens retention cap 3250 may be formed with the FOC retention apparatus 3226 as a single, unitary component. For example, in some instances, the lens retention cap 3250 and the FOC retention apparatus 3226 may be 3D printed, cast, or otherwise formed as a single, unitary component.

In any case, it should be appreciated that the lens retention cap 3250 provides a convenient way to accurately center the diffusing lens 3225 with respect to the FOC 3209, while ensuring that light emitted through the diffusing lens 3225 is not cut off.

As best illustrated in FIG. 70A, the FOC retention apparatus 3226 is configured to receive and retain the FOC 3209 such that the fiber end 3228 of the FOC 3209 is in contact with the diffusing lens 3225 while the diffusing lens 3225 is in contact with the lens retention cap 3250, as described above. As shown, the FOC retention apparatus 3226 includes an FOC bore 3270 configured to receive and retain the FOC 3209. The FOC bore 3270 generally defines a hollow, cylindrical channel extending axially throughout the FOC retention apparatus 3226 and being sized to receive the FOC 3209.

The FOC bore 3270 includes an FOC receiving portion 3272 and an FOC retention portion 3274. The FOC receiving portion 3272 is disposed at a proximal end of the FOC bore 3270 and defines a diameter that is significantly larger than the diameter of the FOC 3209 and is configured to receive and allow for a slight bend to be formed in the FOC 3209. The FOC retention portion 3274 is disposed at a distal end of the FOC bore 3270 and defines a diameter that is approximately the same diameter as the FOC 3209. Accordingly, while assembling the optical box 3205, the FOC 3209 may be fed into the FOC receiving portion 3272, through the FOC bore 3270, through the FOC retention portion 3274, and ultimately into contact with the diffusing lens 3225. With the FOC 3209 inserted into the FOC bore 3270, as described above, an epoxy material may be filled into the open space between the FOC 3209 and the FOC bore 3270 to "lock" or fix the FOC 3209 within the FOC bore 3270.

It should be appreciated that FOC retention apparatuses have traditionally included a fiber optic cable stabilizing tail or stress sleeve. To minimize the distance between the proximal end of the FOC retention apparatus 3226 and the external surface of the emission lens 3223, the FOC retention apparatus 3226 does not include this stabilizing tail, and instead uses the aforementioned epoxy material to stabilize the FOC 3209 within the FOC bore 3270 described above. In some instances, in addition or alternative to the epoxy solution, a pre-bent metal tail extending from the FOC receiving portion 3272 may be used to stabilize the FOC 3209 within the FOC bore 3270. The pre-bent metal tail may have effectively the same bend in the FOC 3209 shown in FIG. 70A to provide substantially the same distance between the proximal end of the FOC retention apparatus 3226 and the external surface of the emission lens 3223.

Referring now to FIGS. 73 and 74, the FOC 3209 includes a fiber ferrule 3278 and a fiber core 3280. As illustrated, the fiber end 3228 is a specialized fiber ending where the fiber core 3280 is recessed into the fiber ferrule 3278 to allow for the diffusing lens 3225 (e.g., the ball lens described above) to extend slightly into the fiber ferrule 3278. Accordingly, when the FOC 3209 is inserted into the FOC retention apparatus 3226, as described above, the diffusing lens 3225 is held against the lens retention cap 3250 by the fiber ferrule 3278. Furthermore, the fiber core 3280 may be recessed into the fiber ferrule 3278 based on the size of the diffusing lens 3225 to allow for the diffusing lens 3225 to abut the end surface of the fiber core 3280 while eliminating or significantly reducing contact pressure between the diffusing lens 3225 and the fiber core 3280. By having the fiber core 3280 directly abutted with the diffusing lens 3225, loses (e.g., heat buildup) due to reflection between the end surface of the fiber core 3280 and the diffusing lens 3225 are minimized.

In a traditional FOC, where the fiber core is not recessed with respect to the fiber ferrule, contact pressure between the diffusing lens and the fiber core may cause damage to the surfaces of the diffusing lens and/or the fiber core, leading to loses (e.g., heat buildup). Accordingly, the configuration of the fiber end 3228 of the FOC 3209 improves light transmission by reducing losses caused by reflection while reducing the likelihood of surface damage to either of the end surface of the fiber core or the surface of the diffusing lens.

In some instances, the surface of the diffusing lens 3225 and/or the end surface of the fiber core 3280 may be coated with a strengthening coating (e.g., a diamond-like coating) and/or an anti-reflective coating to prevent damage and/or improve light transmission properties.

In the illustrated embodiments provided in FIGS. 73 and 74, as described above, the diffusing lens 3225 is a 1 mm ball lens configured to diffract the emitted light from the FOC 3209. Accordingly, the fiber core 3280 may be recessed approximately 100 µm to allow for the ball lens to just abut the fiber core 3280. In some other instances, the fiber core 3280 may be recessed slightly more than necessary, creating a small gap between the fiber core 3280 and the diffusing lens. For example, in some instances, the fiber core 3280 may be recessed between 100 µm to 500 µm, as desired for a given application. However, as the gap between the diffusing lens 3225 (e.g., the ball lens) is increased, the amount of light reflected off of the surface of the diffusing lens 3225 is increased, leading to increased losses due to heat buildup. Accordingly, in many instances, reducing/minimizing the distance between the diffusing lens 3225 and the fiber core 3280 may be desirable. In some instances, the fiber core 3280 is recessed to create a gap of 50 µm to eliminate any potential contact pressure between the surface of the ball lens and the end surface of the fiber core 3280 that may distort the beam transmission and/or cause fracturing/breakage of the fiber core 3280. In some instances, the fiber core 3280 may be recessed to create a gap of between 0 µm (i.e., no gap) and 400 µm.

Figure 75:
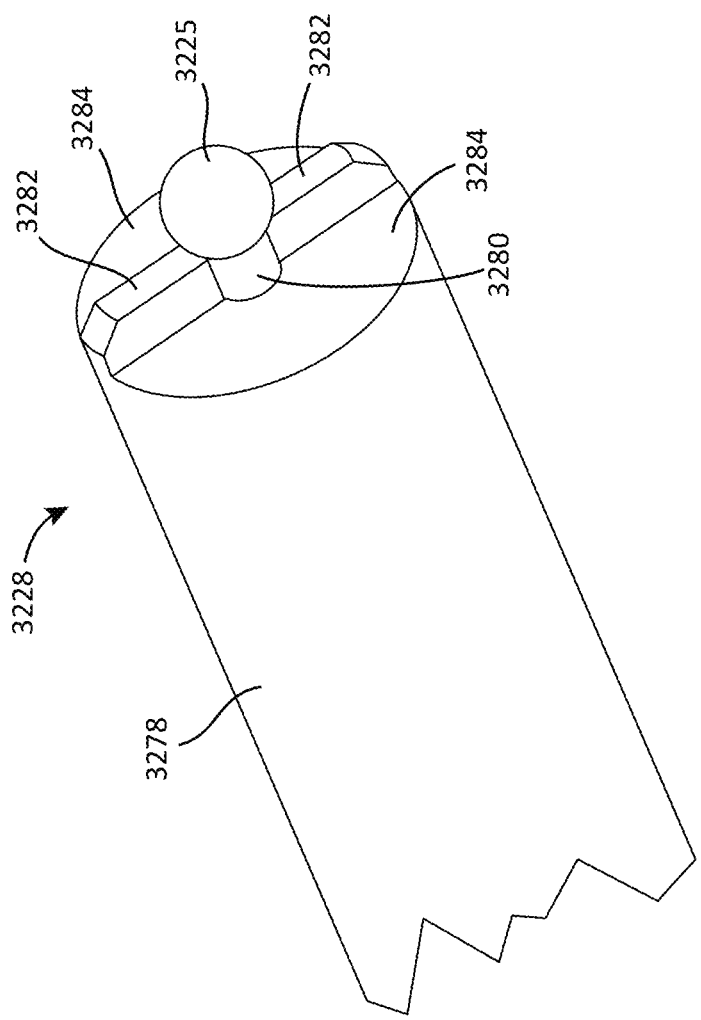
FIG. 75 depicts a ball lens arrangement on a winged fiber ferrule of a fiber optic cable for implementation in the handheld probe device of FIG. 65.

Referring now to FIG. 75, the fiber end 3228 may further include a winged tip end 3282 formed between a pair of recessed surfaces 3284 in the fiber ferrule 3278. The pair of recessed surfaces 3284 may be recessed beyond the fiber core 3280 discussed above, and may be configured to provide additional space around the fiber end 3228 to allow for better heat dissipation to reduce heat buildup during operation. In various other embodiments, other venting options may be utilized. For example, in some instances, apertures may be formed in the fiber ferrule 3278 around the fiber end 3228 to allow for addition heat dissipation. In some instances, instead of the winged tip end 3282, the fiber end 3228 may include a pair of opposed recessed channels extending through the center of the fiber ferrule 3278, generally providing the inverse shape of the winged tip end, which would allow for heat dissipation through the pair of opposed recessed channels.

Referring now to FIG. 76, a simplified depiction of the optical box 3205 is provided. Because the distal side 3286 of the hollow reflection portion 3205a is longer than the proximal side 3288 of the hollow reflection portion 3205a, more of the light rays (shown as 3290) emitted from the diffusing lens 3225 are allowed to reflect off of the distal side 3286 than are reflected off of the proximal side 3288. This reflection pattern creates a unique light density distribution pattern 3292 (shown in FIG. 77).

Figure 77:
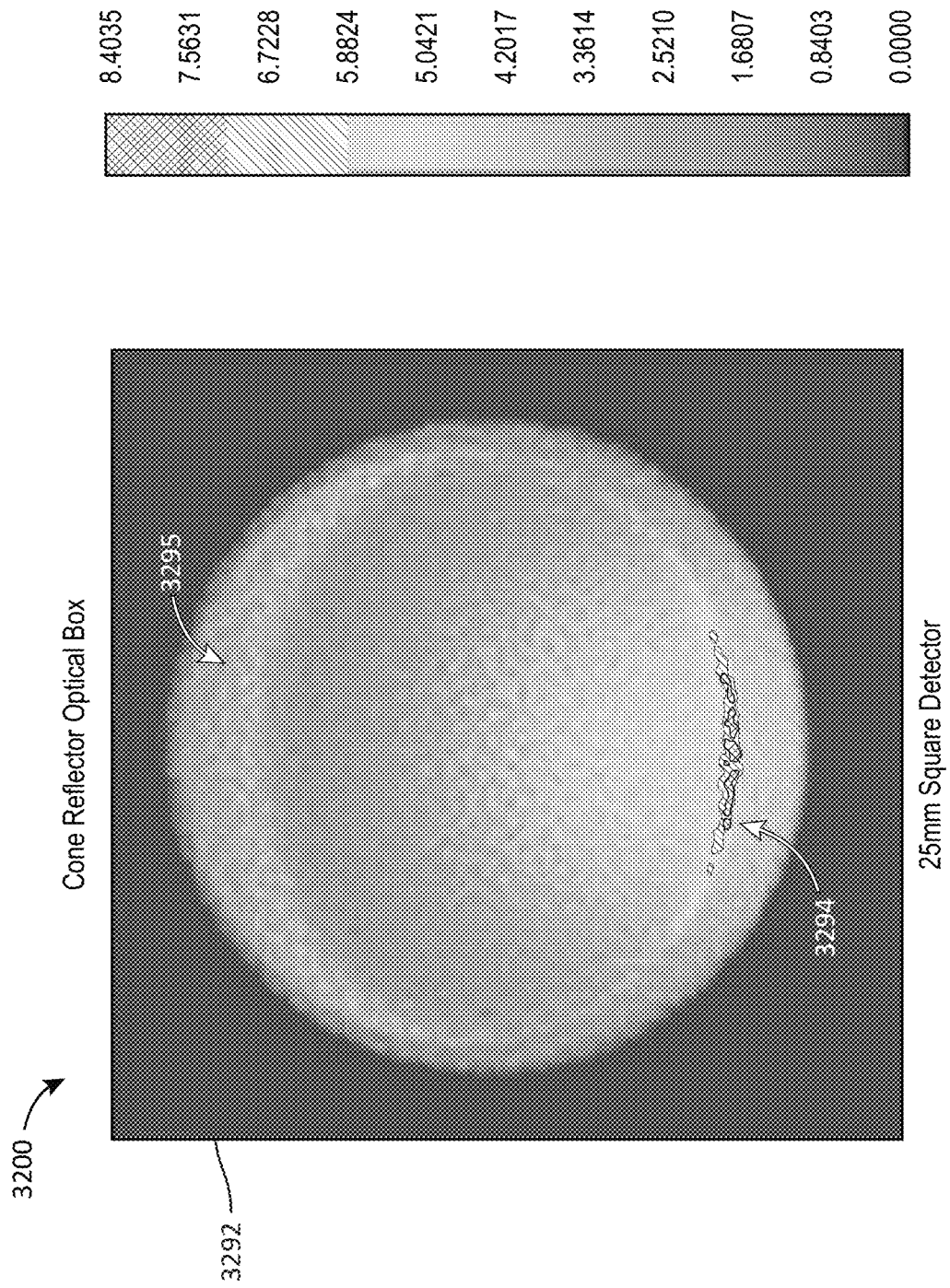
FIG. 77 depicts an intensity mapping of a treatment area based on the ray tracings shown in FIG. 76.

Referring to FIG. 77, a light density distribution map 3293 is illustrated, showing the irradiance levels over an example treatment surface. As illustrated, the light density distribution pattern 3292 created by the handheld probe device 3201 is non-Gaussian and creates a unique primary hot spot 3294 closer to the distal side 3286. In a traditional photobiomodulation probe, the strongest density of light (e.g., the "hot spot") is provided at the center of the beam, with a Gaussian distribution of light density being emitted at larger distances from the center. However, due to the beam mixing created by the reflection pattern of the hollow reflection portion 3205a of the optical box 3205, the handheld probe device 3201 is capable of providing the unique, non-Gaussian distribution having the unique primary hot spot 3294, which defines a generally arc or "half-moon" shaped hot spot. Further, although not depicted in FIG. 76, some light rays also reflect off of the proximal side 3288 of the hollow reflection portion 3205a, creating a secondary hot spot 3295 closer to the proximal side 3288. The secondary hot spot 3295 has a lower irradiance level than the primary hot spot 3294, and as such does not penetrate into the treated tissue as far as the primary hot spot 3294. Accordingly, the secondary hot spot 3295 may be capable of treating tissues at a different depth than the primary hot spot 3294 in the same pass of the probe tip 3204c.

Figure 78:
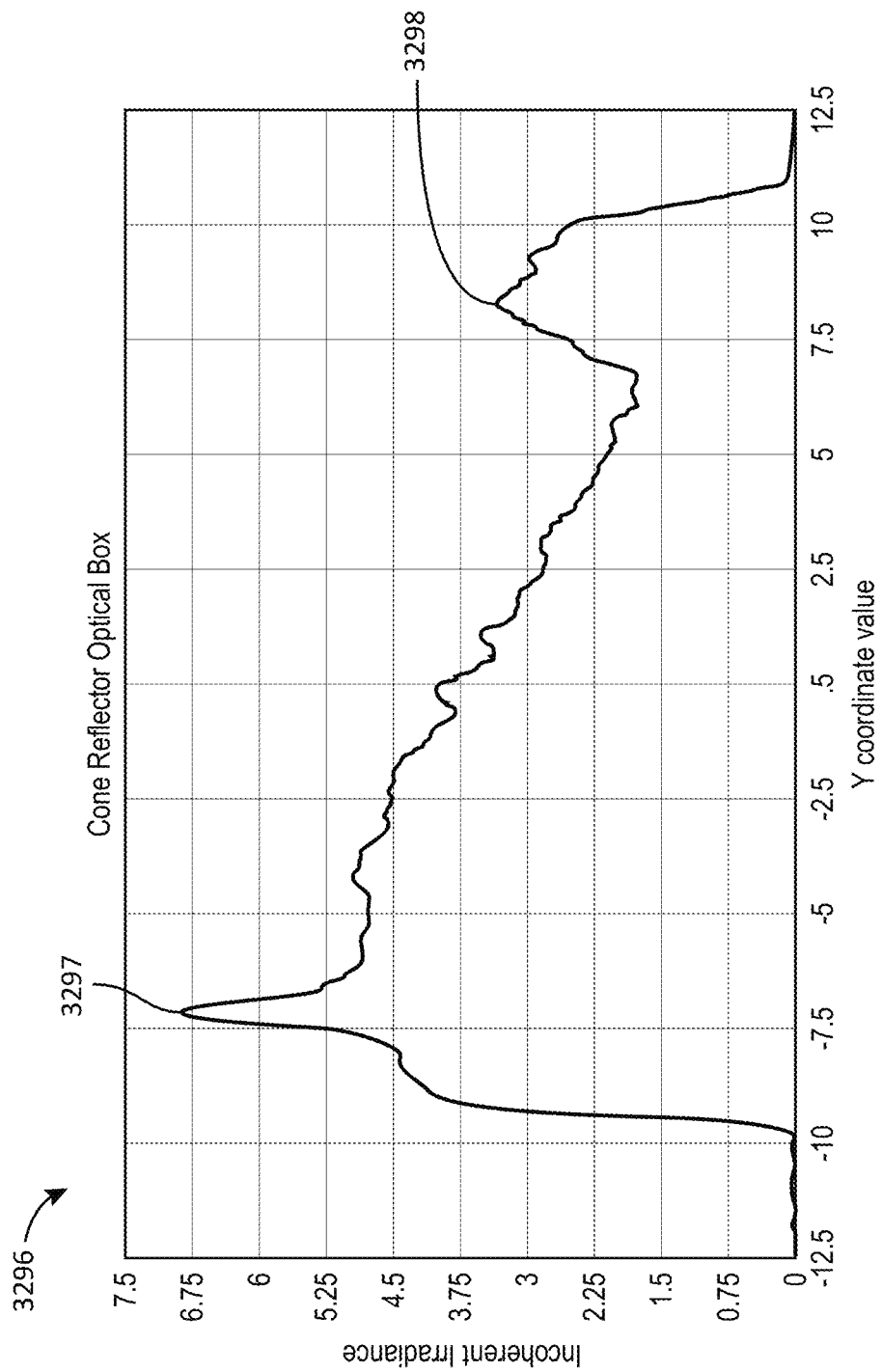
FIG. 78 depicts a graphical representation of light intensity as a function of position on the emission lens of the handheld probe device, based on the intensity mapping of the treatment area of FIG. 77.

Referring now to FIG. 78, a light density distribution plot 3296 is illustrated. The light density distribution plot 3296 shows the irradiance provided by the handheld probe device 3201 based on the longitudinal location (e.g., distal end to proximal end) of the emission lens 3223. As illustrated, the light density distribution plot 3296 has a first peak 3297 corresponding to the primary hot spot 3294 and a second peak 3298 corresponding to the secondary hot spot 3295.

Accordingly, during treatment using the handheld probe device 3201, a larger area of tissue can be effectively treated with each pass of the probe tip 3204c. Specifically, because the primary hot spot 3294 is spread out perpendicular to the direction of movement during treatment, a larger path can be treated with each pass of the probe tip. Further, because the primary hot spot 3294 is thin in the direction of movement during treatment, the primary hot spot 3294 provides a high level of irradiance (allowing for a deeper tissue treatment depth) without creating a risk of tissue damage or inadvertently dilating vessels in the tissues being treated and thereby reducing the effective tissue penetration of the treatment light. As such, the handheld probe device 3201 may be used to treat various tissues more efficiently and effectively by requiring fewer passes and allowing for a deeper tissue penetration than a probe device having a traditional concentrated central hot spot.

Referring again to FIGS. 66 and 68, the handheld probe device 3201 includes control electronics 3206. The control electronics 3206 may comprise a printed circuit board (PCB) that is configured to control and monitor various components of the handheld probe device 3201. For example, the control electronics 3206 may be in communication with the CCU 3217 to receive and transmit various information, as will be described in detail below.

The control electronics 3206 may be in communication with one or more external temperatures sensors 3222, one or more internal temperature sensors 3222b, an internal pressure sensors 3227, one or more external pressure/tactile sensors 3299 (shown in FIG. 72), a probe camera 3300 (shown in FIG. 72), and a motion sensor 3301 via one or more wired or wireless connections. The control electronics 3206 are configured to receive various information from the one or more external temperatures sensors 3222, the one or more internal temperature sensors 3222b, the one or more pressure/tactile sensors 3299, the probe camera 3300, and the accelerometer, and to transmit this information to the CCU 3217 to be used to control and operate the various components of the phototherapy system 3200.

Referring now to FIGS. 70A and 72, one or more external temperatures sensors 3222 may be disposed on the probe tip 3204c. The one or more external temperature sensors 3222 are in communication with the control electronics 3206 and are configured to sense the temperature of treatment tissue during operation of the handheld probe device 3201. This external temperature information may then be communicated to the CCU 3217 by the control electronics 3206 to be used to control and operate the various components of the phototherapy system 3200.

As best illustrated in FIG. 72, in some instances, the handheld probe device 3201 may include a pair of external temperature sensors 3222 disposed on opposing sides of the emission lens 3223. Specifically, the external temperature sensors 3222 may be disposed directly on opposing sides of the emission lens 3223 in line with a direction of movement of the handheld probe device 3201 during treatment. Accordingly, as the probe tip 3204c passes over the treatment tissue during use, the temperature of the treatment tissue directly before and after treatment can be observed using the external temperature sensors 3222. It should be appreciated that, in some instances, there may be more or less than two external temperature sensors 3222, as desired for a given application. Furthermore, in some instances, the external temperature sensors 3222 may be arranged differently on the probe tip 3204c or within the handheld probe device 3201 generally.

As best illustrated in FIG. 70A, the one or more internal temperature sensors 3222b may be implemented into the optical box 3205 within the probe tip 3204c of the handheld probe device 3201. The internal temperature sensors 3222b are similarly in communication with the control electronics 3206 and are configured to sense the temperatures of various internal components of the handheld probe device 3201. For example, the internal temperature sensors 3222b may be arranged and configured to monitor the temperatures of various components and/or locations within the probe tip 3204c and/or elsewhere within the handheld probe device 3201 to detect excessive heat buildup during operation. This internal temperature information may then similarly be communicated to the CCU 3217 by the control electronics 3206 to be used to control and operate the various components of the phototherapy system 3200.

In some instances, the external temperature sensors 3222 and/or internal temperature sensors 3222b may be K-type thermocouples. In some other instances, the external temperature sensors 3222 and/or internal temperature sensors 3222b may be various other thermocouple types or other temperature sensing devices generally as desired for a given application. For example, in some instances, an optical temperature sensor may be implemented within the optical box 3205 to allow for touchless temperature sensing of the treated tissue. In some instances, the touchless temperature sensing may be performed using the same FOC 3209 as is used by the handheld probe device 3201 to provide the therapy treatment light. In these instances, the optical temperature sensing may allow for a temperature of the tissue to be taken in the middle of a treatment zone (as opposed to being taken proximate the edges of the optical window/emission lens 3223, as illustrated in FIG. 72).

The internal pressure sensor 3227 is arranged proximate a coolant outlet 3224 disposed on the distal side 3286 of the hollow reflection portion 3205a. The internal pressure sensor 3227 is similarly in communication with the control electronics 3206 and is configured to detect a pressure generated within the cavity 3230 formed within the optical box 3205. Specifically, the internal pressure sensor 3227 is configured to detect pressure generated within the cavity 3230 due to any imbalance between the coolant flowing in via the coolant inlet 3221 and out of the coolant outlets 3224. The control electronics 3206 are configured to transmit this internal pressure information to the CCU 3217 to be used to control the cooling system 3210 to balance a rate of suction on the coolant vent tubing 3211b to maintain the pressure environment within the cavity 3230 to a pressure of between 0 PSIG to −2 PSIG.

As shown in FIG. 72, in some instances, the one or more external pressure/tactile sensors 3299 may include a pair of external pressure/tactile sensors 3299 arranged on opposite sides of the emission lens 3223. For example, each of the external pressure/tactile sensor 3299 may be approximately 0.2 mm in diameter. The external pressure/tactile sensors 3299 are similarly in communication with the control electronics 3206 and are configured to sense the pressure applied to the probe tip 3204c. In some instances, the external pressure/tactile sensors 3299 may be configured to detect a minimum of 1 PSI of pressure being applied to the probe tip 3204c. In some other instances, the external pressure/tactile sensors 3299 may be configured to detect between 0 and 40 PSI of pressure being applied to the probe tip 3204c.

In some instances, one or more of the external pressure/tactile sensors 3299 may further be configured to sense tactile movement across the external pressure sensor 3299. In some instances, each external pressure/tactile sensor 3299 may include a separate pressure sensor and a separate tactile sensor. In some instances, the external pressure/tactile sensors 3299 may include a combination sensor capable of both sensing pressure and sensing tactile movement. In any case, the control electronics 3206 is configured to transmit the pressure and/or tactile movement information to the CCU 3217 to be used to control and operate the various components of the phototherapy system 3200.

In some instances, the external pressure/tactile sensors 3299, as illustrated in FIG. 72, may be arranged on lateral sides of the probe tip 3204c near the emission lens 3223 (e.g., arranged approximately 90 degrees from the pair of external temperature sensors 3222). In some other instances, the external pressure/tactile sensors 3299 may be arranged differently. Similarly, in some instances, there may be more or fewer external pressure/tactile sensors 3299, as desired for a given application.

For example, in some instances, there may only be one external temperature sensor 3222 disposed on the probe tip 3204c proximate the proximal edge of the emission lens 3223 (i.e., the side of the emission lens 3223 closest to the proximal side 3288 of the hollow reflection portion 3205a), and there may be only one external pressure/tactile sensor 3299 disposed on the probe tip 3204c proximate the distal edge of the emission lens 3223 (i.e., the side of the emission lens 3223 closest to the distal side 3286 of the hollow reflection portion 3205a).

In some instances, as shown in FIG. 65, the external pressure/tactile sensors 3299 may additionally or alternatively include a strain gauge disposed on the shaft 3204b configured to deduce the pressure applied to the probe tip 3204c during operation using the strain detected at the strain gauge on the shaft 3204b. In these instances, a tactile sensor may be provided on the probe tip 3204c to sense the tactile movement across the probe tip 3204c. It will be appreciated that various embodiments are possible, and the provided examples herein are provided as examples.

Referring now to FIG. 72, the probe camera 3300 may be a tiny and/or micro-size camera and/or video recording device disposed within the hollow reflection portion 3205a. The probe camera 3300 is configured to capture video and/or photographs of the treatment tissue through the emission lens 3223. The probe camera 3300 is further in communication with the control electronics 3206, such that the video and/or photographs of the treatment tissue can be transmitted to the CCU 3217. The CCU 3217 may be further configured to provide the video and/or photographs to a user (e.g., a physician) to use while administering treatment using the handheld probe device 3201. For example, the user (e.g., a physician) may utilize the video and/or photographs to help him/her to direct and/or move the probe tip 3204c to inspect the tissues and to identify the desired target for photobiomodulation therapy tissue's surface location to begin the treatment session.

In some instances, the handheld probe device 3201 may utilize the same FOC 3209 used to provide the treatment light to provide an illuminating white light that may illuminate the video and/or photographs captured by the probe camera 3300. In some other instances, a separate FOC may be fed through the handheld probe device 3201 and used to illuminate the treatment tissue. Because the infrared laser wavelengths used for treatment are invisible (with respect to the visible spectrum), they do not obscure the video and/or photographs captured by the probe camera 3300, such that the probe camera 3300 is configured to be used during treatment to provide a live PBMT treatment visual for the physician.

In some other instances, the probe camera 3300 may be disposed elsewhere in the handheld probe device 3201. For example, in some instances, the probe camera 3300 may be provided on or near the probe tip 3204c. Specifically, in some instances, the probe camera 3300 may be arranged proximate or near one of the external temperature sensors 3222. In some other instances, the probe camera 3300 may be integrated with the control electronics 3206, and may receive images via an imaging FOC.

In yet some other instances, there may be multiple probe cameras 3300. For example, there could be the probe camera 3300 discussed above, disposed within the hollow reflection portion 3205a, as well as multiple probe cameras 3300 disposed on the probe tip 3204c around the emission lens 3223, arranged to allow for the operator (e.g., the physician) to view the tissues directly outside of the emission lens 3223, as well as in front of, behind, and to the side of the probe tip 3204c.

Referring now to FIG. 66, the motion sensor 3301 is integrated within and in communication with the control electronics 3206. The motion sensor 3301 is configured to detect motion of the handheld probe device 3201. In some instances, the motion sensor 3301 is configured to detect gradual or slight movements of the handheld probe device 3201, such as the handheld probe device 3201 being moved during treatment. In some instances, the motion sensor 3301 is further configured to detect sudden movements of the handheld probe device 3201, such as a drop event in which the handheld probe device 3201 is dropped. The control electronics 3206 are then configured to transmit this information to the CCU 3217 to be used to control the various components of the phototherapy system 3200. The motion sensor 3301 may be any of a variety of motion sensing mechanisms, such as a capacitive accelerometer, a piezoresistive accelerometer, a piezoelectric accelerometer, a rotational sensor, or any other suitable motion sensing mechanism.

In some instances, the handheld probe device 3201 may further include various detectable chips 3311 embedded in various locations. The detectable chips 3311 may be configured to be detected by an external-to-the-body "probe's internal chip location" (PCL) detection device that allows for the user (e.g., a physician) to visualize where the probe tip 3204c (or other components of the handheld probe device 3201) are located within or on a body tissue surface. In some instances, the detectable chips 3311 may be embedded within the handle 3204a (as shown in FIG. 68). In some instances, the detectable chips 3311 may alternatively or additionally be embedded in other locations within the handheld probe device 3201, such as within the shaft 3204b or within the probe tip 3204c.

In some instances, the handheld probe device 3201 may include as few as 1 detectable chip 3311 embedded therein. In some instances, the handheld probe device 3201 may include as many as 100 detectable chips 3311 embedded therein, as necessary for a given application. In some instances, the detectable chips 3311 may be microsize (e.g., between 0.1 mm and 1 mm in diameter). The detectable chips 3311 may be magnetic in content or may be configured to emit an energy (e.g., radio waves) that an external chip detector device (e.g., the PCL detection device) can detect.

In any case, the detectable chips 3311 are configured to aid in sensing and/or determining a position of the handheld probe device 3201 relative to adjacent tissues or nearby organs that need to be either treated or avoided during a treatment procedure.

Figure 85:
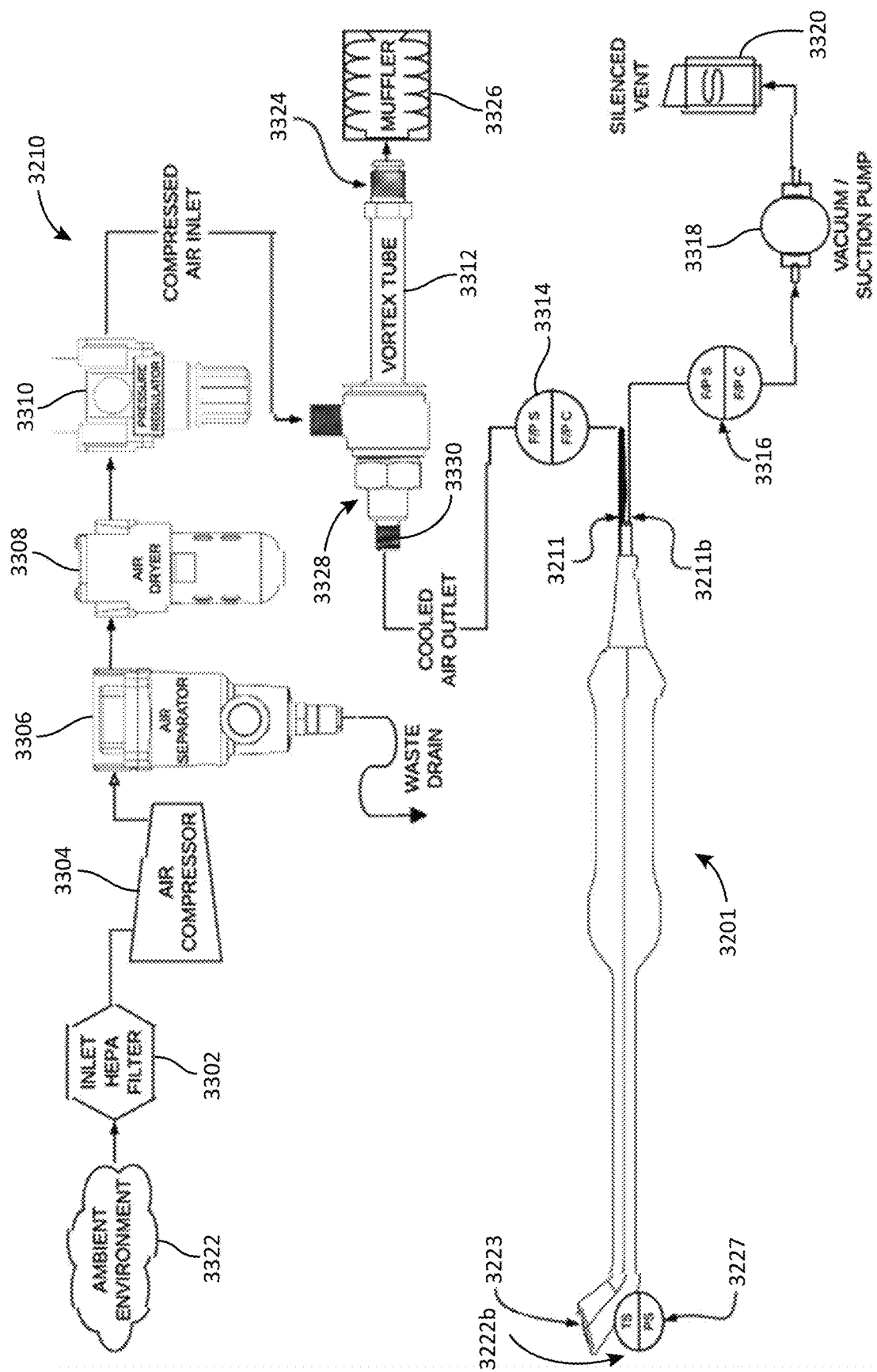
FIG. 85 depicts a schematic representation of a cooling system for integration with the phototherapy system and handheld probe device of FIG. 66.

Referring now to FIG. 85, a schematic diagram of an exemplary embodiment of the cooling system 3210 is provided. The cooling system 3210 shown in FIG. 85 is configured to allow for the use of chilled air as a coolant within the handheld probe device 3201 described above. It should be appreciated that, in some instances, the cooling system 3210 may be configured for use with other gases (e.g., carbon dioxide) that are traditionally used in medical procedures without departing from the scope of the present disclosure. The cooling system 3210 depicted in FIG. 85 utilizes a vacuum/suction pump 3318 on the downstream side of the cooling system 3210 (with respect to the handheld probe device 3201) to ensure that no chilled air escapes from the handheld probe device 3201 during use, thereby eliminating the potential for embolisms to be caused by leaked chilled air within various treatment cavities (e.g., the rectal cavity, the vaginal cavity).

As illustrated, the cooling system 3210 includes an inlet filter 3302, an air compressor 3304, an air moisture separator 3306, an air dryer 3308, a pressure regulator 3310, a vortex tube 3312, an inlet flow/pressure sensor and controller 3314, the handheld probe device 3201 (including internal temperature sensors 3222b and internal pressure sensors 3227), an outlet flow/pressure sensor and controller 3316, a vacuum/suction pump 3318, and an outlet vent 3320.

In the cooling system 3210, ambient air 3322 is pulled in through the inlet filter 3302 by the air compressor 3304. In some instances, the inlet filter 3302 may be a high-efficiency particulate air filter. The filtered air is then fed through the air moisture separator 3306 to separate any water molecules from the incoming air stream. The filtered and separated air is then fed through the air dryer 3308 to ensure that any remaining water vapor contained within the filtered and separated air is removed from the filtered and separated air. The filtered, separated, and dried air is then fed into the vortex tube 3312 to be cooled.

The vortex tube 3312 may function similarly to the vortex tube 3100 described above, with reference to the treatment cylinder device 3001. Accordingly, the vortex tube 3312 is configured to spin compressed air through the body of the vortex tube 3312 toward a hot side 3324, where some of the air escapes through a valve or orifice into a muffler 3326 to be expelled to the ambient surroundings. The remaining air is then forced back toward a cold side 3328, which results in kinetic energy in the form of heat to be transferred to the incoming compressed air (e.g., being directed toward the hot side 3324), such that the compressed air traveling to the cold side 3328 is effectively chilled. It should be appreciated that, although the vortex tube 3312 is utilized in the cooling system 3210, various other cooling or chilling systems may be implemented within the cooling system 3210 in place of the vortex tube 3312. For example, a heat exchanger, a chiller, or any other suitable cooling or chilling mechanism may be implemented within the cooling system 3210.

The chilled air that has been filtered, separated, dried, and cooled then exits the vortex tube 3312 via a cooled air outlet 3330 on the cold side 3328. The chilled air is then fed through the inlet flow/pressure sensor and controller 3314. The inlet flow/pressure sensor and controller 3314 may include a mass flow meter, a pressure differential sensor (e.g., a Venturi flow meter), or any other suitable flow/pressure sensor. The chilled air is then fed into the handheld probe device 3201 via the coolant supply tubing 3211.

Figure 86:
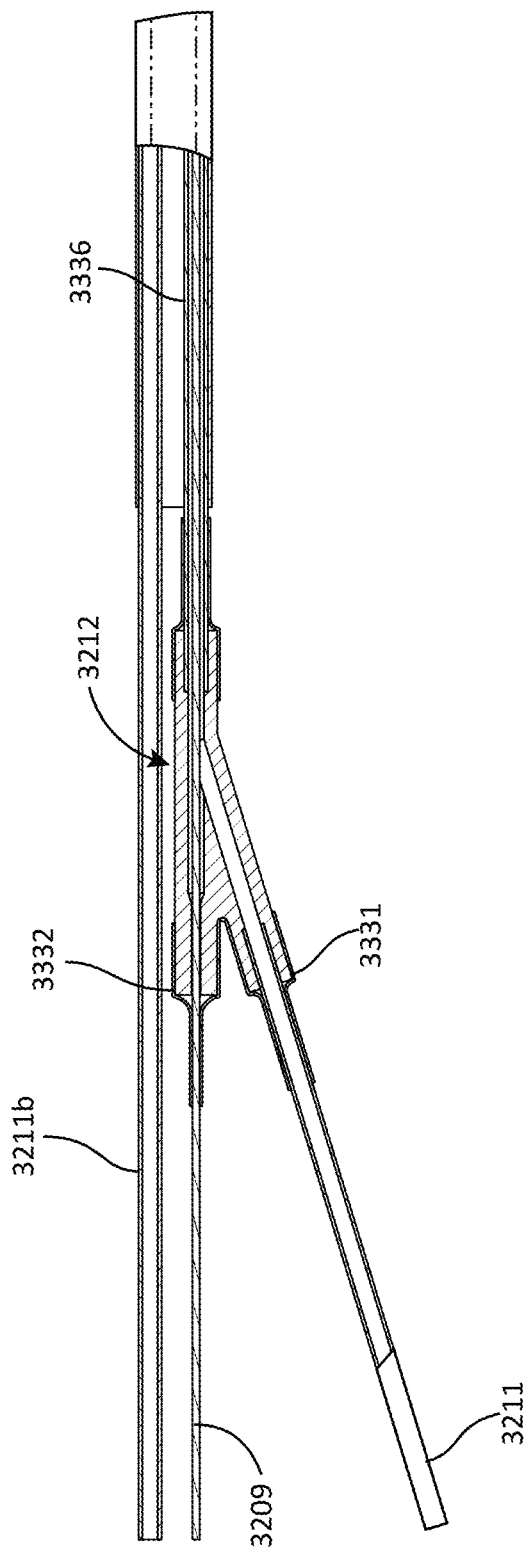
FIG. 86 depicts a wye fitting for coupling the cooling system of FIG. 85 to a fiber optic cable of the handheld probe device of FIG. 65.

As best illustrated in FIG. 86, the coolant supply tubing 3211 is merged with the FOC 3209 using the wye junction 3212. As shown, the wye junction 3212 includes a coolant tubing inlet port 3331 and an FOC inlet port 3332. The FOC 3209 and the coolant supply tubing 3211 are then merged within the wye junction 3212 into a single coaxial outlet tube 3336. The internal wye junction 3212b is substantially similar to the wye junction 3212, but instead separates the single coaxial outlet tube 3336 into the separate FOC 3209 and coolant supply tubing 3211.

From the handheld probe device 3201, the chilled air is then fed out of the coolant vent tubing 3211b and through the outlet flow/pressure sensor and controller 3316. The outlet flow/pressure sensor and controller 3316 may similarly include a mass flow meter, a pressure differential sensor (e.g., a Venturi flow meter), or any other suitable flow/pressure sensor. The chilled air is then fed or pulled into the vacuum/suction pump 3318. The vacuum/suction pump 3318 is configured to provide suction to the back end of the cooling system 3210 to actively prevent any chilled air from leaking within the patient during treatment (e.g., treatment of the rectal or vaginal cavities). The vacuum/suction pump 3318 is then configured to vent the chilled air out of the outlet vent 3320.

It should be appreciated that in some instances, for example if a $CO_2$-based cooling system is implemented, $CO_2$ gas may not provide a risk for potential embolisms. That is, $CO_2$ is a known and safe medical grade gas that is commonly used within the human body during operations, including many invasive procedures. Therefore, any accidental escape of $CO_2$ from the handheld probe device 3201 is not a significant risk to the patient being treated. In these instances, the vacuum/suction pump 3318 may be optionally omitted. However, in some instances, the vacuum/suction pump 3318 may still be used within a $CO_2$-based system. For example, a vacuum/suction pump 3318 may be useful to include when the cooling system 3210 is a system that recirculates the same reusable coolant media (e.g., $CO_2$) throughout the cooling system 3210. Further, an automatic electronic PSI regulator may be used by the CCU 3217 to adjust the system's PSI (e.g., $CO_2$ gas pressure) during the PBMT treatment session depending on the needs of a particular treatment protocol. In yet some other embodiments, cooling systems employing various other types of coolant medias may be implemented.

Further, in some instances, the cooling system 3210 may be configured as a sealed and enclosed cooling system that uses a static amount of coolant media. Accordingly, in some instances, the cooling system 3210 may be configured to recirculate the coolant media within a refrigerator-type chamber to chill the coolant media. For example, in some instances, the cooling system 3210 may include a chiller machine that utilizes liquid refrigerate to cool hollow coils configured to receive the coolant media. The hollow coils may be submerged within the liquid refrigerate. Accordingly, as the coolant media flows through the hollow coils, the liquid refrigerate on the outside of the hollow coils may actively chill the coolant media. This implementation may be applied in any of the various cooling systems described herein.

Additionally, in some instances, the cooling system 3210 may utilize a vortex tube to cool $CO_2$ gas that is circulated through a handheld probe device 3201 within a completely closed-circuit cooling system. In this instance, both the heated $CO_2$ gas escaping from the hot side of the vortex tube and the $CO_2$ vented out of the handheld probe device 3201 may be routed back into a refillable supply tank, such that there is a static volume of $CO_2$ gas within the cooling system 3210 that is recirculated to cool the various components of the handheld probe device 3201. In some instances, the heated $CO_2$ gas escaping from the hot side of the vortex tube may be chilled using a heat exchange device within the cooling system 3210 to remove the heat from (or otherwise chill) the $CO_2$ gas prior to being recirculated.

For example, in the closed-circuit $CO_2$ system described above, the heated $CO_2$ gas may be pumped into a network of hollow coils that are submerged in a bath of cooled liquid refrigerant. As indicated herein, the CCU 3217 may similarly control or automatically adjust the $CO_2$ gas flow rate within the closed-circuit $CO_2$ system (e.g., via an RPM speed of a gas pump motor) to effectively cool the handheld probe device 3201 based on temperature information received from temperature sensors 3222, 3222b.

Now that the various components of the phototherapy system 3200 have been described above, the functionality and control aspects of the phototherapy system 3200, with specific reference to the CCU 3217, will be described below.

As discussed above, the CCU 3217 is configured to receive and monitor various inputs from the handheld probe device 3201 (e.g., via the control electronics 3206), the CLG 3208, and the cooling system 3210, and to use these inputs to control the operation of the handheld probe device 3201, the CLG 3208, and the cooling system 3210. As described above, the CCU 3217 may be connected to the CLG 3208 and the cooling system via wired (e.g., hardwired) and/or wireless (e.g., Bluetooth, Wi-Fi) connections 3213. The CCU 3217 may be connected to the control electronics 3206 of the handheld probe device 3201 via wireless (e.g., Bluetooth, Wi-Fi) connections 3218.

In some instances, the CCU 3217 is configured to control the CLG 3208 to deliver a treatment dosage at the treatment tissue of approximately 10 $W/cm^2$ to the treatment tissue. In some other instances, the CCU 3217 is configured to control the CLG 3208 to deliver a treatment dosage at the treatment tissue between 0 $W/cm^2$ and 30 $W/cm^2$ to the treatment tissue. In some instances, a curvature of a cavity in which tissue is being treated (e.g., the curvature of the vaginal wall) may necessitate a higher treatment dosage as compared to a flat treatment tissue surface. Accordingly, in some instances, the user (e.g., the physician) may manually change the treatment parameters to be administered during treatment based on the tissue to be treated. In some instances, the CCU 3217 may be configured to control the CLG 3208 to deliver an initial treatment photon dose at a light wavelength of 810 nm and a secondary treatment photon dose at a wavelength of 980 nm. In some instances, the CCU 3217 may be configured to control the CLG 3208 to deliver the initial treatment photon dose and the secondary treatment photon dose simultaneously or individually (e.g., each being emitted for a period of time) during the same treatment session. For example, in some instances, the available wavelengths may be pulsed individually (e.g., every other pulse is a differing wavelength). In some other instances, the CCU 3217 may be configured to control the CLG 3208 to deliver treatment doses at various other wavelengths.

The CCU 3217 is further configured to control the CLG 3208 according to various protocols or modes of operation. For example, the CCU 3217 is configured to control the CLG 3208 in a continuous mode (CM), a continuous and pulsed mode (CPM), a pulsed mode (PM, and operations with a combination of CM and PM during the same treatment session.

In some instances, the CCU 3217 is configured to receive temperature information from the control electronics 3206 of the handheld probe device 3201 obtained using the external and/or internal temperature sensors 3222, 3222b. The CCU 3217 may then use this temperature information to control the cooling system 3210 to provide more or less coolant media (e.g., chilled air) to the handheld probe device 3201.

For example, during treatment, the external temperature sensors 3222 may be used by the CCU 3217 to constantly monitor the treatment tissue (e.g., the mucosal surface of the vaginal wall) receiving the PBMT. The CCU 3217 may alert or notify (e.g., via a display of the CCU 3217) the user (e.g., the physician) as to the temperature of the treatment tissue. Accordingly, the user may have a real-time indication of the temperature of the treatment tissue during a treatment procedure. This may be particularly useful while administering treatments within various body cavities (e.g., the vaginal cavity, the rectal cavity), where visibility may be limited.

The CCU 3217 is further configured to automatically adjust the flow rate of the coolant media (e.g., air, $CO_2$, or any other suitable coolant media) based on the temperature information received from the external and/or internal temperature sensors 3222, 3222b during the PBMT session. For example, in some instances, the CCU 3217 is configured to shut off the light emitted from the CLG 3208 if the external temperature sensors 3222 detect that the treatment tissue has reached a first external temperature threshold. For example, in some instances, the first external temperature threshold may be 45 degrees Celsius. The CCU 3217 may then prevent the CLG 3208 from producing light again until the treatment tissue has had sufficient time (e.g., 5-20 seconds) to cool down.

Upon detecting that the treatment tissue has reached the first external temperature threshold, the CCU 3217 may additionally provide an alert or notification to the user via a display of the CCU 3217. Further, in some instances, the handheld probe device 3201 may further include one or more LED and/or audio feedback indicators 3334 (shown in FIG. 65), configured to provide feedback to the user in certain scenarios. Accordingly, the CCU 3217 may additionally or alternatively cause LED and/or audio feedback indicators 3334 to provide a light and/or audio signal to the user indicating that the treatment tissue has reached the first external temperature threshold. For example, in some instances, the LED and/or audio feedback indicator 3334 may include an LED light on the handle 3204a of the handheld probe device 3201. During normal operation, the LED may be lit up with a green light, indicating that the laser beam emission is 'On.' The LED light may then begin to flash red upon the light from the CLG 3208 being shut off, thereby indicating that an error has been detect, specifically a temperature fault has been detected. After flashing red, the LED light may turn to a solid red color to indicate that the laser beam emission has been turned off. The LED and/or audio feedback indicator 3334 may further include an internal audio component configured to verbally notify the user that the temperature has reached the first external temperature threshold, and that the laser beam emission has been turned off.

In some instances, the CCU 3217 is configured to control the cooling system 3210 to provide 100 standard cubic centimeters per minute (SCCM) of coolant media flow through the handheld probe device 3201. However, the CCU 3217 is configured to automatically increase the flow rate of the coolant media provided by the cooling system 3210 if the external temperature sensors 3222 detect that the treatment tissue has reached a second external temperature threshold. For example, in some instances, the second external temperature threshold may be 40 degrees Celsius. In some other instances, the second external temperature threshold may be 42.5 degrees Celsius. In some other instances, the second external temperature threshold may be between 35 degrees Celsius and 44 degrees Celsius. For example, in some instances, the CCU 3217 is configured to maintain the treatment tissue at temperatures between 35 and 40 degrees Celsius during treatment. Depending on the application, the CCU 3217 is also configured to selectively maintain the treatment tissue at even lower temperatures during treatment.

In these instances, the CCU 3217 may also cause the LED and/or audio feedback indicator 3334 to provide a notification to the user that the temperature has reached the second external temperature threshold. For example, the CCU 3217 may cause the LED light to flash green to indicate that the second temperature threshold has been reached. Similarly, the internal audio component may be caused to verbally notify the user that the second temperature threshold has been reached.

Similarly, in some instances, the CCU 3217 is configured to automatically shut off the light emitted from the CLG 3208 if the internal temperature sensors 3222*b* detect that the internal components of the handheld probe device 3201 have reached an internal temperature threshold. For example, in some instances, the internal temperature threshold may be 48 degrees Celsius. The CCU 3217 may then similarly prevent the CLG 3208 from producing light again until the internal components have had sufficient time (e.g., 5-20 seconds) to cool down. Similarly, upon reaching the internal temperature threshold, the CCU 3217 may be configured to notify the user via the LED and/or audio feedback indicators 3334 (e.g., via a specific LED color or pattern or via a verbal notification).

Furthermore, the coolant media provided by the cooling system 3210 cools the emission lens 3223, which thereby provides direct cooling to the treatment tissue. For example, the treatment tissue may be mucosal, submucosal, dermal, and/or various other tissues.

In the case of a transvaginal procedure, by monitoring the temperature of and providing direct cooling to the treatment tissue (e.g., the vaginal mucosa and submucosal tissues), the CCU 3217 allows for the temporary vasoconstriction of the blood vessels within the submucosal layers during the initial 810 nm dose administration. This cooling effect diminishes the number of blood-borne chromophores in the path of the laser beam, which results in more photons reaching the deepest depths within the pelvis (e.g., through the vaginal tissue) where disease may reside. Then, the second treatment photon dose administered with the 980 nm wavelength (which is a less penetrating wavelength) may be administered with less coolant flow. This results in the heating of tissues to still trigger vasodilation and cause increased blood flow to the mucosa and submucosal tissues and organs.

Accordingly, by cooling the treatment tissue using the cooling system 3210, the handheld probe device 3201 allows for a higher power intensity to be used, while also preventing tissue denaturization and/or damage. Further, the cooling provided by the cooling system 3210 may prevent the patient from sensing an intolerable heat buildup within the superficial tissues where the majority of mucosa's and submucosa's sensory nerves reside, deeper within the sacral plexus sensory nerve network, and also where other deeper pain-producing tissues reside. For example, in some instances, the phototherapy system 3200 is capable of safely administering up to 30 W/cm$^2$. In some instances, the phototherapy system 3200 may be capable of even higher intensities, depending on the flow rate of the coolant media provided by the cooling system 3210.

The CCU 3217 is configured to monitor the internal pressure of the handheld probe device 3201 using internal pressure information provided via the internal pressure sensors 3227. The CCU 3217 is further configured to increase or decrease suction provided by the vacuum/suction pump 3318 to maintain the internal pressure within the handheld probe device 3201 between 0 PSIG and −2 PSIG. By maintaining the internal pressure of the handheld probe device 3201 between 0 PSIG and −2 PSIG, the CCU 3217 effectively prevents the instance of chilled air escaping within the treated cavity, thereby preventing the possible of air embolisms (e.g., for transvaginal procedures).

The CCU 3217 is further configured to monitor the pressure and tactile contact on the probe tip 3204*c* using pressure/tactile contact information provided via the pressure/tactile sensors 3299. The CCU 3217 may use the pressure/tactile contact information to confirm that the probe tip 3204*c* is, in fact, in contact with the treatment tissue. Accordingly, by continuously monitoring the pressure/tactile contact information during a treatment procedure, the CCU 3217 may automatically shut off the light emitted by the CLG 3208 if the probe tip 3204*c* comes out of contact with the treatment tissue.

By shutting off the light emitted by the CLG 3208 immediately when the probe tip 3204*c* comes out of contact with the treatment tissue, the phototherapy system 3200 is capable of ensuring that no light emitted from the handheld probe device 3201 can accidentally be shined in the eyes of anyone near the treatment site. Accordingly, this automatic shutting off of the light emitted by the CLG 3208 makes the phototherapy system 3200 safe to be prescribed as an in-home therapy system for a patient to treat himself/herself, even though the CLG 3208 will typically operate as a Class 4 (Power Output 1 or more watts) medical laser device.

For example, in some instances, if the CCU 3217 detects that a pressure exerted on the probe tip 3204*c* is below a pressure threshold, the CCU 3217 may automatically shut off the light emitted by the CLG 3208. In some instances, the pressure threshold may be set at 1 PSI. In some other instances, the pressure threshold may be set between 0 PSI and 5 PSI.

In some instances, in addition to shutting off the light emitted by the CLG 3208, the CCU 3217 is further configured to provide an alert or notification to the user via the display of the CCU 3217 indicating that the pressure exerted on the probe tip 3204*c* has dropped below the pressure threshold. Similarly, upon determining that the pressure exerted on the probe tip 3204*c* has dropped below the pressure threshold, the CCU 3217 may be configured to notify the user via the LED and/or audio feedback indicators 3334 (e.g., via a specific LED color or pattern or via a verbal notification).

Accordingly, in the case of a transvaginal treatment procedure being administered as a self-treatment at home using the phototherapy system 3200, the CCU 3217 may automatically shut off the light emitted by the CLG 3208 immediately if the patient removes or pulls the handheld probe device 3201 out of the vagina prematurely or accidentally, thus improving the safety of using the handheld probe device 3201. Accordingly, even if the patient and/or another individual is not wearing laser goggles that they, and anyone else present, are required to wear during their at-home self-treatment session, the risk of the laser light emitted by the handheld probe device 3201 hitting their eyes is effectively eliminated.

In some instances, when there are multiple pressure/tactile sensors 3299, the CCU 3217 may be configured to automatically shut off the light emitted by the CLG 3208 upon determining that the pressure detected by any of the pressure/tactile sensors 3299 falls below the pressure threshold. In these instances, the CCU 3217 is capable of determining not only whether sufficient pressure is being exerted on the probe tip 3204*c*, but whether sufficient pressure is being exerted on multiple locations, thereby indicating that the emission lens 3223 is in proper contact with the treatment tissue. Furthermore, if multiple pressure/tactile sensors 3299 are employed, the CCU 3217 may be configured to alert or notify the user, via the display of the CCU 3217 and/or via a verbal notification from the audio feedback indicator 3334, that they need to change the angle of pressure so that the probe tip 3204c is lying flat on the treatment tissue.

Accordingly, in the case of a topical or transcutaneous treatment procedure being administered as a self-treatment at home using the phototherapy system 3200, the CCU 3217 may automatically shut off the light emitted by the CLG 3208 immediately if the patient accidentally lifts even one side of the probe tip 3204c off of the skins surface, thus improving the safety of using the handheld probe device 3201. Again, even if the patient and/or another individual is not wearing laser goggles that they, and anyone else present, are required to wear during their at-home self-treatment session, the risk of the laser light emitted by the handheld probe device 3201 hitting their eyes is effectively eliminated.

In some instances, the CCU 3217 may be configured to provide an alert or notification to the user (e.g., a physician) via the display of the CCU 3217 indicating how much pressure is being exerted on the probe tip 3204c (and thus the treatment tissue). In some instances, the CCU 3217 may further be configured to provide an alert or notification to the user via the display of the CCU 3217 indicating that the pressure being exerted on the probe tip 3204c has reached or exceeded a maximum recommended pressure. For example, in some instances, the maximum recommended pressure may be 40 PSI. In some other instances, the maximum recommended pressure may be more or less than 40 PSI depending on the materials of the handheld probe device 3201 and/or the tissue being treated.

Similarly, the CCU 3217 may be configured to provide an alert or notification to the user via the display of the CCU 3217 indicating that the pressure being exerted on the probe tip 3204c is below a recommended pressure for a particular procedure. Similarly, upon determining that the pressure exerted on the probe tip 3204c has dropped below the recommended pressure, the CCU 3217 may be configured to notify the user via the LED and/or audio feedback indicators 3334 (e.g., via a specific LED color or pattern or via a verbal notification).

For example, during a transvaginal procedure, it may be recommended that the user applies at least 15 PSI onto the probe tip 3204c to flex the vaginal tissue inward, to allow for the probe tip 3204c (e.g., the external surface of the emission lens 3223) to be as close as possible to the target tissue (which is generally an internal tissue at a certain depth from the vaginal wall) while providing the treatment. For example, a pressure of approximately 15 PSI applied by the user may force the vaginal (or rectal) tissue to flex inwardly, closer to the deepest targeted diseased tissues that are to be treated, thereby allowing for effective photon fluence dosing to be administered between 2 cm and 3 cm from the central longitudinal axis of the vaginal (or in some cases the rectal) vault. In some cases, the handheld probe device 3201 may be configured to provide effective photon fluence dosing to be administered beyond 3 cm from the central longitudinal axis of the vaginal (or rectal) vault. Accordingly, by ensuring that a sufficient pressure is provided, the handheld probe device 3201 is capable of administering a greater fluence of photons into the deepest areas to be treated, thereby greatly increasing the therapeutic capacity of the handheld probe device 3201.

The CCU 3217 may further be configured to detect that the probe tip 3204c is being continuously moved across the treatment tissue by monitoring the tactile contact information received from the pressure/tactile sensors 3299. For example, if the CCU 3217 determines that the probe tip 3204c has not been moved within a predetermined time period (e.g., 1-2 seconds), the CCU 3217 is configured to automatically shut off the light emitted by the CLG 3208, thereby preventing accidental burning of the treatment tissue. Accordingly, the CCU 3217 may provide an alert or notification to the user (e.g., the physician) via the display of the CCU 3217 indicating that they need to move the probe tip 3204c to continue treatment. Similarly, upon determining that the probe tip 3204c has not been moved within the predetermined time period, the CCU 3217 may be configured to notify the user via the LED and/or audio feedback indicators 3334 (e.g., via a specific LED color or pattern or via a verbal notification).

As discussed above, the CCU 3217 is further configured to receive videos and/or photographs from the probe camera 3300. The CCU 3217 may then provide these videos and/or photographs to the user via the display of the CCU 3217. Accordingly, in some instances, the CCU 3217 may provide the user with a real-time feed received from the probe camera 3300 to allow the user to better arrange the handheld probe device 3201 within the patient.

The CCU 3217 is further configured to receive various movement information from the motion sensor 3301. The CCU 3217 may use the movement information, in addition or alternative to the tactile contact information, detect whether the user is moving the handheld probe device 3201. Similarly, if the CCU 3217 detects that the user has not moved the handheld probe device 3201 within the predetermined time period, the CCU 3217 may shut off the light emitted from the CLG 3208 to prevent the user from burning the treatment tissue. Accordingly, the CCU 3217 may provide an alert or notification to the user (e.g., the physician) via the display of the CCU 3217 indicating that they need to move the probe tip 3204c to continue treatment. Similarly, upon determining that the probe tip 3204c has not been moved within the predetermined time period, the CCU 3217 may be configured to notify the user via the LED and/or audio feedback indicators 3334 (e.g., via a specific LED color or pattern or via a verbal notification).

Further, the CCU 3217 may use the movement information to detect whether there has been a drop event, in which the handheld probe device 3201 has been dropped. In the case of a drop event, the CCU 3217 may prevent the handheld probe device 3201 from being operated until it has been reviewed by a technician to ensure that no damage has occurred. In some instances, the CCU 3217 may further automatically log the date and time of the drop event and inform the manufacturer that the handheld probe device 3201 has been dropped via a network connection (e.g., via the internet).

In some instances, the motion sensor 3301 may further be configured to detect a rotational orientation of the handheld probe device 3201 (e.g., via a rotational sensor). Accordingly, in the case that the handheld probe device 3201 is used to treat multiple rotational quadrants within an internal cavity of the patient (e.g., the vaginal or rectal vault), by using the rotation orientation information in conjunction with the temperature information obtained using the external temperature sensors 3222, the CCU 3217 may be configured to automatically provide an alert or notification to the user (e.g. via the display of the CCU 3217 or via the LED and/or audio feedback indicators 3334 on the handheld probe device 3201) when they should switch between quadrants.

The CCU 3217 is further configured to sense and monitor the detectable chips 3311 disposed within the handheld probe device 3201 (and potentially within other components of the phototherapy system 3200). Accordingly, the CCU 3217 is configured to ensure that the user only uses the system components provided to ensure the safe delivery of the PBMT through the unique set of optics of the handheld probe device 3201. Specifically, the CLG 3208 may include a similar set of detectable chips (similar to the detectable chips 3311 of the handheld probe device 3201), and the CCU 3217 may be configured to prevent operation of the handheld probe device 3201 if the detectable chips 3311 of the handheld probe device 3201 and the detectable chips of the CLG 3208 are both detected. Accordingly, by including the detectable chips within various components of the phototherapy system 3200 and sensing the detectable chips via the CCU 3217, patient treatment sessions using non-approved (e.g., "knock-off") devices in place of the various components provided by the manufacturer may be effectively prevented.

The CCU 3217 is further configured to sense a probe battery charge level of the battery embedded within the control electronics 3206. Accordingly, the CCU 3217 may provide an alert to the user when the handheld probe device 3201 needs to be recharged (e.g., via placing the handheld probe device 3201 on its charging station or by plugging it into a charger).

In some instances, the CCU 3217 may be further configured to automatically transmit various HIPPA-approved test reports to an electronic medical records database (e.g., of a healthcare facility). Additionally, by collecting and storing data from several phototherapy systems similar to the phototherapy system 3200, various modifications can be made to improve the treatment process. Furthermore, the CCU 3217 and the control electronics 3206 of the handheld probe device 3201 may be configured to allow a technician to remotely access either device via Wi-Fi or Bluetooth (or any other suitable wireless communication technology employed in either device) to check and/or troubleshoot problems with the phototherapy system 3200.

The CCU 3217 is further configured to monitor various characteristics of the handheld probe device 3201 to determine if and when the handheld probe device 3201 needs to be sent in for repair. For example, the CCU 3217 may detect whether the handheld probe device 3201 develops clouded optics via the video and/or photographs obtained using the probe camera 3300. The CCU 3217 may further be configured to detect whether a restriction has developed in the coolant supply or vent tubing 3211, 3211*b* via a pressure differential detected between the inlet flow/pressure sensor and controller 3314 and the outlet flow/pressure sensor and controller 3316 of the cooling system 3210. The CCU 3217 may additionally detect whether the handheld probe device 3201 is heating up at an abnormally high rate or if an unusually high flow rate is needed to maintain the handheld probe device 3201 at the necessary temperatures via the temperature information obtained using the external and/or internal temperature sensors 3222, 3222*b*. Upon detecting any of these occurrences, the CCU 3217 is configured to automatically alert the manufacturer of the handheld probe device 3201 and instruct the user to have the handheld probe device 3201 repaired. Similarly, the CCU 3217 is configured to track a number of treatments performed using the handheld probe device 3201, and to provide a similar alert once the handheld probe device 3201 has been used for a predetermined number of treatments (e.g., 100 treatments).

Now that the various components, as well as the functionality and control aspects, of the phototherapy system 3200 have been described above, several exemplary use cases of the phototherapy system 3200 will be described below. It should be appreciated that these use cases are provided as examples and are not meant to be limiting in any way.

The phototherapy system 3200 is configured to allow for the handheld probe device 3201 to deliver a concentrated beam that is approximately 1.85 cm to 2 cm in diameter that can be directed toward specific targeted tissues close to the bladder-pelvic tissues. This concentrated beam may be used to treat female chronic bladder pain, as well as interstitial cystitis (IC) including severe bladder pain episodes called IC flare-ups. That is, the user (e.g., a physician) can use the handheld probe device 3201 to direct the emission lens 3223 within the vaginal vault to deliver a concentrated dose of photon energy (PBMT) toward specific pelvic structures to treat various tissues and organs (and associated diseases or afflictions) like the bladder, the urethra, the pelvic floor musculature (Myofascial Pelvic Floor Pain and Vaginismus), the deep sacral plexus nerve network, the cervix (Chronic Cervicitis), the uterus (Adenomyosis), the endometrium (Chronic Endometritis), as well as the intra-pelvic peritoneal organs like the ovaries, the Fallopian tubes (Acute Pelvic Inflammatory Disease), the posterior cul-de-sac's peritoneum and the uterosacral ligaments (Endometriosis).

The phototherapy system 3200 is similarly configured to allow for the handheld probe device 3201 to be inserted into the rectal vault to administer PBMT transrectally a concentrated dose of photon energy (PBMT) directly toward specific ano-rectal tissues or organs like the prostate gland (Prostatitis), bladder wall base (Intersitial Cystitis), as well as toward upper rectal areas and near or within the lower sigmoid colon (Diverticulitis).

In some instances, the phototherapy system 3200 is configured to allow the user to administer PBMT transcutaneously onto various external skin areas on and around the pelvic girdle. There are several lower body areas that commonly contribute to the pain symptomology in the Chronic Pelvic Pain (CPP) population. Some of these sites may need PBMT treatment to conquer the complex pain of CPP syndrome are lower back pain, *piriformis* muscle pain, hip-gluteal muscle pain, inner thigh & groin pain, lower abdominal wall pain, suprapubic and Mons pubis pain, vulvar pain, and clitoral pain. These additional sites can be treated during the same treatment session as the transvaginal and/or transrectal PBMT. In some instances, this transcutaneous PBMT may be provided using the handheld probe device 3201 itself. In some other instances, this transcutaneous PBMT may be provided using an accessory therapy hand piece with an adjustable 1.5 cm to 4 cm in-diameter beam using the same CLG 3208 described above. This accessory therapy hand piece may be substantially similar to the handheld probe device 3201 and/or may be an additional accessory configured to be coupled to the handheld probe device. This accessory hand piece may similarly be monitored and controlled by the CCU 3217. In either case, the ability to treat these external pelvic girdle's areas provides an enhanced potential for treatment success and may lengthen the state of Remission in pain symptoms relief following a series of 6 to 12 treatments.

The design/construction of the handheld probe device 3201 allows for a cleaning/sterilization protocol that eliminates any cross-contamination risks between treatment sessions and between different patients being treated with the handheld probe device 3201. For example, the handheld probe device 3201 has surfaces and connections that are easily cleanable and possesses no open crevices or large gaps at connection sites to avoid the collection of bodily fluids that would be hard to clean, to decontaminate, and to sterilize between treatment sessions. In some instances, the handheld probe device 3201 may be submerged in a disinfectant for approximately 45 minutes to be effectively sterilized. In some instances, the handheld probe device 3201 may additionally or alternatively be gas sterilized.

Further, in some instances, to avoid the necessity of sterilization, the handheld probe device 3201 may be operated with a transparent sterile covering (e.g., a flexible sheath that is rolled over the handheld probe device 3201) configured to cover the entire handheld probe device 3201 during operation. This sterile covering may then be discarded between uses. In some instances, prior to rolling the sterile covering onto the handheld probe device 3201, a transparent coupling oil or gel may be placed inside of the sterile covering to provide an interface between the probe tip 3204c (e.g., the emission lens 3223 and the external temperature sensors 3222) and the inside of the sterile covering (e.g., to provide improved heat transmission and reduce reflection between the emission lens 3223 and the inside of the sterile covering).

In some instances, the safety precautions and measures enacted by the CCU 3217 may make the phototherapy system 3200 safe for the manufacturer to sell to the end user (e.g., a healthcare facility), and to electronically and remotely (e.g., through electronic activation of the handheld probe device 3201) allow the administration of a set of treatment sessions. In some instances, the phototherapy system 3200 may be configured to allow for various unique preset settings based on specific disease states. Furthermore, the ability for the manufacturer to electronically and remotely control various operational capabilities of the phototherapy system 3200 may allow for the phototherapy system 3200 to be used as an at-home treatment system to be used by the patient to administer self-treatment using the handheld probe device 3201 (e.g., to administer a topical treatment). For example, in some instances, the manufacturer or a prescribing healthcare provider may be able to electronically lock the phototherapy system 3200 out from performing non-prescribed treatment procedures at a patient's home.

Accordingly, the phototherapy system 3200 is capable of safely administering high-intensity PBMT onto mucosal surfaces in an unique concentrated and focused beam methodology where the photon energies can be precisely targeted onto and toward a specific area or spot, and into deep into the soft tissues, beyond the receiving body cavity. Furthermore, because of the safety protocols implemented within the phototherapy system 3200, the handheld probe device 3201 may be used to safely administer treatment in anesthetized patients, in patients who are paralyzed, and in mentally challenged patients who are not able to express to a provider that the heat from the handheld probe device 3201 is intolerable.

Furthermore, due to the cooling system 3210 of the phototherapy system 3200 and the utilization of a variety of sensors, the phototherapy system 3200 allows for significantly improved safety, as compared to traditional PBMT delivery systems. Specifically, the cooling system 3210 provides cooling to three important features during operation of the handheld probe device 3201: a) the internal optical components within the enclosed-sealed system, b) the double convex lens that makes up the optical window that is emitting the photon energy onto the mucosa's or skin's surfaces, and c) the mucosal surface or the skin's surface that the optical window slides over via a thermodynamic conductive transfer of heat from the mucosal or skin's surface into the convex lens' surface.

Additionally, due to the cooling system 3210 and the various sensors, the phototherapy system 3200 has the design capacity and the capability to deliver the a very high amount of photon energy (fluency) of up to 30 W/cm$^2$ deep down into the soft tissues (e.g., up to and beyond 3 cm). In some instances, the photon energy (fluency) may exceed 30 W/cm$^2$ depending on the capabilities of the cooling system 3210.

The handheld probe device 3201 is further capable of being used transcutaneously (topically) onto almost any surface of the skin. Accordingly, the handheld probe device 3201 may be considered a universally useable PBMT wand hand piece.

In some instances, the handheld probe device 3201 may be used for a variety of other treatments, including, for example, skin pigmentation treatments, sexual stimulation treatments, and/or any other suitable treatments that necessitate the use of PBMT. The handheld probe device 3201 is also configured for use in the body cavities of large animals (e.g., race horses) to treat their pelvic floor muscle spasms. The handheld probe device 3201 may also be useable within much smaller animals (e.g., Poodles, German Shepherds) to treat their hip dysplasias and/or previously unreachable pelvic organ inflammatory disease states.

Furthermore, because the handheld probe device 3201 includes the rechargeable battery embedded within the control electronics 3206, and because the control electronics 3206 communicate with the CCU 3217 via wireless communication (e.g., Wi-Fi or Bluetooth) and utilizes a very low voltage battery, the phototherapy system 3200 effectively eliminates the potential for accidental high-voltage shock of the patient through the handheld probe device 3201. Specifically, because nothing within the handheld probe device 3201 is plugged into or electrically coupled to any high power sources, the risk of a high voltage shock of the patient is effectively eliminated.

In some instances, the configuration of the handheld probe device 3201 within the phototherapy system 3200 allows for a total power loss (e.g., from the CLG 3208 to the light being emitted out of the emission lens 3223) to be approximately 9%. In some instances, the total power loss may be even further reduced by using various reflective and anti-reflective coatings, as described above.

Additionally, although shown as different systems, the power source 3216, the AC/DC power inverter 3214, the cooling system 3210, the CLG 3208, the CCU 3217, and/or various other accessories may all be incorporated into a single system or device to be used with the handheld probe device 3201.

Furthermore, it should be appreciated that, in some instances, the phototherapy system 3200 may be operated without the use of the cooling system 3210 and/or the various temperature sensors 3222, 3222b. For example, if the output power (e.g., the photon dosage) required for a particular treatment is low enough, the potential for accidental burning of the treatment tissue may be low enough to omit the cooling system 3210 and/or the various temperature sensors 3222, 3222b.

Now that the phototherapy system 3200 has been described above, a variety of alternative handheld probe devices will be described below. It will be appreciated that the following alternative handheld probe devices are provided as examples, and are not meant to be limiting. Furthermore, it will be appreciated that the various handheld probe devices discussed below may be used in place of the handheld probe device 3201, described above, within the context of the phototherapy system 3200. Accordingly, operation of the following handheld probe devices may similarly be controlled by the CCU 3217, and the following handheld probe devices may be provided with coolant media and/or coherent light by the cooling system 3210 and/or the CLG 3208, respectively.

Referring now to FIG. 88, another handheld probe device 3401 is illustrated. The handheld probe device 3401 is substantially similar to the handheld probe device 3201, but has a replaceable portion 3432 including a shaft 3404b and a probe tip 3404c. The replaceable portion 3432 may be configured to be quickly attached to the handle 3404a using a coupler apparatus 3434. The coupler apparatus 3434 may utilize any of a variety of connection methods. For example, the coupler apparatus 3434 may be a threaded connection configured to align the FOC 3409 and the cooling supply and vent tubing 3411, 3411b within the handle 3404a with the FOC 3209 and the cooling supply and vent tubing 3411, 3411b within the shaft 3404b. In some instances, the coupler apparatus 3434 may be a barb-fitting connection that is configured to form an air-tight seal having the FOC 3209 and the cooling supply and vent tubing 3411, 3411b within the handle 3404a and the shaft 3404b aligned.

Referring now to FIG. 89, another handheld probe device 3501, similar to the handheld probe device 3401, is shown having an alternative replaceable portion 3532 coupled to a handle 3504a via a coupler apparatus 3534. The replaceable portion 3532 similarly includes a shaft 3504b and a probe tip 3504c. The replaceable portion 3532 further includes a sheath 3508 enveloping the shaft 3504b and the probe tip 3504c. The shaft 3504b includes a support shaft 3533, sensor wires 3510, and an air flow baffle 3512. The FOC 3509 and sensor wires 3510 run axially within the sheath 3508 between the handle 3504a and the probe tip 3504c. The air flow baffle 3512 runs axially along the shaft 3504b and splits the shaft 3504b into a coolant inlet channel configured to receive coolant media from the coolant supply tubing 3511 to be provided to the probe tip 3504c and a coolant outlet channel configured to provide a venting route for the coolant media to exit the probe tip 3504c out of the coolant vent tubing 3511b.

The probe tip 3504c includes a fiber end 3528 of the FOC 3509, a reflective mirror 3514, and a temperature sensor 3522. As illustrated, the fiber end 3528 is configured to emit light axially onto the reflective mirror 3514 to be directed radially out of the sheath 3508 onto a treatment site. Accordingly, the sheath 3508 is made of a transparent or translucent material configured to permit light emission therethrough. The external temperature sensor 3522 is substantially similar to the external temperature sensors 3222 of the handheld probe device 3201. The sensor wires 3510 are configured to transmit temperature information obtained by the temperature sensor 3522 back to control electronics 3506 (e.g., similar to the control electronics 3206) to be communicated to the CCU 3217 of the phototherapy system 3200.

Referring now to FIG. 90, another handheld probe device 3601, similar to the handheld probe device 3401, is shown having an alternative replaceable portion 3632 coupled to a handle 3604a via a coupler apparatus 3634. The replaceable portion 3632 similarly includes a sheath 3608 enveloping a shaft 3604b and a probe tip 3604c. The shaft 3604b is substantially similar to the shaft 3504b discussed above. The probe tip 3604c, however, includes an angled emission fiber end 3628 configured to emit coherent light from the FOC 3609 through the sheath 3608 and onto the treatment tissue. The probe tip 3604c similarly includes a temperature sensor 3622 that is similar to the external temperature sensors 3222 of the handheld probe device 3201. The handheld probe device 3601 similarly includes sensor wires 3610 configured to transmit temperature information obtained by the temperature sensor 3622 back to control electronics 3606 (e.g., similar to the control electronics 3206) to be communicated to the CCU 3217 of the phototherapy system 3200.

Referring now to FIG. 91, another handheld probe device 3701, similar to the handheld probe device 3401, is shown having an alternative replaceable portion 3732 coupled to a handle 3704a via a coupler apparatus 3734. The replaceable portion 3732 similarly includes a sheath 3708 enveloping a shaft 3704b and a probe tip 3704c. The sheath 3708 similarly includes an air flow baffle 3712 running axially along the shaft 3704b that is substantially similar to the air flow baffle 3512 discussed above. The shaft 3704b is substantially similar to the shaft 3504b discussed above. The probe tip 3704c, however, includes a circular emission fiber end 3728 configured to emit coherent light from the FOC 3709 approximately 360 degrees through the sheath 3708 and onto the treatment tissue. The probe tip 3704c similarly includes a temperature sensor 3722 that is similar to the external temperature sensors 3222 of the handheld probe device 3201. The handheld probe device 3701 similarly includes sensor wires 3710 configured to transmit temperature information obtained by the temperature sensor 3722 back to control electronics 3706 (e.g., similar to the control electronics 3206) to be communicated to the CCU 3217 of the phototherapy system 3200.

Referring now to FIGS. 92-96, another handheld probe device 3801, similar to the handheld probe device 3401, is shown having an alternative replaceable portion 3832. Coolant supply tubing 3811 and an FOC 3809 (which may be the FOC 3209 described above) similarly enter (coaxially) a handle 3804a of the handheld probe device 3801 via an external interface 3807 disposed at a proximal end of the handheld probe device 3801. It should be noted that the handle 3804a of the handheld probe device 3801 does not include an internal wye junction, such that the FOC 3809 that is coaxially disposed within the coolant supply tubing 3811 is fed through the handle 3804a and into the replaceable portion 3832 via a coupler apparatus 3834.

As best illustrated in FIG. 96, the coupler apparatus 3834 includes a junction body 3838 fixedly coupled to the handle 3804a and including a plurality of circular spring contacts 3837. The plurality of circular spring contacts 3837 are configured to engage and retain a plurality of corresponding grooves 3839 disposed on a sheath 3808 of the replaceable portion 3832. Accordingly, the sheath 3808 may be inserted into the coupler apparatus 3834 to couple the replaceable portion 3832 to the handle 3804a. In some instances, the spring contacts 3837 are further configured to provide electrical contact between wire leads connecting the temperature sensors 3822 to the control electronics 3806.

With the sheath 3808 inserted into the coupler apparatus 3834, the coolant supply tubing 3811 is configured to align with a support shaft 3833 of the replaceable portion 3832. The support shaft 3833 includes the FOC 3809 having an annular gap 3820 (shown in FIG. 95) between the inside of the support shaft 3833 and the outside of the FOC 3809. Accordingly, coolant media provided via the coolant supply tubing 3811 is allowed to flow into the support shaft 3833 within the annular gap 3820 to be provided to the probe tip 3804c. Similarly, the FOC 3809 within the handle 3804a is configured to emit coherent light into the FOC 3809 within the replaceable portion 3832 to be emitted through the probe tip 3804c.

Referring now to FIG. 95, the support shaft 3833 terminates at a shaft end interface 3841 within a cavity 3830 formed by the probe tip 3804c. The shaft end interface 3841 includes a plurality of coolant inlet holes 3821, an internal temperature sensor 3822b, an internal pressure sensor 3827, and a fiber end 3828 of the FOC 3809. The coolant inlet holes 3821 allow for coolant media (e.g., supplied by the cooling system 3210) to flow into the cavity 3830 formed by the probe tip 3804c to provide cooling to the various components within the probe tip 3804c. In some instances, the coolant media may alternatively simply flow into the cavity 3830 axially around the FOC 3809. The coolant may then flow out of the probe tip 3804c via space between the sheath 3808 and the support shaft 3833, through one or more clearances 3836, to coolant vent tubing (similar to the coolant vent tubing 3211b) to be vented out of the handheld probe device 3801.

Figure 97:
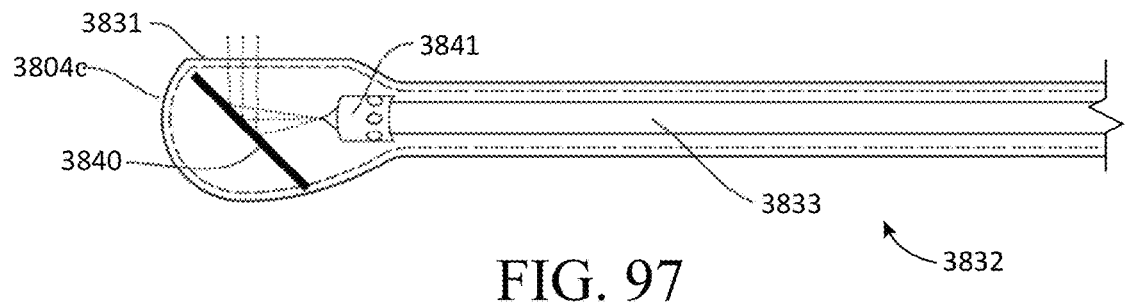
FIG. 97 depicts a side view of another disposable probe tip for implementation with the partially disposable handheld probe device of FIG. 88.

The fiber end 3828 is configured to emit coherently light axially onto a reflector 3840, which is configured to reflect the emitted light out of an optical window 3831 formed within the probe tip 3804c (shown in FIG. 97). The probe tip 3804c further includes an external temperature sensor 3822 arranged adjacent to the optical window 3831. Each of the various temperature and pressure sensors 3822, 3822b, 3827 may function substantially similarly to the various sensors 3222, 3222b, 3227 described above. Accordingly, temperature and pressure information obtained by the various temperature and pressure sensors 3822, 3822b, 3827 may similarly be transmitted to the CCU 3217 via control electronics 3806 (similar to control electronics 3206) of the handheld probe device 3801 (shown in FIG. 93).

Accordingly, the handheld probe device 3801 may be integrated into the phototherapy system 3200 described above, and may similarly be controlled via the CCU 3217 in a similar fashion. In some instances, additional optical elements may be integrated into the support shaft 3833 or replaceable portion 3832 to direct, shape, or otherwise alter the light for delivery. For example, in some instances, the shaft end interface 3841 may include a ball lens configured to spread the light beam emitted from the FOC 3809 into the cavity 3830 formed by the probe tip 3804c. Additionally, in some instances, the coupler apparatus 3834 may include a ball lens configured to aid in the light transmission between the FOC 3809 within the handle 3804a and the FOC 3809 within the replaceable portion 3832. In some other instances, the shaft end interface 3841 may alternatively be substantially similar to the FOC retention apparatus 3226 described above. Furthermore, various additional contacts or other elements including seals may be used in conjunction with or in lieu of the circular spring contacts 3837, as appropriate for an intended application.

Further, although depicted as a single replaceable portion 3832, in some instances, the replaceable portion 3832 may be provided in two or more components, each coupled together via a coupler apparatus (similar to the coupler apparatus 3834). For example, in some instances, a probe tip 3804c of the replaceable portion 3832 may be provided in a separate replaceable portion than a shaft 3804b of the replaceable portion 3832.

Referring generally to FIGS. 98-102, a variety of alternative replaceable portions configured for use with the handheld probe device 3801 are illustrated. Each of the various replaceable portions include substantially similar components to the replaceable portion 3832 discussed above. As such, the description provided below will focus on the differences between the replaceable portion 3832 and the replaceable portions discussed below.

Figure 98:
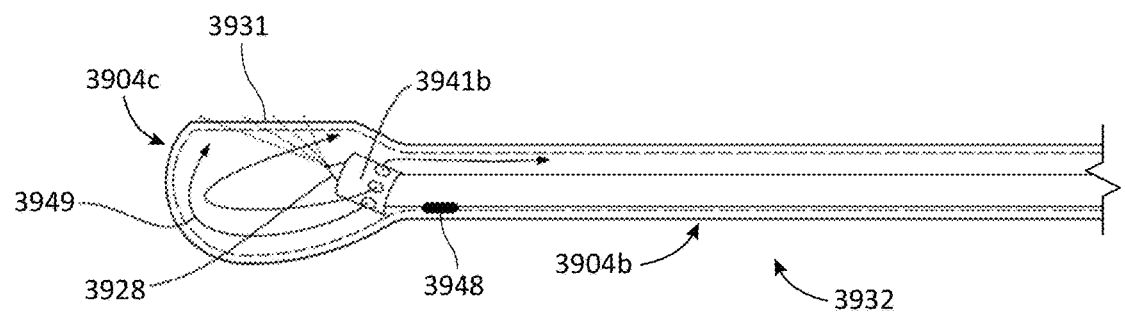

Referring now to FIG. 98, another replaceable portion 3932 is illustrated. The replaceable portion 3932 includes a similar shaft 3904b as the shaft 3804b discussed above. However, the shaft 3904b further includes an air flow restrictor 3948 configured to control the direction and flow of the coolant media within the replaceable portion 3932. It should be noted that, instead of including a reflector (similar to the reflector 3840), the replaceable portion 3932 includes an angled shaft end interface 3941b configured to direct light from a fiber end 3928 directly onto and through an optic window 3931 of the probe tip 3904c. The angled shaft end interface 3941b is substantially similar to the shaft end interface 3841. Accordingly, the angled shaft end interface 3941b includes similar components to the shaft end interface 3841 described above and is configured to function similarly. Further, coolant media 3949 is allowed to flow out of the angled shaft end interface 3941b, within the probe tip 3904c, and out of the shaft 3904b (as depicted by the arrowed flow paths).

Figure 99:
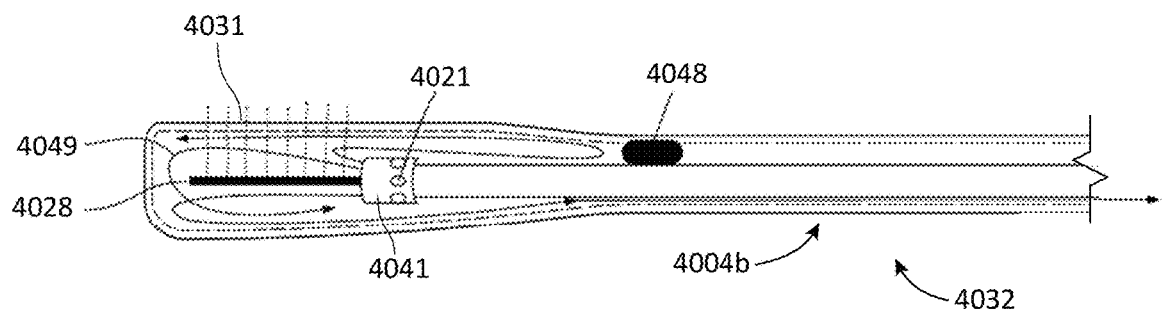

Referring now to FIG. 99, another replaceable portion 4032 is illustrated. The replaceable portion 4032 includes a similar shaft 4004b as the shaft 3804b discussed above. However, the shaft 4004b further includes an air flow restrictor 4048 (similar to the air flow restrictor 3948) that is similarly configured to control the direction and flow of the coolant media within the replaceable portion 4032. It should be noted that, instead of including a reflector (similar to the reflector 3840), the replaceable portion 4032 includes a section of exposed fiber 4028 that is configured to transmit light radially out of an optical window 4031 of the replaceable portion 4032. Similarly, coolant media 4049 is allowed to flow out of coolant inlets 4021 on a shaft end interface 4041, within the probe tip 4004c, and out of the shaft 4004b (as depicted by the arrowed flow paths).

Figure 100:

Referring now to FIG. 100, another replaceable portion 4132 is illustrated. The replaceable portion 4132 includes a similar shaft 4104b and probe tip 4104c as the shaft 3804b and probe tip 3804c discussed above. However, the probe tip 4104c does not include a reflector (similar to the reflector 3840). Instead, light emitted from a fiber end 4128 of the FOC 4109 is configured to be transmitted axially out of a distal end 4116 of the replaceable portion 4132.

Figure 101:
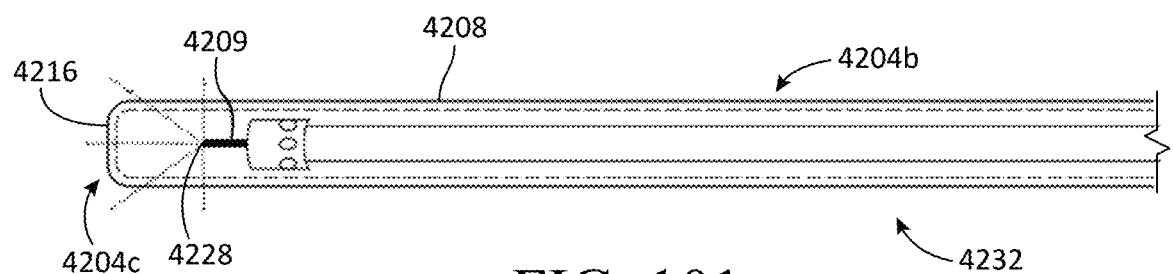

Referring now to FIG. 101, another replaceable portion 4232 is illustrated. The replaceable portion 4232 includes a similar shaft 4204b and probe tip 4204c as the shaft 3804b and probe tip 3804c discussed above. However, the probe tip 4204c does not include a reflector (similar to the reflector 3840). Instead, light emitted from a fiber end 4228 of the FOC 4209 is configured to be transmitted spherically both axially out of a distal end 4216 of the replaceable portion 4232 as well as radially out of a sheath 4208 of the replaceable portion 4232. That is, the light emitted from the FOC 4209 may be emitted radially in 360 degrees, axially, and angularly in 90 degrees between the axial direction and the radial direction.

Figure 102:
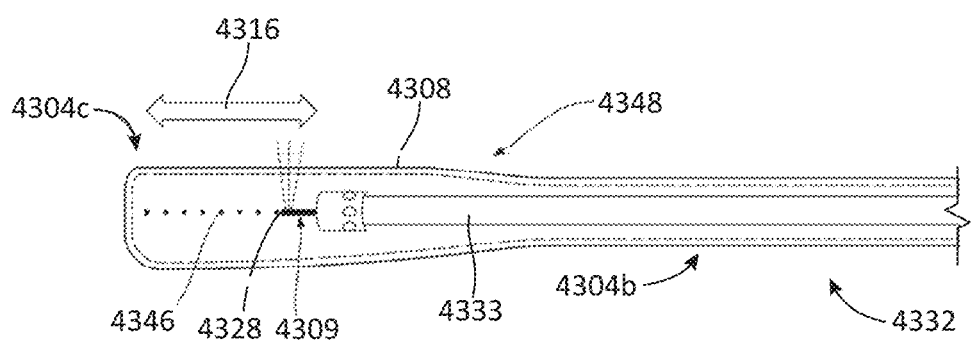

Referring now to FIG. 102, another replaceable portion 4332 is illustrated. The replaceable portion 4332 includes a similar shaft 4304b and probe tip 4304c as the shaft 3804b and probe tip 3804c discussed above. However, instead of including a reflector (similar to the reflector 3840), the replaceable portion 4332 includes an axially-emitting fiber end 4328 that is configured to transmit light radially out of a sheath 4308 of the replaceable portion 4332. In some instances, the FOC 4309 of the replaceable portion 4332 may be moveable in the axial direction (along the dotted line 4346 in the direction of arrows 4316). In some instances, the entire support shaft 4333 may be moveable in the axial direction. Accordingly, by moving the FOC 4309 or the entire support shaft 4333 axially, the light emitted by the axially-emitting fiber end 4328 may be translated along a treatment tissue without having to move the probe device within the patient. Further, the sheath 4308 includes an air flow restriction portion 4348 where the sheath 4308 narrows. This air flow restriction ensures that the coolant media is allowed to swirl within the probe tip 4304c to improve the cooling efficiency of the coolant media before it exits out of the shaft 4304b.

Referring now to FIGS. 103 and 104, another handheld probe device 4401 is illustrated. The handheld probe device 4401 may similarly be incorporated within the phototherapy system 3200 described above. The handheld probe device 4401 similarly includes a handle 4404a, a shaft 4404b, and a probe tip 4404c. The handle 4404a is substantially similar to the handle 3204a of the handheld probe device 3201. However, the handle 4404a further includes a probe tip rotation mechanism 4443, which is shown as a thumb wheel. The probe tip rotation mechanism 4443 is configured to selectively rotated the probe tip 4404c between a raised position 4447a, a nominal position 4447b, and a lowered position 4447c using control cables 4444 the extend within the shaft 4404b. It should be appreciated that the illustrated raised and lowered positions 4447a, 4447c are illustrative and a probe rotating mechanism 4445 of the probe tip 4404c would be axially aligned with the shaft 4404b when the probe tip 4404c is in either of the raised or lowered positions 4447a, 4447c.

The shaft 4404b and the probe tip 4404c are provided on a replaceable portion 4432 coupled to the handle 4404a via a coupler apparatus 4434. The shaft 4404b is substantially similar to the shaft 3804b discussed above, with the exception of the control cables 4444. The probe tip 4404c is substantially similar to the probe tip 3804c, but further includes the probe rotating mechanism 4445. The probe rotating mechanism 4445 is configured to rotate the probe tip 4404c about its central axis 4448 between the raised position 47a, the nominal position 47b, and the lowered position 47c. The probe rotating mechanism 4445 is further configured to be articulated between the various positions via input from the user from the probe tip rotation mechanism 4443, which is configured to move the cables 4444 (shown by a dash-dot-dot line) to rotate the probe rotating mechanism 4445. Accordingly, the user may effectively change an angle at which the emitted light is applied to the treatment tissue. This may be particularly useful for treating uniquely-shaped surfaces within various body cavities.

Referring now to FIGS. 105-107, another handheld probe device 4501 is shown that may be used with the phototherapy system 3200. The handheld probe device 4501 includes a reusable shaft portion 4508 and a disposable tip portion 4510. The reusable shaft portion 4508 includes a support shaft 4533 terminating in a shaft end interface 4541. The shaft end interface 4541 includes a FOC 4509 configured to emit light axially through a ball diffusing lens 4525. In some instances, the ball diffusing lens 4525 may similarly be approximately 1 mm in diameter. The emitted light from the ball diffusing lens 4525 then travels through a collimating lens 4514, which collimates the spread-out beam received from the ball diffusing lens 4525 into a straight collimated beam. In some instances, the collimating lens 4514 may be approximately 1 cm in diameter. The straight collimated beam may then travel into the disposable tip portion 4510. The reusable shaft portion 4508 further includes a coolant inlet port 4516 configured to provide coolant media into a coolant supply line 4518 of the disposable tip portion 4510.

The disposable tip portion 4510 is configured to be coupled within a female-type connection opening at a distal end 4520 of the reusable shaft portion 4508. The disposable tip portion 4510 may be retainably coupled to the reusable shaft portion 4508 via any suitable detachable coupling method. For example, the disposable tip portion 4510 may be retained within the reusable shaft portion 4508 via one or more spring contacts and corresponding grooves (similar to the spring contacts 3837 and grooves 3839 discussed above). In some other instances, the disposable tip portion 4510 may be threadably coupled to the reusable shaft portion 4508.

The disposable tip portion 4510 includes an outer sheath 4521, the coolant supply line 4518, an external temperature sensor 4522, an optical window 4523, and a reflector 4540. When the disposable tip portion 4510 is coupled or attached to the reusable shaft portion 4508, the coolant inlet port 4516 is configured to align with an opening in the coolant supply line 4518, such that coolant media (e.g., provided via a coolant supply line from the cooling system 3210) may flow through the coolant supply line 4518 and be used to cool the optical window 4523, as well as the rest of a distal end 4524 of the disposable tip portion 4510. The coolant media may then flow back through the hollow portion of the disposable tip portion 4510 and out of the hollow portion of the reusable shaft portion 4508. In some instances, there may be an annular gap around the collimating lens 4514 to allow for the coolant media to escape. Accordingly, the coolant media also flows over the collimating lens 4514, the ball diffusing lens 4525, and the support shaft 4533 to cool those components as well. The coolant media may exit the reusable shaft portion 4508 via coolant vent tubing (e.g., similar to the coolant vent tubing 3211b discussed above).

Additionally, when the disposable tip portion 4510 is coupled or attached to the reusable shaft portion 4508, a connection wire 4526 configured to transmit temperature information obtained from the external temperature sensor 4522 is configured to align with electrical contacts disposed within the reusable shaft portion 4508. Accordingly, temperature information obtained by the external temperature sensor 4522 can be transmitted to the control electronics (similar to the control electronics 3206) to be ultimately transmitted back to the CCU 3217. As illustrated, the external temperature sensor 4522 may be arranged adjacent the optical window 4523 by the distal end 4524 of the disposable tip portion 4510.

In some instances, the disposable tip portion 4510 may further include a detectable chip 4511 having a unique identification signal embedded within the distal end 4524 of the disposable tip portion 4510. Accordingly, the control electronics may be configured to sense the unique identification signal of the detectable chip 4511 from a particular disposable tip portion 4510 and transmit that information to the CCU 3217. The CCU 3217 may then limit the number of times a particular disposable tip portion 4510 is allowed to be used to perform a treatment session. For example, in some instances, a particular disposable tip portion 4510 may be limited to 6 to 12 treatment sessions.

Referring specifically to FIG. 106, the disposable tip portion 4510 defines a generally oval shaped cross-section having a large diameter of approximately 1.7 cm and a small diameter of approximately 1.2 cm. Accordingly, the collimated light 4528 traveling within the disposable tip portion 4510 may be a generally circular beam having a diameter of approximately 0.9 cm. As illustrated, the oval shape of the disposable tip portion 4510 provides sufficient space for the coolant supply line 4518 to travel down one side of the disposable tip portion 4510 and the connection wire 4526 to travel down the other side of the disposable tip portion 4510. As shown in FIG. 105, the collimated light 4528 travels down the length of the disposable tip portion 4510 and is reflected off of the reflector 4540 and through the optical window 4523 to be directed onto treatment tissue.

It should be appreciated that, because the most expensive components of the handheld probe device 4501 (e.g., the ball diffusing lens 4525, the collimating lens 4514) are disposed within the reusable shaft portion 4508, the handheld probe device 4501 may provide a more cost-effective probe device, as compared to probe devices that either include these components within the reusable portion or that do not have a reusable portion. For example, the reusable shaft portion 4508 may be configured to be used for up to 500 to 1000 treatment sessions.

In some instances, the reusable shaft portion 4508 may further include a microcamera and/or video system arranged adjacent to the shaft end interface 4541 and configured to obtain images and/or video reflected off of the reflector 4540 and shown down the length of the disposable tip portion 4510.

It should be appreciated that any of the various disposable and/or replaceable portions described herein may be formed with their respective handle components to form a single, unitary handheld probe device.

Figure 108:
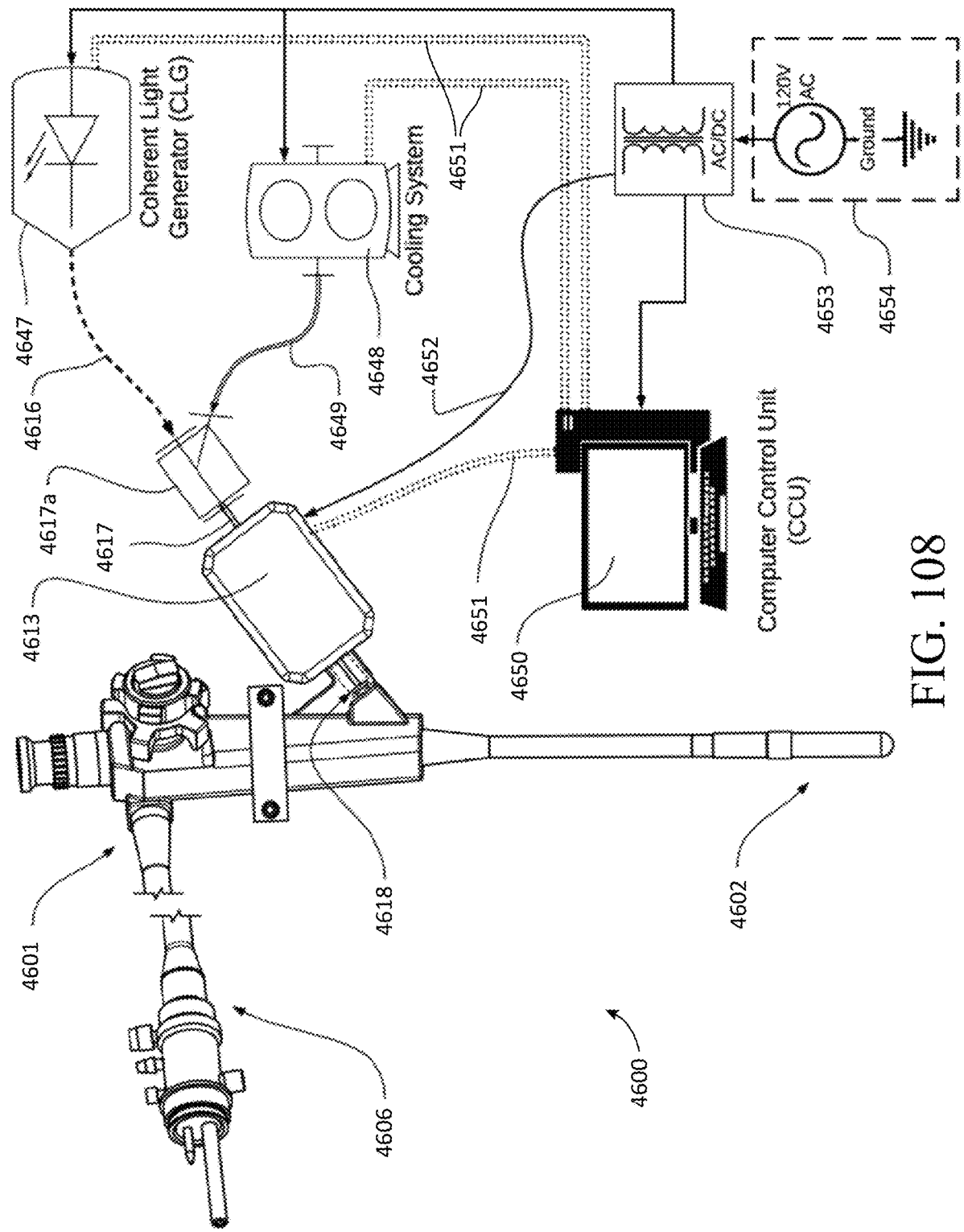

Referring now to FIG. 108, another phototherapy system 4600 is illustrated. The phototherapy system includes scope probe assembly 4601, a coherent light generator (CLG) 4647, a cooling system 4648, a computer control unit (CCU) 4650, and a power source 4654. The scope probe assembly 4601 is configured to provide PBMT to a tissue to be treated via a scope portion 4602. For example, in some instances, the scope portion 4602 may be used to provide a transesophageal PBMT treatment. In some other instances, the scope portion 4602 may be used to provide transbronchial or transcolonic PBMT treatment. However, it will be appreciated that a variety of treatment procedures may be performed using the scope portion 4602 without departing from the scope of the present disclosure. In some instances, the phototherapy system 4600 is configured to be implemented with a standard medical/surgical probe apparatus defined as a standard and/or pre-existing medical/surgical rigid or flexible endoscope apparatus.

The scope probe assembly 4601, the CLG 4647, and the cooling system 4648 are each in communication with the CCU 4650, which is configured to control operation of each of the various components of the phototherapy system 4600. For example, the scope probe assembly 4601, the CLG 4647, and the cooling system 4648 may be communicably coupled to the CCU 4650 via wired and/or wireless connections 4651. Although the CCU 4650 is depicted as a traditional computer, in some instances the CCU 4650 may be implemented using a PLC or other embedded systems.

The CLG 4647, the cooling system 4648, and the CCU 4650 are each configured to receive power from the power source 4654 through an AC/DC power inverter 4653 via electrical wires 4656. The power source 4654 may be substantially similar to the power source 3216 described above.

The scope probe assembly 4601 is configured to receive coherent light generated by the CLG 4647 via a fiber optic cable (FOC) 4616. The CLG 4647 may be substantially similar to the CLG 3208 described above. The scope probe assembly 4601 is further configured to receive a coolant media from the cooling system 4648 via coolant supply tubing 4649. The cooling system 4648 may also be substantially similar to the cooling system 3210 described above. The FOC 4616 and the coolant supply tubing 4649 are similarly combined into a single input line 4617 via a wye junction 4617a. The single input line 4617 similarly contains the FOC 4616 coaxially disposed within the coolant supply tubing 4649.

The single input line 4617 is then fed into an articulation assembly 4613, into the scope probe assembly 4601, and ultimately into the scope portion 4602. The articulation assembly 4613 is configured to selectively move the input line 4617 axially within the scope portion 4602. The articulation assembly 4613 is in communication with the CCU 4650, which is similarly configured to control operation of the articulation assembly 4613, as will be described below.

The coolant media supplied by the cooling system 4648 flows into the scope probe assembly 4601 via an operating channel 4618, into the scope portion 4602 to cool the various components of the scope portion 4602, and is ultimately vented through the operating channel 4618 and out through the articulation assembly 4613.

Referring now to 109 and 110, the scope probe assembly 4601 includes an eyepiece or camera device 4605, a scope umbilical cord end 4606, the articulation assembly 4613, and the scope portion 4602. The eyepiece or camera device 4605 is configured to allow a user (e.g., a physician) to directly view or view via a display screen (e.g., of the CCU 4650) the treatment tissue through the scope portion 4602. The scope umbilical cord end 4606 may be a standard scope umbilical cord for use in traditional healthcare facilities. For example, the scope umbilical cord end 4606 may include an air input 4607, a light input 4608, a gas input 4609, a water input 4610, a suction outlet 4611, and a vent outlet 4612. The articulation assembly 4613 is attached to the scope probe assembly 4601 via a clamp 4614 and bracket 4615.

As shown in FIGS. 111 and 112, the scope portion 4602 includes the FOC 4616 disposed within input line 4617, a disposable bulb 4619, and a coupling sleeve 4620. The scope portion 4602 may be selectively axially articulated via an articulation section 4603 that is controlled using a manual control knob 4604 (shown in FIG. 110). The disposable bulb 4619 may be made of an acrylic material, tempered glass, or any other suitable translucent material. The disposable bulb 4619 is configured to be attached to the articulation section 4603 via the coupling sleeve 4620. The coupling sleeve 4620 may be made of a flexible material that may be rolled over the articulation section 4603 to couple the disposable bulb 4619 onto the articulation section 4603. The coupling sleeve 4620 encapsulates the FOC 4616 and the input line 4617 within the disposable bulb 4619 to allow for the FOC 4616 and input line 4617 to be reused for multiple treatments. Specifically, the coupling sleeve 4620 provides an impervious seal between an internal cavity 4621 disposed within the disposable bulb 4619 and the external treatment environment of the scope portion 4602.

Referring to FIGS. 113-115, after a treatment session, the disposable bulb 4619 may be removed from the articulation section 4603 by rolling back the coupling sleeve 4620 (as best illustrated in FIG. 115). As best shown in FIG. 114, the distal end of the articulation section 4603 (e.g., the distal end of the scope) has an operation interface 4633 including an operating channel 4618, a visible light emitter 4634, an irrigation port 4635, a suction port 4636, and an optical window 4637. The operating channel 4618 receives the FOC 4616 and input line 4617, which protrude therethrough into the internal cavity 4621 of the disposable bulb 4619 during normal operation. Accordingly, the FOC 4616 is configured to extend into and emit light onto a treatment area from within the internal cavity 4621.

Further, coolant media may flow from the cooling system 4648, through the input line 4617, and into the internal cavity 4621 to cool the various components of the scope portion 4602. The coolant media may then be vented out via an annular gap 4643 (shown in FIG. 116) between the input line 4617 and the operating channel 4618. In some instances, additional sensors and/or tubing may be inserted through the operating channel 4618 to support additional device functionality.

Referring now to FIG. 116, in some instances, the scope portion 4602 further includes temperature sensors 4645 and an internal baffle 4646. The temperature sensors 4645 are located on the disposable bulb 4619 near the distal end of the disposable bulb 4619 and proximate the connection to the articulation section 4603. The temperature sensors 4645 are configured to provide temperature information to the CCU 4650 via wire leads that may be fed back through the operating channel 4618. The temperature sensors 4645 may further be integrated within the disposable bulb 4619, such that direct temperature readings of the tissue or other surface external to the disposable bulb 4619 where PBMT is being applied may be obtained. In some instances, instead of including the temperature sensors 4645, the temperature of the coolant media entering the scope portion 4602 and the coolant media exiting the scope portion 4602 may be taken, and the temperature of the disposable bulb 4619 may be inferred via the differential between the inlet and outlet coolant media temperatures, which may indicate the amount of cooling within the internal cavity 4621. In any case, the CCU 4650 may control the cooling system 4648 to increase or decrease a flow rate of the coolant media based on the temperature information obtained using the temperature sensors 4645.

The internal baffle 4646 is positioned along a portion of the axial length of the inside of the disposable bulb 4619. The internal baffle 4646 is configured to force coolant media 4644 (illustrated as lines with two dots and a dash) to travel from the input line 4617, along the axial length of the disposable bulb 4619 to the distal end of the disposable bulb 4619, back through the axial length of the disposable bulb 4619 on the other side of the internal baffle 4646, and out through the annular gap 4643. Accordingly, heat generated by the laser energy emitted from the FOC 4616 is dissipated by the flowing coolant media 4644 as it circulates through the internal cavity 4621.

Referring now to FIGS. 117-20, the articulation assembly 4613 is illustrated. The articulation assembly 4613 includes a housing 4622, a cover 4623, and an articulation mechanism 4625. The housing 4622 and the cover 4623 are configured to collectively envelop and protect the articulation mechanism 4625. The articulation mechanism 4625 includes a body 4626, guide rails 4627, and a carriage 4628. The body 4626 serve as a structural frame for the articulation mechanism 4625. The body 4626 further provides a central interface for the functional elements of the articulation mechanism 4625. The guide rails 4627 are configured to support the carriage 4628 over a range of motion. The carriage 4628 is fixed to the input line 4617 via a clamp 4624. Accordingly, motion of the carriage 4628 results in motion of the input line 4617. In some instances, the carriage 4628 may alternatively be fixed to the FOC 4616 within the input line 4617, such that motion of the carriage 4628 results in motion of the FOC 4616 only.

The articulation mechanism 4625 further includes a motor 4631 (shown in FIG. 118) configured to rotate a disk 4629 having a pin 4630. In some instances, the motor 4631 directly rotates the disk 4629. In some other instances, the motor 4631 is configured to rotate the disk 4629 via a geared interface or another intermediate drive apparatus. The pin 4630 is configured to slidably interface with a slot 4632 on the underside of the carriage 4628. Specifically, rotation of the disk 4629 moves the pin 4630 about the circumference of the disk 4629, which is in turn converted to linear motion of the carriage 4628 by the sliding interface between the pin 4630 and the slot 4632. In some instances, various other mechanisms for converting rotational motion to linear motion may be utilized in place of the articulation mechanism 4625. Further, in some instances, an electric or pneumatic direct linear actuator may be utilized in place of the articulation mechanism 4625.

Referring now to FIGS. 121-126, the articulation mechanism 4625 is moveable between a nominal position 4625a (shown in FIG. 121), an extended position 4625b (shown in FIG. 123), and a retracted position 4625c (shown in FIG. 125). When the articulation mechanism 4625 is in the nominal position 4625a, the distal end of the input line 4617 is disposed approximately in the axial middle of the internal cavity 4621 (as shown in FIG. 122). When the articulation mechanism 4625 is in the extended position 4625b, the distal end of the input line 4617 is disposed proximate a distal end of the internal cavity 4621 (as shown in FIG. 124). When the articulation mechanism 4625 is in the retracted position 4625c, the distal end of the input line 4617 is disposed proximate the proximal end of the internal cavity 4621 (as shown in FIG. 126).

Referring now to FIGS. 127-134, the scope portion 4602 may receive a variety of differing FOC types and may include various reflector types. For example, in some instances, the scope portion 4602 may receive an FOC having a narrow radially-emitting end 4616a configured to emit light 4639 radially out of the disposable bulb 4619 (as shown in FIGS. 127 and 132). In some instances, the scope portion 4602 may receive an FOC having an axially-emitting end 4616b configured to emit light 4639 axially out of the disposable bulb 4619 (as shown in FIG. 128). In some instances, the scope portion 4602 may receive an FOC having an axially-emitting end 4616c configured to emit light 4639 axially onto a flat reflector 4638a configured to reflect the light 4639 radially out of the disposable bulb 4619 (as shown in FIG. 129). In some instances, instead of axially moving the FOC 4616 and/or the input line 4617, the articulation mechanism 4625 may be configured to move the flat reflector 4638a axially within the disposable bulb 4619 (e.g., via a separate support shaft) to treat different areas of tissue without moving the remainder of the scope portion 4602. In some instances, the scope portion 4602 may receive an FOC having a spherically-emitting end 4616d configured to emit light out of the disposable bulb 4619 radially in 360 degrees, axially, and in all directions angular directions between the radial and axial directions (as shown in FIG. 130). In some instances, the scope portion 4602 may receive an FOC having an extended radially-emitting portion 4616e configured to emit light 4639 radially out of the disposable bulb 4619 along an axial length of the disposable bulb 4619 (as shown in FIG. 131).

In some instances, the scope portion 4602 may receive an FOC having a radially-emitting end 4616f at an off-centered location within the disposable bulb 4619 (as shown in FIG.

132). In some instances, the scope portion 4602 may receive an FOC having a spherically-emitting end 4616g at a centered location within the disposable bulb 4619 (as shown in FIG. 133). In some instances, the scope portion 4602 may receive an FOC having a radially-emitting end 4616h at an off-centered location within the disposable bulb 4619 that is configured to emit light 4639 onto a curved reflector 4638b to be reflected radially out of the disposable bulb 4619 (as shown in FIG. 134). By having the radially-emitting end 4616h reflecting off of the curved reflector 4638b, the light 4639 is spread out to cover a larger treatment area. In some instances, the curved reflector 4638b may be a concave mirror (as shown in FIG. 134), a convex mirror, or any other form of mirror that may be used to obtain desired light emission characteristics.

It should be appreciated that the various FOCs and corresponding light emission configurations depicted in FIGS. 127-134 are provided as examples and may be implemented individually or in any combination, as desired for a given application.

Referring now to FIGS. 135-137, the scope portion 4602 is illustrated with the operating channel 4618 receiving a fully-enclosed input line 4617b. The fully-enclosed input line 4617b is closed at the end to fully enclose the FOC 4616. Accordingly, the fully-enclosed input line 4617b is utilized in lieu of the disposable bulb 4619. As such, the operation interface 4633 is exposed, allowing normal, unobstructed use of the scope probe features during application of the PBMT. The fully-enclosed input line 4617b and/or the FOC 4616 may similarly be articulated, independently or in unison, using the articulation assembly 4613, as described above.

Referring now to FIG. 138, another articulation mechanism 4657 is illustrated that may be implemented within the articulation assembly 4613. The articulation mechanism 4657 includes a base structure 4626b configured to support the controlled linear actuation of the FOC 4616 and/or the input line 4617. The articulation mechanism 4657 further includes a carriage 4628b configured to be coupled to the FOC 4616 and/or the input line 4617 via a clamp 4624b. In some instances, the clamp 4624b may be a nut/ferrule or collet-type clamp which securely holds and evenly applies force to the circumference of the FOC 4616 and/or the input line 4617. Accordingly, motion of the carriage 4628b results in motion of the FOC 4616 and/or the input line 4617.

The articulation mechanism 4657 further includes a linear guide shaft 4640 and a lead screw 4641 configured to collectively support the carriage 4628b. The lead screw 4641 is threadably interfaced with the carriage 4628b such that rotational motion of the lead screw 4641 results in linear motion of the carriage 4628b. The lead screw 41 may be rotationally driven by a motor 4631b to axially translate the carriage 4628b with respect to the base structure 4626b. In some instances, the motor 4631b may be a stepper motor configured to provide precise control of the linear position of the carriage 28b, and thus precise control of the position of the FOC 4616 and/or the input line 4617 within the disposable bulb 4619.

In some instances, the phototherapy system 4600 may be configured to provide ablative strength light through the FOC 4616 to allow the scope portion 4602 to be used to administer ablative treatments.

It should be appreciated that the scope portion 4602 of the phototherapy system 4600 may be provided as a standalone disposable medical-surgical rod, handheld pole, or surgical manipulation tool that is not implemented on an endoscope apparatus. In this standalone form, the scope portion 4602 may be either rigid or flexible, as deemed necessary for a given application.

Furthermore, in some instances, the various components of the phototherapy system 4600 (e.g., the power source 4654, the AC/DC power inverter 4653, the CCU 4650, the CLG 4647, the cooling system 4648, and/or the articulation assembly 4613) may be integrated into one device for simplified use with any medical/surgical scope or other probe apparatus having an operating channel (e.g., similar to the operating channel 4618).

It should be appreciated that, the use of the word "disposable" and/or "replaceable" in conjunction with the various components described above is not meant to limit the scope of their use to a "single-use" case. That is, the "disposable" and/or "replaceable" components described above may be used a single time or several times before being disposed and/or replaced. Each of these use cases are contemplated by the present disclosure.

It should further be appreciated that any of the various probes discussed herein may be sized depending on their intended use. For example, the various probes discussed herein may be sized to provide treatment in various body cavities, lumens, vessels, and/or orifices in and/or on the body to allow for various treatments, such as trans-bronchial, trans-laryngeal, trans-sphenoidal (inside the nose), trans-pharyngeal (inside the oral cavity), trans-colonic, trans-aortic, trans-tympanic (membrane inside of the auditory canal of the ear), trans-urethral, and trans-vesical treatments, as well as treatments administered onto the colon, onto the aorta, onto the urethra, and onto the inner bladder (vesical) surface. It will be appreciated that the various probes discussed herein may be sized to allow for various other treatments.

Furthermore, any of the various PBMT devices discussed herein may be used to administer PBMT and/or treat diseases on the surface of the body's skin. Similarly, the various probes discussed herein may be used to administer PBMT and/or treat diseases on the surface of the mucosa, such as the vaginal mucosa and the rectal mucosa. It should also be appreciated that any of the various PBMT devices discussed herein may be used to deliver PBMT or administer photon energy through the body's skin and/or the surface of the mucosa to deliver photon energy beyond the body's skin and/or the surface of the mucosa.

While various embodiments and aspects of the phototherapy device have been described above, it should be understood that they have been presented by way of example only, and not limitation. Thus, the breadth and scope of the present disclosure should not be limited by any of the above exemplary embodiments.

This application—taken as a whole with the abstract, specification, and drawings being combined—provides sufficient information for a person having ordinary skill in the art to practice the features as disclosed herein. Any measures necessary to practice the features described herein are well within the skill of a person having ordinary skill in this art after that person has made a careful study of this disclosure.

Because of this disclosure and solely because of this disclosure, modification of this device and method can become clear to a person having ordinary skill in this particular art. Such modifications are clearly covered by this disclosure.

As used herein, in various embodiments, the term "circuit" includes hardware structured to execute the functions described herein. In some embodiments, each respective "circuit" includes machine-readable media for configuring the hardware to execute the functions described herein. The circuit is embodied as one or more circuitry components including, but not limited to, processing circuitry, network interfaces, peripheral devices, input devices, output devices, sensors, etc. In some embodiments, a circuit takes the form of one or more analog circuits, electronic circuits (e.g., integrated circuits (IC), discrete circuits, system on a chip (SOCs) circuits, etc.), telecommunication circuits, hybrid circuits, and any other type of "circuit." In this regard, the "circuit" includes any type of component for accomplishing or facilitating achievement of the operations described herein. In one example, a circuit as described herein includes one or more transistors, logic gates (e.g., NAND, AND, NOR, OR, XOR, NOT, or XNOR), resistors, multiplexers, registers, capacitors, inductors, diodes, wiring, and so on.

In other embodiments, the "circuit" includes one or more processors communicably coupled to one or more memories or memory devices. In this regard, the one or more processors execute instructions stored in the memory or execute instructions otherwise accessible to the one or more processors. In various arrangements, the one or more processors are embodied in various ways and are constructed in a manner sufficient to perform at least the operations described herein. In some embodiments, the one or more processors are shared by multiple circuits (e.g., circuit A and circuit B include or otherwise share the same processor which, in some example embodiments, executes instructions stored, or otherwise accessed, via different areas of memory). Additionally, in various arrangements, a given circuit or components thereof (e.g., the one or more processors) are disposed locally (e.g., as part of a local server or a local computing system) or remotely (e.g., as part of a remote server such as a cloud-based server). To that end, in certain arrangements, a "circuit" as described herein includes components that are distributed across one or more locations. Further, in various arrangements, the functions of one or more circuits discussed above may be implemented by single circuit (e.g., a processing circuit), or the functions of one circuit discussed above may be implemented by multiple circuits.

As used herein, a processor is implemented as a general-purpose processor, an application specific integrated circuit (ASIC), one or more field programmable gate arrays (FPGAs), a digital signal processor (DSP), a group of processing components, or other suitable electronic processing components. Additionally, in some arrangements, a "processor," as used herein, is implemented as one or more processors. In certain embodiments, the one or more processors are structured to perform or otherwise execute certain operations independent of one or more co-processors. In other example embodiments, two or more processors are coupled via a bus to enable independent, parallel, pipelined, or multi-threaded instruction execution. In some arrangements, the one or more processors take the form of a single core processor, multi-core processor (e.g., a dual core processor, triple core processor, or quad core processor), microprocessor, etc. In some embodiments, the one or more processors are external to the apparatus, for example, the one or more processors are a remote processor (e.g., a cloud-based processor). Alternatively, or additionally, the one or more processors are internal and/or local to the apparatus. Accordingly, an exemplary system for implementing the overall system or portions of the embodiments might include general purpose computing computers in the form of computers, including a processing unit, a system memory, and a system bus that couples various system components including the system memory to the processing unit.

Additionally, as used herein, a memory includes one or more memory devices including non-transient volatile storage media, non-volatile storage media, non-transitory storage media (e.g., one or more volatile and/or non-volatile memories), etc. In some embodiments, the non-volatile media takes the form of ROM, flash memory (e.g., flash memory such as NAND, 3D NAND, NOR, or 3D NOR), EEPROM, MRAM, magnetic storage, hard discs, optical discs, etc. In some embodiments, the volatile storage media takes the form of RAM, TRAM, ZRAM, etc. Combinations of the above are also included within the scope of machine-readable media. In this regard, machine-executable instructions comprise, for example, instructions and data which cause a general purpose computer, special purpose computer, or special purpose processing machines to perform a certain function or group of functions. In various arrangements, each respective memory device is operable to maintain or otherwise store information relating to the operations performed by one or more associated circuits, including processor instructions and related data (e.g., database components, object code components, or script components), in accordance with the example embodiments described herein.

What is claimed is:

1. A device for administering phototherapy, comprising:
   a hollow structure having at least a first open end through which the hollow structure receives at least a portion of patient anatomy, wherein the hollow structure comprises an annular rotatable member configured to rotate around at least one rotary axis;
   one or more coherent light generators mounted to the hollow structure and translatable in an axial direction parallel to the rotary axis along a track on the annular rotatable member, each coherent light generator configured to generate a beam of coherent light;
   for each coherent light generator, one or more lenses or mirrors optically connected to the coherent light generator and mounted to the hollow structure, the one or more lenses or mirrors configured to alter at least one aspect of the beam of coherent light generated by the coherent light generator; and
   a processing circuit comprising a processor and a memory storing instructions that, when executed by the processor, cause the processor to:
      accept an input from an operator; and
      generate one or more beams of coherent light via the one or more coherent light generators according to a plurality of settings configured to produce a therapeutic effect at a targeted treatment site on the patient anatomy;
   wherein the annular rotatable member is configured to be rotated to direct the one or more beams of coherent light to the targeted treatment site on the patient anatomy.

2. The device of claim 1, wherein the input relates to a treatment plan for the patient, and wherein the instructions cause the processor to generate the one or more beams of coherent light based on the treatment plan input.

3. The device of claim 2, wherein the input is a selection of a treatment plan from a plurality of stored treatment plans, and wherein the instructions cause the processor to generate the one or more beams of coherent light based on the selected treatment plan.

4. The device of claim 1, wherein the annular rotatable member is configured to rotate 360 degrees around at least one rotary axis.

5. The device of claim 1, wherein each coherent light generator is configured to generate the beam of coherent light at an infrared or near-infrared wavelength.

6. The device of claim 1, wherein at least one coherent light generator is configured to generate the beam of coherent light at 400 to 1200 nm.

7. The device of claim 1, wherein the one or more coherent light generators are configured to deliver beams of coherent light with a radiant exposure in a range of 0.1 to 50 J/cm$^2$ to the targeted treatment site.

8. The device of claim 1, wherein the device comprises three or more coherent light generators.

9. The device of claim 1, wherein the one or more coherent light coherent light generators are configured to generate beams of coherent light at three or more wavelengths.

10. The device of claim 1, wherein at least one of the lenses or mirrors is mounted on at least one galvanometric gimbal; and
wherein the instructions further cause the processor to direct the beam of coherent light to the target treatment site by moving the at least one galvanometric gimbal.

11. The device of claim 1, wherein the targeted treatment site comprises a primary treatment zone and a secondary treatment zone, the secondary treatment zone comprising a first zone proximal to a heart of the patient and a second zone distal to the heart of the patient; and
wherein the instructions further cause the processor to:
direct the one or more beams of coherent light to each of the primary treatment zone, proximal secondary treatment zone, and distal secondary treatment zone.

12. The device of claim 11, wherein the instructions further cause the processor to modify at least one setting and/or direct a beam of coherent light generated by a different coherent light generator to each of the primary treatment zone, proximal secondary treatment zone, and distal secondary treatment zone.

13. The device of claim 1, wherein the plurality of settings comprises a pulse type for each of the coherent light generators; and
wherein each pulse type is one of a continuous beam, a pulsed beam, a superpulsed beam, or a combination thereof.

14. The device of claim 1, wherein the instructions further cause the processor to:
receive data from at least one camera or sensor, the data relating to at least one of an operation of the device or a parameter of the targeted treatment site; and
in response to the data, perform at least one of:
modifying at least one of the plurality of settings controlling operation of the device; or
redirecting at least one beam of coherent light by at least one of rotating the annular rotatable member or moving at least one of the lenses or mirrors.

15. The device of claim 14, wherein the at least one sensor comprises a temperature sensor.

16. The device of claim 1, further comprising a display, and wherein the instructions further cause the processor to:
display, via the display, one or more user interfaces of the targeted treatment site to an operator;
receive, via the display, an identification of one or more areas within the targeted treatment site from the operator; and
perform one of:
directing one or more beams of coherent light to the one or more areas;
modifying at least one of the plurality of settings and directing one or more beams of coherent light to the one or more areas with the modified plurality of settings; or
avoid directing the one or more beams of coherent light to the one or more areas.

17. The device of claim 1, further comprising a cooling structure configured to deliver a coolant to at least a portion of the device or a portion of the patient anatomy, wherein the cooling structure includes at least one of a fan, a vortex tube, or an air compressor.

18. The device of claim 17, wherein the cooling structure is configured to maintain the portion of the patient anatomy at a temperature below 41° C.

19. The device of claim 1, further comprising a handheld probe configured to be optically connected to a coherent light generator of the one or more coherent light generators;
wherein the handheld probe is configured to receive a beam of coherent light from the coherent light generator and emit the coherent light from the handheld probe after the beam of coherent light is received.

20. The device of claim 19, wherein the handheld probe comprises a closed tip.

21. The device of claim 19, wherein the coherent light generator optically connected to the handheld probe is configured to generate a beam of coherent light of at least 10 W.

22. The device of claim 19, wherein the handheld probe further comprises one or more markers configured to be sensed by an external monitoring device;
wherein the instructions further cause the processor to display to the operator a location of the handheld probe relative to anatomy of the patient based on data received from the external monitoring device.

23. The device of claim 1, wherein the instructions further cause the processor to:
receive images of the targeted treatment site from an external imaging system; and
guide the one or more beams of coherent light to the targeted treatment site based on the images from the external imaging system.

24. The device of claim 1, further comprising a support system on which the hollow structure is mounted, wherein the support system is configured to move the hollow structure according to one or more degrees of freedom.

25. The device of claim 1, wherein the hollow structure is a hollow cylinder.

26. A method for administering phototherapy, comprising:
accepting an input from an operator; and
generating one or more beams of coherent light via one or more coherent light generators, the one or more beams generated according to a plurality of settings configured to produce a therapeutic effect at a targeted treatment site on a patient,
wherein the one or more coherent light generators are mounted to a hollow structure and translatable in an axial direction parallel to at least one rotary axis of an annular rotatable member of the hollow structure along a track on the annular rotatable member,
wherein the hollow structure comprises at least a first open end through which the hollow structure receives at least a portion of patient anatomy comprising the targeted treatment site,
wherein the hollow structure further comprises the annular rotatable member configured to rotate around the at least one rotary axis, and wherein each coherent light generator is optically connected to one or more lenses or mirrors mounted to the hollow structure, the one or more lenses or mirrors configured to alter at least one aspect of the beam of coherent light generated by the coherent light generator, wherein the annular rotatable member is configured to be rotated to direct the one or more beams of coherent light to the targeted treatment site.

27. The method of claim 26, wherein the input relates to a treatment plan for the patient, and wherein generating the one or more beams of coherent light comprises generating the one or more beams of coherent light via the one or more coherent light generators based on the treatment plan input.

28. The method of claim 27, wherein the input is a selection of a treatment plan from a plurality of stored treatment plans, and wherein the generating the one or more beams of coherent light comprises generating the one or more beams of coherent light via the one or more coherent light generators based on the selected treatment plan.

29. The method of claim 26, wherein the annular rotatable member is configured to rotate 360 degrees around at least one rotary axis.

30. The method of claim 26, wherein each coherent light generator is configured to generate the beam of coherent light at an infrared or near-infrared wavelength.

31. The method of claim 26, wherein at least one coherent light generator is configured to generate the beam of coherent light at 400 to 1200 nm.

32. The method of claim 26, wherein the one or more coherent light generators are configured to deliver beams of coherent light with a radiant exposure in a range of 0.1 to 50 $J/cm^2$ to the targeted treatment site.

33. The method of claim 26, wherein three or more coherent light generators are mounted to the hollow structure.

34. The method of claim 26, wherein the one or more coherent light generators are configured to generate beams of coherent light at three or more wavelengths.

35. The method of claim 26, wherein at least one of the lenses or mirrors is mounted on at least one galvanometric gimbal; and
wherein the method further comprises directing the one or more beams of coherent light to the targeted treatment site by moving the at least one galvanometric gimbal.

36. The method of claim 26, wherein the targeted treatment site comprises a primary treatment zone and a secondary treatment zone, the secondary treatment zone comprising a first zone proximal to a heart of the patient and a second zone distal to the heart of the patient; and
wherein directing the one or more beams of coherent light to the targeted treatment zone by rotating the annular rotatable member comprises directing the one or more beams of coherent light to each of the primary treatment zone, proximal secondary treatment zone, and distal secondary treatment zone.

37. The method of claim 36, wherein directing the one or more beams of coherent light to each of the primary treatment zone, proximal secondary treatment zone, and distal secondary treatment zone comprises modifying at least one setting and/or directing a beam of coherent light generated by a different coherent light generator to each of the primary treatment zone, proximal secondary treatment zone, and distal secondary treatment zone.

38. The method of claim 26, wherein the plurality of settings comprises a pulse type for each of the coherent light generators; and
wherein each pulse type is one of a continuous beam, a pulsed beam, a superpulsed beam, or a combination thereof.

39. The method of claim 26, further comprising:
receiving data from at least one camera or sensor, the data relating to at least one of an operation of the device or a parameter of the targeted treatment site; and
in response to the data, perform at least one of:
modifying at least one of the plurality of settings; or
redirecting at least one beam of coherent light by at least one of rotating the annular rotatable member or moving at least one of the lenses or mirrors.

40. The method of claim 39, wherein the at least one sensor comprises a temperature sensor.

41. The method of claim 26, further comprising:
displaying, via a display, one or more user interfaces of the targeted treatment site to an operator;
receiving, via a display, an identification of one or more areas within the targeted treatment site from the operator; and
performing one of:
directing one or more beams of coherent light to the one or more areas;
modifying at least one of the plurality of settings and directing one or more beams of coherent light to the one or more areas with the modified plurality of settings; or
avoiding directing the one or more beams of coherent light to the one or more areas.

42. The method of claim 26, further comprising delivering, by a cooling structure, a coolant to at least a portion of the hollow structure or the targeted treatment site, wherein the cooling structure includes at least one of a fan, a vortex tube, or an air compressor.

43. The method of claim 42, wherein the cooling structure is configured to maintain the portion of the patient anatomy at a temperature below 41° C.

44. The method of claim 26, further comprising optically connecting a handheld probe to a coherent light generator of the one or more coherent light generators, wherein the handheld probe is configured to receive a beam of coherent light from the coherent light generator and emit the coherent light from the handheld probe after the beam of coherent light is received.

45. The method of claim 44, wherein the handheld probe comprises a closed tip.

46. The method of claim 44, wherein the coherent light generator optically connected to the handheld probe is configured to generate a beam of coherent light of at least 10 W.

47. The method of claim 44, wherein the handheld probe further comprises one or more markers configured to be sensed by an external monitoring device; and
wherein the method further comprises displaying to the operator a location of the handheld probe relative to the anatomy of the patient based on data received from the external monitoring device.

48. The method of claim 26, further comprising:
receiving images of the targeted treatment site from an external imaging system; and
guiding the one or more beams of coherent light to the targeted treatment site based on the images from the external imaging system.

49. The method of claim 26, wherein the hollow structure is further mounted on a support system configured to move the hollow structure according to one or more degrees of freedom.

50. The method of claim 26, wherein the hollow structure is a hollow cylinder.

\* \* \* \* \*